US012529097B2

(12) United States Patent
Hutchison et al.

(10) Patent No.: US 12,529,097 B2
(45) Date of Patent: Jan. 20, 2026

(54) DIGITAL ANALYTE ANALYSIS

(71) Applicant: Bio-Rad Laboratories, Inc., Hercules, CA (US)

(72) Inventors: John Brian Hutchison, Medford, MA (US); Jeffrey Charles Olson, Chelmsford, MA (US); Darren Roy Link, Lafayette, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 699 days.

(21) Appl. No.: 17/835,439

(22) Filed: Jun. 8, 2022

(65) Prior Publication Data

US 2022/0307073 A1 Sep. 29, 2022

Related U.S. Application Data

(60) Continuation of application No. 16/838,800, filed on Apr. 2, 2020, now Pat. No. 11,390,917, which is a division of application No. 15/189,672, filed on Jun. 22, 2016, now Pat. No. 10,612,081, which is a division of application No. 13/460,762, filed on Apr. 30, 2012, now Pat. No. 9,399,797, which is a continuation-in-part of application No. 13/026,120, filed on Feb. 11, 2011, now Pat. No. 9,074,242.

(60) Provisional application No. 61/388,937, filed on Oct. 1, 2010, provisional application No. 61/347,158, filed on May 21, 2010, provisional application No. 61/331,490, filed on May 5, 2010, provisional application No. 61/304,163, filed on Feb. 12, 2010.

(51) Int. Cl.
*C12Q 1/686* (2018.01)

(52) U.S. Cl.
CPC .................................... *C12Q 1/686* (2013.01)

(58) Field of Classification Search
None
See application file for complete search history.

(56) References Cited

U.S. PATENT DOCUMENTS

| | | | |
|---|---|---|---|
| 2,097,692 | A | 11/1937 | Fiegel |
| 2,164,172 | A | 6/1939 | Dalton |
| 2,636,855 | A | 4/1953 | Schwartz |
| 2,656,508 | A | 10/1953 | Coulter |
| 2,692,800 | A | 10/1954 | Nichols et al. |
| 2,797,149 | A | 6/1957 | Skeggs |

(Continued)

FOREIGN PATENT DOCUMENTS

| | | | |
|---|---|---|---|
| AT | 140025 | T | 7/1996 |
| AT | 140880 | T | 8/1996 |

(Continued)

OTHER PUBLICATIONS

Mhlanga et al. Using Molecular Beacons to Detect Single-Nucleotide Polymorphisms with Real-Time PCR. Methods 25:463-471 (2001). (Year: 2001).*

(Continued)

*Primary Examiner* — Samuel C Woolwine
(74) *Attorney, Agent, or Firm* — Thomas C. Meyers; Sullivan & Worcester LLP

(57) ABSTRACT

The invention generally relates to droplet based digital PCR and methods for analyzing a target nucleic acid using the same. In certain embodiments, a method for determining the nucleic acid make-up of a sample is provided.

7 Claims, 44 Drawing Sheets

Specification includes a Sequence Listing.

Two Colors THREE Targets

(56) References Cited

U.S. PATENT DOCUMENTS

| | | | |
|---|---|---|---|
| 2,879,141 | A | 3/1959 | Skeggs |
| 2,971,700 | A | 2/1961 | Peeps |
| 3,479,141 | A | 11/1969 | Smythe et al. |
| 3,608,821 | A | 9/1971 | Simm et al. |
| 3,621,059 | A | 11/1971 | Bartlett |
| 3,698,635 | A | 10/1972 | Sickles |
| 3,784,471 | A | 1/1974 | Kaiser |
| 3,816,331 | A | 6/1974 | Brown, Jr. et al. |
| 3,828,085 | A | 8/1974 | Price et al. |
| 3,930,061 | A | 12/1975 | Scharfenberger |
| 3,960,187 | A | 6/1976 | Stock et al. |
| 3,980,541 | A | 9/1976 | Aine |
| 3,982,541 | A | 9/1976 | L'Esperance, Jr. |
| 4,014,469 | A | 3/1977 | Sato |
| 4,022,575 | A | 5/1977 | Hansen et al. |
| 4,034,966 | A | 7/1977 | Suh et al. |
| 4,059,552 | A | 11/1977 | Zweigle et al. |
| 4,091,042 | A | 5/1978 | Alexanderson et al. |
| 4,117,550 | A | 9/1978 | Folland et al. |
| 4,130,394 | A | 12/1978 | Negersmith |
| 4,210,809 | A | 7/1980 | Pelavin |
| 4,253,846 | A | 3/1981 | Smythe et al. |
| 4,266,721 | A | 5/1981 | Sickles |
| 4,279,345 | A | 7/1981 | Allred |
| 4,297,345 | A | 10/1981 | Howarth |
| 4,315,754 | A | 2/1982 | Ruzicka et al. |
| 4,378,957 | A | 4/1983 | Malkin et al. |
| 4,383,767 | A | 5/1983 | Jido |
| 4,439,980 | A | 4/1984 | Biblarz et al. |
| 4,508,265 | A | 4/1985 | Jido |
| 4,533,634 | A | 8/1985 | Maldonado et al. |
| 4,566,908 | A | 1/1986 | Nakatani et al. |
| 4,585,209 | A | 4/1986 | Aine et al. |
| 4,618,476 | A | 10/1986 | Columbus |
| 4,675,285 | A | 6/1987 | Clark et al. |
| 4,676,274 | A | 6/1987 | Brown |
| 4,683,195 | A | 7/1987 | Mullis et al. |
| 4,683,202 | A | 7/1987 | Mullis |
| 4,739,044 | A | 4/1988 | Stabinsky |
| 4,757,141 | A | 7/1988 | Fung et al. |
| 4,767,515 | A | 8/1988 | Scott et al. |
| 4,767,929 | A | 8/1988 | Valentine |
| 4,779,805 | A | 10/1988 | Jackson et al. |
| 4,795,330 | A | 1/1989 | Noakes et al. |
| 4,801,086 | A | 1/1989 | Noakes |
| 4,801,529 | A | 1/1989 | Perlman |
| 4,829,996 | A | 5/1989 | Noakes et al. |
| 4,853,336 | A | 8/1989 | Saros et al. |
| 4,856,363 | A | 8/1989 | LaRocca et al. |
| 4,859,363 | A | 8/1989 | Davis et al. |
| 4,865,444 | A | 9/1989 | Green et al. |
| 4,883,750 | A | 11/1989 | Whiteley et al. |
| 4,908,112 | A | 3/1990 | Pace |
| 4,931,225 | A | 6/1990 | Cheng |
| 4,941,959 | A | 7/1990 | Scott |
| 4,962,885 | A | 10/1990 | Coffee |
| 4,963,498 | A | 10/1990 | Hillman et al. |
| 4,981,580 | A | 1/1991 | Auer |
| 4,996,004 | A | 2/1991 | Bucheler et al. |
| 5,055,390 | A | 10/1991 | Weaver et al. |
| 5,091,652 | A | 2/1992 | Mathies et al. |
| 5,096,615 | A | 3/1992 | Prescott et al. |
| 5,104,813 | A | 4/1992 | Besemer et al. |
| 5,122,360 | A | 6/1992 | Harris et al. |
| 5,149,625 | A | 9/1992 | Church et al. |
| 5,180,662 | A | 1/1993 | Sitkovsky |
| 5,185,099 | A | 2/1993 | Delpuech et al. |
| 5,188,290 | A | 2/1993 | Gebauer et al. |
| 5,188,291 | A | 2/1993 | Cross |
| 5,192,659 | A | 3/1993 | Simons |
| 5,204,112 | A | 4/1993 | Hope et al. |
| 5,207,973 | A | 5/1993 | Harris et al. |
| 5,241,159 | A | 8/1993 | Chatteriee et al. |
| 5,260,466 | A | 11/1993 | McGibbon |
| 5,262,027 | A | 11/1993 | Scott |
| 5,270,163 | A | 12/1993 | Gold et al. |
| 5,296,375 | A | 3/1994 | Kricka et al. |
| 5,304,487 | A | 4/1994 | Wilding et al. |
| 5,310,653 | A | 5/1994 | Hanausek-Walaszek et al. |
| 5,313,009 | A | 5/1994 | Guenkel et al. |
| 5,333,675 | A | 8/1994 | Mullis et al. |
| 5,344,489 | A | 9/1994 | Matijevic et al. |
| 5,344,594 | A | 9/1994 | Sheridon |
| 5,354,670 | A | 10/1994 | Nickoloff et al. |
| 5,376,252 | A | 12/1994 | Ekstrom et al. |
| 5,378,957 | A | 1/1995 | Kelly |
| 5,397,605 | A | 3/1995 | Barbieri et al. |
| 5,399,461 | A | 3/1995 | Van et al. |
| 5,399,491 | A | 3/1995 | Kacian et al. |
| 5,403,617 | A | 4/1995 | Haaland |
| 5,413,924 | A | 5/1995 | Kosak et al. |
| 5,417,235 | A | 5/1995 | Wise et al. |
| 5,427,946 | A | 6/1995 | Kricka et al. |
| 5,445,934 | A | 8/1995 | Fodor et al. |
| 5,452,878 | A | 9/1995 | Gravesen et al. |
| 5,452,955 | A | 9/1995 | Lundstrom |
| 5,454,472 | A | 10/1995 | Benecke et al. |
| 5,460,945 | A | 10/1995 | Springer et al. |
| 5,468,613 | A | 11/1995 | Erlich et al. |
| 5,475,096 | A | 12/1995 | Gold et al. |
| 5,475,610 | A | 12/1995 | Atwood et al. |
| 5,480,614 | A | 1/1996 | Kamahori |
| 5,486,335 | A | 1/1996 | Wilding et al. |
| 5,498,392 | A | 3/1996 | Wilding et al. |
| 5,498,523 | A | 3/1996 | Tabor et al. |
| 5,500,415 | A | 3/1996 | Dollat et al. |
| 5,503,851 | A | 4/1996 | Mank et al. |
| 5,512,131 | A | 4/1996 | Kumar et al. |
| 5,516,635 | A | 5/1996 | Ekins et al. |
| 5,518,709 | A | 5/1996 | Sutton et al. |
| 5,523,162 | A | 6/1996 | Franz et al. |
| 5,587,128 | A | 12/1996 | Wilding et al. |
| 5,589,136 | A | 12/1996 | Northrup et al. |
| 5,602,756 | A | 2/1997 | Atwood et al. |
| 5,604,097 | A | 2/1997 | Brenner |
| 5,610,016 | A | 3/1997 | Sato et al. |
| 5,612,188 | A | 3/1997 | Shuler et al. |
| 5,616,478 | A | 4/1997 | Chetverin et al. |
| 5,617,997 | A | 4/1997 | Kobayashi et al. |
| 5,635,358 | A | 6/1997 | Wilding et al. |
| 5,636,400 | A | 6/1997 | Young |
| 5,641,658 | A | 6/1997 | Adams et al. |
| 5,643,729 | A | 7/1997 | Taniguchi et al. |
| 5,655,517 | A | 8/1997 | Coffee |
| 5,656,155 | A | 8/1997 | Norcross et al. |
| 5,656,493 | A | 8/1997 | Mullis et al. |
| 5,661,222 | A | 8/1997 | Hare |
| 5,662,874 | A | 9/1997 | David |
| 5,670,325 | A | 9/1997 | Lapidus et al. |
| 5,681,600 | A | 10/1997 | Antinone et al. |
| 5,695,934 | A | 12/1997 | Brenner |
| 5,726,026 | A | 3/1998 | Wilding et al. |
| 5,726,404 | A | 3/1998 | Brody |
| 5,733,526 | A | 3/1998 | Trevino et al. |
| 5,739,036 | A | 4/1998 | Parris |
| 5,744,366 | A | 4/1998 | Kricka et al. |
| 5,750,988 | A | 5/1998 | Apffel et al. |
| 5,762,775 | A | 6/1998 | DePaoli |
| 5,779,868 | A | 7/1998 | Parce et al. |
| 5,783,431 | A | 7/1998 | Peterson et al. |
| 5,789,206 | A | 8/1998 | Tavtigian et al. |
| 5,813,988 | A | 9/1998 | Alfano et al. |
| 5,830,633 | A | 11/1998 | Matsumoto |
| 5,830,663 | A | 11/1998 | Embleton et al. |
| 5,840,506 | A | 11/1998 | Giordano |
| 5,846,719 | A | 12/1998 | Brenner et al. |
| 5,849,491 | A | 12/1998 | Radomski et al. |
| 5,851,769 | A | 12/1998 | Gray et al. |
| 5,858,187 | A | 1/1999 | Ramsey et al. |
| 5,858,655 | A | 1/1999 | Arnold |
| 5,858,670 | A | 1/1999 | Lam et al. |
| 5,863,722 | A | 1/1999 | Brenner |
| 5,868,322 | A | 2/1999 | Loucks |
| 5,872,010 | A | 2/1999 | Karger et al. |

(56) References Cited

U.S. PATENT DOCUMENTS

| | | | |
|---|---|---|---|
| 5,876,771 | A | 3/1999 | Sizer et al. |
| 5,880,071 | A | 3/1999 | Parce et al. |
| 5,882,680 | A | 3/1999 | Suzuki et al. |
| 5,882,856 | A | 3/1999 | Shuber |
| 5,884,846 | A | 3/1999 | Tan |
| 5,887,755 | A | 3/1999 | Hood, III |
| 5,888,746 | A | 3/1999 | Tabiti et al. |
| 5,888,778 | A | 3/1999 | Shuber |
| 5,904,933 | A | 5/1999 | Riess et al. |
| 5,921,678 | A | 7/1999 | Desai et al. |
| 5,927,852 | A | 7/1999 | Serafin |
| 5,928,870 | A | 7/1999 | Lapidus et al. |
| 5,932,100 | A | 8/1999 | Yager et al. |
| 5,935,331 | A | 8/1999 | Naka et al. |
| 5,942,056 | A | 8/1999 | Singh |
| 5,942,443 | A | 8/1999 | Parce et al. |
| 5,958,203 | A | 9/1999 | Parce et al. |
| 5,972,187 | A | 10/1999 | Parce et al. |
| 5,980,936 | A | 11/1999 | Krafft et al. |
| 5,989,815 | A | 11/1999 | Skolnick et al. |
| 5,989,892 | A | 11/1999 | Nishimaki et al. |
| 5,995,341 | A | 11/1999 | Tanaka et al. |
| 5,997,636 | A | 12/1999 | Gamarnik et al. |
| 6,008,003 | A | 12/1999 | Haak-Frendscho et al. |
| 6,023,540 | A | 2/2000 | Walt et al. |
| 6,028,066 | A | 2/2000 | Unger |
| 6,042,709 | A | 3/2000 | Parce et al. |
| 6,045,755 | A | 4/2000 | Lebl et al. |
| 6,046,056 | A | 4/2000 | Parce et al. |
| 6,048,551 | A | 4/2000 | Hilfinger et al. |
| 6,048,690 | A | 4/2000 | Heller et al. |
| 6,068,199 | A | 5/2000 | Coffee |
| 6,074,879 | A | 6/2000 | Zelmanovic et al. |
| 6,080,295 | A | 6/2000 | Parce et al. |
| 6,081,612 | A | 6/2000 | Gutkowicz-Krusin et al. |
| 6,086,740 | A | 7/2000 | Kennedy |
| 6,096,495 | A | 8/2000 | Kasai et al. |
| 6,103,537 | A | 8/2000 | Ullman et al. |
| 6,105,571 | A | 8/2000 | Coffee |
| 6,105,877 | A | 8/2000 | Coffee |
| 6,107,059 | A | 8/2000 | Hart |
| 6,116,516 | A | 9/2000 | Ganan-Calvo |
| 6,118,849 | A | 9/2000 | Tanimori et al. |
| 6,119,953 | A | 9/2000 | Ganan-Calvo et al. |
| 6,120,666 | A | 9/2000 | Jacobson et al. |
| 6,124,388 | A | 9/2000 | Takai et al. |
| 6,124,439 | A | 9/2000 | Friedman et al. |
| 6,130,052 | A | 10/2000 | Van Baren et al. |
| 6,130,098 | A | 10/2000 | Handique et al. |
| 6,137,214 | A | 10/2000 | Raina |
| 6,138,077 | A | 10/2000 | Brenner |
| 6,139,303 | A | 10/2000 | Reed et al. |
| 6,140,053 | A | 10/2000 | Koster |
| 6,143,496 | A | 11/2000 | Brown et al. |
| 6,146,828 | A | 11/2000 | Lapidus et al. |
| 6,149,789 | A | 11/2000 | Benecke et al. |
| 6,150,180 | A | 11/2000 | Parce et al. |
| 6,150,516 | A | 11/2000 | Brenner et al. |
| 6,155,710 | A | 12/2000 | Nakajima et al. |
| 6,162,421 | A | 12/2000 | Ordino et al. |
| 6,165,778 | A | 12/2000 | Kedar |
| 6,171,796 | B1 | 1/2001 | An et al. |
| 6,171,850 | B1 | 1/2001 | Nagle et al. |
| 6,172,214 | B1 | 1/2001 | Brenner |
| 6,172,218 | B1 | 1/2001 | Brenner |
| 6,174,160 | B1 | 1/2001 | Lee et al. |
| 6,174,469 | B1 | 1/2001 | Gañan-Calvo |
| 6,177,479 | B1 | 1/2001 | Nakajima |
| 6,180,372 | B1 | 1/2001 | Franzen |
| 6,184,012 | B1 | 2/2001 | Neri et al. |
| 6,187,214 | B1 | 2/2001 | Ganan-Calvo |
| 6,189,803 | B1 | 2/2001 | Ganan-Calvo |
| 6,196,525 | B1 | 3/2001 | Ganan-Calvo |
| 6,197,335 | B1 | 3/2001 | Sherman |
| 6,197,835 | B1 | 3/2001 | Ganan-Calvo |
| 6,203,993 | B1 | 3/2001 | Shuber et al. |
| 6,207,372 | B1 | 3/2001 | Shuber |
| 6,207,397 | B1 | 3/2001 | Lynch et al. |
| 6,208,749 | B1 | 3/2001 | Gutkowicz-Krusin et al. |
| 6,210,396 | B1 | 4/2001 | MacDonald et al. |
| 6,210,891 | B1 | 4/2001 | Nyren et al. |
| 6,210,896 | B1 | 4/2001 | Chan |
| 6,214,558 | B1 | 4/2001 | Shuber et al. |
| 6,221,654 | B1 | 4/2001 | Quake et al. |
| 6,227,466 | B1 | 5/2001 | Hartman et al. |
| 6,234,402 | B1 | 5/2001 | Ganan-Calvo |
| 6,235,383 | B1 | 5/2001 | Hong et al. |
| 6,235,475 | B1 | 5/2001 | Brenner et al. |
| 6,241,159 | B1 | 6/2001 | Ganan-Calvo et al. |
| 6,243,373 | B1 | 6/2001 | Turock |
| 6,248,378 | B1 | 6/2001 | Ganan-Calvo |
| 6,251,661 | B1 | 6/2001 | Urabe et al. |
| 6,252,129 | B1 | 6/2001 | Coffee |
| 6,258,568 | B1 | 7/2001 | Nyren |
| 6,258,858 | B1 | 7/2001 | Nakajima et al. |
| 6,261,661 | B1 | 7/2001 | Ohno et al. |
| 6,261,797 | B1 | 7/2001 | Sorge et al. |
| 6,263,222 | B1 | 7/2001 | Diab et al. |
| 6,266,459 | B1 | 7/2001 | Walt et al. |
| 6,267,353 | B1 | 7/2001 | Friedline et al. |
| 6,267,858 | B1 | 7/2001 | Parce et al. |
| 6,268,152 | B1 | 7/2001 | Fodor et al. |
| 6,268,165 | B1 | 7/2001 | O'Brien |
| 6,268,222 | B1 | 7/2001 | Chandler et al. |
| 6,274,320 | B1 | 8/2001 | Rothberg et al. |
| 6,274,337 | B1 | 8/2001 | Parce et al. |
| 6,280,948 | B1 | 8/2001 | Guilfoyle et al. |
| 6,292,756 | B1 | 9/2001 | Lievois et al. |
| 6,294,344 | B1 | 9/2001 | O'Brien |
| 6,296,020 | B1 | 10/2001 | McNeely et al. |
| 6,296,673 | B1 | 10/2001 | Santarsiero et al. |
| 6,299,145 | B1 | 10/2001 | Ganan-Calvo |
| 6,301,055 | B1 | 10/2001 | Legrand et al. |
| 6,306,659 | B1 | 10/2001 | Parce et al. |
| 6,307,957 | B1 | 10/2001 | Gutkowicz-Krusin et al. |
| 6,309,842 | B1 | 10/2001 | Dower et al. |
| 6,310,354 | B1 | 10/2001 | Hanninen et al. |
| 6,310,653 | B1 | 10/2001 | Malcolm, Jr. et al. |
| 6,316,208 | B1 | 11/2001 | Roberts et al. |
| 6,316,213 | B1 | 11/2001 | O'Brien |
| 6,318,640 | B1 | 11/2001 | Coffee |
| 6,324,417 | B1 | 11/2001 | Cotton |
| 6,326,145 | B1 | 12/2001 | Whitcombe et al. |
| 6,336,463 | B1 | 1/2002 | Ohta |
| 6,344,325 | B1 | 2/2002 | Quake et al. |
| 6,352,828 | B1 | 3/2002 | Brenner |
| 6,355,193 | B1 | 3/2002 | Stott |
| 6,355,198 | B1 | 3/2002 | Kim et al. |
| 6,357,670 | B2 | 3/2002 | Ganan-Calvo |
| 6,386,463 | B1 | 5/2002 | Ganan-Calvo |
| 6,391,559 | B1 | 5/2002 | Brown et al. |
| 6,394,429 | B2 | 5/2002 | Ganan-Calvo |
| 6,399,339 | B1 | 6/2002 | Wolberg et al. |
| 6,399,389 | B1 | 6/2002 | Parce et al. |
| 6,403,373 | B1 | 6/2002 | Scanlan et al. |
| 6,405,936 | B1 | 6/2002 | Ganan-Calvo |
| 6,408,878 | B2 | 6/2002 | Unger et al. |
| 6,409,832 | B2 | 6/2002 | Weigl et al. |
| 6,428,053 | B1 | 8/2002 | Tai et al. |
| 6,429,025 | B1 | 8/2002 | Parce et al. |
| 6,429,148 | B1 | 8/2002 | Chu et al. |
| 6,432,143 | B2 | 8/2002 | Kubiak et al. |
| 6,432,148 | B1 | 8/2002 | Ganan-Calvo |
| 6,432,630 | B1 | 8/2002 | Blankenstein |
| 6,439,103 | B1 | 8/2002 | Miller |
| 6,440,706 | B1 | 8/2002 | Vogelstein et al. |
| 6,440,760 | B1 | 8/2002 | Cho et al. |
| 6,450,139 | B1 | 9/2002 | Watanabe |
| 6,450,189 | B1 | 9/2002 | Ganan-Calvo |
| 6,454,193 | B1 | 9/2002 | Busick et al. |
| 6,464,336 | B1 | 10/2002 | Sharma |
| 6,464,886 | B2 | 10/2002 | Ganan-Calvo |
| 6,469,094 | B1 | 10/2002 | Keoshkerian et al. |
| 6,475,441 | B1 | 11/2002 | Parce et al. |

(56) References Cited

U.S. PATENT DOCUMENTS

| | | | |
|---|---|---|---|
| 6,481,648 | B1 | 11/2002 | Zimmermann |
| 6,489,103 | B1 | 12/2002 | Griffiths et al. |
| 6,503,933 | B1 | 1/2003 | Moloney et al. |
| 6,506,609 | B1 | 1/2003 | Wada et al. |
| 6,508,988 | B1 | 1/2003 | Van Dam et al. |
| 6,511,803 | B1 | 1/2003 | Church et al. |
| 6,520,425 | B1 | 2/2003 | Reneker |
| 6,524,456 | B1 | 2/2003 | Ramsey et al. |
| 6,530,944 | B2 | 3/2003 | West et al. |
| 6,540,395 | B2 | 4/2003 | Muhlbauer et al. |
| 6,540,895 | B1 | 4/2003 | Spence et al. |
| 6,551,836 | B1 | 4/2003 | Chow et al. |
| 6,553,944 | B1 | 4/2003 | Allen et al. |
| 6,553,960 | B1 | 4/2003 | Yoshikawa et al. |
| 6,554,202 | B2 | 4/2003 | Ganan-Calvo |
| 6,557,334 | B2 | 5/2003 | Jager |
| 6,557,834 | B2 | 5/2003 | Ganan-Calvo |
| 6,558,944 | B1 | 5/2003 | Parce et al. |
| 6,558,960 | B1 | 5/2003 | Parce et al. |
| 6,560,030 | B2 | 5/2003 | Legrand et al. |
| 6,565,010 | B2 | 5/2003 | Anderson et al. |
| 6,569,631 | B1 | 5/2003 | Pantoliano et al. |
| 6,576,420 | B1 | 6/2003 | Carson et al. |
| 6,591,852 | B1 | 7/2003 | McNeely et al. |
| 6,592,321 | B2 | 7/2003 | Bonker et al. |
| 6,592,821 | B1 | 7/2003 | Nada et al. |
| 6,601,613 | B2 | 8/2003 | McNeely et al. |
| 6,608,726 | B2 | 8/2003 | Legrand et al. |
| 6,610,499 | B1 | 8/2003 | Fulwyler et al. |
| 6,614,598 | B1 | 9/2003 | Quake et al. |
| 6,627,603 | B1 | 9/2003 | Bibette et al. |
| 6,630,006 | B2 | 10/2003 | Santarsiero et al. |
| 6,630,353 | B1 | 10/2003 | Parce et al. |
| 6,632,619 | B1 | 10/2003 | Harrison et al. |
| 6,632,800 | B1 | 10/2003 | Russell et al. |
| 6,637,463 | B1 | 10/2003 | Lei et al. |
| 6,638,749 | B1 | 10/2003 | Beckman et al. |
| 6,645,432 | B1 | 11/2003 | Anderson et al. |
| 6,646,253 | B1 | 11/2003 | Rohwer et al. |
| 6,653,626 | B2 | 11/2003 | Fischer et al. |
| 6,656,267 | B2 | 12/2003 | Newman |
| 6,659,370 | B1 | 12/2003 | Inoue |
| 6,660,252 | B2 | 12/2003 | Matathia et al. |
| 6,670,142 | B2 | 12/2003 | Lau et al. |
| 6,679,441 | B1 | 1/2004 | Borra et al. |
| 6,680,178 | B2 | 1/2004 | Harris et al. |
| 6,682,890 | B2 | 1/2004 | Mack et al. |
| 6,717,136 | B2 | 4/2004 | Andersson et al. |
| 6,729,561 | B2 | 5/2004 | Hirae et al. |
| 6,738,502 | B1 | 5/2004 | Coleman et al. |
| 6,739,036 | B2 | 5/2004 | Koike et al. |
| 6,744,046 | B2 | 6/2004 | Valaskovic et al. |
| 6,752,922 | B2 | 6/2004 | Huang et al. |
| 6,753,147 | B2 | 6/2004 | Vogelstein et al. |
| 6,766,817 | B2 | 7/2004 | da Silva |
| 6,767,194 | B2 | 7/2004 | Jeon et al. |
| 6,767,704 | B2 | 7/2004 | Waldman et al. |
| 6,790,328 | B2 | 9/2004 | Jacobson et al. |
| 6,793,753 | B2 | 9/2004 | Unger et al. |
| 6,797,056 | B2 | 9/2004 | David |
| 6,800,849 | B2 | 10/2004 | Staats |
| 6,806,058 | B2 | 10/2004 | Jesperson et al. |
| 6,808,382 | B2 | 10/2004 | Lanfranchi |
| 6,808,882 | B2 | 10/2004 | Griffiths et al. |
| 6,814,980 | B2 | 11/2004 | Levy et al. |
| 6,818,395 | B1 | 11/2004 | Quake et al. |
| 6,832,787 | B1 | 12/2004 | Renzi |
| 6,833,242 | B2 | 12/2004 | Quake et al. |
| 6,841,350 | B2 | 1/2005 | Ogden et al. |
| 6,844,377 | B1 | 1/2005 | Auweter et al. |
| 6,872,250 | B2 | 3/2005 | David et al. |
| 6,890,487 | B1 | 5/2005 | Sklar et al. |
| 6,897,018 | B1 | 5/2005 | Yuan et al. |
| 6,905,844 | B2 | 6/2005 | Kim |
| 6,918,404 | B2 | 7/2005 | Dias da Silva |
| 6,926,313 | B1 | 8/2005 | Renzi |
| 6,935,768 | B2 | 8/2005 | Lowe et al. |
| 6,936,417 | B2 | 8/2005 | Omtoft |
| 6,942,978 | B1 | 9/2005 | O'Brien |
| 6,949,342 | B2 | 9/2005 | Golub et al. |
| 6,960,437 | B2 | 11/2005 | Enzelberger et al. |
| 6,964,847 | B1 | 11/2005 | Englert |
| 6,974,667 | B2 | 12/2005 | Horne et al. |
| 6,998,232 | B1 | 2/2006 | Feinstein et al. |
| 7,022,472 | B2 | 4/2006 | Robbins et al. |
| 7,041,481 | B2 | 5/2006 | Anderson et al. |
| 7,049,072 | B2 | 5/2006 | Seshi |
| 7,056,674 | B2 | 6/2006 | Baker et al. |
| 7,057,026 | B2 | 6/2006 | Barnes et al. |
| 7,066,586 | B2 | 6/2006 | da Silva |
| 7,068,874 | B2 | 6/2006 | Wang et al. |
| 7,078,180 | B2 | 7/2006 | Genetta |
| 7,081,192 | B1 | 7/2006 | Wang et al. |
| 7,081,340 | B2 | 7/2006 | Baker et al. |
| 7,090,983 | B1 | 8/2006 | Muramatsu et al. |
| 7,115,230 | B2 | 10/2006 | Sundararajan |
| 7,118,910 | B2 | 10/2006 | Unger et al. |
| 7,129,091 | B2 | 10/2006 | Ismagilov et al. |
| 7,138,233 | B2 | 11/2006 | Griffiths et al. |
| 7,153,700 | B1 | 12/2006 | Pardee et al. |
| 7,156,917 | B2 | 1/2007 | Moriyama et al. |
| 7,163,801 | B2 | 1/2007 | Reed |
| 7,169,560 | B2 | 1/2007 | Lapidus et al. |
| 7,171,311 | B2 | 1/2007 | Dai et al. |
| 7,198,899 | B2 | 4/2007 | Schleyer et al. |
| 7,204,431 | B2 | 4/2007 | Li et al. |
| 7,229,760 | B2 | 6/2007 | Zohlnhofer et al. |
| 7,229,770 | B1 | 6/2007 | Price et al. |
| 7,252,943 | B2 | 8/2007 | Griffiths et al. |
| 7,267,938 | B2 | 9/2007 | Anderson et al. |
| 7,268,167 | B2 | 9/2007 | Higuchi et al. |
| 7,282,337 | B1 | 10/2007 | Harris |
| 7,291,462 | B2 | 11/2007 | O'Brien et al. |
| 7,294,503 | B2 | 11/2007 | Quake et al. |
| 7,300,765 | B2 | 11/2007 | Patel |
| 7,308,364 | B2 | 12/2007 | Shaughnessy et al. |
| 7,314,721 | B2 | 1/2008 | Gure et al. |
| 7,316,906 | B2 | 1/2008 | Chiorazzi et al. |
| 7,323,305 | B2 | 1/2008 | Leamon et al. |
| 7,323,309 | B2 | 1/2008 | Mirkin et al. |
| 7,326,529 | B2 | 2/2008 | Ali et al. |
| 7,332,280 | B2 | 2/2008 | Levy et al. |
| 7,332,590 | B2 | 2/2008 | Nacht et al. |
| 7,341,211 | B2 | 3/2008 | Ganan Calvo et al. |
| 7,348,142 | B2 | 3/2008 | Wang |
| 7,358,231 | B1 | 4/2008 | McCaffey et al. |
| 7,361,474 | B2 | 4/2008 | Siegler |
| 7,364,862 | B2 | 4/2008 | Ali et al. |
| 7,368,255 | B2 | 5/2008 | Bae et al. |
| 7,378,233 | B2 | 5/2008 | Sidransky et al. |
| 7,378,280 | B2 | 5/2008 | Quake et al. |
| 7,390,463 | B2 | 6/2008 | He et al. |
| 7,392,908 | B2 | 7/2008 | Frazier |
| 7,393,634 | B1 | 7/2008 | Ahuja et al. |
| 7,393,665 | B2 | 7/2008 | Brenner |
| 7,405,002 | B2 | 7/2008 | Ying et al. |
| 7,416,851 | B2 | 8/2008 | Davi et al. |
| 7,429,467 | B2 | 9/2008 | Holliger et al. |
| 7,432,064 | B2 | 10/2008 | Salceda et al. |
| 7,442,507 | B2 | 10/2008 | Polsky et al. |
| 7,449,303 | B2 | 11/2008 | Coignet |
| 7,468,271 | B2 | 12/2008 | Golovchenko et al. |
| 7,473,530 | B2 | 1/2009 | Huttemann |
| 7,473,531 | B1 | 1/2009 | Domon et al. |
| 7,476,506 | B2 | 1/2009 | Schleyer et al. |
| 7,479,370 | B2 | 1/2009 | Coignet |
| 7,479,371 | B2 | 1/2009 | Ando et al. |
| 7,479,376 | B2 | 1/2009 | Waldman et al. |
| 7,482,129 | B2 | 1/2009 | Soyupak et al. |
| 7,501,244 | B2 | 3/2009 | Reinhard et al. |
| 7,504,214 | B2 | 3/2009 | Erlander et al. |
| 7,507,532 | B2 | 3/2009 | Chang et al. |
| 7,507,541 | B2 | 3/2009 | Raitano et al. |
| 7,510,707 | B2 | 3/2009 | Platica et al. |

(56) References Cited

U.S. PATENT DOCUMENTS

| | | | |
|---|---|---|---|
| 7,510,842 | B2 | 3/2009 | Podust et al. |
| 7,514,209 | B2 | 4/2009 | Dai et al. |
| 7,514,210 | B2 | 4/2009 | Holliger et al. |
| 7,524,633 | B2 | 4/2009 | Sidransky |
| 7,527,933 | B2 | 5/2009 | Sahin et al. |
| 7,537,897 | B2 | 5/2009 | Brenner et al. |
| 7,541,383 | B2 | 6/2009 | Fu et al. |
| 7,544,473 | B2 | 6/2009 | Brenner |
| 7,556,776 | B2 | 7/2009 | Fraden et al. |
| 7,582,446 | B2 | 9/2009 | Griffiths et al. |
| 7,595,195 | B2 | 9/2009 | Lee et al. |
| 7,604,938 | B2 | 10/2009 | Takahashi et al. |
| 7,622,076 | B2 | 11/2009 | Davies et al. |
| 7,622,081 | B2 | 11/2009 | Chou et al. |
| 7,632,562 | B2 | 12/2009 | Nair et al. |
| 7,635,562 | B2 | 12/2009 | Harris et al. |
| 7,638,276 | B2 | 12/2009 | Griffiths et al. |
| 7,655,435 | B2 | 2/2010 | Holliger et al. |
| 7,655,470 | B2 | 2/2010 | Ismagilov et al. |
| 7,666,593 | B2 | 2/2010 | Lapidus |
| 7,691,576 | B2 | 4/2010 | Holliger et al. |
| 7,698,287 | B2 | 4/2010 | Becker et al. |
| 7,708,949 | B2 | 5/2010 | Stone et al. |
| 7,718,578 | B2 | 5/2010 | Griffiths et al. |
| 7,736,890 | B2 | 6/2010 | Sia et al. |
| 7,741,130 | B2 | 6/2010 | Lee, Jr. et al. |
| RE41,780 | E | 9/2010 | Anderson et al. |
| 7,814,175 | B1 | 10/2010 | Chang et al. |
| 7,824,889 | B2 | 11/2010 | Vogelstein et al. |
| 7,888,017 | B2 | 2/2011 | Quake et al. |
| 7,897,044 | B2 | 3/2011 | Hoyos et al. |
| 7,897,341 | B2 | 3/2011 | Griffiths et al. |
| 7,901,939 | B2 | 3/2011 | Ismagliov et al. |
| 7,915,015 | B2 | 3/2011 | Vogelstein et al. |
| 7,968,287 | B2 | 6/2011 | Griffiths et al. |
| 7,990,525 | B2 | 8/2011 | Kanda |
| 8,012,382 | B2 | 9/2011 | Kim et al. |
| 8,067,159 | B2 | 11/2011 | Brown et al. |
| 8,153,402 | B2 | 4/2012 | Holliger et al. |
| 8,252,539 | B2 | 8/2012 | Quake et al. |
| 8,257,925 | B2 | 9/2012 | Brown et al. |
| 8,278,071 | B2 | 10/2012 | Brown et al. |
| 8,278,711 | B2 | 10/2012 | Rao et al. |
| 8,290,625 | B2 | 10/2012 | Degeal et al. |
| 8,318,434 | B2 | 11/2012 | Cuppens |
| 8,337,778 | B2 | 12/2012 | Stone et al. |
| 8,383,061 | B2 | 2/2013 | Prakash et al. |
| 8,436,993 | B2 | 5/2013 | Kaduchak et al. |
| 8,462,269 | B2 | 6/2013 | Cheng et al. |
| 8,528,589 | B2 | 9/2013 | Miller et al. |
| 8,535,889 | B2 | 9/2013 | Larson et al. |
| 8,592,221 | B2 | 11/2013 | Fraden et al. |
| 8,658,430 | B2 | 2/2014 | Miller et al. |
| 8,673,595 | B2 | 3/2014 | Nakamura et al. |
| 8,715,934 | B2 | 5/2014 | Diehl et al. |
| 8,765,485 | B2 | 7/2014 | Link et al. |
| 8,772,046 | B2 | 7/2014 | Fraden et al. |
| 8,820,538 | B1 | 9/2014 | Lin |
| 8,841,071 | B2 | 9/2014 | Link |
| 8,857,462 | B2 | 10/2014 | Miller et al. |
| 8,871,444 | B2 | 10/2014 | Griffiths et al. |
| 8,889,072 | B2 | 11/2014 | Degeal et al. |
| 8,894,946 | B2 | 11/2014 | Nielsen et al. |
| 9,012,390 | B2 | 4/2015 | Holtze et al. |
| 9,029,083 | B2 | 5/2015 | Griffiths et al. |
| 9,029,085 | B2 | 5/2015 | Agresti et al. |
| 9,038,919 | B2 | 5/2015 | Link et al. |
| 9,074,242 | B2 | 7/2015 | Larson et al. |
| 9,080,056 | B2 | 7/2015 | Glennon et al. |
| 9,127,310 | B2 | 9/2015 | Larson |
| 9,150,852 | B2 | 10/2015 | Samuels et al. |
| 9,176,031 | B2 | 11/2015 | Watson |
| 9,186,643 | B2 | 11/2015 | Griffiths et al. |
| 9,194,772 | B2 | 11/2015 | Lee et al. |
| 9,222,128 | B2 | 12/2015 | Saxonov |
| 9,228,229 | B2 | 1/2016 | Olson et al. |
| 9,266,104 | B2 | 2/2016 | Link |
| 9,273,308 | B2 | 3/2016 | Link et al. |
| 9,273,349 | B2 | 3/2016 | Nguyen et al. |
| 9,297,784 | B2 | 3/2016 | Molho et al. |
| 9,322,511 | B2 | 4/2016 | Davies et al. |
| 9,328,344 | B2 | 5/2016 | Link et al. |
| 9,341,594 | B2 | 5/2016 | Miller et al. |
| 9,364,803 | B2 | 6/2016 | Yurkovetsky et al. |
| 9,366,632 | B2 | 6/2016 | Link |
| 9,399,797 | B2 | 7/2016 | Hutchison |
| 9,410,151 | B2 | 8/2016 | Link et al. |
| 9,441,266 | B2 | 9/2016 | Larson et al. |
| 9,448,172 | B2 | 9/2016 | Griffiths et al. |
| 9,494,520 | B2 | 11/2016 | Link |
| 9,498,761 | B2 | 11/2016 | Holtze et al. |
| 9,534,216 | B2 | 1/2017 | Link et al. |
| 9,556,470 | B2 | 1/2017 | Link et al. |
| 9,562,837 | B2 | 2/2017 | Link |
| 9,562,897 | B2 | 2/2017 | Samuels et al. |
| 9,733,168 | B2 | 8/2017 | Miller et al. |
| 9,745,617 | B2 | 8/2017 | Larson |
| 9,752,141 | B2 | 9/2017 | Link et al. |
| 9,816,121 | B2 | 11/2017 | Agresti et al. |
| 9,839,890 | B2 | 12/2017 | Griffiths et al. |
| 9,840,734 | B2 | 12/2017 | Samuels |
| 9,857,202 | B2 | 1/2018 | Seki |
| 9,857,303 | B2 | 1/2018 | Griffiths et al. |
| 9,896,722 | B2 | 2/2018 | Link |
| 9,919,277 | B2 | 3/2018 | Griffiths et al. |
| 9,925,501 | B2 | 3/2018 | Griffiths et al. |
| 9,944,977 | B2 | 4/2018 | Link et al. |
| 9,981,230 | B2 | 5/2018 | Link et al. |
| 10,011,865 | B2 | 7/2018 | Link |
| 10,041,113 | B2 | 8/2018 | Lee et al. |
| 10,101,260 | B2 | 10/2018 | Reed et al. |
| 10,101,261 | B2 | 10/2018 | Takeda |
| 10,139,411 | B2 | 11/2018 | Link et al. |
| 10,144,950 | B2 | 12/2018 | Nolan |
| 10,151,698 | B2 | 12/2018 | Griffiths et al. |
| 10,155,207 | B2 | 12/2018 | Yurkovetsky et al. |
| 10,166,522 | B2 | 1/2019 | Hindson |
| 10,222,317 | B2 | 3/2019 | Takeda |
| 10,267,721 | B2 | 4/2019 | Takeda |
| 10,324,019 | B2 | 6/2019 | Diebold et al. |
| 10,351,905 | B2 | 7/2019 | Link et al. |
| 10,357,772 | B2 | 7/2019 | Fraden et al. |
| 10,428,369 | B2 | 10/2019 | Miller et al. |
| 10,450,604 | B2 | 10/2019 | Wiyatno et al. |
| 10,466,160 | B2 | 11/2019 | Handique et al. |
| 10,520,500 | B2 | 12/2019 | El Harrak et al. |
| 10,526,605 | B2 | 1/2020 | Liu et al. |
| 10,527,529 | B2 | 1/2020 | Miller et al. |
| 10,533,998 | B2 | 1/2020 | Link et al. |
| 10,551,382 | B2 | 2/2020 | Link et al. |
| 10,578,633 | B2 | 3/2020 | West et al. |
| 10,584,332 | B2 | 3/2020 | Samuels et al. |
| 10,596,541 | B2 | 3/2020 | Weitz et al. |
| 10,611,995 | B2 | 4/2020 | Masaeli et al. |
| 10,612,081 | B2 | 4/2020 | Hutchison |
| 10,620,111 | B2 | 4/2020 | Diebold et al. |
| 10,625,220 | B2 | 4/2020 | Link et al. |
| 10,626,442 | B2 | 4/2020 | Nolan |
| 10,626,451 | B2 | 4/2020 | Davies et al. |
| 10,633,652 | B2 | 4/2020 | Link et al. |
| 10,639,597 | B2 | 5/2020 | Link et al. |
| 10,639,598 | B2 | 5/2020 | Griffiths et al. |
| 10,647,981 | B1 | 5/2020 | Luckey |
| 10,648,899 | B2 | 5/2020 | Takeda |
| 10,650,602 | B2 | 5/2020 | You et al. |
| 10,675,626 | B2 | 6/2020 | Fraden et al. |
| 10,676,786 | B2 | 6/2020 | Davies et al. |
| 10,724,082 | B2 | 7/2020 | Samuels |
| 10,730,051 | B2 | 8/2020 | Davies et al. |
| 10,761,090 | B2 | 9/2020 | Samuels et al. |
| 10,808,279 | B2 | 10/2020 | Link et al. |
| 10,837,883 | B2 | 11/2020 | Kleinschmidt et al. |
| 10,927,407 | B2 | 2/2021 | Link |
| 10,960,397 | B2 | 3/2021 | Fraden et al. |

(56) References Cited

U.S. PATENT DOCUMENTS 11,077,415 B2 8/2021 Yurkovetsky et al.
11,168,353 B2 11/2021 Samuels et al.
11,174,509 B2 11/2021 Link et al.
11,187,702 B2 11/2021 Link et al.
11,254,968 B2 2/2022 Larson
11,390,917 B2 7/2022 Hutchison et al.
12,031,175 B2 7/2024 Larson
2001/0010338 A1 8/2001 Ganan-Calvo
2001/0020011 A1 9/2001 Mathiowitz et al.
2001/0023078 A1 9/2001 Bawendi et al.
2001/0024790 A1 9/2001 Kambara et al.
2001/0029983 A1 10/2001 Unger et al.
2001/0032053 A1 10/2001 Hielscher et al.
2001/0034025 A1 10/2001 Modlin et al.
2001/0034031 A1 10/2001 Short et al.
2001/0041343 A1 11/2001 Pankowsky
2001/0041344 A1 11/2001 Sepetov et al.
2001/0041357 A1 11/2001 Fouillet et al.
2001/0042793 A1 11/2001 Ganan-Calvo
2001/0048900 A1 12/2001 Bardell et al.
2001/0050881 A1 12/2001 Depaoli et al.
2002/0004532 A1 1/2002 Matathia et al.
2002/0005354 A1 1/2002 Spence et al.
2002/0008028 A1 1/2002 Jacobson et al.
2002/0012971 A1 1/2002 Mehta
2002/0015997 A1 2/2002 Lafferty
2002/0022038 A1 2/2002 Biatry et al.
2002/0022261 A1 2/2002 Anderson et al.
2002/0033422 A1 3/2002 Ganan-Calvo
2002/0034737 A1 3/2002 Drmanac
2002/0036018 A1 3/2002 McNeely et al.
2002/0036139 A1 3/2002 Becker et al.
2002/0041378 A1 4/2002 Peltie et al.
2002/0058332 A1 5/2002 Quake et al.
2002/0065609 A1 5/2002 Ashby
2002/0067800 A1 6/2002 Newman et al.
2002/0084417 A1 7/2002 Khalil et al.
2002/0085961 A1 7/2002 Morin et al.
2002/0090720 A1 7/2002 Mutz et al.
2002/0106667 A1 8/2002 Yamamoto et al.
2002/0119455 A1 8/2002 Chan
2002/0119459 A1 8/2002 Griffiths
2002/0127591 A1 9/2002 Wada et al.
2002/0140414 A1 10/2002 Sohn et al.
2002/0142344 A1 10/2002 Akeson et al.
2002/0143437 A1 10/2002 Handique et al.
2002/0155080 A1 10/2002 Glenn et al.
2002/0158027 A1 10/2002 Moon et al.
2002/0164271 A1 11/2002 Ho
2002/0164629 A1 11/2002 Quake et al.
2002/0166582 A1 11/2002 O'Connor et al.
2002/0179849 A1 12/2002 Maher et al.
2003/0008308 A1 1/2003 Enzelberger et al.
2003/0012586 A1 1/2003 Iwata et al.
2003/0015425 A1 1/2003 Bohm et al.
2003/0017305 A1 1/2003 Roitman et al.
2003/0017579 A1 1/2003 Corn et al.
2003/0027150 A1* 2/2003 Katz .................... C12Q 1/6888
435/91.2
2003/0032204 A1 2/2003 Walt et al.
2003/0038865 A1 2/2003 Inamura
2003/0039169 A1 2/2003 Ehrfeld et al.
2003/0040620 A1 2/2003 Langmore et al.
2003/0059764 A1 3/2003 Ravkin et al.
2003/0061687 A1 4/2003 Hansen et al.
2003/0064414 A1 4/2003 Benecky et al.
2003/0082795 A1 5/2003 Shuler et al.
2003/0083276 A1 5/2003 Li et al.
2003/0104372 A1 6/2003 Ahmadian et al.
2003/0108900 A1 6/2003 Oliphant et al.
2003/0124586 A1 7/2003 Griffiths et al.
2003/0143599 A1 7/2003 Makarov et al.
2003/0144260 A1 7/2003 Gilon
2003/0148273 A1 8/2003 Dong et al.
2003/0148335 A1 8/2003 Shen et al.
2003/0148531 A1 8/2003 Hatcher et al.
2003/0148544 A1 8/2003 Nie et al.
2003/0180748 A1 9/2003 Braun et al.
2003/0181574 A1 9/2003 Adam et al.
2003/0183525 A1 10/2003 Elrod et al.
2003/0207295 A1 11/2003 Gunderson et al.
2003/0219754 A1 11/2003 Oleksy et al.
2003/0224509 A1 12/2003 Moon et al.
2003/0229376 A1 12/2003 Sandhu
2003/0230486 A1 12/2003 Chien et al.
2003/0232356 A1 12/2003 Dooley et al.
2004/0005582 A1 1/2004 Shipwash
2004/0005594 A1 1/2004 Holliger et al.
2004/0018525 A1 1/2004 Wirtz et al.
2004/0027915 A1 2/2004 Lowe et al.
2004/0030255 A1 2/2004 Alfano et al.
2004/0031688 A1 2/2004 Shenderov
2004/0037739 A1 2/2004 McNeely et al.
2004/0037813 A1 2/2004 Simpson et al.
2004/0041093 A1 3/2004 Schultz et al.
2004/0050946 A1 3/2004 Wang et al.
2004/0053247 A1 3/2004 Cordon-Cardo et al.
2004/0057906 A1 3/2004 Hsu et al.
2004/0058450 A1 3/2004 Pamula et al.
2004/0068019 A1 4/2004 Higuchi et al.
2004/0071781 A1 4/2004 Chattopadhyay et al.
2004/0079881 A1 4/2004 Fischer et al.
2004/0086892 A1 5/2004 Crothers et al.
2004/0091923 A1 5/2004 Reyes et al.
2004/0092824 A1 5/2004 Stamnes et al.
2004/0096515 A1 5/2004 Bausch et al.
2004/0101822 A1 5/2004 Wiesner et al.
2004/0134854 A1 7/2004 Higuchi et al.
2004/0136497 A1 7/2004 Meldrum et al.
2004/0142329 A1 7/2004 Erikson et al.
2004/0146866 A1 7/2004 Fu
2004/0146921 A1 7/2004 Eveleigh et al.
2004/0159633 A1 8/2004 Whitesides et al.
2004/0166514 A1* 8/2004 Puskas ................. C12Q 1/6818
435/6.12
2004/0180346 A1 9/2004 Anderson
2004/0181131 A1 9/2004 Maynard et al.
2004/0181343 A1 9/2004 Wigstrom et al.
2004/0182712 A1 9/2004 Basol
2004/0185484 A1 9/2004 Costa et al.
2004/0188254 A1 9/2004 Spaid
2004/0209299 A1 10/2004 Pinter et al.
2004/0224325 A1 11/2004 Knapp et al.
2004/0224419 A1 11/2004 Zheng et al.
2004/0229349 A1 11/2004 Daridon
2004/0241693 A1 12/2004 Ricoul et al.
2004/0253731 A1 12/2004 Holliger et al.
2004/0258203 A1 12/2004 Yamano et al.
2004/0259083 A1 12/2004 Oshima
2005/0000970 A1 1/2005 Kimbara et al.
2005/0003380 A1 1/2005 Cohen et al.
2005/0008592 A1 1/2005 Gardel et al.
2005/0019776 A1 1/2005 Callow et al.
2005/0022764 A1 2/2005 Kawai et al.
2005/0032238 A1 2/2005 Karp et al.
2005/0032240 A1 2/2005 Lee et al.
2005/0037392 A1 2/2005 Griffiths et al.
2005/0037397 A1 2/2005 Mirkin et al.
2005/0042639 A1 2/2005 Knapp et al.
2005/0042648 A1 2/2005 Griffiths et al.
2005/0048467 A1 3/2005 Sastry et al.
2005/0064460 A1 3/2005 Holliger et al.
2005/0069920 A1 3/2005 Griffiths et al.
2005/0079501 A1 4/2005 Koike et al.
2005/0079510 A1 4/2005 Berka et al.
2005/0084923 A1 4/2005 Mueller et al.
2005/0087122 A1 4/2005 Ismagliov et al.
2005/0095611 A1 5/2005 Chan et al.
2005/0100895 A1 5/2005 Waldman et al.
2005/0103690 A1 5/2005 Kawano et al.
2005/0123937 A1 6/2005 Thorp et al.
2005/0129582 A1 6/2005 Breidford et al.
2005/0130173 A1 6/2005 Leamon et al.
2005/0152908 A1 7/2005 Liew et al.

(56) References Cited

U.S. PATENT DOCUMENTS

| | | | |
|---|---|---|---|
| 2005/0161669 | A1 | 7/2005 | Jovanovich et al. |
| 2005/0164239 | A1 | 7/2005 | Griffiths et al. |
| 2005/0169797 | A1 | 8/2005 | Oshima |
| 2005/0170373 | A1 | 8/2005 | Monforte |
| 2005/0170431 | A1 | 8/2005 | Ibrahim et al. |
| 2005/0172476 | A1 | 8/2005 | Stone et al. |
| 2005/0183995 | A1 | 8/2005 | Deshpande et al. |
| 2005/0202429 | A1 | 9/2005 | Trau et al. |
| 2005/0202489 | A1 | 9/2005 | Cho et al. |
| 2005/0207940 | A1 | 9/2005 | Butler et al. |
| 2005/0208495 | A1 | 9/2005 | Joseph et al. |
| 2005/0208529 | A1 | 9/2005 | Winther et al. |
| 2005/0214173 | A1 | 9/2005 | Facer et al. |
| 2005/0221339 | A1 | 10/2005 | Griffiths et al. |
| 2005/0221341 | A1 | 10/2005 | Shimkets et al. |
| 2005/0226742 | A1 | 10/2005 | Unger et al. |
| 2005/0227264 | A1 | 10/2005 | Nobile et al. |
| 2005/0248066 | A1 | 11/2005 | Esteban |
| 2005/0251049 | A1 | 11/2005 | Cane et al. |
| 2005/0260566 | A1 | 11/2005 | Fischer et al. |
| 2005/0272159 | A1 | 12/2005 | Ismagilov et al. |
| 2005/0287572 | A1 | 12/2005 | Mathies et al. |
| 2006/0003347 | A1 | 1/2006 | Griffiths et al. |
| 2006/0003429 | A1 | 1/2006 | Frost et al. |
| 2006/0003439 | A1 | 1/2006 | Ismagilov et al. |
| 2006/0008824 | A1 | 1/2006 | Ronaghi et al. |
| 2006/0035386 | A1 | 2/2006 | Hattori et al. |
| 2006/0036348 | A1 | 2/2006 | Handique et al. |
| 2006/0040197 | A1 | 2/2006 | Kabai |
| 2006/0040297 | A1 | 2/2006 | Leamon et al. |
| 2006/0046257 | A1 | 3/2006 | Pollock et al. |
| 2006/0051329 | A1 | 3/2006 | Lee et al. |
| 2006/0068398 | A1 | 3/2006 | McMillan |
| 2006/0078475 | A1 | 4/2006 | Tai et al. |
| 2006/0078888 | A1 | 4/2006 | Griffiths et al. |
| 2006/0078893 | A1 | 4/2006 | Griffiths et al. |
| 2006/0094119 | A1 | 5/2006 | Ismagilov et al. |
| 2006/0096923 | A1 | 5/2006 | Wagler et al. |
| 2006/0100788 | A1 | 5/2006 | Carrino et al. |
| 2006/0105170 | A1 | 5/2006 | Dobson et al. |
| 2006/0108012 | A1 | 5/2006 | Barrow et al. |
| 2006/0110759 | A1 | 5/2006 | Paris et al. |
| 2006/0115821 | A1 | 6/2006 | Einstein et al. |
| 2006/0147909 | A1 | 7/2006 | Rarbach et al. |
| 2006/0153924 | A1 | 7/2006 | Griffiths et al. |
| 2006/0154298 | A1 | 7/2006 | Griffiths et al. |
| 2006/0160762 | A1 | 7/2006 | Zetter et al. |
| 2006/0163385 | A1 | 7/2006 | Link et al. |
| 2006/0169800 | A1 | 8/2006 | Rosell et al. |
| 2006/0177348 | A1 | 8/2006 | Yasuda et al. |
| 2006/0177832 | A1 | 8/2006 | Brenner |
| 2006/0195269 | A1 | 8/2006 | Yeatman et al. |
| 2006/0223127 | A1 | 10/2006 | Yip et al. |
| 2006/0234254 | A1 | 10/2006 | An et al. |
| 2006/0234259 | A1 | 10/2006 | Rubin et al. |
| 2006/0234264 | A1 | 10/2006 | Hardenbol |
| 2006/0245971 | A1 | 11/2006 | Burns et al. |
| 2006/0246431 | A1 | 11/2006 | Balachandran |
| 2006/0247532 | A1 | 11/2006 | Ramanujam et al. |
| 2006/0252057 | A1 | 11/2006 | Raponi et al. |
| 2006/0257893 | A1 | 11/2006 | Takahashi et al. |
| 2006/0258841 | A1 | 11/2006 | Michl et al. |
| 2006/0263888 | A1 | 11/2006 | Fritz et al. |
| 2006/0269558 | A1 | 11/2006 | Murphy et al. |
| 2006/0269934 | A1 | 11/2006 | Woudenberg et al. |
| 2006/0269971 | A1 | 11/2006 | Diamandis |
| 2006/0281089 | A1 | 12/2006 | Gibson et al. |
| 2006/0281098 | A1 | 12/2006 | Miao et al. |
| 2006/0286570 | A1 | 12/2006 | Rowlen et al. |
| 2007/0003442 | A1 | 1/2007 | Link et al. |
| 2007/0009914 | A1 | 1/2007 | Wallace et al. |
| 2007/0009954 | A1 | 1/2007 | Wang et al. |
| 2007/0016078 | A1 | 1/2007 | Hoyt et al. |
| 2007/0020617 | A1 | 1/2007 | Trnovsky et al. |
| 2007/0026439 | A1 | 2/2007 | Faulstich et al. |
| 2007/0031829 | A1 | 2/2007 | Yasuno et al. |
| 2007/0039866 | A1 | 2/2007 | Schroeder et al. |
| 2007/0042400 | A1 | 2/2007 | Choi et al. |
| 2007/0042419 | A1 | 2/2007 | Barany et al. |
| 2007/0045117 | A1 | 3/2007 | Pamula et al. |
| 2007/0048744 | A1 | 3/2007 | Lapidus |
| 2007/0053896 | A1 | 3/2007 | Ahmed et al. |
| 2007/0054119 | A1 | 3/2007 | Garstecki et al. |
| 2007/0056853 | A1 | 3/2007 | Aizenberg et al. |
| 2007/0065823 | A1 | 3/2007 | Dressman et al. |
| 2007/0077572 | A1 | 4/2007 | Tawfik et al. |
| 2007/0077579 | A1 | 4/2007 | Griffiths et al. |
| 2007/0092914 | A1 | 4/2007 | Griffiths et al. |
| 2007/0111303 | A1 | 5/2007 | Inoue et al. |
| 2007/0120899 | A1 | 5/2007 | Ohnishi et al. |
| 2007/0123430 | A1 | 5/2007 | Pasquier et al. |
| 2007/0141593 | A1 | 6/2007 | Lee et al. |
| 2007/0142720 | A1 | 6/2007 | Ridder et al. |
| 2007/0154889 | A1 | 7/2007 | Wang |
| 2007/0156037 | A1 | 7/2007 | Pilon et al. |
| 2007/0166705 | A1 | 7/2007 | Milton et al. |
| 2007/0172873 | A1 | 7/2007 | Brenner et al. |
| 2007/0184439 | A1 | 8/2007 | Guilford et al. |
| 2007/0184489 | A1 | 8/2007 | Griffiths et al. |
| 2007/0195127 | A1 | 8/2007 | Ahn et al. |
| 2007/0202525 | A1 | 8/2007 | Quake |
| 2007/0213410 | A1 | 9/2007 | Hastwell et al. |
| 2007/0241068 | A1 | 10/2007 | Pamula et al. |
| 2007/0242105 | A1 | 10/2007 | Srinivasan et al. |
| 2007/0242111 | A1 | 10/2007 | Pamula et al. |
| 2007/0243634 | A1 | 10/2007 | Pamula et al. |
| 2007/0259351 | A1 | 11/2007 | Chinitz et al. |
| 2007/0259368 | A1 | 11/2007 | An et al. |
| 2007/0259374 | A1 | 11/2007 | Griffiths et al. |
| 2007/0269804 | A1 | 11/2007 | Liew et al. |
| 2007/0275415 | A1 | 11/2007 | Srinivasan et al. |
| 2007/0292869 | A1 | 12/2007 | Becker et al. |
| 2008/0003142 | A1 | 1/2008 | Link et al. |
| 2008/0003571 | A1 | 1/2008 | McKeman et al. |
| 2008/0004436 | A1 | 1/2008 | Tawfik et al. |
| 2008/0009005 | A1 | 1/2008 | Kruk |
| 2008/0014589 | A1 | 1/2008 | Link et al. |
| 2008/0014590 | A1 | 1/2008 | Dahary et al. |
| 2008/0020940 | A1 | 1/2008 | Stedronsky et al. |
| 2008/0021330 | A1 | 1/2008 | Hwang et al. |
| 2008/0023330 | A1 | 1/2008 | Viovy et al. |
| 2008/0032413 | A1 | 2/2008 | Kim et al. |
| 2008/0038754 | A1 | 2/2008 | Farias-Eisner et al. |
| 2008/0044828 | A1 | 2/2008 | Kwok |
| 2008/0050378 | A1 | 2/2008 | Nakamura et al. |
| 2008/0050723 | A1 | 2/2008 | Belacel et al. |
| 2008/0053205 | A1 | 3/2008 | Pollack et al. |
| 2008/0057514 | A1 | 3/2008 | Goldenring |
| 2008/0058432 | A1 | 3/2008 | Wang et al. |
| 2008/0063227 | A1 | 3/2008 | Rohrseitz |
| 2008/0064047 | A1 | 3/2008 | Zetter et al. |
| 2008/0081330 | A1 | 4/2008 | Kahvejian |
| 2008/0081333 | A1 | 4/2008 | Mori et al. |
| 2008/0087585 | A1 | 4/2008 | Tyvoll et al. |
| 2008/0092973 | A1 | 4/2008 | Lai |
| 2008/0113340 | A1 | 5/2008 | Schlegel |
| 2008/0118462 | A1 | 5/2008 | Alani et al. |
| 2008/0124726 | A1 | 5/2008 | Monforte |
| 2008/0138806 | A1 | 6/2008 | Chow et al. |
| 2008/0166772 | A1 | 7/2008 | Hollinger et al. |
| 2008/0166793 | A1 | 7/2008 | Beer et al. |
| 2008/0171078 | A1 | 7/2008 | Gray |
| 2008/0176211 | A1 | 7/2008 | Spence et al. |
| 2008/0176236 | A1 | 7/2008 | Tsao et al. |
| 2008/0181850 | A1 | 7/2008 | Thaxton et al. |
| 2008/0206756 | A1 | 8/2008 | Lee et al. |
| 2008/0213377 | A1 | 9/2008 | Bhatia et al. |
| 2008/0216563 | A1 | 9/2008 | Reed et al. |
| 2008/0220986 | A1 | 9/2008 | Gormley et al. |
| 2008/0222741 | A1 | 9/2008 | Chinnaiyan |
| 2008/0234138 | A1 | 9/2008 | Shaughnessy et al. |
| 2008/0234139 | A1 | 9/2008 | Shaughnessy et al. |
| 2008/0241830 | A1 | 10/2008 | Vogelstein |
| 2008/0261295 | A1 | 10/2008 | Butler et al. |

(56) References Cited

U.S. PATENT DOCUMENTS

2008/0268473 A1 10/2008 Moses et al.
2008/0269157 A1 10/2008 Srivastava et al.
2008/0274513 A1 11/2008 Shenderov et al.
2008/0274908 A1 11/2008 Chang
2008/0280285 A1 11/2008 Chen et al.
2008/0280302 A1 11/2008 Kebebew
2008/0286199 A1 11/2008 Livingston et al.
2008/0286801 A1 11/2008 Arjol et al.
2008/0286811 A1 11/2008 Moses et al.
2008/0293578 A1 11/2008 Shaugnessy et al.
2008/0299565 A1 12/2008 Schneider et al.
2008/0305482 A1 12/2008 Brentano et al.
2008/0311570 A1 12/2008 Lai
2008/0311604 A1 12/2008 Elting et al.
2008/0317632 A1 12/2008 Shimasaki et al.
2009/0004687 A1 1/2009 Mansfield et al.
2009/0005254 A1 1/2009 Griffiths et al.
2009/0009855 A1 1/2009 Nakatsuka et al.
2009/0012187 A1 1/2009 Chu et al.
2009/0017463 A1 1/2009 Bhowmick
2009/0021728 A1 1/2009 Heinz et al.
2009/0023137 A1 1/2009 Van Der Zee et al.
2009/0026082 A1 1/2009 Rothberg et al.
2009/0029372 A1 1/2009 Wewer
2009/0029478 A1 1/2009 Puskas
2009/0035770 A1 2/2009 Mathies et al.
2009/0042737 A1 2/2009 Katz et al.
2009/0053700 A1 2/2009 Griffiths et al.
2009/0053732 A1 2/2009 Vermesh et al.
2009/0060797 A1 3/2009 Mathies et al.
2009/0062144 A1 3/2009 Guo
2009/0068170 A1 3/2009 Weitz et al.
2009/0069194 A1 3/2009 Ramakrishnan
2009/0075265 A1 3/2009 Budiman et al.
2009/0075307 A1 3/2009 Fischer et al.
2009/0075311 A1 3/2009 Karl
2009/0081237 A1 3/2009 D'Andrea et al.
2009/0081685 A1 3/2009 Beyer et al.
2009/0087847 A1 4/2009 Lo
2009/0087849 A1 4/2009 Malinowski et al.
2009/0092973 A1 4/2009 Erlander et al.
2009/0098542 A1 4/2009 Budiman et al.
2009/0098543 A1 4/2009 Budiman et al.
2009/0098555 A1 4/2009 Roth et al.
2009/0105959 A1 4/2009 Braverman et al.
2009/0118128 A1 5/2009 Liu et al.
2009/0118158 A1 5/2009 Quay
2009/0124569 A1 5/2009 Bergan et al.
2009/0124789 A1 5/2009 Yoshida et al.
2009/0127454 A1 5/2009 Ritchie et al.
2009/0127589 A1 5/2009 Rothberg et al.
2009/0131353 A1 5/2009 Insel et al.
2009/0131543 A1 5/2009 Weitz et al.
2009/0134027 A1 5/2009 Jary
2009/0134331 A1 5/2009 Miyamae et al.
2009/0169482 A1 7/2009 Zheng et al.
2009/0191565 A1 7/2009 Lapidus et al.
2009/0197248 A1 8/2009 Griffiths et al.
2009/0197772 A1 8/2009 Griffiths et al.
2009/0215633 A1 8/2009 Van Eijk et al.
2009/0226971 A1 9/2009 Beer et al.
2009/0226972 A1 9/2009 Beer et al.
2009/0233802 A1 9/2009 Bignell et al.
2009/0239308 A1 9/2009 Dube
2009/0246788 A1 10/2009 Albert et al.
2009/0317798 A1 12/2009 Heid et al.
2009/0325217 A1 12/2009 Luscher
2009/0325236 A1 12/2009 Griffiths et al.
2010/0003687 A1 1/2010 Simen et al.
2010/0009353 A1 1/2010 Barnes et al.
2010/0015617 A1 1/2010 Toyama
2010/0021984 A1 1/2010 Edd et al.
2010/0022414 A1 1/2010 Link et al.
2010/0035252 A1 2/2010 Rothberg et al.
2010/0041046 A1 2/2010 Chiu et al.
2010/0055677 A1 3/2010 Colston, Jr. et al.
2010/0055708 A1 3/2010 Maus et al.
2010/0058908 A1 3/2010 O'banion et al.
2010/0075436 A1 3/2010 Urdea et al.
2010/0086914 A1 4/2010 Bentley et al.
2010/0092973 A1 4/2010 Davies et al.
2010/0093107 A1 4/2010 Clarizia et al.
2010/0105112 A1 4/2010 Holtze et al.
2010/0111768 A1 5/2010 Banerjee et al.
2010/0120098 A1 5/2010 Grunenwald et al.
2010/0124759 A1 5/2010 Wang et al.
2010/0129896 A1 5/2010 Knapp et al.
2010/0130369 A1 5/2010 Shenderov et al.
2010/0136544 A1 6/2010 Agresti et al.
2010/0137143 A1 6/2010 Rothberg et al.
2010/0137163 A1 6/2010 Link et al.
2010/0159592 A1 6/2010 Holliger et al.
2010/0172803 A1 7/2010 Stone et al.
2010/0173293 A1 7/2010 Woudenberg et al.
2010/0173394 A1 7/2010 Colston, Jr. et al.
2010/0183504 A1 7/2010 Chen
2010/0184069 A1 7/2010 Fernando et al.
2010/0188073 A1 7/2010 Rothberg et al.
2010/0197507 A1 8/2010 Rothberg et al.
2010/0210479 A1 8/2010 Griffiths et al.
2010/0213628 A1 8/2010 Bausch et al.
2010/0216128 A1 8/2010 Davies et al.
2010/0233026 A1 9/2010 Ismagliov et al.
2010/0233083 A1 9/2010 Dias et al.
2010/0240101 A1 9/2010 Lieberman et al.
2010/0248237 A1 9/2010 Froehlich et al.
2010/0252118 A1 10/2010 Fraden et al.
2010/0273173 A1 10/2010 Hirai
2010/0273219 A1 10/2010 May et al.
2010/0282617 A1 11/2010 Rothberg et al.
2010/0285975 A1 11/2010 Mathies et al.
2010/0300559 A1 12/2010 Schultz et al.
2010/0300895 A1 12/2010 Nobile et al.
2010/0301398 A1 12/2010 Rothberg et al.
2010/0304378 A1 12/2010 Griffiths et al.
2010/0304982 A1 12/2010 Hinz et al.
2011/0000560 A1 1/2011 Miller et al.
2011/0009294 A1 1/2011 Jones et al.
2011/0024455 A1 2/2011 Bethuy et al.
2011/0030808 A1 2/2011 Chiou et al.
2011/0033854 A1 2/2011 Drmanac et al.
2011/0045462 A1 2/2011 Fu et al.
2011/0053151 A1 3/2011 Hansen et al.
2011/0053798 A1 3/2011 Hindson et al.
2011/0059435 A1 3/2011 Vogelstein et al.
2011/0059556 A1 3/2011 Strey et al.
2011/0104725 A1 5/2011 Pamula et al.
2011/0104816 A1 5/2011 Pollack et al.
2011/0111981 A1 5/2011 Love et al.
2011/0142734 A1 6/2011 Smagliov et al.
2011/0151444 A1 6/2011 Albers et al.
2011/0159499 A1 6/2011 Hindson et al.
2011/0174622 A1 7/2011 Ismagilov et al.
2011/0176966 A1 7/2011 Ismagilov et al.
2011/0177494 A1 7/2011 Ismagilov et al.
2011/0177586 A1 7/2011 Ismagilov et al.
2011/0177609 A1 7/2011 Ismagilov et al.
2011/0188717 A1 8/2011 Baudry et al.
2011/0190146 A1 8/2011 Boehm et al.
2011/0218123 A1 9/2011 Weitz et al.
2011/0223314 A1 9/2011 Zhang et al.
2011/0244455 A1 10/2011 Larson et al.
2011/0250597 A1 10/2011 Larson et al.
2011/0257031 A1 10/2011 Bodeau et al.
2011/0267457 A1 11/2011 Weitz et al.
2011/0274706 A1 11/2011 Nelson et al.
2011/0275063 A1 11/2011 Weitz et al.
2011/0311978 A1 12/2011 Makarewicz, Jr. et al.
2012/0010085 A1 1/2012 Rava et al.
2012/0010098 A1 1/2012 Griffiths et al.
2012/0010107 A1 1/2012 Griffiths et al.
2012/0014977 A1 1/2012 Furihata et al.
2012/0015382 A1 1/2012 Weitz et al.
2012/0015822 A1 1/2012 Weitz et al.

(56) References Cited

U.S. PATENT DOCUMENTS

2012/0021919 A1 1/2012 Scholl et al.
2012/0021930 A1 1/2012 Schoen et al.
2012/0028724 A1 2/2012 Ensing
2012/0058908 A1 3/2012 Li et al.
2012/0088691 A1 4/2012 Chen et al.
2012/0122714 A1 5/2012 Samuels et al.
2012/0132288 A1 5/2012 Weitz et al.
2012/0164652 A1 6/2012 Clemens et al.
2012/0165219 A1 6/2012 Van Der Zaag et al.
2012/0167142 A1 6/2012 Hey
2012/0171667 A1 7/2012 Shoemaker et al.
2012/0190032 A1 7/2012 Ness et al.
2012/0208241 A1 8/2012 Link
2012/0208705 A1 8/2012 Steemers et al.
2012/0208724 A1 8/2012 Steemers et al.
2012/0219947 A1 8/2012 Yurkovetsky et al.
2012/0220494 A1 8/2012 Samuels et al.
2012/0231972 A1 9/2012 Golyshin et al.
2012/0244043 A1 9/2012 Leblanc et al.
2012/0252012 A1 10/2012 Armougom et al.
2012/0253689 A1 10/2012 Rogan
2012/0258516 A1 10/2012 Schultz et al.
2012/0264646 A1 10/2012 Link et al.
2012/0288857 A1 11/2012 Livak
2012/0289414 A1 11/2012 Mitra et al.
2012/0302448 A1 11/2012 Hutchison et al.
2012/0309002 A1 12/2012 Link
2012/0322058 A1 12/2012 Regan et al.
2013/0064776 A1 3/2013 El Harrak et al.
2013/0090248 A1 4/2013 Link et al.
2013/0099018 A1 4/2013 Miller et al.
2013/0109575 A1 5/2013 Kleinschmidt et al.
2013/0109577 A1 5/2013 Korlach et al.
2013/0116130 A1 5/2013 Fu et al.
2013/0123339 A1 5/2013 Heyes et al.
2013/0143745 A1 6/2013 Christen et al.
2013/0143749 A1 6/2013 Ghadessy
2013/0157870 A1 6/2013 Pushkarev et al.
2013/0157872 A1 6/2013 Griffiths et al.
2013/0178368 A1 7/2013 Griffiths et al.
2013/0178378 A1 7/2013 Hatch et al.
2013/0183659 A1 7/2013 Link et al.
2013/0196324 A1 8/2013 Larson et al.
2013/0203606 A1 8/2013 Pollack et al.
2013/0210638 A1 8/2013 Olson et al.
2013/0210639 A1 8/2013 Link et al.
2013/0210659 A1 8/2013 Watson et al.
2013/0217071 A1 8/2013 Montesclaros et al.
2013/0217583 A1 8/2013 Link et al.
2013/0217601 A1 8/2013 Griffiths et al.
2013/0224751 A1 8/2013 Olson et al.
2013/0225418 A1 8/2013 Watson
2013/0225623 A1 8/2013 Buxbaum et al.
2013/0244906 A1 9/2013 Collins
2013/0260447 A1 10/2013 Link
2013/0261196 A1 10/2013 Diamond et al.
2013/0274117 A1 10/2013 Church et al.
2013/0288254 A1 10/2013 Pollack et al.
2013/0295567 A1 11/2013 Link et al.
2013/0295568 A1 11/2013 Link
2013/0296535 A1 11/2013 Church et al.
2014/0045712 A1 2/2014 Link et al.
2014/0057799 A1 2/2014 Johnson et al.
2014/0065631 A1 3/2014 Froehlich et al.
2014/0076430 A1 3/2014 Miller et al.
2014/0099637 A1 4/2014 Nolan et al.
2014/0113300 A1 4/2014 Samuels
2014/0154695 A1 6/2014 Miller et al.
2014/0155274 A1 6/2014 Xie et al.
2014/0235452 A1 8/2014 Rothberg et al.
2014/0256568 A1 9/2014 Link
2014/0256585 A1 9/2014 McCoy
2014/0256595 A1 9/2014 Link et al.
2014/0274786 A1 9/2014 McCoy et al.
2014/0295421 A1 10/2014 Link et al.
2014/0323317 A1 10/2014 Link et al.
2014/0329239 A1 11/2014 Larson et al.
2015/0018236 A1 1/2015 Green et al.
2015/0027892 A1 1/2015 Miller et al.
2015/0038356 A1 2/2015 Karlin-Neumann et al.
2015/0099266 A1 4/2015 Samuels et al.
2015/0126400 A1 5/2015 Watson et al.
2015/0167066 A1 6/2015 Link et al.
2015/0184256 A1 7/2015 Samuels et al.
2015/0197790 A1 7/2015 Tzonev
2015/0217246 A1 8/2015 Holtze et al.
2015/0247191 A1 9/2015 Zhang et al.
2015/0258520 A1 9/2015 Griffiths et al.
2015/0298091 A1 10/2015 Weitz et al.
2015/0336072 A1 11/2015 Weitz et al.
2016/0060621 A1 3/2016 Agresti et al.
2016/0200847 A1 7/2016 Chiari
2016/0201125 A1 7/2016 Samuels et al.
2016/0209303 A1 7/2016 Miller et al.
2016/0222433 A1 8/2016 Larson et al.
2016/0281140 A1 9/2016 Miller et al.
2016/0289670 A1 10/2016 Samuels et al.
2016/0304954 A1 10/2016 Lin et al.
2016/0346748 A1 12/2016 Yurkovetsky et al.
2017/0002400 A1 1/2017 Hutchison et al.
2017/0028365 A1 2/2017 Link et al.
2017/0067047 A1 3/2017 Link et al.
2017/0128941 A1 5/2017 Sadri et al.
2017/0131279 A1 5/2017 Link et al.
2017/0176429 A1 6/2017 Samuels et al.
2017/0183722 A1 6/2017 Link
2017/0304785 A1 10/2017 Link et al.
2017/0336306 A1 11/2017 Miller et al.
2018/0057863 A1 3/2018 Larson et al.
2018/0057868 A1 3/2018 Walder et al.
2018/0080020 A1 3/2018 Link et al.
2018/0100185 A1 4/2018 Samuels
2018/0135117 A1 5/2018 Link
2018/0178174 A1 6/2018 Link et al.
2018/0223348 A1 8/2018 Link et al.
2018/0272294 A1 9/2018 Griffiths et al.
2018/0272295 A1 9/2018 Link et al.
2018/0272296 A1 9/2018 Link et al.
2018/0272299 A1 9/2018 Griffiths et al.
2018/0280897 A1 10/2018 Link et al.
2018/0298324 A1 10/2018 Takeda et al.
2018/0304222 A1 10/2018 Weitz et al.
2018/0305747 A1 10/2018 Link
2018/0353913 A1 12/2018 Link et al.
2018/0355350 A1 12/2018 Link et al.
2018/0361346 A1 12/2018 Griffiths et al.
2018/0363050 A1 12/2018 Hutchison et al.
2019/0024261 A1 1/2019 Griffiths et al.
2019/0094226 A1 3/2019 Link et al.
2019/0107489 A1 4/2019 Griffiths et al.
2019/0134581 A1 5/2019 Yurkovetsky et al.
2019/0227021 A1 7/2019 Han et al.
2019/0255530 A1 8/2019 Fraden et al.
2019/0316119 A1 10/2019 Samuels et al.
2019/0330683 A1 10/2019 Link et al.
2020/0002748 A1 1/2020 Miller et al.
2020/0217843 A1 7/2020 El Harrak et al.
2020/0225129 A1 7/2020 Miller et al.
2020/0225232 A1 7/2020 Link et al.
2020/0249230 A1 8/2020 Link et al.
2020/0254400 A1 8/2020 Griffiths et al.
2020/0270600 A1 8/2020 Samuels et al.
2020/0318157 A1 10/2020 Hutchison et al.
2020/0360876 A1 11/2020 Link et al.
2020/0399635 A1 12/2020 Samuels et al.
2021/0002703 A1 1/2021 Link et al.
2021/0041432 A1 2/2021 Samuels et al.
2021/0088424 A1 3/2021 Kleinschmidt et al.
2021/0088519 A1 3/2021 Link et al.
2021/0230681 A1 7/2021 Patterson et al.
2021/0262020 A1 8/2021 Link
2022/0042995 A1 2/2022 Link et al.
2022/0047998 A1 2/2022 Link et al.
2022/0050108 A1 2/2022 Link et al.

(56) References Cited

U.S. PATENT DOCUMENTS

| | | | |
|---|---|---|---|
| 2022/0064711 | A1 | 3/2022 | Samuels et al. |
| 2022/0213530 | A1 | 7/2022 | Larson et al. |
| 2022/0307073 | A1 | 9/2022 | Hutchison et al. |
| 2024/0002910 | A1 | 1/2024 | Larson |
| 2024/0132939 | A1 | 4/2024 | Larson |

FOREIGN PATENT DOCUMENTS

| | | | |
|---|---|---|---|
| AT | 155711 | T | 8/1997 |
| AT | 167816 | T | 7/1998 |
| AU | 4032078 | A | 4/1980 |
| AU | 6415380 | A | 5/1981 |
| AU | 1045983 | A | 6/1984 |
| AU | 2177292 | A | 1/1993 |
| AU | 4222393 | A | 11/1993 |
| AU | 4222593 | A | 11/1993 |
| AU | 4222693 | A | 11/1993 |
| AU | 4222793 | A | 11/1993 |
| AU | 4223593 | A | 11/1993 |
| AU | 677197 | B2 | 4/1997 |
| AU | 677781 | B2 | 5/1997 |
| AU | 680195 | B2 | 7/1997 |
| AU | 2935197 | A | 1/1998 |
| AU | 3499097 | A | 1/1998 |
| AU | 3501297 | A | 1/1998 |
| AU | 1276099 | A | 6/1999 |
| AU | 4955799 | A | 12/1999 |
| AU | 3961100 | A | 10/2000 |
| AU | 4910300 | A | 11/2000 |
| AU | 747464 | B2 | 5/2002 |
| AU | 768399 | B2 | 12/2003 |
| AU | 2004225691 | A1 | 10/2004 |
| AU | 2010224352 | A1 | 10/2010 |
| BR | 9710052 | A | 1/2000 |
| CA | 1093344 | A1 | 1/1981 |
| CA | 2258481 | A1 | 1/1998 |
| CA | 2520548 | A1 | 10/2004 |
| CH | 563 087 | A5 | 6/1975 |
| CH | 563807 | A5 | 7/1975 |
| CN | 101910415 | A | 12/2010 |
| CN | 104812915 | A | 7/2015 |
| DE | 2100685 | A1 | 7/1972 |
| DE | 3042915 | A1 | 9/1981 |
| DE | 43 08 839 | A1 | 9/1994 |
| DE | 69126763 | T2 | 2/1998 |
| DE | 199 61 257 | A1 | 7/2001 |
| DE | 100 15 109 | A1 | 10/2001 |
| DE | 100 41 823 | A1 | 3/2002 |
| DE | 10322893 | A1 | 12/2004 |
| EP | 0047130 | A2 | 3/1982 |
| EP | 0402995 | A2 | 12/1990 |
| EP | 0249007 | A3 | 3/1991 |
| EP | 0418635 | A1 | 3/1991 |
| EP | 0476178 | A1 | 3/1992 |
| EP | 0528580 | A1 | 2/1993 |
| EP | 0540281 | A2 | 5/1993 |
| EP | 0546174 | A1 | 6/1993 |
| EP | 0618001 | A1 | 10/1994 |
| EP | 620432 | A1 | 10/1994 |
| EP | 0637996 | A1 | 2/1995 |
| EP | 0637997 | A1 | 2/1995 |
| EP | 0718038 | A2 | 6/1996 |
| EP | 0486351 | B1 | 7/1997 |
| EP | 0895120 | A1 | 2/1999 |
| EP | 1362634 | A1 | 11/2003 |
| EP | 1447127 | A1 | 8/2004 |
| EP | 1462517 | A1 | 9/2004 |
| EP | 04782399.2 | | 5/2006 |
| EP | 1741482 | | 1/2007 |
| EP | 2017910 | A1 | 1/2009 |
| EP | 2127736 | | 12/2009 |
| EP | 2212437 | A1 | 8/2010 |
| EP | 2047910 | B1 | 1/2012 |
| EP | 13165665.4 | | 11/2013 |
| EP | 13165667.0 | | 11/2013 |
| EP | 2363205 | A3 | 6/2014 |
| EP | 2534267 | B1 | 4/2018 |
| ES | 2 095 413 | T3 | 2/1997 |
| FR | 2 404 834 | A1 | 4/1979 |
| FR | 2 451 579 | A1 | 10/1980 |
| FR | 2 469 714 | A1 | 5/1981 |
| FR | 2 470 385 | A1 | 5/1981 |
| FR | 2 650 657 | A1 | 2/1991 |
| FR | 2 669 028 | A1 | 5/1992 |
| FR | 2 703 263 | A1 | 10/1994 |
| GB | 1148543 | | 4/1969 |
| GB | 1 446 998 | | 8/1976 |
| GB | 2 005 224 | | 4/1979 |
| GB | 2 047 880 | | 12/1980 |
| GB | 2 062 225 | | 5/1981 |
| GB | 2 064 114 | | 6/1981 |
| GB | 2097692 | A | 11/1982 |
| GB | 2 210 532 | | 6/1989 |
| IE | 922432 | A1 | 2/1993 |
| JP | S5372016 | A | 6/1978 |
| JP | S5455495 | A | 5/1979 |
| JP | 55125472 | | 9/1980 |
| JP | S5636053 | A | 4/1981 |
| JP | 56-124052 | | 9/1981 |
| JP | 59-49832 | A | 3/1984 |
| JP | 59-102163 | | 6/1984 |
| JP | H0665609 | A | 3/1994 |
| JP | 6-265447 | A | 9/1994 |
| JP | 7-489 | A | 1/1995 |
| JP | 8-153669 | | 6/1996 |
| JP | 10-217477 | | 8/1998 |
| JP | 3-232525 | | 10/1998 |
| JP | 2000-271475 | | 10/2000 |
| JP | 2001-301154 | A | 10/2001 |
| JP | 2001-517353 | A | 10/2001 |
| JP | 2002-085961 | A | 3/2002 |
| JP | 2003-501257 | A | 1/2003 |
| JP | 2003-502655 | A | 1/2003 |
| JP | 2003-502656 | A | 1/2003 |
| JP | 2003-149136 | A | 5/2003 |
| JP | 2003-222633 | A | 8/2003 |
| JP | 2005-037346 | A | 2/2005 |
| JP | 2005-192944 | A | 7/2005 |
| JP | 2006-220423 | A | 8/2006 |
| JP | 2007-190364 | A | 8/2007 |
| JP | 2007-533971 | A | 11/2007 |
| JP | 2009-0536313 | A | 10/2009 |
| JP | 2009-265751 | A | 11/2009 |
| JP | 2010-198393 | A | 9/2010 |
| JP | 2012-204765 | A | 10/2012 |
| JP | 2013-143959 | A | 7/2013 |
| JP | 2016063824 | A | 4/2016 |
| NZ | 264353 | A | 5/1996 |
| WO | 84/02000 | | 5/1984 |
| WO | 90/15807 | A1 | 12/1990 |
| WO | 91/05058 | A1 | 4/1991 |
| WO | 91/07772 | | 5/1991 |
| WO | 91/16966 | A1 | 11/1991 |
| WO | 92/03734 | | 3/1992 |
| WO | 92/21746 | | 12/1992 |
| WO | 93/03151 | | 2/1993 |
| WO | 93/08278 | | 4/1993 |
| WO | 93/22053 | | 11/1993 |
| WO | 93/22054 | | 11/1993 |
| WO | 93/22055 | | 11/1993 |
| WO | 93/22058 | | 11/1993 |
| WO | 93/22421 | | 11/1993 |
| WO | 94/16332 | | 7/1994 |
| WO | 94/23738 | | 10/1994 |
| WO | 94/24314 | | 10/1994 |
| WO | 94/26766 | | 11/1994 |
| WO | 98/00705 | | 1/1995 |
| WO | 95/11922 | | 5/1995 |
| WO | 95/19922 | | 7/1995 |
| WO | 95/24929 | | 9/1995 |
| WO | 95/33447 | | 12/1995 |
| WO | 96/29629 | A2 | 9/1996 |
| WO | 96/34112 | | 10/1996 |
| WO | 96/38730 | | 12/1996 |

(56) References Cited

FOREIGN PATENT DOCUMENTS

| | | | |
|---|---|---|---|
| WO | 96/40057 | | 12/1996 |
| WO | 96/40062 | | 12/1996 |
| WO | 96/40723 | | 12/1996 |
| WO | 97/00125 | | 1/1997 |
| WO | 97/00442 | | 1/1997 |
| WO | 97/04297 | | 2/1997 |
| WO | 97/04748 | | 2/1997 |
| WO | 97/23140 | | 7/1997 |
| WO | 97/28556 | | 8/1997 |
| WO | 97/38318 | A1 | 10/1997 |
| WO | 97/39814 | | 10/1997 |
| WO | 97/40141 | | 10/1997 |
| WO | 97/45644 | | 12/1997 |
| WO | 97/47763 | A1 | 12/1997 |
| WO | 98/00231 | | 1/1998 |
| WO | 98/02237 | | 1/1998 |
| WO | 98/10267 | | 3/1998 |
| WO | 98/13502 | | 4/1998 |
| WO | 98/22625 | A1 | 5/1998 |
| WO | 98/23733 | | 6/1998 |
| WO | 98/31700 | | 7/1998 |
| WO | 98/33001 | | 7/1998 |
| WO | 98/34120 | | 8/1998 |
| WO | 98/37186 | | 8/1998 |
| WO | 98/41869 | | 9/1998 |
| WO | 98/52691 | | 11/1998 |
| WO | 98/58085 | | 12/1998 |
| WO | 99/02671 | | 1/1999 |
| WO | 99/22858 | | 5/1999 |
| WO | 99/28020 | | 6/1999 |
| WO | 99/28507 | | 6/1999 |
| WO | 99/31019 | | 6/1999 |
| WO | 99/42539 | | 8/1999 |
| WO | 99/54730 | | 10/1999 |
| WO | 99/61888 | | 12/1999 |
| WO | 00/04139 | A1 | 1/2000 |
| WO | 00/47322 | | 2/2000 |
| WO | 00/52455 | | 2/2000 |
| WO | 00/37924 | A1 | 6/2000 |
| WO | 00/40712 | | 6/2000 |
| WO | 00/54735 | | 9/2000 |
| WO | 00/61275 | | 10/2000 |
| WO | 00/70080 | | 11/2000 |
| WO | 00/76673 | | 12/2000 |
| WO | 00/078455 | A1 | 12/2000 |
| WO | 0078454 | A1 | 12/2000 |
| WO | 01/12327 | | 2/2001 |
| WO | 01/14589 | | 3/2001 |
| WO | 01/18244 | | 3/2001 |
| WO | 01/64332 | | 9/2001 |
| WO | 01/68257 | | 9/2001 |
| WO | 01/69289 | | 9/2001 |
| WO | 01/72431 | | 10/2001 |
| WO | 01/80283 | | 10/2001 |
| WO | 01/089787 | A2 | 11/2001 |
| WO | 01/89788 | A2 | 11/2001 |
| WO | 01/94635 | A2 | 12/2001 |
| WO | 02/16017 | | 2/2002 |
| WO | 02/18949 | | 3/2002 |
| WO | 02/22869 | | 3/2002 |
| WO | 02/23163 | A1 | 3/2002 |
| WO | 02/27660 | A2 | 4/2002 |
| WO | 02/31203 | | 4/2002 |
| WO | 2002/036815 | A2 | 5/2002 |
| WO | 02/47665 | | 8/2002 |
| WO | 02/060275 | | 8/2002 |
| WO | 02/060591 | A1 | 8/2002 |
| WO | 02/066992 | A1 | 8/2002 |
| WO | 02/068104 | A1 | 9/2002 |
| WO | 02/078845 | | 10/2002 |
| WO | 02/103011 | | 12/2002 |
| WO | 02/103363 | | 12/2002 |
| WO | 03/011443 | | 2/2003 |
| WO | 03/026798 | A1 | 4/2003 |
| WO | 03/037302 | | 5/2003 |
| WO | 03/044187 | | 5/2003 |
| WO | 03/078659 | | 9/2003 |
| WO | 2003/003015 | | 10/2003 |
| WO | 03/099843 | | 12/2003 |
| WO | 2004/002627 | | 1/2004 |
| WO | 2004/018497 | A2 | 3/2004 |
| WO | 2004/024917 | | 3/2004 |
| WO | 2004/026453 | A2 | 4/2004 |
| WO | 2004/037374 | A2 | 5/2004 |
| WO | 2004/038363 | | 5/2004 |
| WO | 04/071638 | A2 | 8/2004 |
| WO | 2004/069849 | A2 | 8/2004 |
| WO | 2004/074504 | | 9/2004 |
| WO | 2004/083443 | A1 | 9/2004 |
| WO | 2004/087308 | | 10/2004 |
| WO | 2004/088314 | | 10/2004 |
| WO | 2004/091763 | | 10/2004 |
| WO | 2004/102204 | | 11/2004 |
| WO | 2004/103565 | A2 | 12/2004 |
| WO | 2005/000970 | | 1/2005 |
| WO | 2005/002730 | A1 | 1/2005 |
| WO | 2005/003375 | A2 | 1/2005 |
| WO | 2005/11867 | A2 | 2/2005 |
| WO | 2005/023427 | A1 | 3/2005 |
| WO | 2005/028674 | A2 | 3/2005 |
| WO | 2005021151 | A1 | 3/2005 |
| WO | 2005/033283 | A2 | 4/2005 |
| WO | 2005/041884 | A2 | 5/2005 |
| WO | 05/049787 | A2 | 6/2005 |
| WO | 2005/103106 | | 11/2005 |
| WO | 2005/118138 | | 12/2005 |
| WO | 2005/118867 | A2 | 12/2005 |
| WO | 2006/002641 | | 1/2006 |
| WO | 2006/009657 | | 1/2006 |
| WO | 2006/027757 | A2 | 3/2006 |
| WO | 2006/038035 | A2 | 4/2006 |
| WO | 2006/040551 | | 4/2006 |
| WO | 2006/040554 | | 4/2006 |
| WO | 2006/042303 | A2 | 4/2006 |
| WO | 2006/076810 | A1 | 7/2006 |
| WO | 2006/078841 | | 7/2006 |
| WO | 2006/096571 | | 9/2006 |
| WO | 2006/101851 | | 9/2006 |
| WO | 2007/012638 | A1 | 2/2007 |
| WO | 2007/021343 | | 2/2007 |
| WO | 2007/030501 | | 3/2007 |
| WO | 2007/033385 | A2 | 3/2007 |
| WO | 2007026884 | A1 | 3/2007 |
| WO | 2007/081385 | A2 | 7/2007 |
| WO | 2007/081387 | A1 | 7/2007 |
| WO | 2007/089541 | | 8/2007 |
| WO | 2007/092473 | A2 | 8/2007 |
| WO | 2007/114794 | A1 | 10/2007 |
| WO | 2007/123744 | A2 | 11/2007 |
| WO | 2007/133710 | | 11/2007 |
| WO | 2007/133710 | A2 | 11/2007 |
| WO | 2007/138178 | | 12/2007 |
| WO | 2007/140015 | A2 | 12/2007 |
| WO | 2008/021123 | | 2/2008 |
| WO | 2008/021123 | A1 | 2/2008 |
| WO | 2008/052138 | A2 | 5/2008 |
| WO | 2008/063227 | | 5/2008 |
| WO | 2008/097559 | | 8/2008 |
| WO | 2008/115626 | A2 | 9/2008 |
| WO | 2008/121342 | | 10/2008 |
| WO | 2008/130623 | | 10/2008 |
| WO | 2008/134153 | A1 | 11/2008 |
| WO | 2008143646 | A2 | 11/2008 |
| WO | 2009/013492 | A1 | 1/2009 |
| WO | 2009/015296 | A1 | 1/2009 |
| WO | 2009/029229 | | 3/2009 |
| WO | 2009/037266 | A2 | 3/2009 |
| WO | 2009/049889 | A1 | 4/2009 |
| WO | 2009/059430 | A1 | 5/2009 |
| WO | 2009/085929 | A1 | 7/2009 |
| WO | 2009/094623 | A2 | 7/2009 |
| WO | 2009/117485 | A2 | 9/2009 |
| WO | 2009/137415 | A2 | 11/2009 |
| WO | 2009/137606 | A1 | 11/2009 |

(56) References Cited

FOREIGN PATENT DOCUMENTS

| | | | |
|---|---|---|---|
| WO | 2010/009365 | A1 | 1/2010 |
| WO | 2010/056728 | A1 | 5/2010 |
| WO | 2010/040006 | | 8/2010 |
| WO | 2010/115154 | A1 | 10/2010 |
| WO | 2010/127550 | A1 | 11/2010 |
| WO | 2010/151776 | | 12/2010 |
| WO | 2011005221 | A1 | 1/2011 |
| WO | 2011/042564 | | 4/2011 |
| WO | 2011/079176 | | 6/2011 |
| WO | 2011/100604 | A2 | 8/2011 |
| WO | 2012/022976 | A1 | 2/2012 |
| WO | 2012/036679 | A1 | 3/2012 |
| WO | 2012/045012 | A2 | 4/2012 |
| WO | 2012/047297 | A2 | 4/2012 |
| WO | 2012/048341 | A1 | 4/2012 |
| WO | 2012/083225 | A2 | 6/2012 |
| WO | 2012103339 | A1 | 8/2012 |
| WO | 2012106385 | A2 | 8/2012 |
| WO | 2012/142213 | A2 | 10/2012 |
| WO | 2012/167142 | A2 | 12/2012 |
| WO | 2013/14356 | A2 | 1/2013 |
| WO | 2013/120089 | A1 | 8/2013 |
| WO | 2013/165748 | A1 | 11/2013 |
| WO | 2014/026031 | A1 | 2/2014 |
| WO | 2014/065756 | A1 | 5/2014 |
| WO | 2014/165559 | A2 | 10/2014 |
| WO | 2014/194131 | A2 | 12/2014 |
| WO | 2014/204939 | A2 | 12/2014 |
| WO | 2015/013681 | A1 | 1/2015 |
| WO | 2015/164212 | A1 | 10/2015 |
| WO | 2015/200541 | A1 | 12/2015 |
| WO | 2015200893 | A2 | 12/2015 |
| WO | 2017/100350 | A1 | 6/2017 |
| WO | 2017/117358 | A1 | 7/2017 |

OTHER PUBLICATIONS

Kozbor, 1984, A human hybrid myeloma for production of human monoclonal antibodies, J. Immunol., 133:3001-3005.
Krafft, 1991, Synthesis and preliminary data on the biocompatibility and emulsifying properties of perfluoroalkylated phosphoramidates as injectable surfactants, Eur. J. Med. Chem., 26:545-550.
Krafft, 2001, Fluorocarbons and fluorinated amphiphiles in drug delivery and biomedical research, Adv Rev Drug Disc 47:209-228.
Krafft, 2003, Emulsions and microemulsions with a fluorocarbon phase, Colloid and Interface Science 8(3):251-258.
Kralj, 2005, Surfactant-enhanced liquid-liquid extraction in microfluidic channels with inline electric-field enhanced coalescence, Lab Chip 5:531-535.
Kricka, 1996, Micromachining: a new direction for clinical analyzers, Pure and Applied Chemistry 68(10):1831-1836.
Kricka, 2003, Microchip PCR, Anal Bioanal Chem 377(5):820-825.
Kritikou, 2005, It's cheaper in the Picolab, Nature 6:668.
Krumdiek, 1980, Solid-phase synthesis of pteroylpolyglutamates, Methods Enzymol, 524-29.
Kruth, 2003, Lasers and materials in selective laser sintering, Assembly Automation, 23(4):357-371.
Kuhlmann, 2009, Fixation of biological specimens, Division of Radiooncology, Germany, 12 pages.
Kumagai, 1994, Ablation of polymer films by a femtosecond high-peak-power Ti:sapphire laser at 798 nm, Applied Physics Letters, 65(14):1850-1852.
Kumar, 1989, Activity and kinetic characteristics of glutathione reductase in vitro in reverse micellar waterpool, Biochem Biophys Acta, 996(1-2):1-6.
Kumaresan, 2008, High-throughput single copy DNA amplification and cell analysis in engineered nanoliter droplets, Anal Chem, 80:3522-3529.
Lage, 2003, Whole genome analysis of genetic alterations in small DNA samples using hyperbranched strand displacement amplification and array-CGH, Genome Res 13:294-307.
Laird, 2013, Rapid Quantification of the Latent Reservoir for HIV-1 Using a Viral Outgrowth Assay, Plos Pathogens 9(5):e1003398.
Lamprecht, 2004, pH-sensitive microsphere delivery increases oral bioavailability of calcitonin, J Control Rel 98(1):1-9.
Lancet, 1993, Probability model for molecular recognition in biological receptor repertoirs, PNAS 90(8):3715-9.
Landergren, 1988, A ligase mediated gene detection technique, Science 241(4869):1077-80.
Lasheras, 1998, Breakup and atomization of a round water jet by a high speed annular air jet, J Fluid Mech 357:351-379.
Laufer, 1996, Introduction to Optics and Lasers in Engineering, Cambridge University Press, Cambridge UK:156-162.
Leamon, 2003, A massively parallel pictoterplate based platform for discrete picoliter-scale PCR, Electrophoresis 24:3769-3777.
Leary, 2000, Application of advanced cytometric and molecular technologies to minimal residual disease monitoring, Proc SPIE 3913:36-44.
Lee, 2000, Circulating flows inside a drop under time-periodic non-uniform electric fields, Phys Fuilds 12(8):1899-1910.
Lee, 2001, Preparation of silica particles encapsulating retinol using O/W/O multiple emulsions, J Coll Interface Sci 240 (1):83-89.
Lee, 2002, Effective formation of silicone-in-fluorocarbon-in-water double emulsions, J Disp Sci Tech 23(4):491-497.
Lee, 2002, Investigating the target recognition of DNA cytosine-5 methyltransferase Hhal by library selection using in vitro compartmentalisation (IVC), Nucleic Acids Res 30:4937-4944.
Lee, 2003, Miniaturization of polymerase chain reacton, Biotechnology and Bioprocess Engineering, 8.4:213-220.
Lee, 2004, Special issue on biomedical applications for MEMS and microfluidics, Proc IEEE 92(1):3-5.
Lemof, 2003, An AC magnetohydrodynamic microfluidic switch for Micro Total Analysis Systems, Biomed Microdev 5(I):55-60.
Leng, 2009, Microfluidic crystalizaiton, Lab Chip 9:24-23.
Leng, 2010, Agarose droplet microfluidics for highly parallel and efficient single molecule emulsion PCR, Lab Chip 10:2841-2843.
Lesley, 1991, Use of in vitro protein synthesis from PCR-generated templates to study interaction of *E coli* transcription factors with core RNA polymerase, J Biol Chem 266(4):2632-8.
Lesley, 1995, Preparation and use of *E. coli* S-30 extracts, Methods Mol Biol 37:265-78.
Leung, 1989, A method for random mutagenesis of a defined DNA segment using a modified polymerase chain reaction, Technique 1:11-15.
Li, 1995, Single-step procedure for labeling DNA strand breaks with flourescein-or BODIPY-conjugated deoxynucleotides, Cytometry 20:172-180.
Li, 1997, Transport, manipulation, and reaction of biological cells on-chip using electrokinetic effects, Anal Chem 69 (8):1564-1568.
Li, 2005, Multiplexed detection of pathogen DNA with DNA-based fluorescence nanobarcodes, Nat Biotech 23 (7):885-889.
Li, 2006, Nanoliter microfluidic hybrid method for simultaneous screening and optimization validated with crystallization of membrane proteins, PNAS 103:19243-19248.
Li, 2018, Microfluidic fabrication of microparticles for biomedical applications, Chem Soc Rev 47(15):5646-5683.
Liao, 1986, Isolation of a thermostable enzyme variant by cloning and selection in a thermophile, PNAS 83:576-80.
Lim, 1980, Microencapsulated islets as bioartificial endocrine pancreas, Science 210(4472):908-10.
Lin, 2007, Self-assembled combinatorial encoding nanoarrays for multiplexed biosensing, Nano Lett 7(2):507-512.
Link, 2004, Geometrically mediated breakup of drops in microfluidic devices, Phys Rev Lettv92(5):054503-1-4.
Link, 2006, Electric control droplets in microfluidic devices, Angew Chem Int Ed 45:2556-2560.
Lipinski, 2001, Experimental and computational approaches to estimate solubility and permeability in drug discovery, , Adv Drug Deliv Rev 46:3-26.
Lipkin, 1988, Biomarkers of increased susceptibility to gastreointestinal cancer: new application to studies of cancer prevention in human subjects, Cancer Res 48:235-245.
Liu, 2000, Passive mixing in a three-dimensional serpentine microchannel, J MEMS 9(2):190-197.

(56) References Cited

OTHER PUBLICATIONS

Liu, 2002, Fabrication and characterization of hydrogel-based microvalves, Mecoelectromech. Syst. 11:45-53.
Lizardi, 1998, Mutation detection and single-molecule counting using isothermal rolling-circle amplification. Nat Genet 19(3):225-32.
Abate, 2011, Synthesis of monidisperse microparticles from non-Newtonian polymer solutions with microfluidic devices, Adv Mat 23(15):1757-1760.
Adang, 2001, The contribution of combinatorial chemistry to lead generation: an interim analysis, Curr Med Chem 8:985-998.
Affholter 1999, Engineering a Revolution, Chemistry in Britain 48-51.
Agrawal, 1990, Site-specific functionalization of oligodeoxynucleotides for non-radioactive labelling, Tetrahedron Let 31:1543-1546.
Aharoni, 2005, High-Throughput screens and selections of enzyme-encoding genes, Curr Opin Chem Biol, 9(2):210-6.
Ahn, 2006, Dielectrophoretic manipulation of drops for high-speed microluidic sorting devices, Applied Phys Lett 88:024104.
Akasheh, 2004, Development of piezoelectric micromachined ultrasonic transducers, Sensors and Actuators A Physical, 111:275-287.
Allen, 2000, High throughput fluorescence polarization: a homogeneous alternative to radioligand binding for cell surface receptors J Biomol Screen. 5(2):63-69.
Ammar, 2003, UV/Vis absorption and fluorescence spectroscopic study of novel symmetrical biscoumarin dyes, Dyes and Pigments 57:259-265.
Amstutz, 2001, In vitro display technologies: novel developments and applications. Curr Opin Biotech 12:400-405.
Anarbaev, 1998, Klenow fragment and DNA polymerase alpha-primase fromserva calf thymus in water-in-oil microemulsions, Biochim Biophy Acta 1384:315-324.
Anderson, 1983, Preparation of a cell-free protein-synthesizing system from wheat germ, Methods Enz 101:635-644.
Anderson, 1993, Restriction endonucleases and modification methylases, Curr Op Struct Biol 3:24-30.
Ando, 1999, PLGA microspheres containing plasmid DNA: preservation of supercoiled DNA via cryopreparation and carbohydrate stabilization, J Pharm Sci 88(1):126-130.
Angell, 1983, Silicon micromechanical devices, Scientific Am 248:44-55.
Anhuf, 2003, Determination of SMN1 and SMN2 copy number using TaqMan technology, Hum Mutat 22(1):74-78.
Anna, 2003, Formation of dispersions using flow focusing in microchannels, Appl Phys Lett82(3):364-366.
Armstrong, 1996, Multiple-Component condensation strategies for combinatorial library synthesis, Acc Chem Res 29 (3):123-131.
Ashkin, 1987, Optical trapping and manipulation of single cells using infrared laser beams, Nature 330:769-771.
Ashkin, 1987, Optical trapping and manipulation of viruses and bacteria, Science 235(4795):1517-20.
Auroux, 2002, Micro Total Analysis Systems 2: Analytical standard operations and applications, Anal Chem 74 (12):2637-2652.
Baccarani, 1977, *Escherichia coli* dihydrofolate reductase: isolation and characterization of two isozymes, Biochemistry 16(16):3566-72.
Bagwe, 2001, Improved drug delivery using microemulsions: rationale, recent progress, and new horizons, Crit Rev Ther Drug Carr Sys 18(1):77-140.
Baker, 2010, Clever PCR: more genotyping, smaller vols. Nat Meth 7:351-356.
Ballantyne, 1973, Selective area metallization by electron-beam controlled direct metallic deposition, J Vac Sci Tech 10:1094.
Barany, 1991, Genetic disease detection and DNA amplification using cloned thermostable ligase, PNAS 88(1):189-93.
Barany, 1991, The ligase chain reaction in a PCR World, PCR Meth App 1(1):5-16.
Baret, 2009, Fluorescence-activated droplet sorting (FADS): efficient microfluidic cell sorting based on enzymatic activity, Lab Chip 9:1850-1858.
Baret, 2009, Kinetic aspects of emulsion stabilization by surfactants: a microfluidic analysis, Langmuir 25:6088-6093.
Baroud, 2004, Multiphase flows in microfluidics, Physique 5:547-555.
Bauer, 1999, Advances in cell separation: recent developments in counterflow centrifugal elutriation and continuous low cell separation, J Chromot 722:55-69.
Beebe, 2000, Functional hydrogel structures for autonomous flow control inside microfluidic channels, Nature 404:588-590.
Beer, 2007, On-chip, real-time, single-copy polymerase chain reaction in picoliter droplets, Anal Chem 79 (22):8471-8475.
Beer, 2008, On-chip single-copy real-time reverse transcription PCR in isolated picoliter droplets, Anal Chem 80 (6):1854-1858.
Bein, 1999, Efficient assays for combinatorial methods for the eiscovery of catalysts, Agnew Chem Int Ed 38:3:323-26.
Benichou, 2002, Double emulsions stabilized by new molecular recognition hybrids of natural polymers, Polym Adv Tech 13:1019-1031.
Benner, 1994, Expanding the genetic lexicon, Trends Biotech 12:158-63.
Benning, 2000, The binding of substrate analogs to phosphotriesterase. J Biol Chem 275:30556-30560.
Berman, 1987, An agarose gel electrophoresis assay for the detection of DNA-binding activities in yeast cell extracts, Meth Enz 155:528-37.
Bernath, 2004, In Vitro Compartmentalization by double emulsions: sorting and gene enrichment by FACS Anal Biochem 325:151-157.
Bernath, 2005, Directed evolution of protein inhibitors of DNA-nucleases by in vitro compartmentalization (IVC) and nano-droplet delivery, J Mol Biol 345(5):1015-26.
Betlach, 1976, A restriction endonuclease analysis of the bacterial plasmid controlling the EcoRI restriction and modification of DNA, Fed Proc 35:2037-2043.
Bibette, 1999, Emulsions: basic principles, Rep Prog Phys 62:969-1033.
Bico, 2002, Rise of liquids and bubbles in angular capillary tubes, J Colloid & Interface Sc 247:162-166.
Bico, 2002, Self-Propelling Slugs, J. Fluid Mech., 467:101-127.
Binder, 2009, Mismatch and G-stack modulated probe signals on SNP microarrays, PLoS One, 4(11):e7862.
Binladen, 2007, The use of coded PCR primers enables high-throughput sequencing of multiple homolog amplification products by 454 parallel sequencing, PLOSOne 2(2):e197.
Blanchet, 1993, Laser Ablation and the Production of Polymer Films, Science, 262(5134):719-721.
Boder, 1997, Yeast surface display for screening combinatorial polypeptide libraries, Nat Biotech 15(6):553-7.
Bosque, 2009, Induction of HIV-1 latency and reactivation in primary memory CD4+ T cells, Blood, 113(1):58-65.
Haynes, 2012, Digital PCR: A Technology Primer, Principles of Digital PCR and Measurement Issues: The certification of Cytomegalovirus Standard Reference Material (SRM 2366) as a model for future SRMs, National Institute of Standards and Tecnology, San Diego, CA, 4 pages.
Hayward, 2006, Dewetting Instability during the Formation of Polymersomes from BloceCopolymer-Stabilized Double Emulsions, Langmuir, 22(10): 4457-4461.
He, 2005, Selective encapsulation of single cells and subcellular organelles into picoliter- and femtoliter-volume droplets, Anal Chem 77(6):1539-1544.
Head, 2014, Library construction for next generation sequencing, Biotech Rap Disp 56(2):61.
Heim, 1996, Engineering Green Fluorescent Protein for Improved Brightness, Longer Wavelengths and Fluorescence Response Energy Transfer, Carr. Biol, 6(2): 178-182.
Hellman, 2009, Differential tissue-specific protein markers of vaginal carcinoma, Br J Cancer, 100(8): 1303-131.
Henrich, 2012, Low-level detection and quantitation of cellular HIV-1 DNA and 2-ILTR circles using droplet dPCR, J Virol Meth 186(1-2):68-72.
Hergenrother, 2000, Small-Molecule Microarrays: Covalent Attachment and Screening of Alcohol-Containing Small Molecules on Glass Slides, J. Am. Chem. Soc, 122: 7849-7850.

(56) References Cited

OTHER PUBLICATIONS

Hermankova, 2003, Analysis of human immunodeficiency virus type 1 gene expression in lately infected reseting CD4 T lymphocytes in vivo, J Virology 77(13):7383-7392.
Herzer, 2001, DNA Purification, in Molecular Biology Problem Solver: A Laboratory Guide, Edited by Alan S. Gerstein, Ch.1.
Heyries, 2011, Megapixel digital PCR, Nat. Methods 8, 649-651.
Hildebrand, 1949, Liquid-Liquid Solubility of Perfluoromethylcyclohexane with Benzene, Carbon Tetrachloride, Chlorobenzene, Chloroform and Toluene, J. Am. Chem. Soc, 71:22-25.
Hindson, 2011, High-Throughput Droplet Digital PCR System for Absolute Quantitation of DNA Copy Number, Anal. Chem., 83, 8604-8610.
Hjelmfelt, 1993, Pattern-Recognition in Coupled Chemical Kinetic Systems, Science, 260(5106):335-337.
Ho, 1989, Site-directed mutageneiss by overlap extension using the polymerase chain reaction, Gene, 77(1):51-9.
Hochuli, 1987, New metal chelate adsorbent selective for proteins and peptides containing neighbouring histidine residues, J Chromatogr 411: 177-84.
Holmes, 1995, Reagents for Combinatorial Organic Synthesis: Development of a New O-Nitrobenzyl Photolabile inder for Solid Phase Synthesis, J. OrgChem., 60: 2318-2319.
Holtze, 2008, Biocompatible surfactants for water-in-fluorocarbon emulsions, Lab Chip, 8, 1632-1639.
Hong, 1999, Stereochemical constraints on the substrate specificity of phosphodiesterase, Biochemistry, 38: 1159-1165.
Hoogenboom, 1997, Designing and optimizing library selection strategies for generating high-affinity antibodies, Trends Biotechnol, 15:62-70.
Hopfinger, 1996, Explosive Breakup of a Liquid Jet by a Swirling Coaxial Jet, Physics of Fluids 8(7):1696-1700.
Hopman, 1998, Rapid synthesis of biotin-, digoxigenin-, trinitrophenyl-, and fluorochrome-labeled tyramides and their application for In situ hybridization using CARD amplification, J of Histochem and Cytochem, 46(6):771-77.
Horton, 1989, Engineering hybrid genes without the use of restriction enzymes: gene splicing by overlap extension, Gene 77(1): 61-8 (.
Hosokawa, 1999, Handling of Picoliter Liquid Samples in a Poly(dimethylsiloxane)- Based Microfluidic Device, Analytical Chemistry, 71(20):4781-4785.
Hsieh, 2009, Rapid label-free DNA analysis in picoliter microfluidic droplets using FRET probes, Microfluidics and nanofluidics 6(3):391-401.
Hsu, 1999, et al., Comparison of process parameters for microencapsulation of plasmid DNA in poly(D, L-lactic-co-glycolic acid microspheres, J Drug Target, 7:313-23.
Hua, 2010, Multiplexed Real-Time Polymerase Chain Reaction on a Digital Microfluidic Platform, Analytical Chemistry 82(6):2310-2316.
Huang, 1991, Kinetic assay of fluorescein mono-beta-D-galactosidase hydrolysis by beta-galactosidase: a front-face measurement for strongly absorbing fluorogenic substrates, Biochemistry, 30:8530-4.
Huang, 1992, A sensitive competitive ELISA for 2,4-dinitrophenol using 3,6-fluorescein diphosphate as a fluorogenic substrate, J Immunol Meth, 149:261.
Huang, 2004, Continuous particle separation through deterministic lateral displacement, Science 304(5673):987-990.
Hubert, 2003, Data Concordance from a Comparison between Filter Binding and Fluorescence Polarization Assay Formats for Identification of RUOCK-II Inhibitors, J biomol Screen 8(4):399-409.
Huebner, 2007, Quantitative detection of protein expression in single cells using droplet microfluidics, Chem Com 12:1218-1220.
Hug, 2003, Measurement of the number of molecules of a single mRNA species in a complex mRNA preparation. J Theor Biol.; 221(4):615-24.
Hung, 2004, Controlled Droplet Fusion in Microfluidic Devices, MicroTAS 2004, Sep. 26-30, Malmo, Sweden.
Hung, 2004, Optimization of Droplet Generation by controlling PDMS Surface Hydrophobicity, 2004 ASME International Mechanical Engineering Congress and RD&D Expo, Nov. 13-19, Anaheim, CA, 47-48.
Hutchison, 2005, Cell-free cloning using Phi29 polymerase, PNAS 102(48):17332-17336.
Hutter, 2005, Detection of proteinases in Saccharomyces cervisiae by flow cytometry, J Inst Brewing 111(1):26-32.
Ibrahim, 2003, High-speed cell sorting: fundamentals and recent advances, Curr Opin Biotchnol, 14(1):5-12.
Ikeda, 2000, Bioactivation of tegafur to 5-fluorouracil is catalyzed by cytochrome P-450 2A6 in human liver microsomes in vitro, Clin Cancer Res 6(11):4409-4415.
Illumina, 2010, Genomic Sequencing, data Sheet, 6 pages.
Inai, 1993, Immunohistochemical detection of an enamel protein-related epitope in rat bone at an early stage of osteogenesis, Histochemistry, 99(5):335-362.
Invitrogen, 2008, Specification sheet for Dynabeads® Oligo (dT)25, http://www.invitrogen.com, 2 pages.
Isegawa, 1992, Selective amplification of cDNA sequence from total RNA by cassette-ligation mediated polymerase chain reaction (PCR): Application to sequencing 6-5 kb genome segment of hantavirus strain B-1, Molecular and Cellular Probes, 6:467-475.
Ismagilov, 2003, Integrated Microfluidic SYstems, Angew. Chem. Int. Ed., 42:4130-4132.
Jakobovits, 1993, Analysis of homozygous mutant chimeric mice:deletion of the immunoglobulin heavy-chain joining region blocks B-cell development and antibody production, PNAS USA 90:2551-255.
Jakobovits, 1993, Germ-line transmission and expression of a human-derived yeast artificial chromosome, Nature 362:255-258.
Janda, 1997, Chemical selection for catalysis in combinatorial antibody libraries, Science, 275:945-948.
Jang, 2003, Controllable delivery of non-viral DNA from porous scaffold, J Controlled Release 86(1):157-168.
Jarvie, 2007, Amplicon Sequencing, Roche Dx Application Note No. 5 (16 pages).
Kakuta, 2006, Development of the microchip-based repeatable immunoassay system for clinical diagnosis, Measurement Science and Technology 17(2):3189-3194.
Klein, 2015, Droplet Barcoding for Single-Cell Transcriptomics Applied to Embryonic Stem Cells, Cell, 161:1187-1201.
Okada, 2004, An immunoassay chip using the electrostatic droplet manipulation technique, Proceedings of MicroTas, 3 pages.
Sista, 2008, Heterogeneous immunoassays using magnetic beads on a digital microfluidic platform, Lab on a Chip, 8 (12):2188-2196.
Compton, 1991, Nucleic acid sequence-based amplification, Nature, 350(6313):91-2.
Cook, 2007, Use and misuse of receiver operating characteristic curve in risk prediction, Circulation 115(7):928-35.
Cooper, 2000, The Central Role of Enzymes as Biological Catalysts, The Cell: A Molecular Approach, 2nd Edition, pp. 1-6.
Cormack, 1996, FACS-optimized mutants of the green fluorescent protein (GFP), Gene 173(1):33-38.
Cortesi, 2002, Production of lipospheres as carriers for bioactive compounds, Biomateials, 23(11): 2283-2294.
Courrier, 2004, Reverse water-in-fluorocarbon emulsions and microemulsions obtained with a fluorinated surfactant, Colloids and Surfaces A: Physicochem. Eng. Aspects 244:141-148.
Craig, 1995, Fluorescence-based enzymatic assay by capillary electrophoresis laser-induced fluoresence detection for the determinination of a few alpha-galactosidase molecules, Anal. Biochem. 226:147.
Creagh, 1993, Structural and catalytic properties of enzymes in reverse micelles, Enzyme Microb Technol 15 (5):383-92.
Crosland-Taylor, 1953, A Device for Counting Small Particles suspended in a Fluid through a Tube, Nature 171:37-38.
Crowley, 1973, Electrical breakdown of bimolecular lipid membranes as an electromechanical instability, Biophys J. 13 (7):711-724.

(56) References Cited

OTHER PUBLICATIONS

Cull, 1992, Screening for receptor ligands using large libraries of peptides linked to the C terminus of the lac repressor, PNAS 89:1865-9.
Curcio, 2003, Continuous Segmented-Flow Polymerase Chain Reaction for High-Throughput Miniaturized DNA Amplification, Anal Chem 75(1):1-7.
Curran, 1998, Strategy-level separations in organic synthesis: from planning to practice. Angew Chem Int Ed, 37:1174-11-96.
Czarnik, 1997, Encoding methods for combinatorial chemistry, Curr Opin Chem Biol 1:60-66.
Dankwardt, 1995, Combinatorial synthesis of small-molecule libraries using 3-amino-5-hydroxybenzoic acid, 1:113-120.
David, 1974, Protein iodination with solid-state lactoperoxidase, Biochemistry 13:1014-1021.
Davis, 1987, Multiple emulsions as targetable delivery systems, Meth Enzymol 149:51-64.
Davis, 2006, Deterministic hydrodynamics: Taking blood apart, PNAS 103:14779-14784.
De Gans, 2004, Inkjet printing of polymers: state of the art and future developments, Advanced materials, 16: 203-213.
De Wildt, 2002, Isolation of receptor-ligand pairs by capture of long-lived multivalent interaction complexes, Proceedings of the National Academy of Sciences of the United States, 99, 8530-8535.
DelRaso, 1993, In vitro methodologies for enhanced toxicity testing, Toxicol. Lett. 68:91-99.
Deng, 2008, Design and analysis of mismatch probes for long oligonucleotide microarrays, BMC Genomics; 9:491, 13 pages.
Dickinson, 1992, Interfacial interactions and the stability of oil-in-water emulsions, Pure Appl Chem 64(11):1721-1724.
Dickinson, 1994, Emulsions and droplet size control, Wedlock, D.J., Ed., in Controlled Particle Droplet and Bubble Formulation, ButterWorth-Heine-mann, 191-257.
DiMatteo, 2008, Genetic conversion of an SMN2 gene to SMN1: A novel approach to the treatment of spinal muscular atrophy, Exp Cell Res. 314(4):878-886.
Ding, 2001, Scheduling of microfluidic operations for reconfigurable two-dimensional electrowetting arrays, IEEE Trans CADICS 20(12):1463-1468.
Ding, 2003, Direct molecular haplotyping of long-range genomic DNA with M1-PCR, Proc. Natl. Acad. Sci. USA, 100 (33):7449-7453.
Dinsmore, 2002, Colioidosomes: Selectively Permeable Capsules Composed of Colloidal Particles, Science 298 (5595):1006-1009.
Dittrich, 2005, A new embedded process for compartmentalized cell-free protein expression and on-line detection in microfluidic devices, Chembiochem 6(5):811-814.
Doi, 1999, STABLE: protein-DNA fusion system for screening of combinatorial protein libraries in vitro, FEBS Lett., 457: 227-230.
Doi, 2004, In vitro selection of restriction endonucleases by in vitro compartmentilization, Nucleic Acids Res, 32(12): e95.
Doman, 2002, Molecular docking and high-throughput screening for novel inhibitors of protein tyrosine phosphatase-1B, J Med Chem, 45: 2213-2221.
Domling, 2000, Multicomponent Reactions with Isocyanides, Angew Chem Int Ed 39(18):3168-3210.
Domling, 2002, Recent advances in isocyanide-based multicomponent chemistry, Curr Opin Chem Biol, 6(3):306-13.
Dorfman, 2005, Contamination-free continuous flow microfluidic polymerase chain reaction for quantitative and clinical applications, Anal Chem 77:3700-3704.
Dove, 2002, Research News Briefs, Nature Biotechnology 20:1213, 1 page.
Dower, 1988, High efficiency transformation of *E. coli* by high voltage electroporation, Nucleic Acids Res 16:6127-6145.
Dressman, 2003, Transforming single DNA molecules into fluorescent magnetic particles for detection and enumeration of genetic variations, PNAS 100:8817-22.
Dreyfus, 2003, Ordered and disordered patterns in two phase flows in microchannels, Phys Rev Lett 90 (14):144505-1-144505-4.
Drmanac, 1992, Sequencing by hybridization: towards an automated sequencing of one million M13 clones arrayed on membranes, Elctrophoresis 13:566-573.
Du, 2009, SlipChip, Lab Chip, 9, 2286-2292.
Dubertret, 2002, In vivo imaging of quantum dots encapsulated in phospholipid micelles, Science, 298: 1759-1762.
Duffy, 1998, Rapid Protyping of Microfluidic Systems and Polydimethylsiloxane, Anal Chem 70:474-480.
Duggleby, 1995, Analysis of Enzyme Progress Curves by Nonlinear Regression, Pt D. Academic Press 249:61-90.
Dumas, 1989, Purification and properties of the phosphotriesterase from Psuedomonas diminuta, J Biol Chem 264: 19659-19665.
Eckert, 1991, DNA polymerase fidelity and the polymerase chain reaction, Genome Res 1:17-24.
Ecole Polytech Federale de Lausanne, 2014, Tracing water channels in cell surface receptors, PhysOrg News (2 pages).
Edel, 2002, Microfluidic Routes to the Controlled Production of Nanopaticles, Chemical Communications, 1136-1137.
Edris, 2001, Encapsulation of orange oil in a spray dried double emulsion, Nahrung/Food, 45(2):133-137.
Effenhauser, 1993, Glass chips for high-speed capillary electrophoresis separations with submicrometer plate heights, Anal Chem 65:2637-2642.
Tan, 2003, Microfluidic liposome generation from monodisperse droplet emulsion, Summer Bioeng Conf, Florida, 2 pages.
Tan, 2003, Monodisperse droplet emulsions in co-flow microfluidic channels, Micro TAS, 2 pages.
Tan, 2004, Design of microluidic channel geometries for the control of droplet volume, chemical concentration, and sorting, Lab Chip 4(4):292-298.
Tan, 2005, Microfluidic separation of satellite droplets as the basis of a monodispersed micron and submicron emulsification system, Lab on a Chip, 5.10, 1178-1183.
Tang, 2009, A multi-color fast-switching microfluidic droplet dye laser, Lab Chip 9:2767-2771.
Taniguchi, 2002, Chemical reactions in microdroplets by electrostatic manipulation of droplets in liquid media, Lab Chip 2:19-23.
Tawfik, 1998, Man-made cell-like compartments for molecular evolution, Nat Biotech 7(16):652-56.
Taylor, 1934, The formation of emulsions in definable field of flow, Proc R Soc London A 146(858):501-523.
Taylor, 1991, Characterization of chemisorbed monolayers by surface potential measurments, J Phys D Appl Phys 24:1443.
Tencza, 2000, Development of a fluorescence polarization-based diagnostic assay for equine infectious anemia virus, J Clin Microbiol 38(5):1854-185.
Terray, 2002, Fabrication of linear colloidal structures for microfluidic applications, Applied Phys Lett 81(9):1555-1557.
Terray, 2002, Microfluidic control using colloidal devices, Science 296(5574):1841-1844.
Tewhey, 2009, Microdroplet based PCR environment for large scale targeted sequence, Nat Biotech 27(11):1025-1031.
Theberge, 2010, Microdroplets in microfluidics: an evolving platform for discoveries in chemistry and biology, Angew Chem Int Ed 49(34):5846-5868.
Thompson, 1983, Introduction to Lithography, ACS Symp Ser 219:1-13.
Thorsen, 2001, Dynamic pattern formation in a vesicle-generating microfluidic device, Phys Rev Lett 86(18):4163-4166.
Thorsen, 2002, Microfluidic Large-Scale Integration, Science, 298:580-584.
Thorsen, 2003, Microfluidic technologies for highthroughput screening applications, California Institute of Technology.
Tice, 2003, Formation of droplets and mixing in multiphase microfluidics at low values of the reynolds and the capillary numbers, Langmuir 19:9127-9133.
Tice, 2004, Effects of Viscosity on Droplet Formation and Mixing in Microfluidic Channels, ANalytica Chimica Acta, 507:73-77.
Titomanlio, 1990, Capillary experiments of flow induced crystallization of HDPE, AlChe J 36(1):13-18.
Tleugabulova, 2004, Evaluating formation and growth mechanisms of silica particles using fluorescence anisotropy decay analysis, Langmuir 20(14):5924-5932.

(56) References Cited

OTHER PUBLICATIONS

Tokatlidis, 1995, Nascent chains: folding and chaperone intraction during elongation on ribosomes, Philos Trans R Soc Lond B Biol Sci, 348:89-95.
Tokeshi, 2002, Continuous-flow chemical processing on a microchip by combining microunit operations and a multiphase flow network, Anal Chem 74(7):1565-1571.
Tokumitsu, 1999, Preparation of gadopentetic acid-loaded chitosan microparticles for gadolinium neutron-capture therapy of cancer by a novel emulsion-droplet coalescence technique, Chem Pharm Bull 47(6):838-842.
Tonelli et al., 2002, Perfluoropolyether functional oligomers: unusual reactivity in organic chemistry, Journal of fluorine Chemistry, 118; 107-121.
Trolier-McKinstry, 2004, Thin Film Piezoelectric for MEMS, Journal of Electroceramics 12:7-17.
Tsuchiya, 2007, On-chip polymerase chain reaction microdevice employing a magnetic droplet-manipulation system, Sens Actuators B 130:583-588.
Tuzel, 2006, Region Covariance: A Fast Descriptor for Detection and Classification, European Conference on Computer Vision (ECCV), 14 pages.
Umbanhowar, 2000, Monodisperse Emulsion Generation via Drop Break Off in a Coflowing Stream, Langmuir 16 (2):347-351.
Unger, 2000, Monolithic microfabricated valves and pumps by multylayer soft lithography, Science 288(5463):113-116.
Utada, 2005, Monodisperse double emulsions generated from a microcapillary device, Science, 308:537-541.
Vainshtein, 1996, Peptide rescue of an N-terminal truncation of the stoffel fragment of Taq DNA polymerase, Protein Science, 5:1785-92.
Van der Sluis, 2013, Dendritic Cell-induced Activation of Latent HIV-1 Provirus in Actively Proliferating Primary T Lymphocytes, PLOS Pathog. 9(3): 16 pages.
Van Dilla, 1968, The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105.
Van Dilla, 1969, Cell Microfluorometry: A Method for Rapid Fluorescence Measurement, Science 163(3872):1213-1214.
Vanhooke, 1996, Three-dimensional structure of the zinc-containing phosphotrieesterase with the bound substrate analog diethy 4-methylbenzylphosphonate, Biochemistry 35:6020-6025.
Varga, 1991, Mechanism of allergic cross-reactions-I. Multispecific binding of ligands to a mouse monoclonal anti-DNP lgE antibody. Mol Immunol 28(6), 641-54.
Vary, 1987, A homogeneous nucleic acid hybridization assay based on strand displacement, Nucl Acids Res 15 (17):6883-6897.
Venkateswaran, 1992, Production of Anti-Fibroblast Growth Factor Receptor Monoclonal Antibodies by In Vitro Immunization, Hybirdoma, 11(6):729-739.
Verhoeyen, 1988, Reshaping human antibodies: grafting an antilysozyme activity, Science, 239:1534-1536.
Viswanathan, 2019, DNA Analysis by Restriction Enzyme (DARE) enables concurrent genomic and epigenomic characterization of single cells, Nucleic Acids Research, 47(19), e122.
Vogelstein, 1999, Digital PCR, PNAS 96(16):9236-9241.
Voss, 1993, Kinetic measurements of molecular interactions by spectrofluorometry, J Mol Recognit, 6:51-58.
Wahler, 2001, Novel methods for biocatalyst screening. Curr Opin Chem Biol, 5: 152-158.
Walde, 1988, Structure and activity of trypsin in reverse micelles, Eur J Biochem, 173(2):401-9.
Walde, 1993, Spectroscopic and kinetic studies of lipases solubilized in reverse micelles, Biochemistry, 32(15):4029-34.
Walde, 1994, Oparin's reactions revisited: enzymatic synthesis of poly(adenylic acid) in micelles and self-reproducing vesicles. J Am Chem Soc, 116: 7541-7547.
Walker, 1992, Isothermal in vitro amplification of DNA by a restriction enzyme/DNA polymerase system, PNAS 89 (1):392-6.
Walker, 1992, Strand displacement amplification-an isothermal, in vitro DNA amplification technique, Nucleic Acid Res, 20(7):1691-6.
Eggers, 1999, Coalescence of Liquid Drops, J. Fluid Mech., 401:293-310.
Ehrig, 1995, Green-fluorescent protein mutants with altered fluorescence excitation spectra, Febs Lett, 367(2):163-66.
Eigen, 1980, Hypercycles and compartments: compartments assists—but does not replace—hypercyclic organization of early genetic information, J Theor Biol, 85:407-11.
Eijk-Van Os, 2011, Multiplex ligation-dependent probe amplification (MLPA(R)) for the detection of copy number variation in genomic sequences, Meth Mol Biol 688:97-126.
Elghanian, 1997, Selective colorimetric detection of polynucleotides based on the distance-dependent optical properties of gold nanoparticles, Science, 277(5329):1078-1080.
Ellington, 1990, In vitro selection of RNA molecules that bind specific ligands, Nature, 346:818-822.
Ellman, 1991, Biosynthetic method for introducing unnatural amino acids site-specifically into proteins, Methods Enzymol, 202:301-36.
Endo, 1996, Autocatalytic decomposition of cobalt complexes as an indicator system for the determination of trace amounts of cobalt and effectors, Analyst 121:391-394.
Endo, 1998, Kinetic determination of trace cobalt by visual autocatalytic indication, Talanta 47:349-353.
Engl, 2005, Droplet Traffic at a Simple Junction at Low Capillary Numbers Physical Review Letters, vol. 95, 208304, 1 page.
Eow, 2002, Electrocoalesce-separators for the separation of aqueous drops from a flowing dielectric viscous liquid, Separation and Purification Tech 29:63-77.
Eow, 2002, Electrostatic and hydrodynamic separation of aqueous drops in a flowing viscous oil, Chemical Eng Proc 41:649-657.
Eow, 2002, Electrostatic enhancement of coalescence of water droplets in oil: a review of the technology, Chemical Engineeing Journal 85:357-368.
Eow, 2003, Motion, deformation and break-up of aqueous drops in oils under high electric field strengths, Chemical Eng Proc 42:259-272.
Eow, 2003, The behavior of a liquid-liquid interface and drop-interface coalescence under the influence of an electric field, Colloids and Surfaces A: Physiochern. Eng. Aspects 215:101-123.
Eriksson, 2013, Comparative analysis of measures of viral reservoirs in HIV-1 eradication studies, PLoS Pathogens 9 (2):e1003174, 17 pages.
Faca, 2008, A mouse to human search for plasma proteome changes associated with pancreatic tumor development, PLoS Med 5(6):el23:0953-0967.
Fahy, 1991, Self-sustained sequence replication (3SR): an isothermal transcription-based amplification system alternative to PCR, PCR Methods Appl 1:25-33.
Fan, 1994, Micromachining of capillary electrophoresis injectors and separators on glass chips and evaluation of flow at capillary intersections, Anal Chem 66:177-184.
Fan, 2007, Detection of Aneuploidy with Digital PCR, available at https://arxiv.org/ftp/arxiv/papers /0705/0705.1 030.pdf, 16 pages.
Fastrez, 1997, In vivo versus in vitro screening or selection for catalytic activity in enzymes and abzymes, Mol Biotechnol 7(1):37-55.
Fettinger, 1993, Stacked modules for micro flow systems in chemical analysis: concept and studies using an enlarged model, Sens Actuat B. 17:19-25.
Fiedler, 1998, Dielectrophoretic sorting of particles and cells in a microsystem, Anal Chem 70(9):1909-1915.
Field, 1988, Purification of a RAS-responsive adenylyl cyclase complex from *Saccharomyces cervisiae* by use of an epitope addition method. Mol Cell Biol, 8: 2159-2165.
Fields, 1989, A novel genetic system to detect protein-protein interactions, Nature 340(6230):245-6.
Filella, 1994, TAG-72, CA 19.9 and CEA as tumor markers in gastric cancer, Acta Oncol. 33(7):747-751.

(56) References Cited

OTHER PUBLICATIONS

Finch, 1993, Encapsulation and controlled release, Spec Publ R Soc Chem, 138:35, 12 pages.
Finettie, 2015, Thesis, Novel Functional Hydrophilic Polymers and Hydrogels for Microanalytical Systems, Universita Degli Studi Di Milano, 203 pages.
Fingas, 1997, Studies of Water-In-Oil Emulsions: Stability Studies, Environment Canada, Proceedings of the Twentieth Arctic Marine Oilspill Program Technical Seminer, 1-20.
Fire, 1995, Rolling replication of short DNA circles, PNAS 92(10):4641-5.
Firestine, 2000, Using an AraC-based three hybrid system to detect biocatalysts in vivo, Nat Biotechnol 18: 544-547.
Fisher, 2004, Cell Encapsulation on a Microfluidic Platform, The Eighth International Conference on Miniaturised Systems for Chemistry and Life Scieces, MicroTAS, Malmo, Sweden.
Flanagan, 2004, Fab Antibody Fragments: Some Applications in Clinical Toxicology, Drug Safety, 27(14):1115-1133.
Fletcher, 2002, Micro reactors: principles and applications in organic synthesis, Tetrahedron 58:4735-4757.
Fluri, 1996, Integrated capillary electrophoresis devices with an efficient postcolumn reactor in planar quartz and glass chips, Anal Chem 68:4285-4290.
Fornusek, 1986, Polymeric microspheres as diagnostic tools for cell surface marker tracing, Crit Rev Ther Drug Carrier Syst, 2:137-74.
Fowler, 2002, Enhancement of Mixing by Droplet-Based Microfluidics, Int Conf MEMS 97-100.
Frenz, 2008, Reliable microfluidic on-chip incubation of droplets in delay-lines, Lab on a Chip 9:1344-1348.
Fu, 1999, A microfabricated fluorescence-activated cell sorter, Nature Biotechnology, 17(11):1109-1111.
Fu, 2002, An Integrated Microfabricated Cell Sorter, Anal. Chem., 74: 2451-2457.
Fulton, 1997, Advanced multiplexed analysis with the FlowMetrix system, Clin Chem 43:1749-1756.
Fulwyler, 1965, Electronic Separation of Biological Cells by Volume, Science 150(3698):910-911.
Galan, 2010, A 454 multiplex sequencing method for rapid and reliable genotyping of highly polymorphic genes in large-scale studies., BMC Genomics 11(296):1-15.
Gallarate, 1999, On the stability of ascorbic acid in emulsified systems for topical and cosmetic use, Int J Pharm 188 (2):233-241.
Ganan-Calvo, 1998, Generation of Steady Liquid Microthreads and Micron-Sized Monodisperse Sprays and Gas Streams, Phys Rev Lett 80(2):285-288.
Ganan-Calvo, 2001, Perfectly Monodisperse Microbubbling by Capillary Flow Focusing, Phys Rev Lett 87(27): 274501-1-4.
Garcia-Ruiz, 1994, Investigation on protein crystal growth by the gel acupuncture method, Acta, Cryst., D50, 99. pp. 484-490.
Garcia-Ruiz, 2001, A super-saturation wave of protein crystallization, J. Crystal Growth, 232:149-155.
Garstecki, 2004, Formation of monodisperse bubbles in a microfiuidic flow-focusing device, Appl Phys Lett 85 (13):2649-2651.
Gasperlin, 1994, The structure elucidation of semisolid w/o emulsion systems containing silicone surfactant, Intl J Pharm, 107:51-6.
Lo, 2007, Digital PCR for the molecular detection of fetal chromosomal aneuploidy, PNAS 104(32):13116-13121.
Loakes, 1994, 5-Nitroindole as a universal base analogue, Nucleic Acids Res 22:4039-4043.
Loakes, 1997, Stability and structure of DNA oligonucleotides containing non-specific base analogues, J Mol Biol 270:426-435.
Lodish, 2000, Structure of Nucleic Acids, Section 4.1 , Molecular Cell Biology, 4th edition, New York, 1-3.
Loeker, 2003, FTIR analysis of water in supercritical carbon dioxide microemulsions using monofunctional perfluoropolyether surfanctants, Colloids and Surfaces A: Phys Eng Asp 214:143-150.
Loo, 2004, Nanoshell Enabled Photonics-Based Imaging and Therapy of Cancer, Technology in Cancer Research & Treatment 3(1):33-40.
Lopez-Herrera, 1995, The electrospraying of viscous and non-viscous semi-insulating liquids: scaling laws, Bull Am Phys Soc 40 (12):2041.
Lopez-Herrera, 1999, One-dimensional simulation of the breakup of capillary jets of conducting liquids application to EHD spraying, Aerosol Set 30(7):895-912.
Lopez-Herrera, 2003, Coaxial jets generated from electrified Taylor cones, Aerosol Sci 34:535-552.
Lorenceau, 2005, Generation of polymerosomes from double-emulsions, Langmuir 21(20):9183-9186.
Lorenz, 1991, Isolation and expression of a cDNA encoding Renilla reniformis luciferase, PNAS 88(10):4438-42.
Loscertales, 2002, Micro/nano encapsulation via electrified coaxial liquid jets, Science 295(5560):1695-1698.
Lowe, 2002, Perfluorochemical respiratory gas carriers: benefits to cell culture systems, J Fluorine Chem 118:19-26.
Lu, 2007, Robust fluorescein-doped silica nanoparticles via dense-liquid treatment, Colloids and Surfaces a Phys Eng Asp 303(3):207-210.
Luft, 20001, Detection of integrated papillomavirus sequences by ligation-mediaated PCR (DIPS-PCR) and molecular characterization in cervical cancer cells, In J Cancer 92:9-17.
Luisi, 1987, Activity and conformation of enzymes in reverse micellar solutions, Meth Enzymol 136:188-216.
Lund, 1988, Assesment of methods for covalent binding of nucleic acids to magnetic beads, Dynabeads, and the characteristics of the bound nucleic acids in hybridization reactions, Nucleic Acids Res 16(22):10861-10880.
Lunderberg, 1995, Solid-phase technology: magnetic beads to improve nucleic acid detection and analysis, Biotech Ann Rev 1:373-401.
Lundstrom, 2002, Breakthrough in cancer therapy: Encapsulation of drugs and viruses, Curr Drug Disc 19-23.
Lyne, 2002, Structure-based virtual screening: an overview, Drug Disc Tod 7(20):1047-1055.
Ma, 1993, In vitro protein engineering using synthetic tRNA(Ala) with different anticodons, Biochemistry 32 (31):7939-45.
Mackenzie, 1985, IABS Symposium on Reduction of Animal Usage in the Development and Control of Biological Products, London, UK, 16 pages.
Mackenzie, 1986, The application of flow microfluorimetry to biomedical research and diagnosis: a review, Dev Biol Stand 64:181-193.
Maclean, 1999, Glossary of terms used in combinatorial chemistry, Pure Appl. Chem. 71(12):2349-2365.
Maenaka, 2008, Continuous and size-dependent sorting of emulsion droplets using hydrodynamics in pinched microchannels, Langmuir, 24.8:4405-4410.
Magdassi, 1984, Multiple Emulsions: HLB Shift Caused by Emulsifier Migration to External Interface, J. Colloid Interface Sci 97:374-379.
Mahajan, 1998, Bcl-2 and Bax Interactions in Mitochondria Probed with Green Florescent Protein and Fluorescence Resonance Energy Transfer, Nat. Biotechnol. 16(6): 547-552.
Mahjoob, 2008, Rapid microfluidic thermal cycler for polymerase chain reaction nucleic acid amplification. Int J HeatMass Transfer;51:2109-22.
Manafi, 2000, New developments in chromogenic and fluorogenic culture media, 2000, International Journal of Food Microbiology, 60, 205-218.
Manley, 1983, In vitro transcription: whole cell extract, Methods Enzymol, 101:568-82.
Manz, 1991, Micromachining of monocrystalline silicon and glass for chemical analysis systems a look into next century's technology or just a fashionable craze, Trends in Analytical Chemistry 10(5):144-149.
Mao, 1991, Substrate effects on the enzymatic activity of alphachymotrypsin in reverse micelles, Biochem Biophys Res Commun, 178(3):1105-12.
Mao, 1992, Kinetic behaviour of alpha-chymotrypsin in reverse micelles: a stopped-flow study, Eur J Biochem 208 (1):165-70.
Mardis, 2008, The impact of next-generation sequencing technology on genetics, Trends Genet 24:133-141.

(56) References Cited

OTHER PUBLICATIONS

Margulies, 2005, Genome sequencing in microfabricated high-density picolitre reactors, Nature, 437(7057):376-380.
Marks, 1992, Bypassing immunization: building high affinity human antibodies by chain shuffling, BioTechnol 10:779-783.
Marques, 1996, Porous Flow within Concentric Cylinders, Bull Am Phys Soc Div Fluid Dyn 41:1768, 1 page.
Maruno, 1991, Fluorine containing optical adhesives for optical communications systems, J. Appl. Polymer. Sci. 42:2141-2148.
Mason, 1997, Shear Rupturing of Droplets in Complex Fluids, Langmuir, 13(17):4600-4613.
Mastrobattista, 2005, High-throughput screening of enzyme libraries: in vitro evolution of a beta-galactosidase by fluorescence-activated sorting of double emulsions, Chem. Biol. 12(12): 1291-1300.
Masui, 1998, Probing of DNA-Binding Sites of *Escherichia coli* RecA Protein Utilizing 1-anilinonaphthalene-8-Sulfonic Acid, Biochem 37(35):12133-12143.
Matayoshi, 1990, Novel fluorogenic substrates for assaying retroviral proteases by resonance energy transfer, Science 247:954.
Matsubara, 2003, Detection of Single Nucleotide Substitution by Competitive Allele-Specific Short Oligonucleotide Hybridization (CASSOH) With Ummunochromatographic Strip, Human Mutation 22:166-172.
Mattheakis, 1994, An in vitro polysome display system for identifying ligands from very large peptide libraries, PNAS 91:9022-6.
Mayr, 2008, The Future of High-Throughput Screening, JBiomol Screen 13:443-448.
Mazutis, 2009, Droplet-Based Microfluidic Systems for High-Throughput Single DNA Molecule Isothermal Amplification and Analysis, Anal Chem 81(12):4813-4821.
Mazutis, 2009, Multi-step microfluidic droplet processing: kinetic analysis of an in vitro translated enzyme, Lab Chip 9:2902-2908.
McDonald, 2000, Fabrication of microfluidic systems in poly(dimethylsiloxane), Electrophoresis 21(1):27-40.
McDonald, 2002, Poly(dimethylsiloxane) as a material for fabricating microfluidic devices, Account Chem. Res. 35:491-499.
Melton, 1984, Efficient in vitro synthesis of biologically active RNA and RNA hybridization probes from plasmids containing a bacteriophage SP6 promoter, Nucl. Acids Res. 12(18):7035-7056.
Mendel, 1995, Site-Directed Mutagenesis with an Expanded Genetic Code, Annu Rev Biophys Biomol Struct, 24:435-62.
Mendieta, 1996, Complementary sequence correlations with applications to reflectometry studies, Instrumentation and Development 3(6):37-46.
Meng, 2015, Self-assembling amphiphilic poly(propargyl methacrylate) grafted DNA copolymers into multi-strand helices, Soft Matter 11(28):5610-5613.
Metzker, 2010, Sequencing Technologies—the next generation, Nature Reviews, vol. 11, pp. 31-46.
Meylan, 1995, Atom/fragment contribution method for estimating octanol-water partition coefficients, J Pharm Sci. 84 (1):83-92.
Michalatos-Beloin, 1996, Molecular haplotyping of genetic markers 10 kb apart by allele-specific long-range PCR, Nucleic Acids Research, 24:4841-4843.
Miele, 1983, Autocatalytic replication of a recombinant Rna, J Mol Biol, 171:281-95.
Milstein, 1983, Hybrid hybridomas and their use in immunohistochemistry, Nature 305:537-540.
Mindlin, 1936, A force at a point of a semi-infinite solid, Physics, 7:195-202.
Minshuil, 1999, Protein evolution by molecular breeding, Curr Opin Chem Biol 3(3): 284-90.
Miroux, 1996, Over-production of proteins in *Escherichia coli*: mutant hosts that allow synthesis of some membrane proteins and globular proteins at high levels, J of Mol Biol 260(3):289-98.
Miyawaki, 1997, Fluorescent Indicators for Ca2+ Based on Green Fluorescent Proteins and Calmodulin, Nature, 388: 882-887.
Mize, 1989, Dual-enzyme cascade—an amplified method for the detection of alkaline phosphatase, Anal Biochem 179 (2): 229-35.
Mock, 1985, A fluorometric assay for the biotin-avidin interaction based on displacement of the fluorescent probe 2-anilinonaphthalene-6-sulfonic acid, Anal Biochem, 151:178-81.
Moldavan, 1934, Photo-electric technique for the counting of microscopical cells, Science 80:188-189.
Monie, 2005, A Novel Assay Allows Genotyping of the Latent Reservoir for Human Immunodeficiency Virus Type 1 in the Resting CD4+ T Cells of Viremic Patients, Journal of Virology, 79(8):5185-5202.
Montigiani, 1996, Alanine substitutions in calmodulin-binding peptides result in unexpected affinity enhancement, J Mol Biol, 258:6-13.
Moore, 1995, Exploration by lamp light, Nature, 374:766-7.
Morrison, 1984, Chimeric human antibody molecules: mouse antigen-binding domains with human constant region domains, PNAS 81:6851-6855.
Moudrianakis, 1965, Base sequence determination in nucelic acids with the electron microscope 3. Chemistry and microscopy of guanine-labeled DNA, PNAS 53:564-71.
Mueller, 1992, Thermotropic Aqueous Gels and Solutions of N, N-Dimethylacrylamide-acrylate Copolymers, Polymer, 33(1):3470-3476.
Mueth, 1996, Origin of stratification in creaming emulsions, Physical Review Letters 77(3):578-581.
Mulbry, 1989, Parathion hydrolase specified by the Flavobacterium opd gene: relationship between the gene and protein. J Bacteriol, 171: 6740-6746.
Mulder, 1993, Characterization of two human monoclonal antibodies reactive with HLA-B12 and HLA-B60, respectively, raised by in vitro secondary immunization of peripheral blood lymphocytes, Hum. Immunol 36(3):186-192.
Munson, 1980, Ligand: a versatile computerized approach for characterization of ligand-binding systems, Analytical Biochemistry, 107:220-239.
Nakano, 1994, High speed polymerase chain reaction in constant flow, Biosci Biotech and Biochem, 58:349-52.
Nakano, 2003, Single-molecule PCR using water-in-oil emulsion, J Biotech, 102:117-124.
Nakano, 2005, Single-molecule reverse transcription polymerase chain reaction using water-in-oil emulsion, J Biosci Bioeng 99:293-295.
Nametkin, 1992, Cell-free translation in reversed micelles, FEB Letters, 309(3):330-32.
Narang, 1979, Improved phosphotriester method for the synthesis of gene fragments, Methods Enzymol, 68:90-98.
Neiman, 2011, Decoding a substantial set of samples in parallel by massive sequencing, PLoS ONE 6(3):1-7.
Nelson, 1989, Bifunctional oligonucleotide probes synthesized using a novel CPG support are able to detect single pase pair mutations, Nucl Acids Res 17(18): 7187-7194.
Nemoto, 1997, In vitro virus: bonding of mRNA bearing puromycin at the 3 terminal end to the C-terminal end of its encoded protein on the ribosome in vitro, Federation of European Biochemical Societies, 414:405-8.
Ness, 2000, Molecular Breeding: the natural approach to protein design. Adv Protein Chem, 55: 261-292.
Ng, 2003, Protein crystallization by capillary counter-diffusion for applied crystallographic structure determination, J. Struct. Biol, 142:218-231.
Ng, 2006, Factors affecting flow karyotype resolution, Cytometry, Part A 69A: 1028-1036.
Nguyen, 2006, Optical detection for droplet size control in microfluidic droplet-based analysis systems, Sensors and Actuators B 117(2):431-436.
Nihant, 1994, Polylactide Microparticles Prepared by Double Emulsion/Evaporation Technique. I. Effect of Primary Emulsion Stability, Pharmaceutical Research, 11(10):1479-1484.
Nisisako, 2002, Droplet formation in a microchannel network, Lab Chip 2:24-26.
Nisisako, 2002, Formation of droplets using branch channels in a microfluidic circuit, Proceedings of the SICE Annual Conference. International Session Papers 1262-1264.

(56) References Cited

OTHER PUBLICATIONS

Nisisako, 2005, Controlled formulation of monodisperse double emulsions in a multiple-phase microluidic system, Sot Matter, 1:23-27.
Nisisako, 2008, Microstructured Devices for Preparing Controlled Multiple Emulsions. Chem. Eng. Technol 31 (8):1091-1098.
Nof, 2002, Drug-releasing scaffolds fabricated from drug-loaded microspheres, J. Biomed Mater Res 59:349-356.
Norman, 1980, Flow Cytometry, Med. Phys., 7(6):609-615.
Nygren, 1982, Conjugation of horseradish peroxidase to Fab fragments with different homobifunctional and heterobifunctional cross-linking reagents. A comparative study, J. Histochem. and Cytochem. 30:407-412.
Obeid, 2003, Continuous-flow DNA and RNA amplification chip combined with laser-induced fluorescence detection, Anal Chimica Acta 494(1-2):1-9.
Oberholzer, 1995, Enzymatic RNA replication in self-reproducing vesicles: an approach to a minimal cell, Biochem Biophys Res Commun 207(1):250-7.
Oberholzer, 1995, Polymerase chain reaction in liposomes, Chem. Biol. 2(10):677-82.
Obukowicz, 1988, Secretion and export of IGF-1 in *Escerichia coli* strain JM101, Mol Gen Genet, 215:19-25.
Ogura, 1955, Catalase activity at high concentrations of hydrogen peroxide, Archs Biochem Biophys, 57: 288-300.
Gasperlin, 2000, Viscosity prediction of lipophillic semisolid emulsion systems by neural network modeling, Intl J Pharm, 196:37-50.
Gelderblom, 2008, Viral complemntation allows HIV-1 replication without integration, Retrovirology 5:60.
Georgiou, 1997, Display of heterologous proteins on the surface of microorganisms: from the screenign of combinatiorial libraires to live recombinant vaccines. Nat Biotechnol 15(1), 29-34.
Georgiou, 2000, Analysis of large libraries of protein mutants using flow cytometry, Adv Protein Chem, 55: 293-315.
Gerdts, 2004, A Synthetic Reaction Network: Chemical Amplification Using Nonequilibrium Autocatalytic Reactions Coupled in Time, J. Am. Chem. Soc. 126-6327-6331.
Ghadessy, 2001, Directed Evolution of Polymerase Function by Compartmentalized Self-Replication, PNSAS 98(8): 4552-4557.
Gibbs, 1989, Detection of single DNA base differences by competitive oligonucleotide priming, Nucleic Acids Res. 17 (7): 2437-48.
Gilliland, 1990, Analysis of cytokine mRNA and DNA: Detection and quantitation by competitive polymerase chain reaction, PNAS, 87(7):2725-9.
Giusti, 1993, Synthesis and characterization of 5' fluorescent dye labeled oligonucleotides, Genome Res 2:223-227.
Glass, 1995, Development of primer sets designed for use with the PCR to amlify conserved genes from filamentous ascomycetes, Applied and Environmental Microbiology, vol. 6, pp. 1323-1330.
Gold, 1995, Diversity of Oligonucleotide Functions Annu Rev Biochem, 64: 763-97.
Gong, 2015, Simple method to prepare oligonucleotide conjugated antibodies and its applicaiotn in multiplex protein detection in single cells, Bioconjugate Chm 27(1):271-225.
Goodall, 1998, Operation of mixed-culture immobilized cell reactors for the metabolism of meta- and para-nitrobenzoate by Comamonas Sp. JS46 and Comamonas Sp. JS47, Biotech Bioeng 59 (1):21-27.
Gordon, 1999, Solid phase synthesis—designer linkers for combinatorial chemistry: a review, J. Chem. Technol. Biotechnol., 74(9):835-851.
Grasland-Mongrain, 2003, Droplet coalescence in microfluidic devices, 30 pages, From internet: http://www.eleves.ens.fr/home/grasland/rapports/stage4.pdf.
Gray, 1987, High speed crhomosome sorting, Science 238(4825):323-329.
Green, 1992, Selection of a Ribozyme That Functions as a Superior Template in a Self Copying Reaction, Science, 258: 1910-5.
Gregoriadis, 1976, Enzyme entrapment in liposomes, Methods Enzymol 44:218-227.
Griffiths, 2000, Man-made enzymes-from design to in vitro compartmentalisation, Curr Opin Biotechnol 11:338-353.
Griffiths, 2003, Directed evolution of an extremely fast phosphotriesterase by in vitro compartmentalization, EMBO J, 22:24-25.
Griffiths, 2006, Miniaturising the laboratory in emulsion droplets, Trend Biotech 24(9):395-402.
Grinwood, 2004, The DNA sequence and biology of human chromosome 19, Nature 428:529-535.
Grothues, 1993, PCR amplification of megabase DNA with tagged random primers (T-PCR), Nucl. Acids Res vol. 21 (5):1321-1322.
Grund, 2010, Analysis of biomarker data:logs, odds, ratios and ROC curves, Curr Opin HIV AIDS 5(6):473-479.
Gruner, 2015, Stabilisers for water-in-fluorinated-oil dispersions, Curr Op Coll Int Sci 20:183-191.
Guatelli, 1990, Isothermal, in vitro amplification of nucleic acids by a multienzyme reaction modeled after retroviral replication, PNAS, 87(5):1874-8.
Guixe, 1998, Ligand-Induced Conformational Transitions in *Escherichia coli* Phosphofructokinase 2: Evidence for an Allosteric Site for MgATP2n, Biochem., 37: 13269-12375.
Guo, 2010, Simultaneous detection of trisomies 13, 18, and 21 with multiplex ligation dependent probe amplification-based real-time PCR, Clin Chem 56(9):1451-1459.
Gupta, 1991, A general method for the synthesis of 3'-sulfhydryl and phosphate group containing oligonucleotides, Nucl Acids Res 19 (11): 3019-3026.
Haber, 1993, Activity and spectroscopic properties of bovine liver catalase in sodium bis(2-ethylhexyl) sulfosuccinate/ sooctane reverse micelles, Eur J Biochem 217(2): 567-73.
Habig, 1981, Assays for differentiation of glutathione S-transferases, Methods in Enzymology, 77: 398-405.
Hadd, 1997, Microchip Device for Performing Enzyme Assays, Anal. Chem 69(17): 3407-3412.
Haeberle, 2007, Microfluidic platforms for lab-on-a-chip applications, Lab on a Chip 7:1081-1220.
Hagar, 1992, The effect of endotoxemia on concanavalin A induced alterations in cytoplasmic free calcium in rat spleen cells as determined with Fluo-3, Cell Calcium 13:123-130.
Hai, 2004, Investigation on the release of fluorescent markers from the w/o/w emulsions by fluorescence-activated cell sorter, J Control Release, 96(3): 393-402.
Haies, 1981, Morphometric study of rat lung cells. I. Numerical and dimensional characteristics of parenchymal cell population, Am. Rev. Respir. Dis. 123:533-54.
Hall, 2003, The EBG system of *E. coli*: origin and evolution of a novel beta-galactosidase for the metabolism of lactose, Genetica 118(2-3):143-56.
Hamady, 2008, Error-correcting barcoded primers for pyrosequencing hundreds of samples in multiplex. Nature Nethods vol. 5, No. 3, p. 235-237.
Han, 2001, Quantum-dot-tagged Microbeads for Multiplexed Optical Coding of Biomolecules, Nat Biotech 19(7): 631-635.
Handen, 2002, High-throughput screening-challenges for the future, Drug Discov World, 47-50.
Handique, 2001, On-Chip Thermopneumatic Pressure for Discrete Drop Pumping, Analytical Chemistry, 73:1831-1838.
Hanes, 1997, In vitro selection and evolution of functional proteins by using ribosome display, PNAS 94:4937-42.
Hanes, 1998, Degradation of porous poly(anhydide-co-imide) microspheres and implication for controlled macromolecule delivery, Biomaterials, 19(1-3): 163-172.
Hansen, 2002, A Robust and Scalable Microfluidic Metering Method That Allows Protein Crystal Growth by Free Interface Diffusion, PNAS, 99(26):16531-16536.
Harada, 1993, Monoclonal antibody G6K12 specific for membrane-associated differentiation marker of human stratified squamous epithelia and squamous cell carcinoma, J. Oral Pathol. Med 22(4):145-152.
Harder, 1994, Characterization and kinetic analysis of the intracellular domain of human protein tyrosine phosphatase peta (HPTP beta) using synthetic phosphopeptides, Biochem J 298 (Pt 2): 395-401.

(56) References Cited

OTHER PUBLICATIONS

Harries, 2006, A Numerical Model for Segmented Flow in a Microreactor, Int J of Heat and Mass Transfer, 46:3313-3322.
Harris, 2008, Single-molecule DNA sequencing of a viral genome, Science 320(5872):106-109.
Harrison, 1993, Micromachining a miniaturized capillary electrophoresis-based chemical analysis system on a chip, Science 261(5123):895-897.
Hasina, 2003, Plasminogen activator inhibitor-2: a molecular biomarker for head and neck cancer progression, Cancer Research 63:555-559.
Jermutus, 1998, et al., Recent advances in producing and selecting functional proteins by using cell-free translation, Curr Opin Biotechnol 9(5): 534-48.
Jo, 2003, Encapsulation of Bovine Serum Albumin in Temperature-Programmed Shell-in-Shell Structures, Macromol. Rapid Comm 24:957-962.
Joerger, 1995, Analyte detection with DNA-labeled antibodies and polymerase chain reaction, Clin. Chem. 41 (9):1371-7.
Johannsson, 1988, Amplification by Second Enzymes, In ELISA and Other Solid Phase Immunoassays, Kemeny et al (ed.), Chapter 4, pp. 85-106 John Wiley.
Johannsson, 1991, Heterogeneous Enzyme Immunoassays, In Principles and Practice of Immunoassay, pp. 295-325 Stockton Press.
Johnson, 1993, Human antibody engineering: Current Opinion in Structural Biology, 3:564-571.
Johnson, 2002, Protein tyrosine phosphatase 1B inhibitors for diabetes, Nature Review Drug Discovery 1, 696-709.
Jones, 1986, Replacing the complementarity-determining regions in a human antibody with those from a mouse, Nature, 321:522-525.
Jones, 1997, Quenched BODIPY dye-labeled casein substrates for the assay of protease activity by direct fluorescence measurement, Anal Biochem, 251:144-152.
Jones, 1999, Glowing jellyfish, luminescence and a molecule called coelenterazine, Trends Biotechnol. 17(12):477-81.
Joo, 1999, Laboratory evolution of peroxide-mediated cytochrome P450 hydroxylaion, Nature 399:670.
Joos, 1997, Covalent attachment of hybridizable oligonucleotides to glass supports, Analytical Biochemistry 247:96-101.
Joyce, 1994, In vitro Evolution of Nucleic Acids, Curr. Opp. Structural Biol, 4: 331-336.
Kadir, 1990, Haem binding to horse spleen ferritin, Febs Lett, 276: 81-4.
Kallen, 1966, The mechanism of the condensation of formaldehyde with tetrahydrofolic acid, J. Biol. Chem., 241:5851-63.
Kambara, 1988, Optimization of Parameters in a DNA Sequenator Using Fluorescence Detection, Nature Biotechnology 6:816-821.
Kamensky, 1965, Spectrophotometer: new instrument for ultrarapid cell analysis, Science 150(3696):630-631.
Kanouni, 2002, Preparation of a stable double emulsion (W1/0/W2): role of the interfacial films on the stability of the system, Adv. Collid. Interf. Sci., 99(3): 229-254.
Karapatis, 1998, Direct rapid tooling:a review of current research, Rapid Prototyping Journal, 4(2):77-89.
Katanaev, 1995, Viral Q beta RNA as a high expression vector for mRNA translation in a cell-free system, Febs Lett, 359:89-92.
Katsura, 2001, Indirect micromanipulation of single molecules in water-in-oil emulsion, Electrophoresis, 22:289-93.
Kawakatsu, 1997, Regular-sized cell creation in microchannel emulsification by visual microprocessing method, Journal of the American Oil ChemistS Society, 74:317-21.
Keana, 1990, New reagents for photoaffinity labeling: synthesis and photolysis of functionalized perfluorophenyl azides, J. Org. Chem. 55(11):3640-3647.
Keefe, 2001, Functional proteins from a random-sequence library, Nature, 410: 715-718.
Keij, 1994, High-speed photodamage cell sorting: An evaluation of the ZAPPER prototype, Methods in cell biology, 42: 371-358.
Kelly, 2005, Detection of Vascular Adhesion Molecule-1 Expression Using a Novel Multimodal Nanoparticle, Circulation Research 96:327-336.
Kelly, 2007, Miniaturizing chemistry and biology in microdroplets, Chem Commun 18:1773-1788.
Kerker, 1983, Elastic and inelastic light scattering in flow cytometry, Cytometry, 4:1-10.
Khandjian, 1986, UV crosslinking of RNA to nylon membrane enhances hybridization signals, Mol. Bio. Rep. 11: 107-115.
Kheir, 2012, Oxygen gas-filled microparticles provide intravenous oxygen delivery, Sci Trans Med 4(140):140ra88.
Kim, 2003, Type II quantum dots: CdTe/CdSe (core/shell) and CdSe/ZnTe (core/shell) heterostructures, J. Am Chem Soc. 125:11466-11467.
Kim, 2004, Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125.
Kircher, 2010, High-throughput DNA sequencing-concepts and limitations, Bioessays 32(6):524-536.
Kiss, 2008, High-throughput quantitative polymerase chain reaction in picoliter droplets, Anal. Chem 80:8975-8981.
Kitagawa, 1995, Manipulation of a single cell with microcapillary tubing based on its electrophoretic mobility, Electrophoresis 16:1364-1368.
Klug, 1994, All you wanted to know about selex, Molecular Biology Reports, 20:97-107.
Klug, 1995, Gene Regulatory Proteins and Their Interaction with DNA, Ann NY Acad Sci, 758: 143-60.
Klug, 1995, Protein motifs 5. Zinc fingers, Faseb J 9(8):597-604.
Knaak, 1995, Development of partition coefficients, Vmax and Km values, and allometric relationships, Toxicol Lett. 79 (I-3):87-98.
Knight, 1998, Hydrodynamic Focusing on a Silicon Chip: Mixing Nanoliters in Microseconds, Physical Review Lett 80 (17):3863-3866.
Koeller, 2001, Enzymes for chemical synthesis, Nature 409:232-240.
Kohara, 2002, DNA probes on beads arrayed in a capillary, 'Bead array',-exhibited high hybridization performance, Nucl Acids Res 30(16):e87.
Kohara, 2002, DNA probes on beads arrayed in a capillary, Nucleic Acids Research 30:e87.
Kohler, 1975, Continuous cultures of fused cells secreting antibody of predefined specificity, Nature, 256:495-7.
Kojima, 2005, PCR amplification from single DNA molecules on magnetic beads in emulsion: application for high-throughput screening of transcription factor targets. Nucleic Acids Res. 33:e150, 9 pages.
Kolb, 1995, Cotranslational folding of proteins, Biochem Cell Biol, 73:1217-20.
Komatsu, 2001, Roles of cytochromes P450 1A2, 2A6, and 2C8 in 5-fluorouracil formation rom tegafur, an anticancer prodrug, in human liver microsomes. Drug Met. Disp., 28:1457-1463.
Kopp, 1998, Chemical amplification: continuous flow PCR on a chip, Science, 280:1046-48.
Koster, 2008, Drop-based microfluidic devices for encapsulation of single cells, Lab on a Chip 8:1110-1115.
Kowalczykowski, 1994, Biochemistry of homologous recombination in *Escherichia coli*, Microbiol Rev 58(3):401-65.
Wang, 1989, Quantitation of mRNA by the polymerase chain reaction. Proc natl Acad Sci USA 86(24), 9717-21.
Wang, 1990, Design and synthesis of new fluorogenic HIV protease substrates based on resonance energy transfer, Tetrahedron Lett., 31:6493.
Wang, 2002, Preparation of Titania Particles Utilizing the Insoluble Phase Interface in a MicroChannel Reactor, Chemical Communications 14:1462-1463.
Wang, 2008, DEP actuated nanoliter droplet dispensing using feedback control, Lab on a Chip 9:901-909.
Wang, 2010, Quantifying EGFR Alterations in the Lung Cancer Genome with Nanofluidic Digital PCR Arrays, Clinical Chemistry 56:4.
Wang, 2010, Single cell analysis: the new frontier in 'omics', Trends Biotech 28:281-290.

(56) References Cited

OTHER PUBLICATIONS

Warburton, 1993, Microcapsules for Multiple Emulsions, Encapsulation and Controlled Release, Spec Publ R Soc Chem, 35-51.
Wasserman, 1989, Structure and reactivity of allyl-siloxane monolayers formed by reaction of allcyltrichlorosilanes on silicon substrates, Langmuir 5:1074-1087.
Weaver, 1997, Gel microdrop technology for rapid isolation of rare and high producer cells, Nat Med 3(5):583-585.
Weaver, 2010, Taking qPCR to a higher level: Analysis of CNV reveals the power of high throughput qPCR to enhance quantitative resolution, Methods 50, 271-276.
Weil, 1979, Selective and accurate initiation of transcription at the Ad2 major late promotor in a soluble system dependent on purified RNA polymerase II and DNA, Cell, 18(2):469-84.
Werle, 1994, Convenient single-step, one tube purification of PCR products for direct sequencing, Nucl Acids Res 22 (20): 4354-4355.
Wetmur, 2005, Molecular haplotyping by linking emulsion PCR: analysis of paraoxonase 1 haplotypes and phenotypes, Nucleic Acids Res 33(8):2615-2619.
White, 2009, Digital PCR provides sensitive and absolute calibration for high throughput sequencing, BMC Genomics 10:116.
Wick, 1996, Enzyme-containing liposomes can endogenously produce membrane-constituting lipids, Chem Biol 3 (4):277-85.
Wiggins, 2004, Foundations of chaotic mixing, Philos Transact A Math Phys Eng Sci 362(1818):937-70.
Williams, 1979, Methotrexate, a high-affinity pseudosubstrate of dihydrofolate reductase, Biochemistry, 18(12):2567-73.
Williams, 2006, Amplification of complex gene libraries by emulsion PCR, Nature Methods 3(7):545-550.
Wilson, 1999, In vitro selection of functional nucleic acids, Ann. Rev. Biochem. 68: 611-647.
Wittrup, 2001, Protein engineering by cell-surface display. Curr Opin Biotechnology, 12: 395-399.
Wittwer, 1989, Automated polymerase chain reaction in capillary tubes with hot air, Nucleic Acids Res., 17(11) 4353-4357.
Wittwer, 1990, Minimizing the Time Required for DNA Amplification by Efficient Heat Transfer to Small Samples, Anal. Biochem., 186, 328-331.
Wolff, 2003, Integrating advanced functionality in a microfabricated high-throughput fluorescent-activated cell sorter, Lab Chip, 3(1): 22-27.
Woolley, 1994, Ultra-high-speed DNA fragment separations using microfabricated capillary array electrophoresis chips. Proc. Natl. Acad. Sci. USA, 91, 11348-11352.
Woolley, 1996, Functional Integration of PCR Amplification and Capillary Electrophoresis in a Microfabricated DNA Analysis Device, Anal. Chem. 68, 4081-4086.
Wronski, 2002, Two-color, fluorescence-based microplate assay for apoptosis detection. Biotechniques, 32:666-668.
Wu, 1989, The ligation amplification reaction (LAR)-amplification of specific DNA sequences using sequential rounds of template-dependent ligation, Genomics 4(4):560-9.
Wyatt, 1991, Synthesis and purification of large amounts of RNA oligonucleotides, Biotechniques 11(6):764-9.
Xia, 1998, Soft Lithography, Angew. Chem. Int. Ed. 37:550-575.
Xia, 1998, Soft Lithography, Ann. Rev. Mat. Sci. 28:153-184.
Xiao, 2007, Rapid DNA mapping by fluorescent single molecule detection, Nucleic Acids Research 35:1-12.
Xing, 2011, Novel structurally related compounds reactivate latent HIV-1 in a bcl-2-transduced primary CD4+ T cell model without inducing global T cell activation, Journal of Antimicrobial Chemotherapy, 67(2):398-403.
Xu, 2005, Generation of monodisperse particles by using microfluidics: control over size, shape, and composition, Angew. Chem. Int. Ed. 44:724-728.
Xu, 2009, Design of 240, 000 orthogonal 25mer DNA barcode probes, PNAS, 106(7) p. 2289-2294.
Yamagishi, 1990, Mutational analysis of structure-activity relationships in human tumor necrosis factor-alpha, Protein Eng, 3:713-9.
Yamaguchi, 2002, Insulin-loaded biodegradable PLGA microcapsules: initial burst release controlled by hydrophilic additives, Journal of Controlled Release, 81(3): 235-249.
Yelamos, 1995, Targeting of non-lg sequences in place of the V segment by somatic hypermutation. Nature 376 (6537):225-9.
Yershov, 1996, DNA analysis and diagnostics on oligonucleotide microchips, PNAS 93(10):4913-4918.
Yonezawa, 2003, DNA display for in vitro selection of diverse peptide libraries, Nucleic Acids Research, 31(19): e118, 5 pages.
Yu, 1997, Specific inhibition of PCR by non-extendable oligonucleotides using a 5' to 3' exonuclease-deficient DNA polymerase, Biotechniques 23(4):714-6, 718-20.
Yu, 2001, Responsive biomimetic hydrogel valve for microfluidics. Appl. Phys. Lett 78:2589-2591.
Yu, 2002, Environmental Carcinogenic Polycyclic Aromatic Hydrocarbons: Photochemisrty and Phototoxicity, J Environ Scie Health C Environ Carcinog Exotoxicol Rev, 20(2), 1-43.
Yu, 2007, Quantum dot and silica nanoparticle doped polymer optical fibers, Optics Express 15(16):9989-9994.
Zaccolo, 1996, An approach to random mutagenesis of DNA using mixtures of triphosphate derivatives of nucleoside analogues. J Mol Biol 255(4):589-603.
Zakrzewski, 1980, Preparation of tritiated dihydrofolic acid of high specific activity, Methods Enzymol, 529-533.
Zaug, 1986, The intervening sequence RNA of Tetrahymena is an enzyme, Science 231(4737):470-5.
Zaug, 1986, The Tetrahymena intervening sequence ribonucleic acid enzyme is a phosphotransferase and an acid phosphatase, Biochemistry 25(16):4478-82.
Zaug, 1986, The Tetrahymena ribozyme acts like an RNA restriction endonuclease, Nature 324(6096):429-33.
Zhang, 1993, Substrate specificity of the protein tyrosine phosphatases, PNAS 90: 4446-4450.
Zhang, 1999, A Simple Statistical Parameter for Use in Evaluation and Validation of High Throughput Screening Assays, Journal of Biomolecular Screening, 4(2): 67-73.
Oh, 2002, Distribution of Macropores in Silica Particles Prepared by Using Multiple Emulsions, Journal of Colloid and Interface Science, 254(1): 79-86.
Oh, 2005, World-to-chip microfluidic interface with built-in valves for multichamber chip-based PCR assays, Lab Chip, 5, 845-850.
Okuno, 2003, Recent Advances in Optical Switches Using Silica-based PLC Technology, NTT Technical Review 1 (7):20-30.
Okushima, 2004, Controlled production of monodisperse double emulsions by two-step droplet breakup in microfluidic devices, Langmuir 20(23): 9905-8.
Olsen, 2000, Function-based isolation of novel enzymes from a large library, Nat Bioteoltnol 13(10):1071-4.
Omburo, 1992, Characterization of the zinc binding site of bacterial phosphotriesterase, J of Biological Chem, 267:13278-83.
Oroskar, 1996, Detection of immobilized amplicons by ELISA-like techniques, Clin. Chem. 42:1547-1555.
Ostermeier, 1999, A combinatorial approach to hybrid enzymes independent of DNA homology, Nat Biotechnol, 17 (12):1205-9.
Ott, 1967, Biological and medical research annual report, Los Alamos Scientific Laboratory, 14 pages.
Ouelette, 2003, A new wave of microfluidic devices, Indust Physicist pp. 14-17.
Pabit, 2002, Laminar-Flow Fluid Mixer for Fast Fluorescence Kinetics Studies, Biophys J 83:2872-2878.
Paddison, 2002, Stable suppression of gene expression by RNAi in mammalian cells, PNAS 99(3):1443-1448.
Pain, 1981, Preparation of protein A-peroxidase mono conjugate using a heterobifunctional reagent, and its use in enzyme immunoassays, J Immunol Methods, 40:219-30.
Pamme, 2007, Continuous flow separations in microfluidic devices, Lab on a Chip, 1644-1659.
Pannacci, 2008, Equilibrium and Nonequilibrium States in Microluidic Double Emulsions Physical Review Leters, 101 (16):164502.
Park, 2001, Model of Formation of Monodispersed Colloids, J. Phys. Chem. B 105:11630-11635.
Park, 2003, Cylindrical compact thermal-cycling device for continuous-flow polymeras chain reaction, Anal Chem, ACS, 75:6029-33.

(56) References Cited

OTHER PUBLICATIONS

Parker, 2000, Development of high throughput screening assays using fluorescence polarization: nuclear receptor-ligand-binding and kinase/phosphatase assays, J Biomol Screen, 5(2): 77-88.
Pasternak, 2013, Cell-associated Hiv Rna: a dynmic biomarker of viral persistence, Retrovirology 10:41.
Patel, 2003, Formation of Fluorinated Nonionic Surfactant Microemulsions in Hydrfuorocarbon 134a, Journal of Colloid and Interface Science, 258, 345-353.
Pedersen, 1998, A method for directed evolution and functional cloning of enzymes, PNAS 95(18):10523-8.
Pekin, 2011, Quantitative and sensitive detection of rare mutations using droplet-based microfluidics, Lab on a Chip 11 (13):2156-2166.
Pelham, 1976, An efficient mRNA-dependent translation system from reticulocyte lysates, Eur J Biochem 67:247-56.
Pelletier, 1999, An in vivo library-versus-library selection of optimized protein-protein interactions, Nature Biotechnology, 17:683-90.
Peng, 1998, Controlled Production of Emulsions Using a Crossflow Membrane, Particle & Particle Systems Characterization 15:21-25.
Pepe, 2004, Limitations of the odds ratio in gauging the performance of a diagnostic, prognostic, or screening marker, American Journal of Epidemiology 159(9):882-890.
Perelson, 1979, Theorectical studies of clonal selection: minimal antibody repertoire size and relaibility of self-non-self discrimination. J Theor Biol 81(4):645-70.
Perez-Gilabert, 1992, Application of active-phase plot to the kinetic analysis of lipoxygenase in reverse micelles, Biochemistry J. 288:1011-1015.
Petrounia, 2000, Designed evolution of enzymatic properties, Curr Opin Biotechnol, 11:325-330.
Pirrung, 1996, A General Method for the Spatially Defined Immobilization of Biomolecules on Glass Surfaces Using Caged' Biotin, Bioconjug Chem 7: 317-321.
Ploem, 1993, in Fluorescent and Luminescent Probes for Biological Activity Mason, T. G. Ed., Academic Press, Landon, pp. 1-11.
Pluckthun, 2000, In vitro selection and evolution of proteins, Adv Protein Chem, 55: 367-403.
Pollack, 1986, Selective chemical catalysis by an antibody, Science 234(4783):1570-3.
Pollack, 2002, Electrowetting-based actuation of droplets for integrated microfluidics, Lab Chip, 2:96-101.
Pons, 2009, Synthesis of Near-Infrared-Emitting, Water-Soluble CdTeSe/CdZnS Core/Shell Quantum Dots, Chemistry of Materials 21(8):1418-1424.
Pooley, 2010, Hydrogels From Acrylic Acid with N, N-Dimethylacrylamide: Synthesis, Characterization, and Water Absorption Properties, J. Chil. Chem. Soc. 55(1):19-24.
Poon, 2002, Differential DNA Methylation between Fetus and Mother as a Strategy for Detecting Fetal DNA in Maternal Plasma, Clinical Chemistry, 48:35-41.
Posner, 1996, Engineering specificity for folate into dihydrofolate reductase from *Escherichia coli*, Biochemistry, 35: 1653-63.
Priest, 2006, Generation of Monodisperse Gel Emulsions in a Microfluidic Device, Applied Physics Letters, 88:024106, 3 pages.
Qi, 1998, Acid Beta-Glucosidase: Intrinsic Fluorescence and Conformational Changes Induced by Phospholipids and Saposin C, Biochem., 37(33): 11544-11554.
Raghuraman, 1994, Emulston Liquid Membranes for Wastewater Treatment: Equilibrium Models for Some Typical Metal-Extractant Systems, Environ. Sci. Technol 28:1090-1098.
Ralhan, 2008, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173.
Ramanan, 2016, Algae-bacteria interactions, Biotech ADv 34:14-29.
Ramsey, 1999, The burgeoning power of the shrinking laboratory, Nat Biotechnol 17(11):1061-2.
Ramstrom, 2002, Drug discovery by dynamic combinatorial libraries, Nat Rev Drug Discov 1:26-36.
Rasmussen, 2013, Comparison of HDAC inhibitors in clinical development, Human Vacc Immunother 9(5):993-1001.
Raushel, 2000, Phosphotriesterase: an enzyme in search of its natural substrate, Adv Enzymol Relat Areas Mol Biol, 74: 51-93.
Rech, 1990, Introduction of a yeast artificial chromosome vector into *Sarrachomyeces cervesia* by electroporation, Nucleic Acids Res 18:1313.
Reyes, 2002, Micro Total Analysis Systems. 1. Introduction, Theory and Technology, Anal Chem 74(12):2623-2636.
Riechmann, 1988, Reshaping human antibodies for therapy, Nature, 332:323-327.
Davies, 1997, Activated Alzheimer Disease Platelets Retain More Beta Amyloid Precursor Protein, Neurobiology of Aging, 18(2):147-153.
Santos, 2007, Detection of Amyloid-b Oligomers in Human Cerebrospinal Fluid by Flow Cytometry and Fluorescence Resonance Energy Transfer, J of Alzheimer's Disease, 11:117-125.
Zhao, 1998, Molecular evolution by staggered extension process (StEP) in vitro recombination. Nat Biotechnol 16 (3):258-61.
Zhao, 2002, Control and Applications of Immiscible Liquids in Microchannels, J. Am. Chem. Soc, vol. 124:5284-5285.
Zheng, 2003, Screening of Protein Crystallization Conditions on a Microfluidic Chip Using Nanoliter-Size Droplets, J Am Chem Soc 125(37):11170-11171.
Zheng, 2004, A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem., 116:1-4.
Zheng, 2004, Formation of droplets of alternating composition in microlfluidic channels and applications to indexing of concentrations in droplet-based assays, Anal Chem 76:4977-4982.
Zheng, 2005, A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17):2520-2523.
Zhong, 2011, Multiplex digital PCR: breaking the one target per color barrier of quantitative PCR, Lab on a Chip 11 (13):2167-2174.
Zhou, 2001, Counting alleles reveals a connection between chromosome 18q loss and vascular invasion, Nat Biotechnol 19(1):78-81.
Zimmermann, 1974, Dielectric Breakdown of Cell Membranes, Biophys J 14(11):881-889.
Zimmermann, 1992, Microscale Production of Hybridomas by Hypo-Osmolar Electrofusion, Hum. Antibod. Hybridomas, 3(1): 14-18.
Zimmermann, 2008, Digital PCR: a powerful new tool for noninvasive prenatal diagnosis?, Prenat Diagn 28, 1087-1093.
Zubay, 1973, In vitro synthesis of protein in microbial systems, Annu Rev Genet, 7: 267-87.
Zubay, 1980, The isolation and properties of CAP, the catabolite gene activator, Methods Enzymol, 65: 856-77.
Zuckermann, 1987, Efficient Methods for Attachment of Thiol-Specific Probes to the 3-end of Synthetic Oligodeoxyribonucleotides, Nucleic Acids Res. 15:5305-5321.
Bougueleret, 1984, Characterization of the gene coding for the EcoRV restriction and modification system of *E coli*, Nucleic Acids Res 12(8):3659-76.
Branebjerg, 1996, Fast mixing by lamination, MEMS Proc 9th Ann 9:441-446.
Braslavsky, 2003, Sequence information can be obtained from single DNA molecules, PNAS, 100(7):3960-3964.
Breslauer, 2006, Microfluidics based systems biology, Mol Bio Syst 2:97-112.
Bringer, 2004, Microfluidic systems for chemical kinetics that rely on chaotic mixing in droplets, Phil Trans A Math Phys Eng Sci 362:1-18.
Brown, 1979, Chemical synthesis and cloning of a tyrosine tRNA gene, Methods Enzymol 68:109-151.
Bru, 1991, Product inhibition of alpha-chymotrypsin in reverse micelles. Eur J Biochem 199(1):95-103.

(56) References Cited

OTHER PUBLICATIONS

Bru, 1993, Catalytic activity of elastase in reverse micelles, Biochem Mol Bio Int, 31(4):685-92.
Brummelkamp, 2002, A system for stable expression of short interfering RNAs in mammalian cells, Science 296 (5567):550-3.
Buican, 1987, Automated single-cell manipulation and sorting by light trapping, Appl Optics 26(24):5311-5316.
Burbaum, 1998, Miniaturization technologies in HTS, Drug Disc Today 3:313-322.
Burns, 1996, Microfabricated structures for integrated DNA analysis, PNAS 93:5556-5561.
Burns, 1998, An Integrated Nanoliter DNA Analysis Device, Science, 282:484-487.
Burns, 2002, The intensification of rapid reactions in multiphase systems using slug flow in capillaries, Lab on a Chip 1:10-15.
Byrnes, 1982, Sensitive fluorogenic substrates for the detection of trypsin-like proteases and pancreatic elastase, Anal Biochem 126:447.
Cahill, 1991, Polymerase chain reaction and Q beta replicase amplification, Clin Chem 37(9):1482-5.
Caldwell, 1991, Limits of diffusion in the hydrolysis of substrates by the phosphodiesterase from Pseudomonas diminuta, Biochem 30:7438-7444.
Calvert, 2001, Inkjet printing for materials and devices, Chem Mater 13:3299-3305.
Cantor, 2003, Direct molecular haplotyping of long-range genomic DNA with M1-PCR; PNAS 100(13):7449-7453.
Caruccio, 2009, Nextura technology for NGS DNA library preparation: simulaneous fragmentation and tagging by in vitro transposition, Epibio Newsletter.
Caruthers, 1985, Gene synthesis machines: DNA chemistry and its uses, Science 230:281-285.
Cavalli, 2010, Nanosponge formulations as oxygen delivery systems, Int J Pharmaceutics 402:254-257.
Chakrabarti, 1994, Production of RNA by a polymerase protein encapsulated within phospholipid vesicles, J Mol Evol 39(6):555-9.
Chamberlain, 1973, Characterization of T7-specific ribonucleic acid polymerase. 1. General properties of the enzymatic reaction and the template specificity of the enzyme, J Biol Chem 248:2235-44.
Chan, 2003, Size-Controlled Growth of CdSe Nanocrystals in Microfluidic Reactors, Nano Lett 3(2):199-201.
Chan, 2008, New trends in immunoassays, Adv Biochem Engin/Biotech 109:123-154.
Chang, 1987, Recycling of NAD(P) by multienzyme systems immobilized by microencapsulation in artifical cells, Methods Enzymol, 136(67):67-82.
Chang, 2008, Controlled double emulsification utilizing 3D PDMS microchannels, Journal of Micromechanics and Microengineering 18:1-8.
Chao, 2004, Control of Concentration and Volume Gradients in Microfluidic Droplet Arrays for Protein Crystallization Screening, 26th Annual International Conference of the IEEE Engineering in Medicine and Biology Society, San Francisco, California Sep. 1-5.
Chao, 2004, Droplet Arrays in Microfluidic Channels for Combinatorial Screening Assays, Hilton Head: A Solid State Sensor, Actuator and Microsystems Workshop, Hilton Head Island, South Carolina, Jun. 6-10.
Chapman, 1994, In vitro selection of catalytic RNAs, Curr. op. Struct. Biol., 4:618-22.
Chayen, 1999, Crystallization with oils: a new dimension in macromolecular crystal growth Journal of Crystal Growth, 196:434-441.
Chen, 2001, Capturing a Photoexcited Molecular Structure Through Time-Domain X-ray Absorption Fine Structure, Science 292(5515):262-264.
Chen, 2003, Microfluidic Switch for Embryo and Cell Sorting the 12th International Conference on Solid State Sensors, Actuators, and Microsystems, Boston, MA, Transducers, 1: 659-662.
Chen-Goodspeed, 2001, Enhancement, relaxation, and reversal of the stereoselectivity for phosphotriesterase by rational evolution of active site residues, Biochemistry, 40: 1332-1339.
Chen-Goodspeed, 2001, Structural Determinants of the substrate and stereochemical specificity of phosphotriesterase, Biochemistry, 40(5):1325-31.
Cheng, 2003, Electro flow focusing inmicrofluidic devices, Microfluidics Poster, presented at DBAS, Frontiers in Nanoscience, 1 page.
Cheng, 2006, Nanotechnologies for biomolecular detection and medical diagnostics, Current Opinion in Chemical Biology, 10:11-19.
Chetverin, 1995, Replicable RNA vectors: prospects for cell-free gene amplification, expression, and cloning, Prog Nucleic Acid Res Mol Biol, 51:225-70.
Chiang, 1993, Expression and purification of general transcription factors by FLAG epitope-tagging and peptide elution, Pept Res, 6:62-64.
Chiba, 1997, Controlled protein delivery from biodegradable tyrosino-containing poly(anhydride-co-imide) microspheres, Biomaterials, 18(13):893-901.
Chiou, 2001, A closed-cycle capillary polymerase chain reaction machine, Analytical Chemistry, American Chamical Society, 73:2018-21.
Chiu, 1999, Chemical transformations in individual ultrasmall biomimetic containers, Science, 283:1892-1895.
Chiu, 2008, Noninvasive prenatal diagnosis of chromosomal aneuploidy by massively paralel genomic seuqencing of DNA in maternal plasma, PNAS 105(51):20458-20463.
Chou, 1998, A microfabricated device for sizing and sorting DNA molecules 96:11-13.
Clackson, 1994, In vitro selection from protein and peptide libraries, Trends Biotechnol, 12:173-84.
Clausell-Tormos, 2008, Droplet-based microfluidic platforms for the encapsulation and screening of Mammalian cells and multicellular organisms, Chem Biol 15(5):427-437.
Cohen, 1991, Controlled delivery systems for proteins based on poly(lactic/glycolic acid) microspheres, Pharm Res, 8 (6):713-720.
Collins, 2003, Optimization of Shear Driven Droplet Generation in a Microluidic Device, ASME International Mechanical Engineering Congress and R&D Expo, Washington, 4 pages.
Collins, 2004, Microfluidic flow transducer based on the measurements of electrical admittance, Lab on a Chip, 4:7-10.
Riess, 2002, Fluorous micro- and nanophases with a biomedical perspective, Tetrahedron 58(20):4113-4131.
Roach, 2005, Controlling nonspecific protein adsorption in a plug-based microfluidic system by controlling inteifacial chemistry using fluorous-phase surfactants, Anal. Chem. 77:785-796.
Roberts, 1969, Termination factor for RNA synthesis, Nature, 224: 1168-74.
Roberts, 1975, Simian virus 40 DNA directs synthesis of authentic viral polypeptides in a linked transcription-translation cell-free system 72(5):1922-1926.
Roberts, 1997, RNA-peptide fusion for the in vitro selection of peptides and proteins, PNAS 94:12297-302.
Roberts, 1999, In vitro selection of nucleic acids and proteins: What are we learning, Curr Opin Struct Biol 9(4): 521-9.
Roberts, 1999, Totally in vitro protein selection using mRNA-protein fusions and ribosome display. Curr Opin Chem Biol 3(3), 268-73.
Roche, 2011, 454 Sequencing System Guidelines for Amplicon Experimental Design, 50 pages.
Rodriguez-Antona, 2000, Quantitative RT-PCR measurement of human cytochrome P-450s: application to drug induction studies. Arch. Biochem. Biophys., 376:109-116.
Rogers, 2005, Closing bacterial genoimc sequence gaps with adaptor-PCR, BioTechniques 39(1):1-3.
Rolland, 1985, Fluorescence Polarization Assay by Flow Cytometry, J. Immunol. Meth., 76(1): 1-10.
Rosenberg, 1975, Inhibition of Human Factor IX by Human Antithrombin, J Biol Chem, 250: 4755-64.
Rosenberry, 1975, Acetylcholinesterase, Adv Enzymol Relat Areas Mol Biol, 43: 103-218.
Rotman, 1961, Measurement of activities of single molecules of beta-galactosidase, PNAS, 47:1981-91.
Rouzioux, 2013, How to best measure HIV reservoirs, Curr Op HIV AIDS 8(3):170-175.

(56) References Cited

OTHER PUBLICATIONS

Russon et al., Single-nucleotide polymorphism analysis by allele-specific extension of fluorescently labeled nucleotides in a microfluidic flow-through device, Electrophoresis, 24:158-61 (2003).
Saarela, 2006, Re-usable multi-inlet PDMS fluidic connector, Sensors Actuators B 114(1):552-57.
Sadtler, 1996, Achieving stable, reverse water-in-fluorocarbon emulsions, Angew Chem Int Ed 35(17):1976-1978.
Sadtler, 1999, Reverse water-In-fluorocarbon emulsions as a drug delivery system: an in vitro study, Colloids & Surfaces A: Phys Eng Asp 147:309-315.
Saiki, 1988, Primer directed enzymatic amplification of DNA with a thermostable DNA polymerase, Science 239 (4839):487-91.
Sakamoto, 2005, Rapid and simple quantification of bacterial cells by using a microfluidic device, Appl Env Microb 71:2.
Salomon, 2019, Droplet-based single cell RNAseq tools: a practical guide, Lab on a Chip 19:1706-1727.
Sano, 1992, Immuno-PCR: very sensitive antigen-detection by means of sepcific Ab-DNA conjugates, Science 258 (5079):120-122.
Santalucia, 1998, A unified view of polymer, dumbbell, and oligonucleotide DNA nearest-neighbor thermodynamics, PNAS 95(4):1460-5.
Santra, 2006, Fluorescence lifetime measurements to determine the core-shell nanostructure of FITC-doped silica nanoparticles, J Luminescence 117(1):75-82.
Sawada, 1996, Synthesis and surfactant properties of novel fluoroalkylated amphiphilic oligomers, Chem Commun 2:179-190.
Schatz, 1996, Screening of peptide libraries linked to lac repressor, Meth Enzymol 267:171-91.
Schneegass, 2001, Miniaturized flow-through PCR with different template types in a silicone chip thermocycler, Lab on a Chip 1:42-9.
Schopman, 2012, Selective packaging of cellular miRNAs in HIV-1 particles, Virus Res 169(2):438-47.
Schubert, 2002, Designer Capsules, Nat Med 8:1362.
Schweitzer, 2000, Immunoassays with rolling circle DNA amplification, PNAS 97(18):10113-10119.
Schweitzer, 2001, Combining nucleic acid amplification and detection. Curr Opin Biotechnol 12(1):21-7.
Scott, 1948, The solubility of fluorocarbons, J Am Chem Soc 70:4090-4093.
Sedlak, 2013, Viral diagnostics in the era of digital polymerase chain reaction, Diag Microb Inf Dis 75(1):1-4.
Seethala, 1997, Homogeneous fluorescence polarization assay for Src-Family tyrosine kinases, Anal Biochem 253 (2):210-218.
Seiler, 1993, Planar glass chips for capillary electrophoresis: repetitive sample injection, quantitation, and separation efficiency, Anal Chem 65(10):1481-1488.
Selwyn, 1965, A simple test for inactivation of an enzyme during assay, Biochim Biophys Acta 105:193-195.
Seo, 2007, Microfluidic consecutive flow-focusing droplet generators, Soft Matter 3:986-992.
Seong, 2002, Efficient mixing and reactions within microfluidic channels using microbead-supported catalysts, J Am Chem Soc 124(45):13360-1.
Seong, 2002, Fabrication of microchambers defined by photopolymerized hydrogels and weirs within microfluidic systems, Anal Chem 74(14):3372-3377.
Sepp, 2002, Microbead display by in vitro compartmentalisation: selection for binding using flow cytometry, FEBS Letters 532:455-58.
Serpersu, 1985, Reversible and irreversible modification of erythrocyte membrane permeability by electric field, Biochim Biophys Acta 812(3):779-785.
Shapiro, 1983, Multistation multiparameter flow cytometry: a critical review and rationale, Cytometry 3: 227-243.
Shastry, 2006, Directing droplets using microstructured surfaces, Langmuir 22:6161-6167.
Shen, 2006, Eigengene-based linear discriminant model for tumor classification using gene expression microarray data, Bioinformatics 22(21):2635-2642.
Shendure, 2008, Next-generation DNA sequencing, Nature Biotechnology, 26(10):1135-1145.
Shestopalov, 2004, Multi-step synthesis of nanoparticles performed on millisecond time scale in a microfluidic droplet-based system, Royal Soc Chem, 4:316-321.
Shim, 2007, Using microfluidics to decouple nucleation and growth of protein crystals, Cryst Growth Des 7 (11):2192-2194.
Shimizu, 1995, Encapsulation of biologically active proteins in a multiple emulsion, Biosci Biotech Biochem 59 (3):492-496.
Shtern, 1996, Hysteresis in swirling jets, J Fluid Mech 309:1-44.
Sia, 2003, Microfluidic devices fabricated in poly(dimethylsiloxane) for biological studies, Electrophoresis 24 (21):3563-3576.
Siemering, 1996, Mutations that suppress the thermosensitivity of green fluorescent protein, Curr Biol 6:1653-1663.
Silva-Cunha, 1998, W/O/W multiple emulsions of insulin containing a protease inhibitor and an absorption enhancer: biological activity after oral administration to normal and diabetic rats, Int J Pharm 169:33-44.
Sims, 2000, Immunopolymerase chain reaction using real-time polymerase chain reaction for detection, Anal. Biochem. 281(2):230-2.
Sista, 2007, Development of a Digital Microfluidic Lab-on-a-Chip for Automated Immunoassay with Magnetically Responsive Beads, Doctoral Thesis, Florida State University, 128 pages.
Sista, 2008, Development of a digital microfluidic platform for point care testing, Lab on a Chip 8:2091-2104.
Siwy, 2003, Electro-responsive asymmetric nanopores in polyimide with stable ion-current signal, Appl Phys A: Mat Sci Proc 76:781-785.
Slappendel, 1994, Normal cations and abnormal membrane lipids in the red blood cells of dogs with familial stomatocytosis hypertrophic gastritis, Blood 84:904-909.
Slob, 1997, Structural identifiability of PBPK models: practical consequences for modeling strategies and study designs, Crit Rev Toxicol. 27(3):261-72.
Smith, 1985, The synthesis of oligonucleotides containing an aliphatic amino group at the 5' terminus: synthesis of fluorescent DNA primers for use in DNA sequence analysis, Nucl Acid Res 13:2399-2412.
Smith, 1986, Fluorescence detection in automated DNA sequence analysis, Nature 321:674-679.
Smith, 1989, Absolute displacement measurements using modulation of the spectrum of white light in a Michelson interferometer, Applied Optics, 28(16):3339-3342.
Smith, 1992, Direct mechanical measurements of the elasticity of single DNA molecules by using magnetic beads, Science 258(5085):1122-1126.
Smith, 1996, Environmental Degradation of Polyacrylamides, 1. Effects of Artificial Environmental Conditions: Temperature, Light and pH, Ecotoxicology and Environmental Safety, 35:121-135.
Smith, 2010, Highly-multiplexed barcode sequencing: an efficient method for parallel analysis of pooled samples, Nucleic Acids Res 38(13):e142.
Smyth, 2000, Markers of apoptosis: methods for elucidating the mechanism of apoptotic cell death from the nervous system, Biotechniques 32:648-665.
Sohn, 2000, Capacitance cytometry: Measuring biological cells one by one, PNAS 97(20):10687-10690.
Sola, 2014, Fabrication of a microfluidic cell made of thiolene for microarray applications, 18th Int Conf Miniaturized Systems for Chem and Life Sciences, MicroTAS, San Antonio, TX 1719-1721.
Somasundaram, 1999, Gain studies of Rhodamine 6G dye doped polymer laser, J Photochem Photobiol 125 (1-3):93-98.
Song, 2002, Experimental test of scaling of mixing by chaotic advection in droplets moving through microfluidic channels, App Phy Lett 83(22):4664-4666.
Song, 2003, A Microfluidic System for Controlling Reaction Networks in Time, Angew. Chem. Int. Ed., 42(7):768-772.
Song, 2003, Millisecond kinetics on a microluidic chip using nanoliters of reagents, J Am Chem Soc 125:14613-14619.

(56) References Cited

OTHER PUBLICATIONS

Song, 2006, Reactions in droplets in microfluidic channels, Angew chem Int ed 45(44):7336-7356.
Soni, 2007, Progress toward ultrafast DNA sequencing using solid-state nanopores, Clin Chem 53:1996-2001.
Soumillion, 2001, Novel concepts for the selection of catalytic activity. Curr Op Biotech 12:387-394.
Spiro, 2000, A bead-based method for multiplexed identification and quantitation of DNA sequences using flow cytometry, Appl Env Micro 66:4258-4265.
Sproat, 1987, The synthesis of protected 5'-mercapto-2',5'-dideoxyribonucleoside-3'-0-phosphorainidites, uses of 5'-mercapto-oligodeoxyribonucleotides, Nucleic Acids Res 15:4837-4848.
Squires, 2005, Microfluidics: fluid physics at the nanoliter scale, Rev Mod Phys 77:977-1026.
Stauber, 1993, Rapid generation of monoclonal antibody-secreting hybridomas against African horse sickness virus by In vitro immunization and the fusion/cloning technique, J Immunol Meth 161(2):157-168.
Stemmer, 1994, DNA shuffling by random fragmentation and reassembly: in vitro recombination for molecular evolution. PNAS 91(22):10747-51.
Stemmer, 1994, Rapid evolution of a protein in vitro by DNA shuffling, Nature 370(6488):389-91.
Stober, 1998, Controlled growth of monodisperse silica spheres in the micron size range, J Colloid Interface Sci 26 (1):62-69.
Stofko, 1992, A single step purification for recombinant proteins, Febs Lett 302:274-278.
Stone, 2004, Engineering flows in small devices: microfluidics toward a lab-on-a-chip, Ann Rev Fluid Mech 36:381-441.
Strizhkov, 2000, PCR amplification on a microarray of gel-immobilized oligonucleotides: Detection of bacterial toxin- and drug-resistant genes and their mutations, BioTechniques 29(4):844-857.
Strommenger, 2003, Multiplex PCR assay for simultaneous detection of nine clinicly relevant antibiotic resistance genes in *S aureus*, J Clin Microb 41(9):4089-4094.
Stroock, 2002, Chaotic mixer for microchannels, Science 295(5555):647-651.
Studer, 1997, Fluorous synthesis: a fluorous-phase strategy for improving separation efficiency in organic synthesis, Science 275:823-826.
Sugiura, 2001, Interfacial tension driven monodispersed droplet formation from mtcrofabricated channel array, Langmuir 17:5562-5566.
Sugiura, 2002, Effect of channel structure on microchannel emuisification, Langmuir 18:5708-5712.
Sundberg, 1995, Spatially-addressable immobilisation of macromolecules on solid supports, J Am Chem Soc 117:12050-12057.
Sung, 2005, Chip-based microfluidic devices coupled with electrospray ionization-mass spectrometry, Electrophoresis 26:1783-1791.
Sutcliffe, 1986, Dynamics of UV laser ablation of organic polymer surfaces, J Appl Phys 60(9):3315-3322.
Suzuki, 1996, Random mutagenesis of thermus aquaticus DNA polmerase I: concordance of immutable sites in vivo with the crystal structure, PNAS 93:96701-9675.
Syed, 2009, Next-generation sequencing library preparation: simultaneous fragmentation and tagging using in vitro transposition, Nat Meth 6:1-2.
Takagi, 2005, Continuous particle separation in a microchannel having asymmetrically arranged multiple branches, Lab on a Chip, 5.7:778-784.
Takayama, 1999, Patterning cells and their environmnets using multiple laminar fluid flows in cappillary networks, PNAS 96:5545-5548.
Takeuchi, 2005, An axisymmetric flow-focusing microfluidic device, Adv Mater 17(8):1067-1072.
Taly, 2007, Droplets as microreactors for high-throughput biology, Chembiochem 8(3):263-272.
Tan, 2003, Controlled fission of droplet emulsions in bifurcating microfluidic channels, 12th Int Conf SSAM 28-31.
Fan, 2007, Detection of aneuploidy with digital polymerase chain reaction, Anal Chem 79:75767579.
Huang, 2007, Identification of 8 foodborne pathogens by multicolor combinational probe coding technology in a single realtime PCR, Clin Chem 53(10):17418.
Kiss, 2008, High throughput quantitative polymerase chain reaction in picoliter droplets, Anal Chem 80(23):897581.
Li, 2009, Sensitive digital quantificaiton of DNA methylation in clinical samples, Nat Biotech 27(9):85863.
Sapsford, 2006, Materials for fluorescence resonance energy transfer analysis, Angew Chem Int Ed Engl 45 (28):456289.

* cited by examiner

- Mixture of multiple primers and probes
- 5 Taqman Assays in each droplet
  - Expression Analysis
  - Precise Quantification of copy number
  - Requires 1/5 the DNA of 5 opti-plex reactions
- Each reaction has a unique location in 2D scatter plot

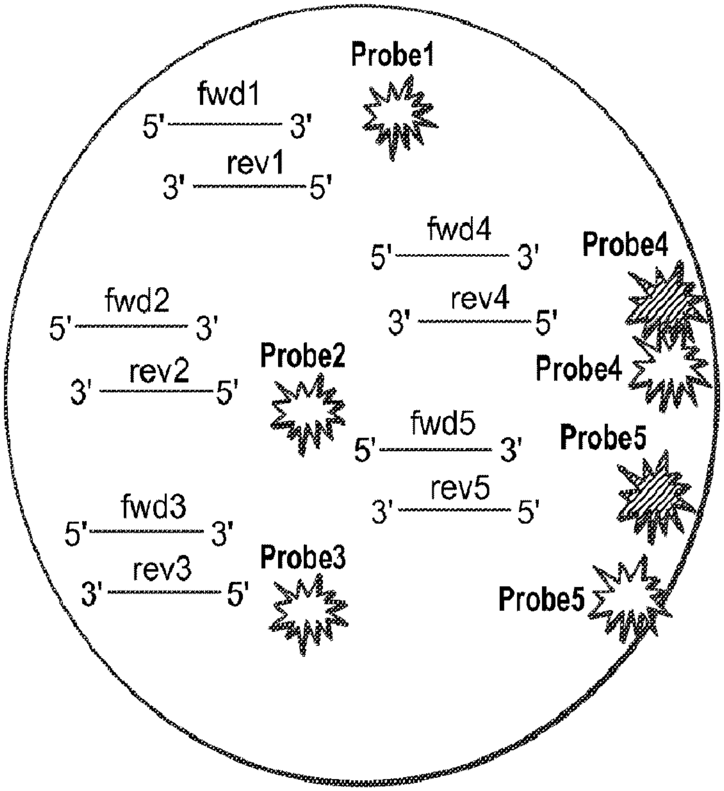
- Off-axis populations are generated by making blends of probes
- Expands optical space available for multiplexing assays
FIG. 6A
FIG. 6B
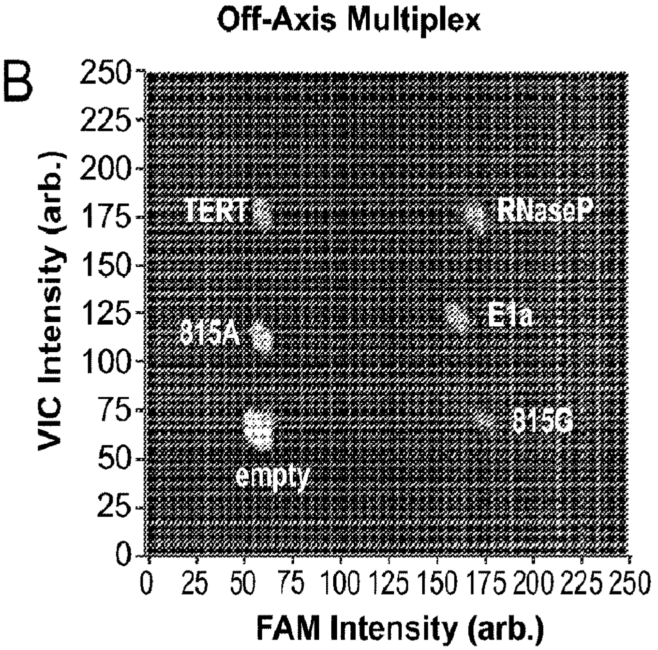
FIG. 6C
| NA03814+815G 215,897 drops | Copy Number | Measured Ratio/TERT |
|---|---|---|
| RNaseP | 2 | 1.01 |
| E1a | 2 | 0.997 |
| 815A | 6 | 3.02 |
| 815G | 1 | 0.497 |
| TERT | 2 | 1 |

Two Colors THREE Targets

Histogram showing four populations of droplets; with target1, with target2, with target3 and without any of the three targets.

FIG. 12A

Tuning the Intensity of Target 2

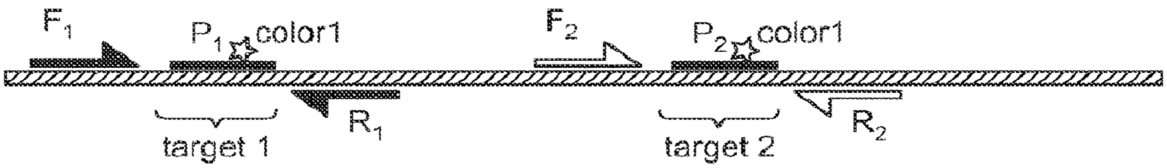

Probe 2 has a single base missmatch to target two and will produce a digital read-out of lower signal intensity

FIG. 12B

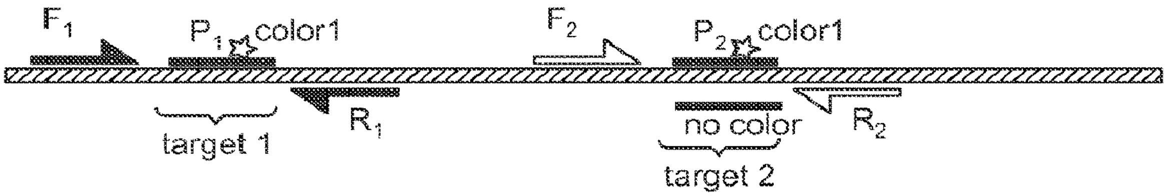

Probe 2 is a blend of identical probes doth with and without a fluorophore to reduce the overall intensity of the fluorescent signal

FIG. 12C

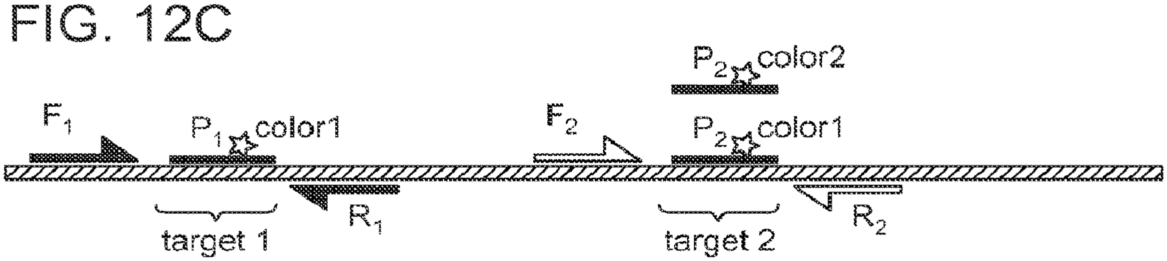

Probe 2 is a blend of identical probes each with a different color fluorophore to produce a multi-color fluorescent burst.

Relative intensity of signals from multiple targets of the same color can be generated in a variety of ways. Examples include: FIG.12A) using a single base missmatch of the probe and target to distinguish different targets. FIG.12B) blend identical probes with and without fluorophores. FIG.12C) blend identical probes with two or more different color fluorophores.

DIGITAL ANALYTE ANALYSIS

SEQUENCE LISTING

This application contains a sequence listing which has been submitted in ASCII format via EFS-Web and is hereby incorporated by reference in its entirety. The ASCII-formatted sequence listing, created on Jun. 8, 2022, is named "RDT-564-Seqs.txt," and is 3,042 bytes in size.

FIELD OF THE INVENTION

The invention generally relates to droplet based digital PCR and methods for analyzing a target nucleic acid using the same.

BACKGROUND

The widespread availability of archived tissue samples has proved to be a valuable resource for the advancement of genetic research. Formalin-fixed, paraffin-embedded (FFPE) tissue specimens, for example, can be stored indefinitely at room temperature and provide a wealth of genetic material for various molecular biology studies, such as expression profiling and sequence analysis. Although genetic material is recoverable from these samples, sample processing and extensive storage times can lead to significant degradation of nucleic acids within the specimen. This degradation can adversely affect the accuracy of results when the sample is tested. Unfortunately, the researcher will not know that a particular sample contains degraded genetic material until after the test has been conducted, when it is too late. Further compounding the problem, genetic tests are relatively expensive, and therefore, conducting these tests without knowing the quality of the sample beforehand may lead to a waste of resources. In addition, limited quantities of genetic starting material in the samples present further challenges.

The advent of PCR and real-time PCR methodologies has greatly improved the analysis of nucleic acids from both throughput and quantitative perspectives. While traditional PCR techniques typically rely on end-point, and sometimes semi-quantitative, analysis of amplified DNA targets via agarose gel electrophoresis, real-time PCR (or qPCR) methods are geared toward accurately quantifying exponential amplification as the reaction progresses. qPCR reactions are monitored either using a variety of highly sequence specific fluorescent probe technologies, or by using non-specific DNA intercalating fluorogenic dyes.

As the need for higher throughput in analyzing multiple targets in parallel continues to escalate in the fields of genomics and genetics, and as the need for more efficient use of sample grows in medically related fields such as diagnostics, the ability to perform and quantify multiple amplifications simultaneously within the same reaction volume (multiplexing) is paramount for both PCR and qPCR. While end-point PCR can support a high level of amplicon multiplexing, such ample capacity for multiplexing probe-based qPCR reactions remains elusive for a number of reasons. For example, most commercial real-time thermal cyclers only support up to four differently colored fluorophores for detection as a consequence of the limited spectral resolution of common fluorophores, translating into a multiplexing capacity of 4×. Additionally, while optimization of single target primer/probe reactions is now standard practice, combining primers and probes for multiple reactions changes the thermodynamic efficiencies and/or chemical kinetics, necessitating potentially extensive troubleshooting and optimization. Very high multiplexing of greater than100× has been demonstrated in a "one of many" detection format for pathogen identification using "sloppy" molecular beacons and melting points as fingerprints, however the approach is restricted to applications with a slim likelihood of the presence of multiple simultaneous targets. A half-multiplexing method achieved 19× in a two step reaction with general multiplexed preamplification in the first step, followed by separate single-plex quantitative PCR in the second step. However a general purpose single-pot solution to qPCR multiplexing does not yet exist.

Digital PCR (dPCR) is an alternative quantitation method in which dilute samples are divided into many separate reactions. See for example, Brown et al. (U.S. patent numbers 6,143,496 and 6,391,559) and Vogelstein et al. (U.S. Pat. Nos. 6,440,706, 6,753,147, and 7,824,889), the content of each of which is incorporated by reference herein in its entirety. The distribution from background of target DNA molecules among the reactions follows Poisson statistics, and at so called "terminal dilution" the vast majority of reactions contain either one or zero target DNA molecules for practical intents and purposes. In another case, at so called "limiting dilution" some reactions contain zero DNA molecules, some reactions contain one molecule, and frequently some other reactions contain multiple molecules, following the Poisson distribution. It is understood that terminal dilution and limiting dilution are useful concepts for describing DNA loading in reaction vessels, but they have no formal mathematical definition, nor are they necessarily mutually exclusive. Ideally, at terminal dilution, the number of PCR positive reactions (PCR(+)) equals the number of template molecules originally present. At limiting dilution, Poisson statistics are used to uncover the underlying amount of DNA. The principle advantage of digital compared to qPCR is that it avoids any need to interpret the time dependence of fluorescence intensity—an analog signal-along with the main underlying uncertainty of non-exponential amplification during early cycles.

SUMMARY

The invention generally relates to the manipulation of nucleic acid in droplets, and in particular, nucleic acid amplification and detection. In one aspect, the invention provides a droplet that contains a single nucleic acid template and a plurality of primer pairs specific for multiple target sites on the template. The single nucleic acid template can be DNA (e.g., genomic DNA, cDNA, etc.) or RNA. The template is amplified in the droplet for detection; and may preferably be amplified using a plurality of primer pairs as described herein.

The ability to amplify and detect single nucleic acids in droplets enables digital PCR, detection, counting, and differentiation among nucleic acids, especially those present in heterogeneous samples. Thus, the invention applies to digital amplification techniques and, in specific embodiments enables multiplex PCR in droplets. For example, multiplexing primers in droplets enables the simultaneous increase in the number of PCR droplets while keeping the amount of input DNA the same or lower and generate the same or greater amplicon yield. This results in an overall increase in the amount of PCR positive droplets and amplicon yield without the consumption of more DNA. Even though the number of PCR primer pairs per droplet is greater than one, there is only one template molecule per droplet, and thus, in some implementations, there is only one primer pair per droplet that is being utilized at one time. As such, the advantages of droplet PCR for eliminating bias from either allele specific PCR or competition between different amplicons is maintained. However, as described below in relation to detection of haplotypes, other implementations advantageously allow detection of multiple loci on a single template using multiple primer pairs, preferably designed to minimize bias.

Microfluidic droplets for multiplex analysis according to the invention contain a plurality of probes that hybridize to amplicons produced in the droplets. Preferably, the droplet contains two or more probes, e.g., 2, 3, 4, 5, 6, 7, 8, 9, 10, 12, 14, 16, 18, 20, 25, 30, 35, 40, 45, 50, 55, 60, 65, 60, 75, 80, 85, 90, 95, 100, 110, 120, 130, 140, 150, 160, 170, 180, 190, 200, 500, or more probes. Certain members of the plurality of probes include a detectable label. Members of the plurality of probes can each include the same detectable label, or a different detectable label. The detectable label is preferably a fluorescent label. The plurality of probes can include one or more groups of probes at varying concentrations. The one or more groups of probes can include the same detectable label which will vary in intensity upon detection, due to the varying probe concentrations. The droplets of the invention can further contain one or more reagents for conducting a polymerase chain reaction, such as a DNA or RNA polymerase, and/or dNTPs.

The present invention additionally relates to a method for detecting a plurality of targets in a biological sample using digital PCR in microfluidic droplets. The sample may be a human tissue or body fluid. Exemplary body fluids pus, sputum, semen, urine, blood, saliva, and cerebrospinal fluid.

One or more droplets are formed, each containing a single nucleic acid template and a heterogeneous mixture of primer pairs and probes, each specific for multiple target sites on the template. For example, a first fluid (either continuous, or discontinuous as in droplets) containing a single nucleic acid template (DNA or RNA) is merged with a second fluid (also either continuous, or discontinuous as in droplets) containing a plurality of primer pairs and a plurality of probes, each specific for multiple targets sites on the nucleic acid template to form a droplet containing the single nucleic acid template and a heterogeneous mixture of primer pairs and probes. The second fluid can also contain reagents for conducting a PCR reaction, such as a polymerase and dNTPs.

Certain members of the plurality of probes include a detectable label. Members of the plurality of probes can each include the same detectable label, or a different detectable label. The detectable label is preferably a fluorescent label. The plurality of probes can include one or more groups of probes at varying concentrations. The one or more groups of probes can include the same detectable label which varies in intensity upon detection, due to the varying probe concentrations.

The first and second fluids can each be in droplet form. Any technique known in the art for forming droplets may be used with methods of the invention. An exemplary method involves flowing a stream of the sample fluid containing the nucleic acid template such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the first fluid. The carrier fluid may be any fluid that is immiscible with the sample fluid. An exemplary carrier fluid is oil. In certain embodiments, the carrier fluid includes a surfactant, such as a fluorosurfactant. The same method may be applied to create individual droplets from the second fluid containing the primer pairs (and, in some implementations, the amplification reagents). Either the droplets containing the first fluid, the droplets containing the second fluid, or both, may be formed and then stored in a library for later merging, aspects of certain implementations of which are described in U.S. patent application Ser. No. 12/504,764, hereby incorporated herein in its entirety for all purposes. Once formed, droplets containing the first and second fluids can be merged to form single droplets containing the single nucleic acid template and heterogeneous mixture of primer pairs and probes. Merging can be accomplished, for example, in the presence of an electric field. Moreover, it is not required that both fluids be in the form of droplets when merging takes places. One exemplary method for merging of fluid portions with droplets is taught, for example, in co-pending U.S. Patent Application No. 61/441,985, filed on even date herewith.

The nucleic acid template in each of the merged/formed droplets is amplified, e.g., by thermocycling the droplets under temperatures/conditions sufficient to conduct a PCR reaction. The resulting amplicons in the droplets can then be analyzed. For example, the presence of absence of the plurality of targets in the one or more droplets is detected optically, e.g., by the detectable label on the plurality of probes.

The invention further relates to methods for analyzing a target nucleic acid. More particularly, methods of the invention are able to detect polymerase errors that occur during a PCR reaction and are able to exclude from analysis amplification products that are a result of a polymerase error. Methods of the invention are particularly useful in digital PCR where a polymerase error may result in a partitioned section of sample being incorrectly identified as containing a mutant allele, i.e., a false positive. Such false positives greatly impact the validity and precision of digital PCR results. Methods of the invention are able to uniquely detect multiple targets with the same optical color. Methods of the invention are particularly useful in digital PCR where it is desirable to identify multiple different target molecules that may be present in the starting test fluid.

Methods of the invention involve forming sample droplets containing target nucleic acid. Ideally, methods of the invention comprise forming droplets for digital PCR. Preferred digital PCR droplets contain one copy of a nucleic acid to be amplified, although they may contain multiple copies of the same nucleic acid sequence. Any technique known in the art for forming sample droplets may be used with methods of the invention. One exemplary method involves flowing a stream of sample fluid including nucleic acids such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets. The carrier fluid may be any fluid that is immiscible with the sample fluid. An exemplary carrier fluid is oil. In certain embodiments, the carrier fluid includes a surfactant, such as a fluorosurfactant.

The targets are then amplified in the droplets. Any method known in the art may be used to amplify the target nucleic acids either linearly or exponentially. A preferred method is the polymerase chain reaction (PCR). For purposes of the invention, any amplification technique commonly known in the art may be implemented such as rolling circle amplification, isothermal amplification, or any combination of amplification methods using loci specific primers, nested-primers, or random primers (such primers, and/or primers used for PCR, are included in the term "amplification reagents"). Once amplified, droplets containing amplicon from the target and amplicon from a variant of the target are excluded. One method to exclude droplets that contain a heterogeneous population of amplicons from droplets that contain a homogeneous population of amplicons includes hybridizing detectably-labeled probes to the amplicons, flowing the droplets through a microfluidic channel, and excluding those droplets in which both amplicon from the target and amplicon from a variant of the target are detected.

Once droplets containing a heterogeneous population of amplicons are excluded, droplets that contain a homogeneous population of amplicons are analyzed. Any analytical technique known in the art may be used. In certain embodiments, analyzing the droplets involves determining a number of droplets that contain only wild-type target, and determining a number of droplets that contain only a variant of the target. Generally, the presence of droplets containing only the variant is indicative of a disease, such as cancer. The variant may be an allelic variant. An exemplary allelic variant is a single nucleotide polymorphism. The variant may also be a specific haplotype. Haplotypes refer to the presence of two or more variants on the same nucleic acid strand. Haplotypes can be more informative or predictive than genotypes when used to determine such things as the presence or severity of disease, response to drug therapy or drug resistance of bacterial or viral infections. Because each droplet contains only one template strand it is an ideal vessel for the determination of haplotypes. The detection of two or more variants in a single droplet that contains a single intact nucleic acid strand identifies the haplotype of the variants on that strand. The presence of two or more markers in the same droplet can be identified by such methods as the presence of dyes of multiple colors or the increase in the intensity of a single dye or a combination of both. Any method that allows the identification of multiple variants in a single droplet enables the determination of a samples haplotype.

In accordance with some implementations of the invention, a method is provided for analyzing a target nucleic acid that includes compartmentalizing a first fluid into portions, each portion containing a single target nucleic acid; amplifying the target in the portions; excluding portions containing amplicon from the target and amplicon from a variant of the target; and analyzing target amplicons.

In other aspects, the invention generally provides methods for detecting a recurrence of a cancer in a patient. Those methods may involve forming sample droplets containing a single target nucleic acid derived from a patient sample, flowing the sample droplets through a channel, amplifying the target in the droplets, detecting amplified target in the droplets, excluding droplets including a heterogeneous population of amplicons, and analyzing non-excluded droplets to determine the presence of mutant alleles indicative of recurrence. In certain embodiments, the analyzing step includes capturing amplicon obtained from the droplets using labeled capture probes. The sample may be a human tissue or body fluid. Exemplary body fluids are pus, sputum, semen, urine, blood, saliva, stool, and cerebrospinal fluid. In other aspects of the invention generally provide a method for forensic identification of low levels of target nucleic acid in an environment having multiple other sources of nucleic acid. Such methods may also be practiced using fluids compartmentalized in containers other than or in addition to droplets.

In further aspects of the invention, methods of determining the nucleic acid make-up of a sample are provided. More specifically, these methods can be used to detect contiguous, intact sequences of RNA or DNA within a sample as well as fragments of those sequences. For certain experiments, samples comprising a higher proportion of contiguous, intact sequences are better candidates for additional testing than samples comprising mostly fragmented sequences. These methods may include partitioning a nucleic acid sample of different lengths into a plurality of different portions, where each portion includes, on average, a single nucleic acid molecule. A first and second primer pairs and a first and second detectably labeled probes are also introduced into the partitioned portions, where the first and second primer pairs are specific for first and second locations on the nucleic acid. If the nucleic acid contains the first and second locations spaced apart from each other, when the first probe hybridizes to the first location and the second probe hybridizes to the second location, an amplicon is created spanning a length. Thus, by amplifying the nucleic acid in the partitioned portions and detecting amplicons in the partitioned portions, the presence of signal from both probes indicates the presence of a nucleic acid that is contiguous between the first and second locations. By making this measurement for the plurality of portions, it is possible to determine a nucleic acid make-up of the sample based on the detecting step. In certain embodiments, the determining step may include comparing relative amounts of contiguous nucleic acid to relative amounts of non-contiguous nucleic acid. In other embodiments, the determining step may include comparing relative amounts of contiguous nucleic acid or non-contiguous nucleic acid to a total amount of nucleic acid.

Methods in accordance with the invention also encompass the use of a single primer pair. The method includes providing a fluid comprising the sample nucleic acid and a plurality of one or more primer pairs, wherein each primer pair has at least one unique related probe and is selected to be complementary to one or more sequences of known length. The method also includes partitioning the fluid into a plurality of partitions, wherein at least a first portion of the partitions comprise one molecule of the nucleic acid sample having sequences complementary to one or more of the primer pairs, and at least one related probe, and a second portion of the partitions comprise no molecules of the sample nucleic acid having sequences complementary to one or more of the primer pairs. The method further includes conducting a PCR reaction in the partitions, thereby changing a fluorescent property of the first portion of the partitions, detecting the fluorescent property of each partition, and determining the number of occurrences in the sample nucleic acid of one or more sequences of known length based on the detecting step. In some aspects of the invention, the method further includes comparing a first number of occurrences of a first sequence of known length to a second number of occurrences of a second sequence of a second known length.

Additional embodiments of the invention may also contemplate the use of a single primer pair as well as rely on something other than a probe for detecting the amplified sequence. In certain embodiments, the method comprises partitioning a sample comprising nucleic acid of different lengths into a plurality of partitioned portions, wherein each portion comprises, on average a single nucleic acid molecule. The method further includes introducing at least one primer pair, in which each primer of the pair is specific for a first and second location on the nucleic acid, the first and second locations being spaced apart from each other. The method further includes amplifying the nucleic acid in the partitioned portions, detecting the amplicons in the partitioned portions, and determining a nucleic acid make-up of the sample based on the results of the detecting step.

Methods in accordance with the invention also encompass the analysis of cell-free nucleic acids in a biological sample. In some embodiments, the biological sample can be blood, saliva, sputum, urine, semen, transvaginal fluid, cerebrospinal fluid, sweat, breast milk, breast fluid (e.g., breast nipple aspirate), stool, a cell or a tissue biopsy.

The methods of the invention can also be used to evaluate the quality of cell-free nucleic acids, for example cell-free DNA or RNA, which can be obtained from a biological sample. The invention allows the cell-free nucleic acid to be evaluated for quality, e.g., continuity, prior to amplification and sequencing. Thus, a cell-free nucleic acid sample can be partitioned into samples comprising nucleic acids of different lengths, primer pairs can be introduced along with appropriate probes, the nucleic acids amplified, and the make-up, e.g., the continuity of the cell-free nucleic acid sample can be determined.

BRIEF DESCRIPTION OF THE DRAWINGS

FIG. 3*a* depicts the droplet generation chip; FIG. 3*b* depicts the droplet spacing for readout; and FIG. 3*c* depicts a cartoon of droplet readout by fluorescence.

FIG. 4*a* shows droplet fluorescence during readout for the most concentrated sample. Each discrete burst of fluorescence corresponded to an individual droplet. Two different groups of droplets were evident: PCR(+) droplets peaking at ~0.8 V and PCR(−) droplets at ~0.1 V; FIG. 4*b* shows a histogram of the peak fluorescence intensities of droplets from the complete data trace in (a). PCR(+) and PCR(−) droplets appeared as two very distinct populations centered at 0.78 and 0.10 V, respectively; FIG. 4*c* shows the serial dilution of template DNA. Open circles: measured occupancies; solid line: the best fit to Eqn 2 (A=0.15, f=4.8, $R^2$—0.9999).

FIG. 6A is a schematic representation of a droplet having 5 sets of primers for PCR amplification of a template sequence and 5 probes, each labeled with a fluorescent dye, that binds specifically to the amplified sequences; FIG. 6B is a scatter plot showing clusters representing droplets that contain specific amplified sequences (TERT, 815A, RNaseP, Ela, and 815G); FIG. 6C is a table showing the copy number of specific sequences shown in FIG. 6B.

FIG. 11*a* depicts a histogram of droplet peak fluorescence intensities; FIG. 11*b* shows a comparison of gene copy numbers measured by monochromatic dPCR.

FIGS. 12A-C show a schematic for tuning the intensity of a detectable label to a particular target with a microfluidic device.

FIG. 14*a* is a 2D histogram of droplet fluorescence intensities, shown as a heat map, for the 5-plex assay, against the synthetic model chromosome for validation. The six well resolved droplet populations corresponded to the five individual assays plus the empty droplets; FIG. 14*b* shows the results of the SMA pilot study.

FIG. 15 shows 2-D histograms of droplet fluorescence intensity, shown as heat maps with hotter colors representing higher droplet counts, for the 9-plex assay against the synthetic model chromosome (left panel=Before optimization; right panel=after optimization).

DETAILED DESCRIPTION

Figure 1:
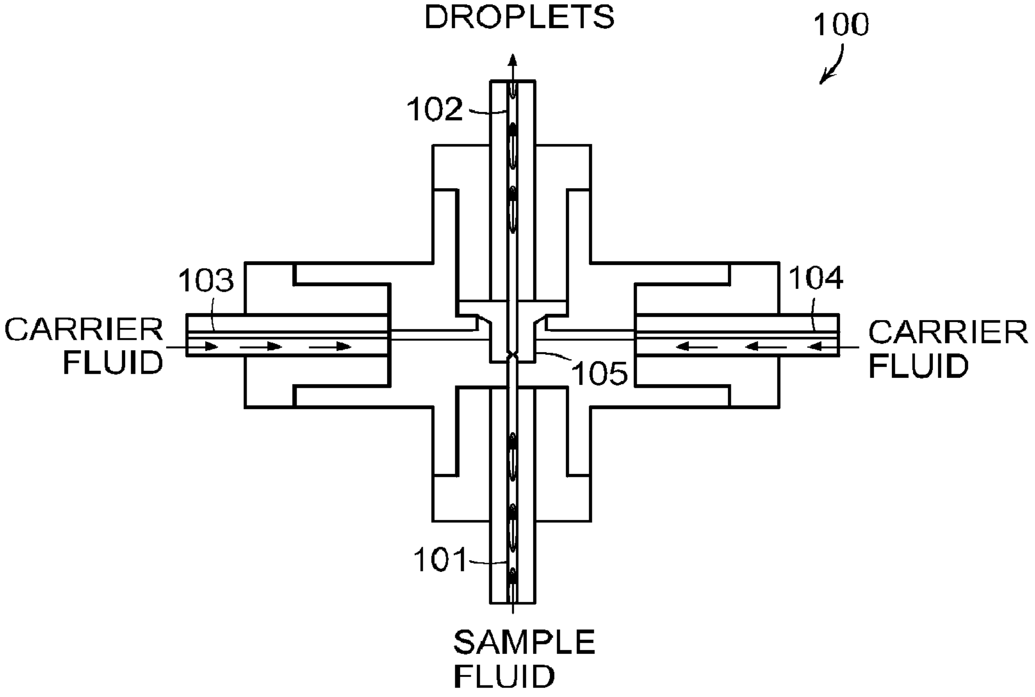
FIG. 1 depicts a droplet formation device.

The invention provides materials and methods for analysis of biomolecules. In one aspect, the invention provides for digital analysis in droplets, such as microfluidic droplets. The invention allows digital PCR to be conducted and provides for significantly reduced or eliminated errors.

Ideally, the sensitivity of digital PCR is limited only by the number of independent amplifications that can be analyzed, which has motivated the development of several ultra-high throughput miniaturized methods allowing millions of single molecule PCR reactions to be performed in parallel (discussed in detail elsewhere). In a preferred embodiment of the invention, digital PCR is performed in aqueous droplets separated by oil using a microfluidics system. In another preferred embodiment, the oil is a fluorinated oil such as the Fluorinert oils (3M). In a still more preferred embodiment the fluorinated oil contains a surfactant, such as PFPE-PEG-PFPE triblock copolymer, to stabilize the droplets against coalescence during the amplification step or at any point where they contact each other. Microfluidic approaches allow the rapid generation of large numbers (e.g., $10^6$ or greater) of very uniformly sized droplets that function as picoliter volume reaction vessels (see reviews of droplet-based microfluidics). But as will be described, the invention is not limited to dPCR performed in water-in-oil emulsions, but rather is general to all methods of reaction compartmentalization for dPCR. In the description that follows, the invention is described in terms of the use of droplets for compartmentalization, but it is understood that this choice of description is not limiting for the invention, and that all of the methods of the invention are compatible with all other methods of reaction compartmentalization for dPCR.

Methods of the invention involve novel strategies for performing multiple different amplification reactions on the same sample simultaneously to quantify the abundance of multiple different DNA targets, commonly known to those familiar with the art as “multiplexing”. Methods of the invention for multiplexing dPCR assays promise greater plexity—the number of simultaneous reactions—than possible with existing qPCR or dPCR techniques. It is based on the singular nature of amplifications at terminal or limiting dilution that arises because most often only a single target allele is ever present in any one droplet even when multiple primers/probes targeting different alleles are present. This alleviates the complications that otherwise plague simultaneous competing reactions, such as varying arrival time into the exponential stage and unintended interactions between primers.

In one aspect, the invention provides materials and methods for improving amplicon yield while maintaining the sensitivity and specificity in droplet based digital PCR. More specifically, the invention provides droplets containing a single nucleic acid template and multiplexed PCR primers and methods for detecting a plurality of targets in a biological sample by forming such droplets and amplifying the nucleic acid templates using droplet based digital PCR.

Reactions within microfluidic droplets yield very uniform fluorescence intensity at the end point, and ultimately the intensity depends on the efficiency of probe hydrolysis. Thus, in another aspect of the methods of the invention, different reactions with different efficiencies can be discriminated on the basis of end point fluorescence intensity alone even if they have the same color. Furthermore, in another method of the invention, the efficiencies can be tuned simply by adjusting the probe concentration, resulting in an easy-to-use and general purpose method for multiplexing. In one demonstration of the invention, a 5-plex TaqMan® dPCR assay worked “right out of the box”, in contrast to lengthy optimizations that typify qPCR multiplexing to this degree. In another aspect of the invention, adding multiple colors increases the number of possible reactions geometrically, rather than linearly as with qPCR, because individual reactions can be labeled with multiple fluorophores. As an example, two fluorophores (VIC and FAM) were used to distinguish five different reactions in one implementation of the invention.

Methods of the invention are able to detect polymerase errors that occur during an amplification reaction and are able to exclude from analysis those products that are a result of polymerase errors. In essence, methods of the invention increase the sensitivity of digital PCR by identifying amplification products that are false positives, and excluding those products from analysis.

Methods of the invention involve forming sample droplets containing a single target nucleic acid, amplifying the target in the droplets, excluding droplets containing amplicon from the target and amplicon from a variant of the target, and analyzing target amplicons.

Nucleic Acid Target Molecules

Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain, embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule and serve as a surrogate for quantifying and/or detecting the target molecule.

Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures).

Droplet Formation

Methods of the invention involve forming sample droplets where some droplets contain zero target nucleic acid molecules, some droplets contain one target nucleic acid molecule, and some droplets may or may not contain multiple nucleic acid molecules (corresponding to limiting or terminal dilution, respectively, as defined above). In the preferred embodiment, the distribution of molecules within droplets obeys the Poisson distribution. However, methods for non-Poisson loading of droplets are known to those familiar with the art, and include but are not limited to active sorting of droplets, such as by laser-induced fluorescence, or by passive one-to-one loading. The description that follows assumes Poisson loading of droplets, but such description is not intended to exclude non-Poisson loading, as the invention is compatible with all distributions of DNA loading that conform to limiting or terminal dilution.

The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety.

Figure 2:
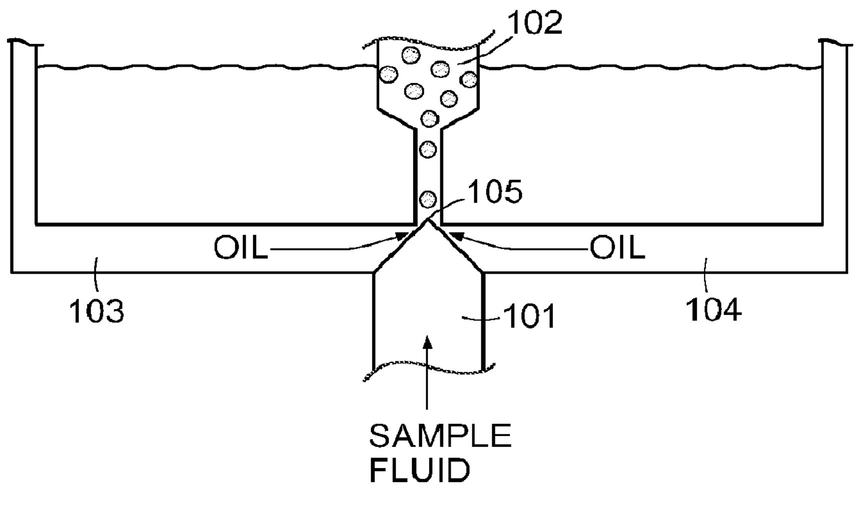
FIG. 2 depicts a portion of the droplet formation device of FIG. 1.

FIG. 1 shows an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 2). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA-(TE) buffer, phosphate buffer saline (PBS) or acetate buffer. Any liquid or buffer that is physiologically compatible with nucleic acid molecules can be used. The carrier fluid is one that is immiscible with the sample fluid. The carrier fluid can be a non-polar solvent, decane (e.g., tetradecane or hexadecane), fluorocarbon oil, silicone oil or another oil (for example, mineral oil).

In certain embodiments, the carrier fluid contains one or more additives, such as agents which increase, reduce, or otherwise create non-Newtonian surface tensions (surfactants) and/or stabilize droplets against spontaneous coalescence on contact. Surfactants can include Tween, Span, fluorosurfactants, and other agents that are soluble in oil relative to water. In some applications, performance is improved by adding a second surfactant, or other agent, such as a polymer or other additive, to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant or a mixture of surfactants. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM; and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated/mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the carrier fluid.

One approach to merging sample fluids, using a device called a lambda injector, involves forming a droplet, and contacting the droplet with a fluid stream, in which a portion of the fluid stream integrates with the droplet to form a mixed droplet. In this approach, only one phase needs to reach a merge area in a form of a droplet. Further description of such method is shown in the co-owned and co-pending U.S. patent application to Yurkovetsky, et al. (U.S. patent application Ser. No. 61/441,985), the content of which is incorporated y reference herein in its entirety.

According to a method for operating the lambda injector, a droplet is formed as described above. After formation of the sample droplet from the first sample fluid, the droplet is contacted with a flow of a second sample fluid stream. Contact between the droplet and the fluid stream results in a portion of the fluid stream integrating with the droplet to form a mixed droplet.

The droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. Preferably, the channels are oriented perpendicular to each other. However, any angle that results in an intersection of the channels may be used.

The bolus of the second sample fluid stream continues to increase in size due to pumping action of a positive displacement pump connected to channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet to form a mixed droplet. In certain embodiments, each incoming droplet of first sample fluid is merged with the same amount of second sample fluid.

In certain embodiments, an electric charge is applied to the first and second sample fluids. Description of applying electric charge to sample fluids is provided in Link et al. (U.S. patent application number 2007/0003442) and European Patent Number EP2004316 to Raindance Technologies Inc, the content of each of which is incorporated by reference herein in its entirety. Electric charge may be created in the first and second sample fluids within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or -embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of bolus of the second sample fluid and the first sample fluid droplet. The forming mixed droplet continues to increase in size until it a portion of the second sample fluid breaks free or segments from the second sample fluid stream prior to arrival and merging of the next droplet containing the first sample fluid. The segmenting of the portion of the second sample fluid from the second sample fluid stream occurs as soon as the shear force exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel.

In other embodiments, the rupture of the interface can be spontaneous, or the rupture can be facilitated by surface chemistry. The invention is not limited in regard to the method of rupture at the interface, as rupture can be brought about by any means.

In the context of PCR, in a preferred embodiment, the first sample fluid contains nucleic acid templates. Droplets of the first sample fluid are formed as described above. Those droplets will include the nucleic acid templates. In certain embodiments, the droplets will include only a single nucleic acid template, and thus digital PCR can be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. A droplet containing the nucleic acid is then caused to merge with the PCR reagents in the second fluid as described above, producing a droplet that includes Taq polymerase, deoxynucleotides of type A, C, G and T, magnesium chloride, forward and reverse primers, detectably labeled probes, and the target nucleic acid. In another embodiment, the first fluid can contain the template DNA and PCR master mix (defined below), and the second fluid can contain the forward and reverse primers and the probe. The invention is not restricted in any way regarding the constituency of the first and second fluidics for PCR or digital PCR. For example, in some embodiments, the template DNA is contained in the second fluid inside droplets.

Target Amplification

Methods of the invention further involve amplifying the target nucleic acid in each droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, ligase chain reaction (Barany F. (1991) PNAS 88:189-193; Barany F. (1991) PCR Methods andApplications 1:5-16), ligase detection reaction (Barany F. (1991) PNAS 88:189-193), strand displacement amplification, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other and by cycling parameters, and therefore, this length is a controllable parameter.

Methods for performing PCR in droplets are shown for example in Link et al. (U.S. patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

The sample droplet may be pre-mixed with a primer or primers, or the primer or primers may be added to the droplet. In some embodiments, droplets created by segmenting the starting sample are merged with a second set of droplets including one or more primers for the target nucleic acid in order to produce final droplets. The merging of droplets can be accomplished using, for example, one or more droplet merging techniques described for example in Link et al. (U.S. patent application numbers 2008/0014589, 2008/0003142, and 2010/0137163) and European publication number EP2047910 to Raindance Technologies Inc.

In embodiments involving merging of droplets, two droplet formation modules are used. In one embodiment, a first droplet formation module produces the sample droplets consistent with limiting or terminal dilution of target nucleic acid. A second droplet formation or reinjection module inserts droplets that contain reagents for a PCR reaction. Such droplets generally include the "PCR master mix" (known to those in the art as a mixture containing at least Taq polymerase, deoxynucleotides of type A, C, G and T, and magnesium chloride) and forward and reverse primers (known to those in the art collectively as "primers"), all suspended within an aqueous buffer. The second droplet also includes detectably labeled probes for detection of the amplified target nucleic acid, the details of which are discussed below. Different arrangements of reagents between the two droplet types is envisioned. For example, in another embodiment, the template droplets also contain the PCR master mix, but the primers and probes remain in the second droplets. Any arrangement of reagents and template DNA can be used according to the invention.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Another method for determining the melting temperature of primers is the nearest neighbor method Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

In one embodiment, the droplet formation modules are arranged and controlled to produce an interdigitation of sample droplets and PCR reagent droplets flowing through a channel. Such an arrangement is described for example in Link et al. (U.S. patent application numbers 2008/0014589, 2008/0003142, and 2010/0137163) and European publication number EP2047910 to Raindance Technologies Inc.

A sample droplet is then caused to merge with a PCR reagent droplet, producing a droplet that includes the PCR master mix, primers, detectably labeled probes, and the target nucleic acid. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/0014589, 2008/0003142, and 2010/0137163) and European publication number EP2047910 to Raindance Technologies Inc. Further description of producing and controlling dielectrophoretic forces on droplets to cause the droplets to merge is described in Link et al. (U.S. patent application number 2007/0003442) and European Patent Number EP2004316 to Raindance Technologies Inc.

In another embodiment, called simple droplet generation, a single droplet formation module, or a plurality of droplet formation modules are arranged to produce droplets from a mixture already containing the template DNA, the PCR master mix, primers, and detectably labeled probes. In yet another embodiment, called co-flow, upstream from a single droplet formation module two channels intersect allowing two flow streams to converge. One flow stream contains one set of reagents and the template DNA, and the other contains the remaining reagents. In the preferred embodiment for co-flow, the template DNA and the PCR master mix are in one flow stream, and the primers and probes are in the other. However, the invention is not limited in regard to the constituency of either flow stream. For example, in another embodiment, one flow stream contains just the template DNA, and the other contains the PCR master mix, the primers, and the probes. On convergence of the flow streams in a fluidic intersection, the flow streams may or may not mix before the droplet generation nozzle. In either embodiment, some amount of fluid from the first stream, and some amount of fluid from the second stream are encapsulated within a single droplet. Following encapsulation, complete mixing occurs.

Once final droplets have been produced by any of the droplet forming embodiments above, or by any other embodiments, the droplets are thermal cycled, resulting in amplification of the target nucleic acid in each droplet. In certain embodiments, the droplets are collected off-chip as an emulsion in a PCR thermal cycling tube and then thermally cycled in a conventional thermal cycler. Temperature profiles for thermal cycling can be adjusted and optimized as with any conventional DNA amplification by PCR.

In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, New York, 2001).

In certain embodiments, the three temperature zones are controlled to have temperatures as follows: 95° C. ($T_H$), 55° C. ($T_L$), 72° C. ($T_M$). The prepared sample droplets flow through the channel at a controlled rate. The sample droplets first pass the initial denaturation zone ($T_H$) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. Methods for controlling the temperature in each zone may include but are not limited to electrical resistance, peltier junction, microwave radiation, and illumination with infrared radiation.

The nucleic acids undergo the same thermal cycling and chemical reaction as the droplets passes through each thermal cycle as they flow through the channel. The total number of cycles in the device is easily altered by an extension of thermal zones or by the creation of a continuous loop structure. The sample undergoes the same thermal cycling and chemical reaction as it passes through N amplification cycles of the complete thermal device.

In other embodiments, the temperature zones are controlled to achieve two individual temperature zones fora PCR reaction. In certain embodiments, the two temperature zones are controlled to have temperatures as follows: 95° C. (Tx) and 60° C. (TL). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately, 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

In another embodiment the droplets are created and/or merged on chip followed by their-storage either on the same chip or another chip or off chip in some type of storage vessel such as a PCR tube. The chip or storage vessel containing the droplets is then cycled in its entirety to achieve the desired PCR heating and cooling cycles.

In another embodiment the droplets are collected in a chamber where the density difference between the droplets and the surrounding oil allows for the oil to be rapidly exchanged without removing the droplets. The temperature of the droplets can then be rapidly changed by exchange of the oil in the vessel for oil of a different temperature. This technique is broadly useful with two and three step temperature cycling or any other sequence of temperatures.

The invention is not limited by the method used to thermocycle the droplets. Any method of thermocycling the droplets may be used.

Target Detection

After amplification, droplets are flowed to a detection module for detection of amplification products. For embodiments in which the droplets are thermally cycled off-chip, the droplets require re-injection into either a second fluidic circuit for read-out—that may or may not reside on the same chip as the fluidic circuit or circuits for droplet generation—or in certain embodiments the droplets may be reinjected for read-out back into the original fluidic circuit used for droplet generation. The droplets may be individually analyzed and detected using any methods known in the art, such as detecting the presence or amount of a reporter. Generally, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In certain embodiments, amplified target are detected using detectably labeled probes. In particular embodiments, the detectably labeled probes are optically labeled probes, such as fluorescently labeled probes. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.TM. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are FAM and VICT™ (from Applied Biosystems). Labels other than fluorescent labels are contemplated by the invention, including other optically-detectable labels.

In certain aspects, the droplets of the invention contain a plurality of detectable probes that hybridize to amplicons produced in the droplets. Members of the plurality of probes can each include the same detectable label, or a different detectable label. The plurality of probes can also include one or more groups of probes at varying concentration. The groups of probes at varying concentrations can include the same detectable label which vary in intensity, due to varying probe concentrations.

In some embodiments, the droplets of the invention contain a plurality of barcodes that hybridize to amplicon's produced in the droplets or are incorporated into the amplicons. The barcodes may be used in lieu of fluorescent probes, to detect the presence of a target sequence, or the barcodes can be used in addition to fluorescent probes, to track a multitude of sample sources. A detectable barcode-type label can be any barcode-type label known in the art including, for example, barcoded magnetic beads (e.g., from Applied Biocode, Inc., Santa Fe Springs, CA), and nucleic acid sequences. Nucleic acid barcode sequences typically include a set of oligonucleotides ranging from about 4 to about 20 oligonucleotide bases (e.g., 8-10 oligonucleotide bases) and uniquely encode a discrete library member without containing significant homology to any sequence in the targeted sample.

The barcode sequence generally includes features useful in sequencing reactions. For example, the barcode sequences are designed to have minimal or no homopolymer regions, i.e., 2 or more of the same base in a row such as AA or CCC, within the barcode sequence. The barcode sequences are also designed so that they are at least one edit distance away from the base addition order when performing base-by-base sequencing, ensuring that the first and last base do not match the expected bases of the sequence. In certain embodiments, the barcode sequences are designed to be correlated to a particular subject, allowing subject samples to be distinguished. Designing barcodes is shown U.S. Pat. No. 6,235,475, the contents of which are incorporated by reference herein in their entirety.

In some instances, the primers used in the invention may include barcodes such that the barcodes will be incorporated into the amplified products. For example, the unique barcode sequence could be incorporated into the 5' end of the primer, or the barcode sequence could be incorporated into the 3' end of the primer. In some embodiments, the barcodes may be incorporated into the amplified products after amplification. For example, a suitable restriction enzyme (or other endonuclease) may be introduced to a sample, e.g., a droplet, where it will cut off an end of an amplification product so that a barcode can be added with a ligase.

Attaching barcode sequences to nucleic acids is shown in U.S. Pub. 2008/0081330 and PCT/US09/64001, the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety.

In a separate embodiment the detection can occur by the scanning of droplets confined to a monolayer in a storage device that is transparent to the wavelengths or method or detection. Droplets stored in this fashion can be scanned either by the movement of the storage device by the scanner or the movement of the scanner over the storage device.

The invention is not limited to the TaqMan assay, as described above, but rather the invention encompasses the use of all fluorogenic DNA hybridization probes, such as molecular beacons, Solaris probes, scorpion probes, and any other probes that function by sequence specific recognition of target DNA by hybridization and result in increased fluorescence on amplification of the target sequence.

Digital PCR Performance in Droplets

Digital PCR performance in the emulsion format was validated by measuring a serial dilution of a reference gene, branched chain keto acid dehydrogenase El (BCKDHA). Mixtures of the PCR master mix, 1× primers and probe for BCKDHA, and varying concentrations of a mixture of human genomic DNA (1:1 NA 14091 and NA13705) were compartmentalized into over one million 5.3 pL droplets in a water-in-fluorinated oil emulsion using the droplet generation microfluidic chip. The emulsion was thermally cycled off-chip and afterwards the fluorescence of each droplet was analyzed by fluorescence in the readout chip (see FIGS. 3*a-c*).

Figure 3A:
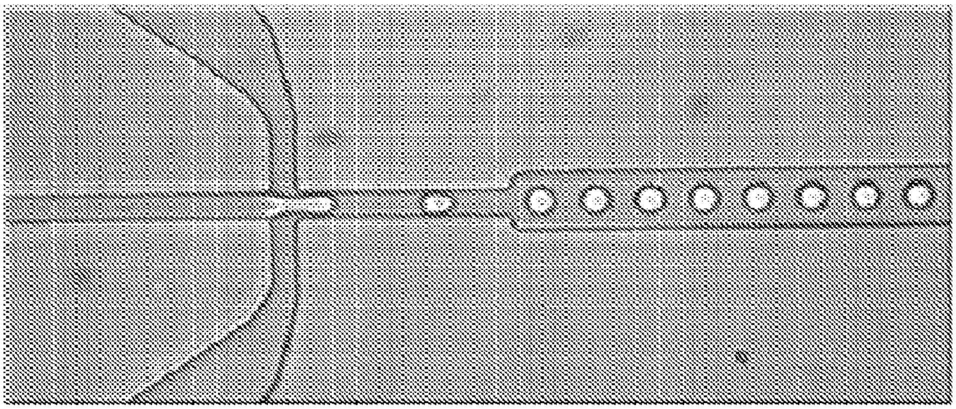
FIGS. 3*a*-*c* depict an exemplary microfluidic system for droplet generation and readout.
Figure 3B:
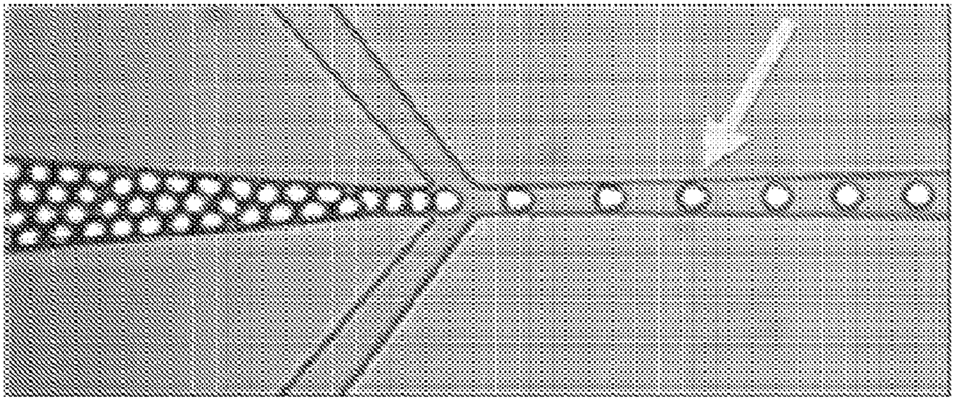
Figure 3C:
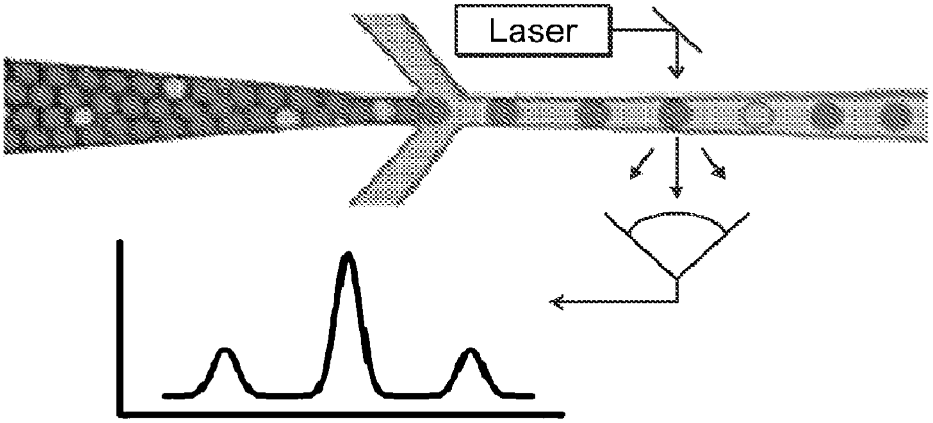

An exemplary microfluidic system for droplet generation and readout is depicted in FIGS. 3*a-c*. The microfluidic system for droplet generation and readout. As shown in FIG. 3*a* (droplet generation chip), a continuous aqueous phase containing the PCR master mix, primers, and probes, and template DNA flowed into the fluidic intersection from the left, and the carrier oil entered from the top and bottom. An emerging bolus of aqueous liquid was imaged inside the intersection just prior to snapping off into a discrete 4 pL droplet as the fluidic strain began to exceed the surface tension of the aqueous liquid. The steady train of droplets leaving the intersection toward the right was collected off chip as a stable emulsion for thermal cycling. FIG. 3*b* depicts the droplet spacing for readout. Flows were arranged as in 3a, except instead of a continuous phase, the emulsion from (a) was injected from the left into the intersection after thermal cycling. The oil drained from the emulsion during off-chip handling, hence the emulsion appeared tightly packed in the image before the intersection. The oil introduced in the intersection separated the droplets and the fluorescence of each droplet was measured at the location marked by the arrow. FIG. 3*c* depicts a cartoon of droplet readout by fluorescence. The relatively infrequent PCR(+) droplets (light gray) flow along with the majority of PCR(−) droplets (dark gray) toward the detector. The droplets were interrogated sequentially by laser induced fluorescence while passing through the detection region.

In a serial dilution the average number of target DNA molecules per droplet-called the "occupancy" from this point forward-should decrease in direct proportion to the DNA concentration. The occupancy was calculated from Poisson statistics using the following equation well known to those experienced in the art:

$$\text{occupancy}=\ln((P+N)/N), \qquad (1)$$

where P and N are the numbers of PCR(+) and PCR(−) droplets respectively.

Figure 4A:
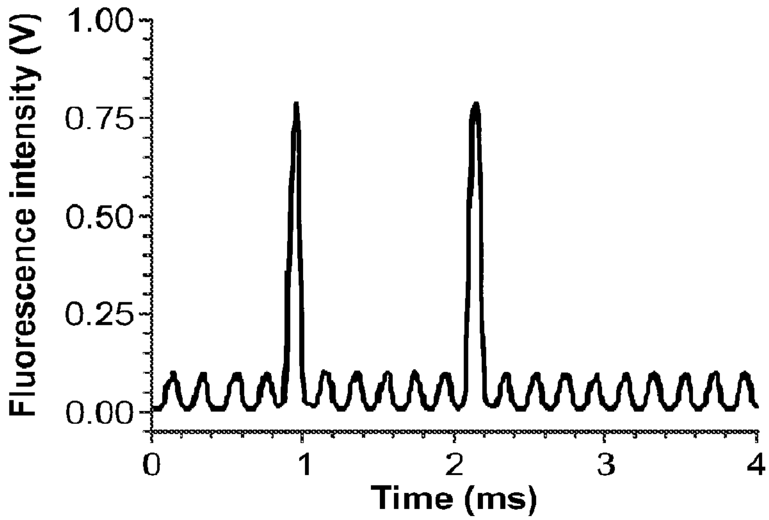
FIGS. 4*a*-*c* depict the serial dilution of template DNA quantified by dPGR.
Figure 4B:
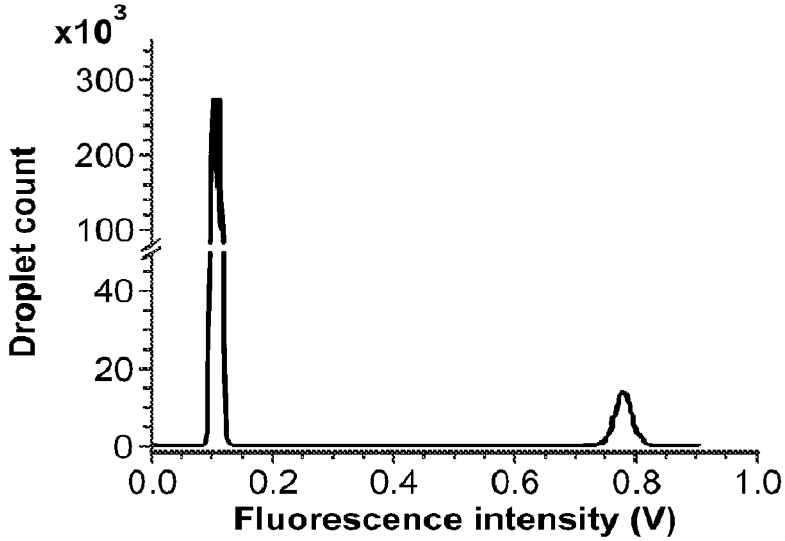
Figure 4C:
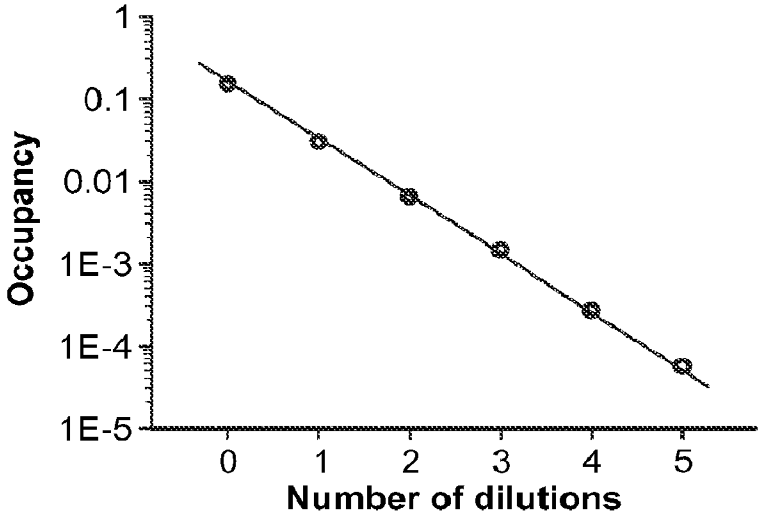

Droplets were analyzed by fluorescence while flowing through the readout chip to count the numbers of PCR(+) and PCR(−) droplets (see FIG. 3*c*). As each droplet passed the detection zone (marked with an arrow in FIG. 3*b*), a burst of fluorescence was observed. To account for small run-to-run differences in the fluorescence intensity that can occur due to different chip positioning, etc., each set of data was scaled such that the average fluorescence intensity of the empty droplets was 0.1 V. FIG. 4*a* shows a very short duration of a typical trace of fluorescence bursts from individual droplets for the sample with the highest DNA concentration in the series. PCR(+) and PCR(−) droplets were easily discriminated by fluorescence intensity. The two large bursts of fluorescence peaking at ~0.8 V arose from the PCR(+) droplets, whereas the smaller bursts due to incomplete fluorescence quenching in the PCR(−) droplets peaked at ~0.1 V. A histogram of peak intensities from the complete data set revealed two clear populations centered at 0.10 and 0.78 V (FIG. 4*b*), demonstrating that the trend evident in the short trace in FIG. 4*a* was stable over much longer periods of time. Integration over the two populations in FIG. 4*b* yielded a total of 197,507 PCR(+) and 1,240,126 PCR(−) droplets. Hence the occupancy was 0.15 for this sample by Eqn. 1, corresponding to the expected occupancy of 0.18 based on the measured DNA concentration of 110 ng/μL. The occupancy was measured for each sample in the serial dilution and fit to the dilution equation:

$$\text{occupancy}(n)=A/f^n, \qquad (2)$$

where n is the number of dilutions, A is the occupancy at the starting concentration (n=0), and f is the dilution factor. The linear fit was in excellent agreement with the data, with an $R^2$ value of 0.9999 and the fitted dilution factor of 4.8 in close agreement with the expected value of 5.0.

Multiplexing Primers in a Digital PCR Reaction

Droplet based digital PCR technology, as described in Link et al. (U.S. patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc, (the contents of each of which are incorporated by reference herein in their entireties) utilizes a single primer pair per library droplet. This library droplet is merged with a template droplet which contains all the PCR reagents including genomic DNA except for the primers. After merging of the template and the primer library droplets the new droplet now contains all the reagents necessary to perform PCR. The droplet is then thermal cycled to produce amplicons. In one embodiment, the template DNA is diluted in the template mix such that on average there is less than one haploid genome per droplet.

Having only one haploid genome (i.e., one allele) per droplet gives droplet PCR advantages over standard singleplex or multiplex PCR in tubes or microwells. For example, in traditional PCR, both alleles are present in the reaction mix so if there is a difference in the PCR efficiency between alleles, the allele with the highest efficiency will be over represented. Additionally, there can be variances in the sequence to which the PCR primers hybridize, despite careful primer design. A variance in the primer hybridization sequence can cause that primer to have a lower efficiency for hybridization for the allele that has the variance compared to the allele that has the wild type sequence. This can also cause one allele to be amplified preferentially over the other allele if both alleles are present in the same reaction mix.

These issues are avoided in droplet based PCR because there is only one template molecule per droplet, and thus one allele per droplet. Thus, even if primer variance exists that reduces the PCR efficiency for one allele, there is no competition between alleles because the alleles are separated and thus uniformly amplified.

Optimization of traditional multiplexing of standard PCR primers in tubes or wells is known to be difficult. Multiple PCR amplicons being generated in the same reaction can lead to competition between amplicons that have differing efficiencies due to differences in sequence or length. This results in varying yields between competing amplicons which can result in non uniform amplicon yields. However, because droplet based digital PCR utilizes only one template molecule per droplet, even if there are multiple PCR primer pairs present in the droplet, only one primer pair will be active. Since only one amplicon is being generated per droplet, there is no competition between amplicons, resulting in a more uniform amplicon yield between different amplicons.

A certain amount of DNA is required to generate either a specific quantity of DNA and/or a specific number of PCR positive droplets to achieve sufficient sequencing coverage per base. Because only a percentage of the droplets are PCR positive, approximately 1 in 3 in the standard procedure, it takes more DNA to achieve the equivalent PCR yield per template DNA molecule. The number of PCR positive droplets and thus the amplicon yield can be increased by adding more genomic DNA. For instance, increasing the amount of genomic DNA twofold while maintaining the number of droplets constant will double the amplicon yield. However there is a limit to the amount of genomic DNA that can be added before there is a significant chance of having both alleles for a gene in the same droplet, thereby eliminating the advantage of droplet PCR for overcoming allele specific PCR and resulting in allelic dropout.

One way to allow the input of more genomic DNA is by generating more droplets to keep the haploid molecules per droplet ratio constant. For instance doubling the amount of DNA and doubling the amount of droplets increases the amplicon yield by 2× while maintaining the same haploid genome per droplet ratio. However, while doubling the number of droplets isn't problematic, increasing the amount of DNA can be challenging to users that have a limited amount of DNA.

The multiplexing of PCR primers in droplets enables the simultaneous increase in the number of PCR droplets while keeping the amount of input DNA the same or lower to generate an equal or greater amplicon yield. This results in an overall increase in the amount of PCR positive droplets and amplicon yield without the consumption of more DNA.

By way of example, if there is an average of 1 haploid genome per every 4 droplets or 1/4 of the haploid genome per droplet and one PCR primer pair per droplet, the chances of the correct template being present for the PCR primer in the droplet is 1 out of 4. However, if there are 2 PCR primer pairs per droplet, then there is double the chance that there will be the correct template present in the droplet. This results in 1 out of 2 droplets being PCR positive which doubles the amplicon yield without doubling the input DNA. If the number of droplets containing the 2× multiplexed primers is doubled and the DNA kept constant, then the number of PCR positive droplets drops back to 1 in 4, but the total number of PCR droplets remains the same because the number of droplets have been doubled. If the multiplexing level in each droplet is increased to 4× and the input DNA is the same, the chance of the correct template molecule being present in each droplet doubles. This results in the number of PCR positive droplets being increased to 1 in 2 which doubles the amount of amplicon yield without increasing the amount of input DNA. Thus, by increasing the multiplexing of PCR primers in each droplet and by increasing the number of droplets overall, the amplicon yield can be increased by 4-fold without increasing the amount of input DNA.

Alternatively, if the amplicon yield is already sufficient, by increasing the multiplexing level for the PCR primers in each droplet, the amount of input genomic DNA can be dropped without sacrificing amplicon yield. For example if the multiplexing level of the PCR primers goes from 1× to 2×, the amount of input genomic DNA can be decreased by 2× while still maintaining the same overall amplicon yield.

Even though the number of PCR primer pairs per droplet is greater than one, there is still only one template molecule per droplet and thus there is only one primer pair per droplet that is being utilized at one time. This means that the advantages of droplet PCR for eliminating bias from either allele specific PCR or competition between different amplicons is maintained.

An example demonstration of droplet-based amplification and detection of multiple target sequences in a single droplet is shown here. Multiple copies of 5 sets of primers (primers for TERT, RNaseP, Ela, SMN1 and SMN2) were encapsulated in a single droplet at various concentrations along with the template DNA and the PCR master mix. Probes that specifically bind to TERT, RNaseP, Ela, SMN1 or SMN2 were also encapsulated in the droplets containing the primers. Probes for TERT, RNaseP and Ela were labeled with the VIC dye and probes for SMN1 and SMN2 were labeled with the FAM dye. The sequences for TERT RNaseP, Ela, SMN1 and SMN2 were amplified by PCR. The PCR was conducted with a standard thermal cycling setting. For example:

95° C. for 10 min
31 cycles
  92° C. for 15 s
  60° C. for 60 s

Figure 5A:
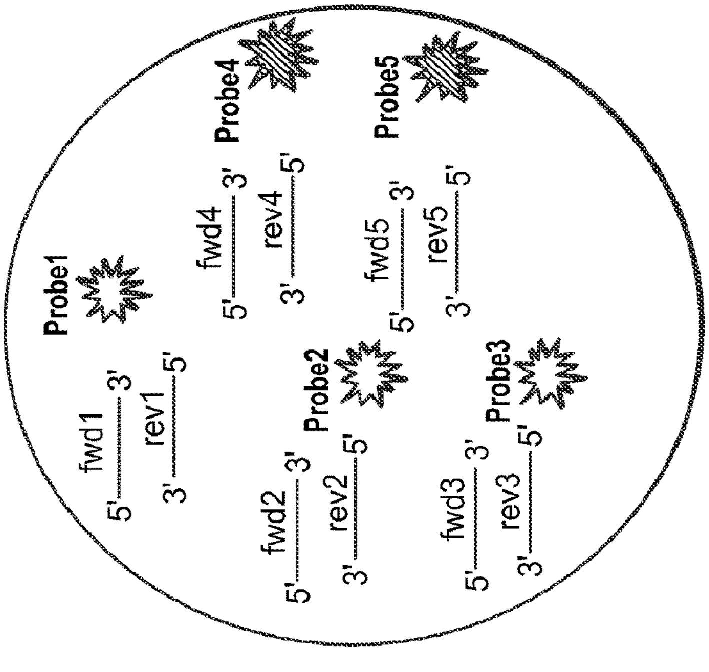
FIG. 5A is a schematic representation of a droplet having 5 sets of primers for PCR amplification of a template sequence and 5 probes, each labeled with a fluorescent dye, that binds specifically to the amplified sequences.
Figure 5B:
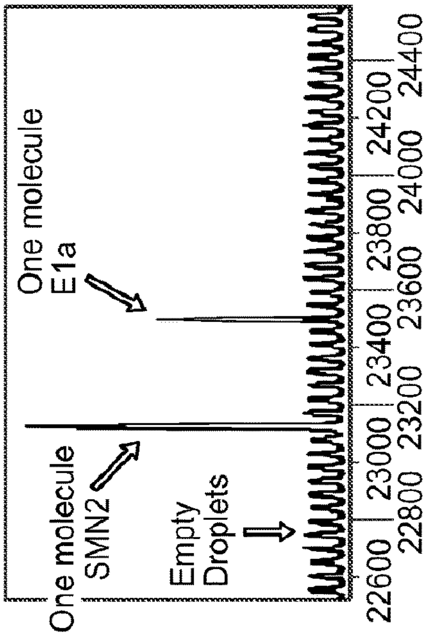
FIG. 5B is a time trace of fluorescence intensity detected from droplets after PCR amplification.
Figure 5C:
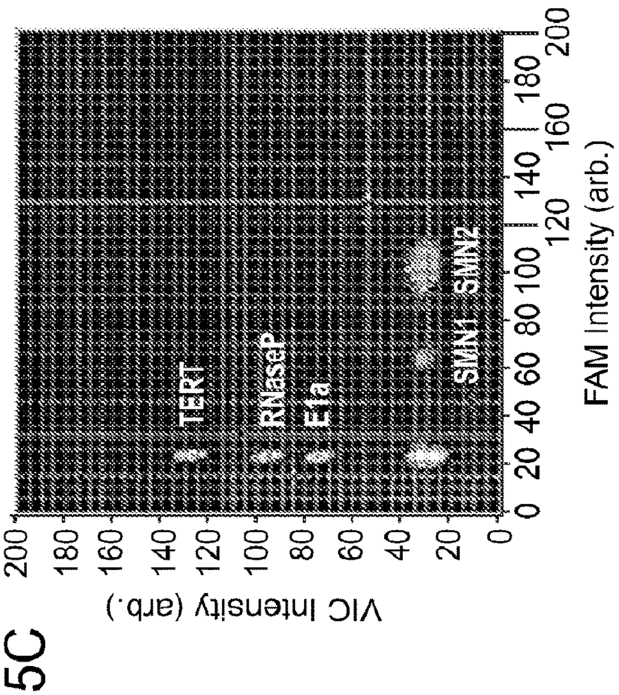
FIG. 5C is a scatter plot showing clusters representing droplets that contain specific amplified sequences (TERT, RNaseP, Ela, SMN1 and SMN2).

At the end of the PCR, the fluorescence emission from each droplet was determined and plotted on a scattered plot based on its wavelength and intensity. Six clusters, each representing droplets having the corresponding fluorescence wavelength and intensity were shown. The TERT, RNaseP and Ela clusters showed the fluorescence of the VIC dye at three distinct intensities and SMN1 and SMN1 clusters showed the fluorescence of the FAM dye at two distinct intensities (FIG. 5). The number of droplets, each having one or more sequences selected from TERT, RNaseP, Ela, SMN1 and SMN2, can be determined from the scattered plot.

In an another demonstration of droplet-based amplification and detection of multiple target sequences in a single droplet, 5 sets of primers (primers for TERT, RNaseP, Ela, 815A and 815G) were encapsulated in a single droplet at various concentrations along with the template DNA, the PCR master mix, and the probes. The five different probes TERT, RNaseP, Ela, 815A and 815G were also encapsulated in the droplets containing the primers. Probes for TERT and 815A were labeled with the VIC dye and probes for 815G were labeled with the FAM dye. For each of RNaseP and Ela, two probes, one labeled with the VIC dye and the other labeled with the FAM dye, were encapsulated.

The droplets containing both the primers and probes were fused with droplets containing the template. PCR reactions were conducted with the fused droplets to amply the sequences for TERT, RNaseP, Ela, 815A and 815G. The PCR was conducted with a standard thermal cycling setting.

At the end of the PCR, the fluorescence emission from each fused droplet was determined and plotted on a scattered plot based on its wavelength and intensity. Six clusters, each representing droplets having the corresponding fluorescence wavelength and intensity were shown. The TERT and 815A clusters showed the fluorescence of the VIC dye at two distinct intensities; the 815G clusters showed the fluorescence of the FAM dye; and the RNaseP and Ela clusters showed the fluorescence of both the FAM and the VIC dye at distinct intensities (FIG. 6). The number of droplets, each having one or more sequences selected from TERT, RNaseP, Ela, 815A and 815G, can be determined from the scattered plot. The copy number of RNaseP, Ela, 815A and 815G in the template were determined by the ratio between the number of droplets having the RNaseP, Ela, 815A and/or 815G sequences and the number of droplets having the TERT sequence (FIG. 6).

In yet another exemplary demonstration of multiplexed primer pairs in a droplet-based digital PCR reaction, two droplet libraries were generated: droplet library A was generated where each droplet contained only one primer pair; and droplet library B was generated where the primer pairs were multiplexed at 5× level in each droplet. HaμMap sample NA18858 was processed in duplicate with droplet libraries A or B using standard procedures. Two pg sample DNA was used for droplet library A and one pg sample DNA was used for the 5× multiplex droplet library B. After PCR amplification, both droplet libraries were broken and purified over a Qiagen MinElute column and then run on an Agilent Bioanalyzer. Samples were sequenced by Illumina on the Illumina GAII with 50 nucleotide reads and the sequencing results were analyzed using the standard sequencing metrics. The results from the 5× multiplexed droplet library B were compared to the singleplex droplet library A using standard metrics shown in the Table below.

The results obtained from the 5× multiplexed droplet library B were equivalent or better than what was obtained from droplet library A. The multiplexing of primers delivers the same sequencing results for base coverage, specificity and uniformity that the singleplexing does with the added advantage of reduced input DNA.

Figure 8A:
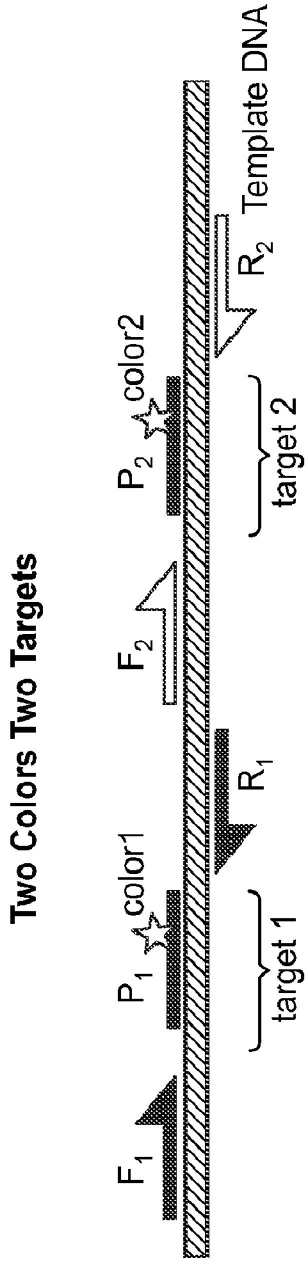
FIGS. 8A-D show a schematic depicting two-color detection of two genetic sequences with a microfluidic device.
Figure 8B:
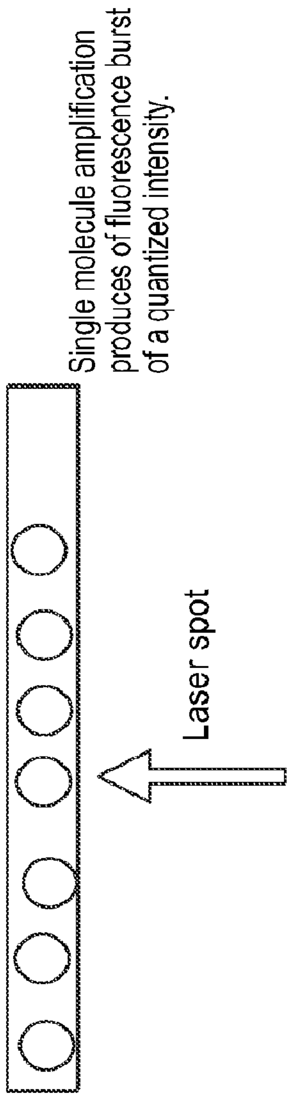
Figure 8C:
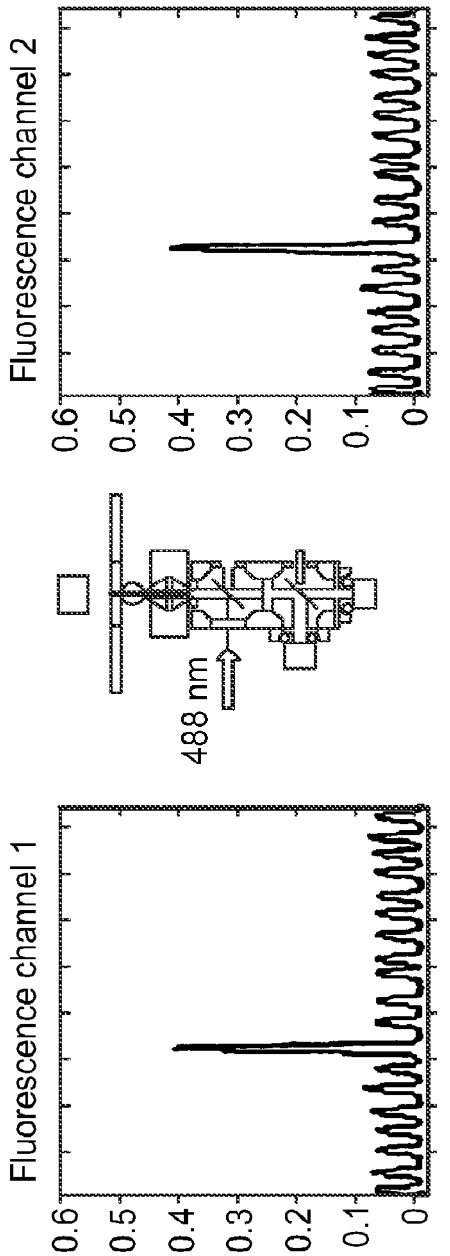
Figure 8D:
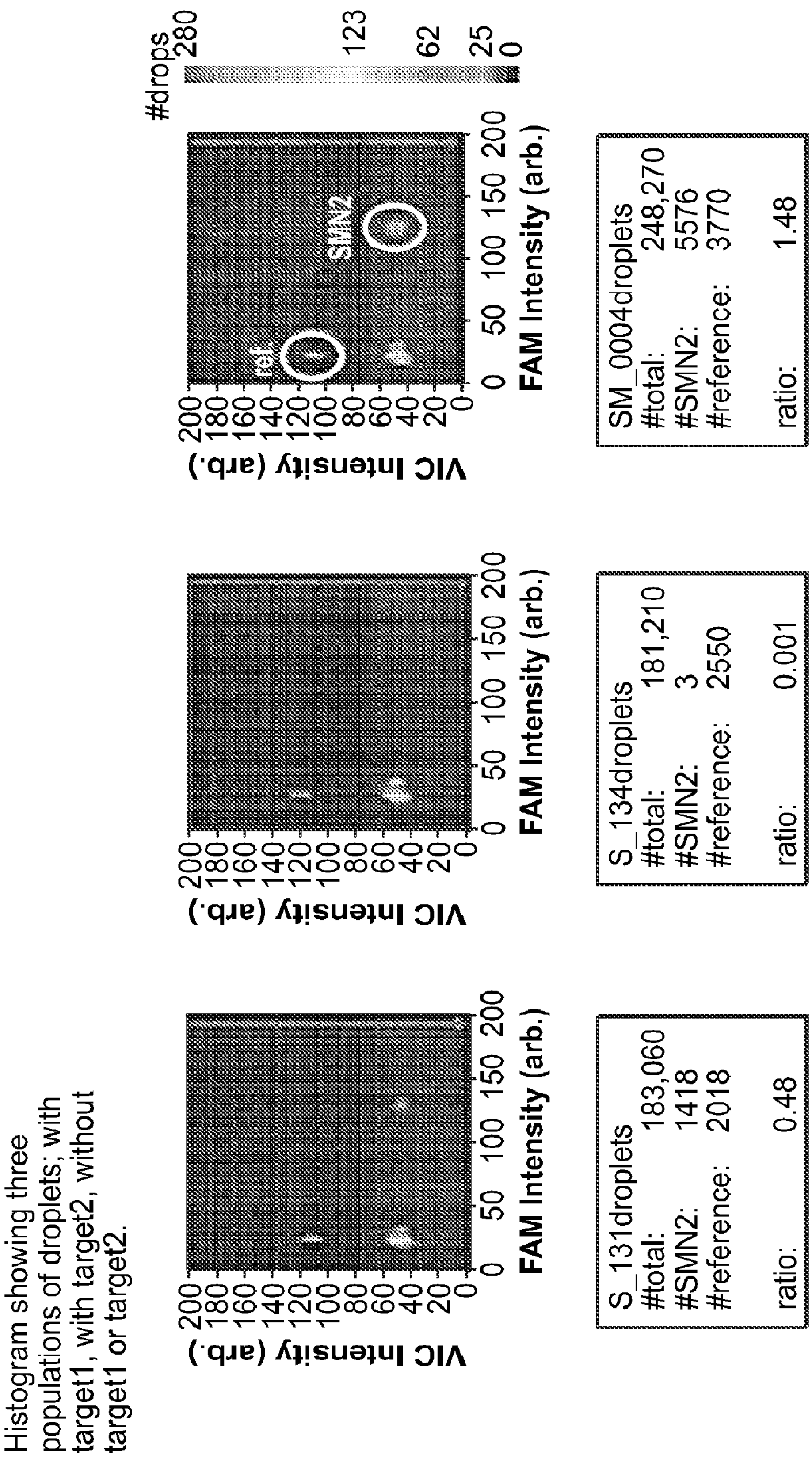

Probe (P1) labeled with a fluorophore of color 1 binds to the target 1 and probe (P2) labeled with a fluorophore of color 2 binds to the target 2 (FIGS. 8B and 8C). Droplets are made of diluted solution of template DNA under conditions of limiting or terminal dilution. Droplets containing the target sequence 1 or 2 emit fluorescence of color 1 or 2 respectively and are optically detected by laser (FIGS. 8B and 8C). The number of microcapsules containing target 1 or 2 is shown by histogram in FIG. 8D.

Figure 9A:
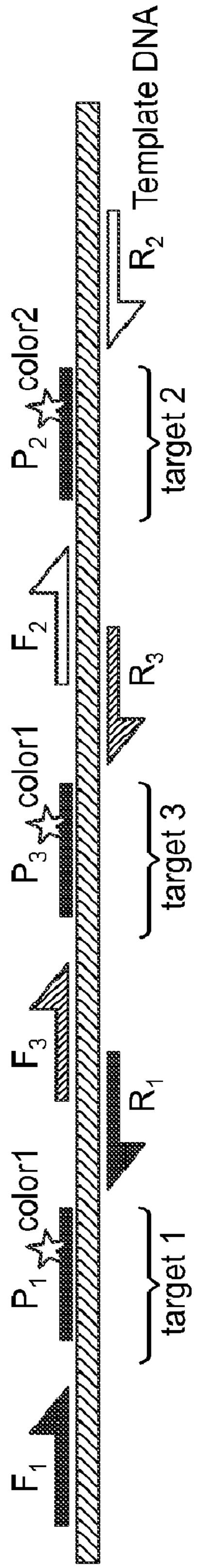
FIGS. 9A-D show a schematic depicting two-color detection of three genetic sequences with a microfluidic device.
Figure 9B:
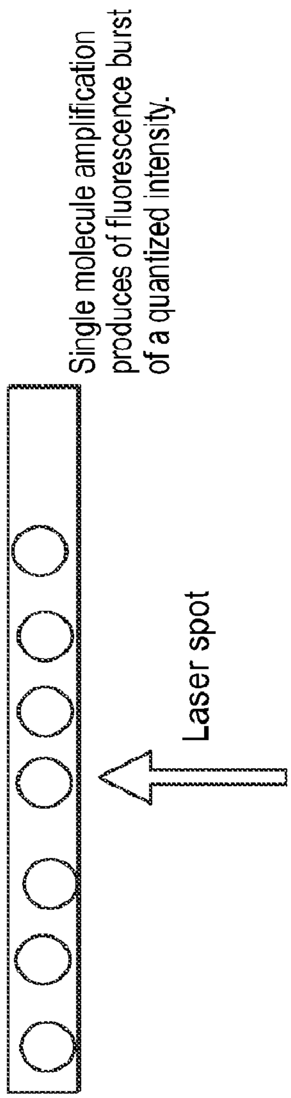
Figure 9C:
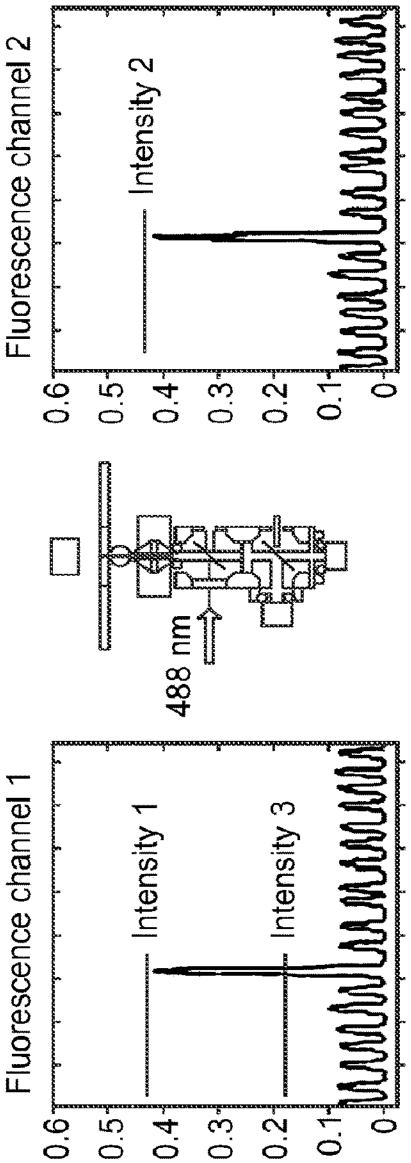
Figure 9D:
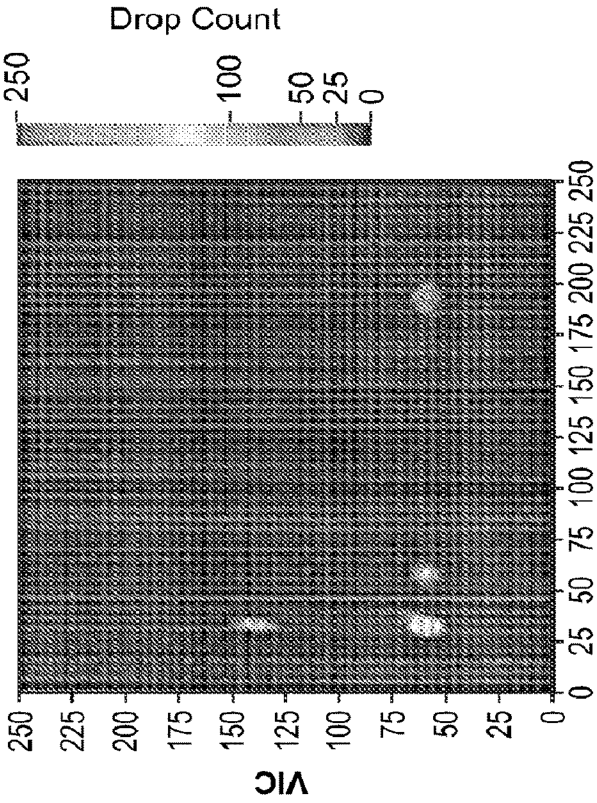

Methods of the invention involve performing accurate quantitation of multiple different DNA targets by dPCR using probes with the same fluorophore. FIGS. 9A-D show a schematic depicting two-color detection of three genetic sequences with a microfluidic device. As shown in FIG. 9A, a template DNA is amplified with three sets of primers: forward primers (F1, F2 and F3) and reverse primers (R1, R2 and R3). Probes (P1, P2 and P3) are labeled with fluorophores (color 1, color 2 and color 1) and bind to the target genetic sequences (target 1, target 2 and target 3) (FIGS. 9B and C). Microdroplets are made of diluted solution of template DNA under conditions of limiting or terminal dilution. Microdroplets containing target sequence 1 or 3 emit fluorescence of color 1 at two different intensities; and microdroplets containing target sequence 2 emit fluorescence of color 2. The number of microdroplets containing target 1, 2 or 3 is shown by histogram in FIG. 9D.

| Sample | Total reads | Mapped reads | Specificity | Mean base coverage | C1 | C20 | C100 | Base coverage (0.2x of mean) |
|---|---|---|---|---|---|---|---|---|
| Library A with sample 1 | 27431697 | 99.4% | 0.813 | 1394 | 99.5% | 99.0% | 98.2% | 92.8% |
| Library A with sample 2 | 15147288 | 99.4% | 0.862 | 819 | 99.1% | 98.2% | 87.6% | 78.0% |
| Library B with sample 1 | 27861378 | 99.5% | 0.847 | 1472 | 99.7% | 99.3% | 97.6% | 89.9% |
| Library B with sample 2 | 25758406 | 99.1% | 0.837 | 1321 | 99.8% | 99.4% | 97.9% | 91.3% |

Total reads: total number of sequencing read found within the provided sample data.

Mapped reads (%): percentage of total reads that mapped to the human genome.

Specificity: percentage of mapped reads that include the target. The target includes all amplicon sequences with primer sequences excluded.

Mean base coverage: average base coverage within the target. The target includes all amplicon sequences with primer sequences excluded.

C1: % of target that has at least 1x base coverage.

Note:

non-unique sequencing reads are mapped randomly.

C20: % of target that has at least 20x base coverage.

C100: % of target that has at least 100x base coverage.

Base coverage (0.2x of mean): % of target that has at least 20% of mean base coverage.

Monochromatic Gene Copy Number Assay

Figure 7A:
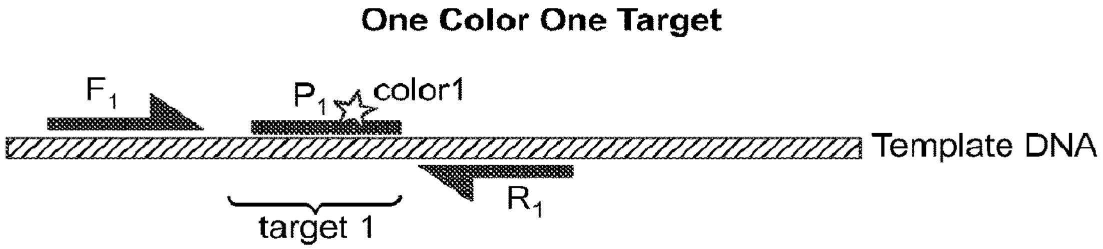
FIGS. 7A-E show a schematic depicting one-color detection of a genetic sequence with a microfluidic device.
Figure 7B:
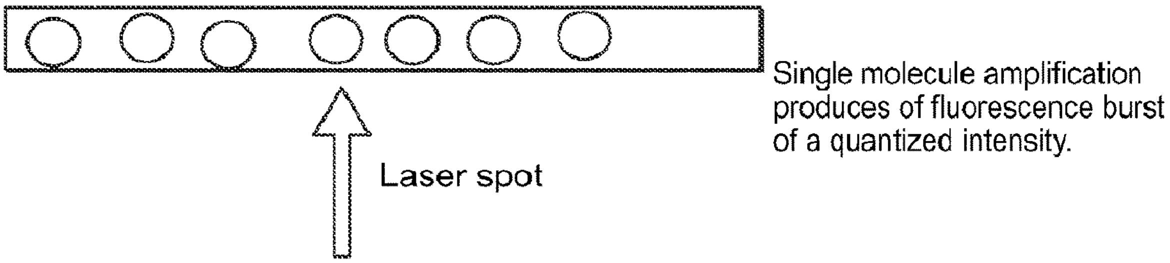
Figure 7C:
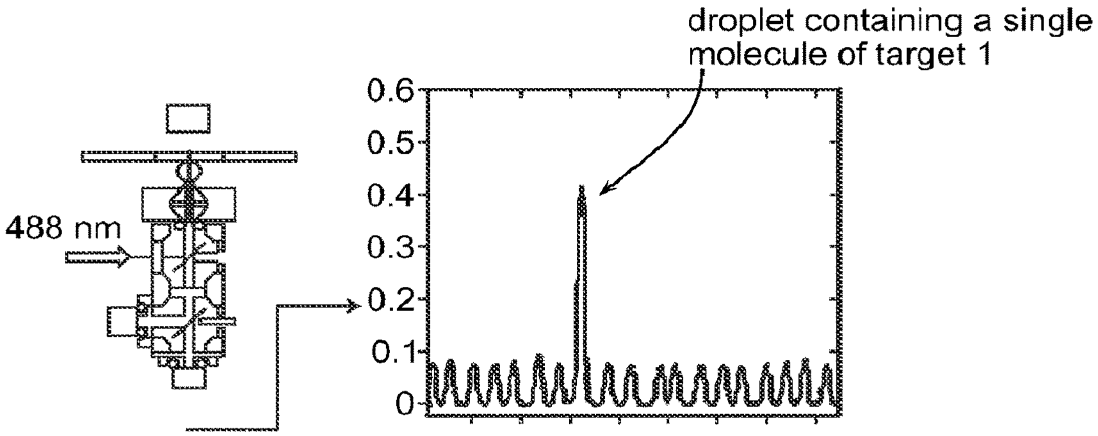
Figure 7E:
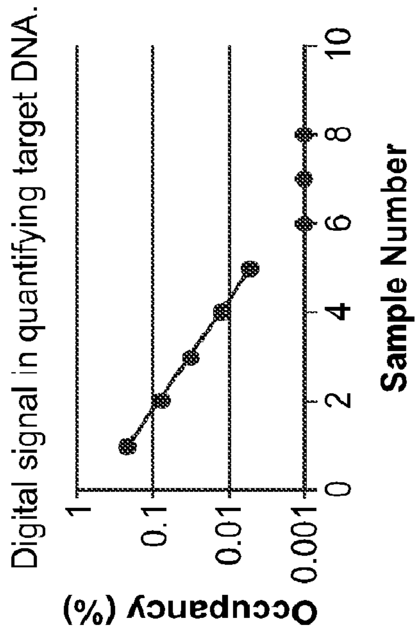
Figure 7D:
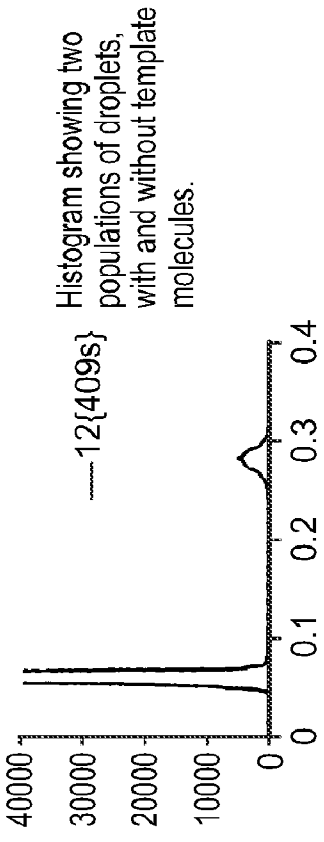

Traditional digital PCR methods involve the use of a single labeled probe specific for an individual target. FIGS. 7A-E show a schematic depicting one-color detection of a target sequence using droplet based digital PCR. As shown in FIG. 7A, a template DNA is amplified with a forward primer (F1) and a reverse primer (R1). Probe (P1) labeled with a fluorophore of color 1 binds to the target genetic sequence (target 1). Microdroplets are made of diluted solution of template DNA under conditions of limiting or terminal dilution. Droplets containing the target sequence emit fluorescence and are detected by laser (FIGS. 7B and 7C). The number of microcapsules either containing or not containing the target sequence is shown in a histogram (FIG. 7D) and quantified (FIG. 7E).

FIGS. 8A-D show a schematic depicting two-color detection of two genetic sequences with a microfluidic device. As shown in FIG. 8A, a template DNA is amplified with two sets of primers: forward primer (F1) and a reverse primer (R1), and forward primer (F2) and a reverse primer (R2).

Recent results from the droplet digital PCR (dPCR) shows that multiple independent PCR reactions can be run and separately quantified using the same fluorophore. Specifically, an SMN2 assay yields an unexpected population of droplets with slightly elevated signal in the FAM detection channel.

Figure 10:
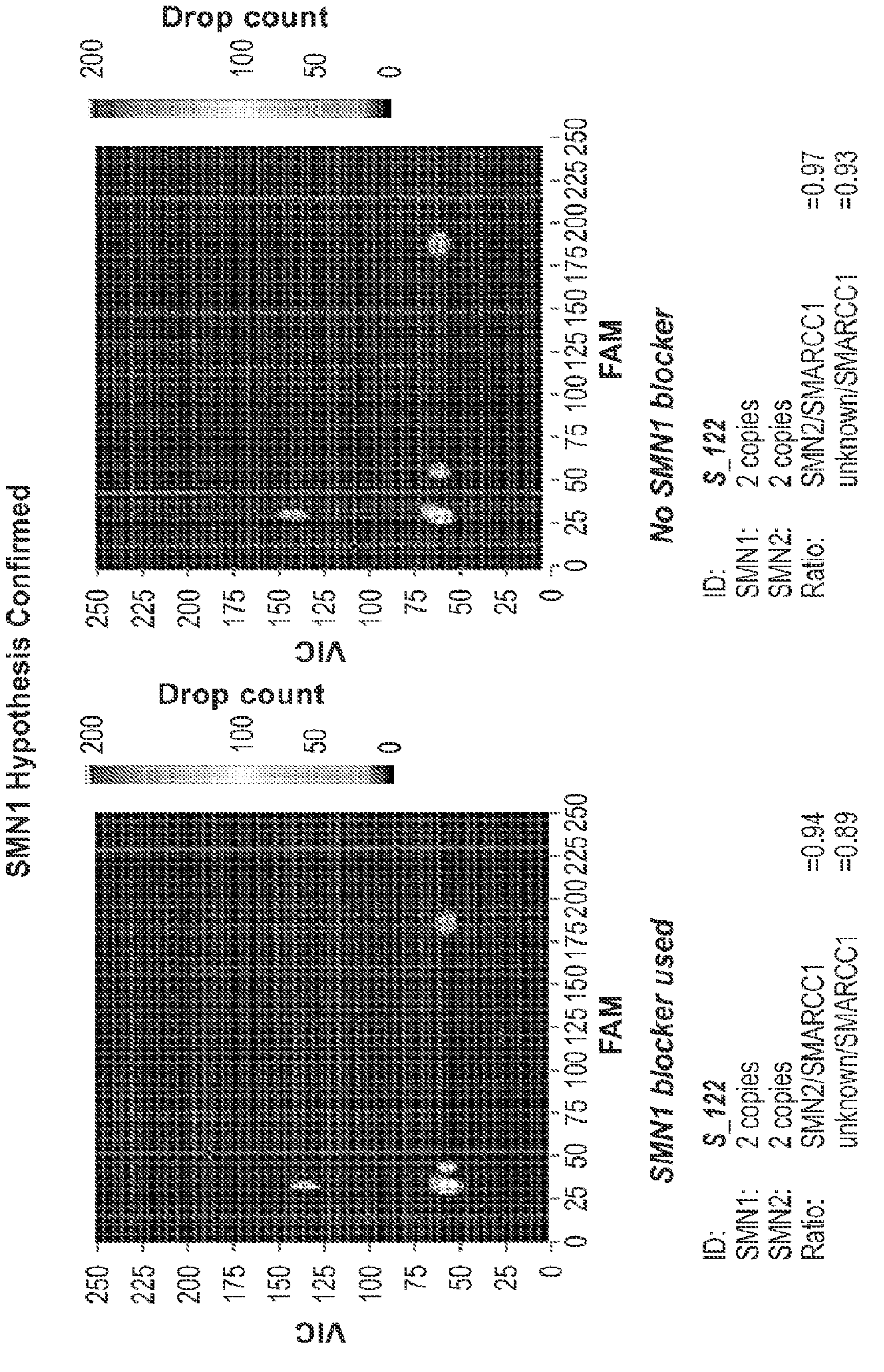
FIG. 10 shows two dot plots depicting clusters of genetic sequences detected through fluorescence intensity. Left panel is a dot plot showing four clusters. Block for SMN1 sequence was present. Top left: microdroplets containing the reference sequence (SMARCC1); bottom left: microdroplets not containing any sequence; bottom middle: microdroplets containing sequence for SMN1; and bottom right: microdroplets containing sequence for SMN2. Right panel is a dot plot showing four clusters. No block for SMN1 sequence was present. Top left: microdroplets containing, the reference sequence (SMARCC1); bottom left: microdroplets not containing any sequence; bottom middle: microdroplets containing sequence for SMN1; and bottom right: microdroplets containing sequence for SMN2. The shift of the bottom middle cluster in right panel as compared to left panel confirms that fluorescence intensity provides a very sensitive measurement for the presence of a sequence.

The results are depicted in FIG. 10. The left-side dot plot in FIG. 10 depicts the effect of having the SMN1 blocker present in the reaction. The four clusters depicted in the left-side dot plot are as follows: the top left cluster includes microdroplets containing the reference sequence (SMARCC1); the bottom left cluster includes microdroplets not containing any sequence; the bottom middle cluster includes microdroplets containing sequence for SMN1; and the bottom right cluster includes microdroplets containing sequence for SMN2. The dot plot on the right-side of FIG. 10 depicts four clusters where no SMN1 blocker was present in the reaction: the top left cluster includes microdroplets containing the reference sequence (SMARCC1); the bottom left cluster includes microdroplets not containing any sequence; the bottom middle cluster includes microdroplets containing sequence for SMN1; and the bottom right cluster includes microdroplets containing sequence for SMN2. The shift of the bottom middle cluster in right panel as compared to left panel confirms that fluorescence intensity provides a very sensitive measurement for the presence of a sequence.

Without intending to be bound by any theory, the simplest explanation is that the cluster arises from weak association of the SMN2 probe to the SMN1 gene despite the presence of a blocker to that gene (a nonfluorescent complementary probe to the SMN1 gene).

One definitive confirmation of SMN1 as the source of the unexpected cluster was an observed dependence of the intensity of this feature on the presence of the SMN1 blocker. A clear shift toward higher FAM fluorescent intensities was observed in the absence of the blocker (FIG. 10). In another definitive confirmation the ratio of the SMN1 (putative) population size to the reference size of 0.96 in perfect agreement with expectation (two copies of each) (S_131 sample). Another sample, S 122, with the same number of SMN1 copies yielded a ratio of 0.88 in one run and 0.93 in another, also consistent with the proposed explanation of the unexpected cluster.

Without intending to be bound by any theory, these observations indicate that SMN2 probe binding to SMN1 DNA yields an elevated fluorescent signal. A simple kinetic model explaining this phenomenon assumes that the hybridization of the SMN2 probe to the SMN1 DNA achieves equilibrium at a faster rate than the polymerase fills in the complementary strand. The amount of probe fluorophore that is released in each thermal cycle is therefore proportional to (or even equal to) the number of bound probes. Thus the lower the binding affinity the fewer the number of probe fluorophores that are released. Due to SMN1 sequence mismatch(es) with the SMN2 probe, the affinity of the probe is certainly expected to be lower to SMN1 than SMN2. This model also explains the signal dependence on the sMN1 blocker: the blocker competitively inhibits the SMN2 probe hydrolysis by the polymerase exonuclease activity.

It may also be, however, that the probe hybridization does not reach equilibrium before exonuclease activity. In this case, the association rates would play a more dominant role. Similar logic applies. The binding rate to the matching site is likely to be faster than to the mismatch site, and the blocker would act to decelerate probe binding to the mismatch site. The binding of SMN2 probe to SMN1 DNA might be detectable by conventional bulk qPCR, especially in absence of SMN2, but highly quantitative results like those shown here are very unlikely. Definitely, there is no report of qPCR or any other technique quantifying two different DNA sequence motifs with the same color fluorophore. Sequestration of the individual reactions by single molecule amplification within droplets eliminates any confusion regarding mixed contributions to the signal.

The advantage of quantifying DNA with multiple probes of the same color fluorophore extends beyond the example of two highly homologous sequences shown here. Rather, any plurality of sequences of any degree of similarity or dissimilarity can be quantified so long as the different probes have significantly different binding occupancies to their respective DNA binding sites.

Another advantage of the dPCR approach for multiplexed reactions is that the different reactions do not compete with each other for reagents as they would in a bulk qPCR assay. However, the possibility for unintended cross-reactivity remains. A multiplexes assay can require a more dilute sample. For instance, at 10% occupancy a duplex reaction would have double occupancy 1% of the time. Hence 1 in 10 PCR+ droplets would be doubles, resulting in a final intensity at least as high and possibly higher than the brighter of the two probes. For a simple duplex system the contribution from each probe could be recovered. In this example the total number of PCR+ droplets for probe 1 would be (Probe 1)+(Probe1+Probe2). Higher degrees of multiplexing would require greater dilution. For example, for a 4-plex at 1% occupancy the probability of one probe overlapping any of the other 3 is ~3%, and that error may be too high for some applications. The need for large dilutions strongly favors the large number of dPCR reactions.

In another example of the invention, a single fluorophore (FAM) was used in a gene copy number assay for both the reference and the target DNA. A model system was used with varying concentrations of plasmid DNA to represent a change in the target gene copy number, relative to a reference gene, equivalent to 0-16 copies of the target gene per cell. BCKDHA and SMN2 plasmid DNA served as the reference and target with 1× and 0.5× primers and probes respectively. With a starting ratio of 8:1 SMN2 to BCKDHA, the sample was diluted serially by 2× into a solution of BCKDHA at the same concentration to vary just the amount of SMN2. The resultant samples were emulsified, thermally cycled, and over 105 droplets were analyzed for each sample as described in the previous section. The process was repeated in triplicate.

Figure 11A:
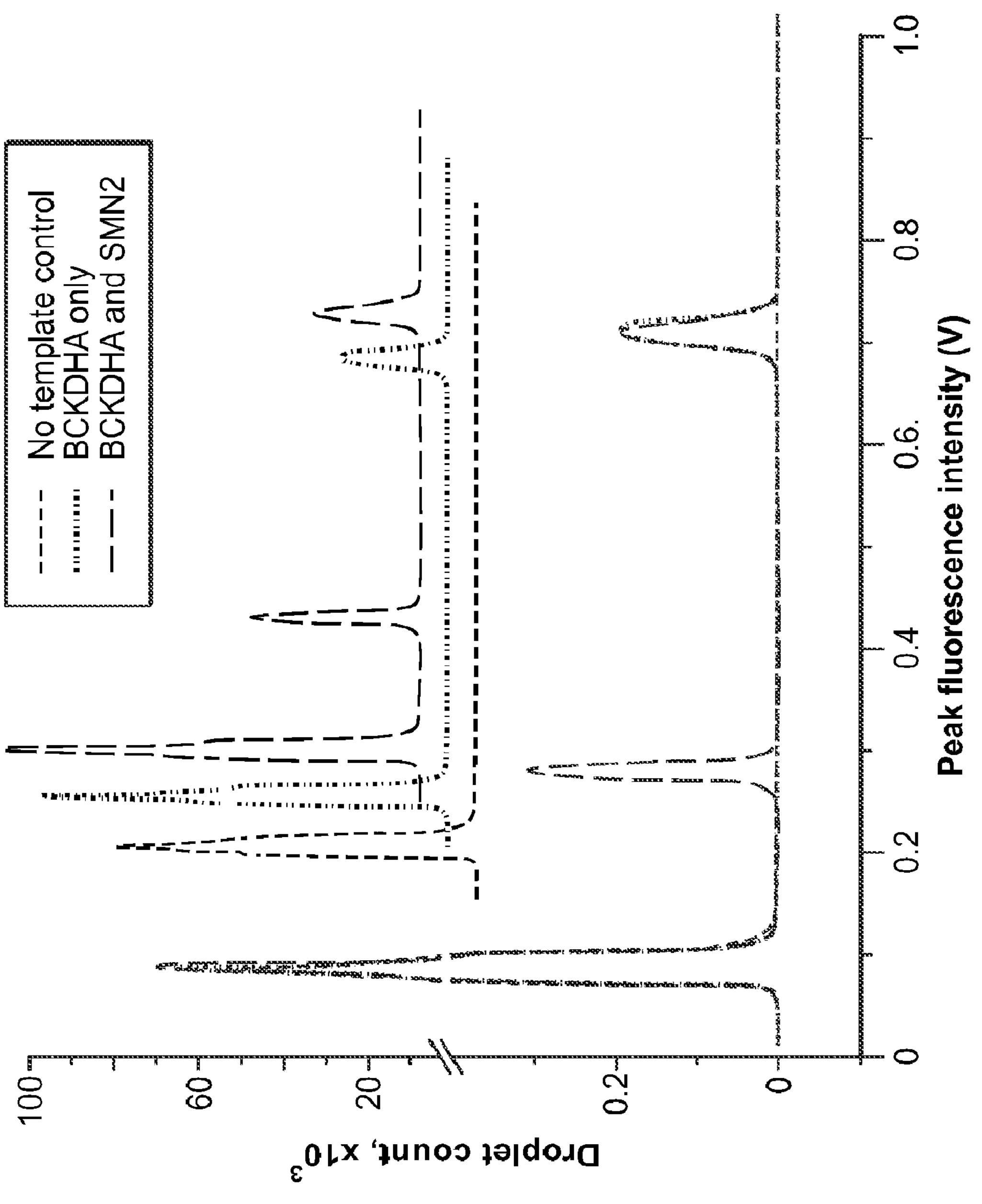
FIGS. 11*a*-*b* depict histograms of a duplex gene copy number assay using only one type of fluorophore by digital PCR.
Figure 11B:
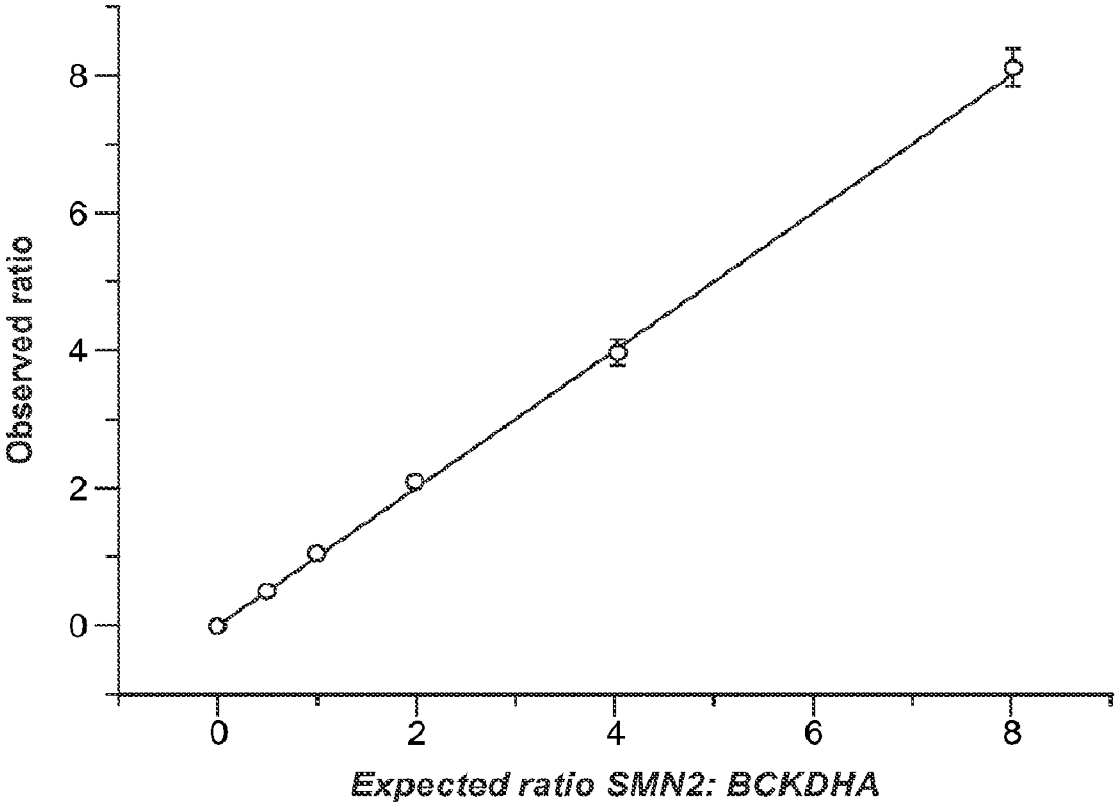

Methods of the invention also include analytical techniques for identification of fluorescence signatures unique to each probe. In this example of the invention, histograms of the droplet fluorescence intensities are shown in FIG. 11*a* for three different template DNA samples: a no template control (dotted line), BCKDHA only (solid line), and 1:1 BCKDHA to SMN2 (dashed line). For clarity, the histograms are shown both overlapped to highlight the similarity for certain peaks, and offset from each other to reveal all of the features. In the case of 1:1 BCKDHA to SMN2, three populations were readily apparent: a dominant feature appeared at 0.08 V, and two smaller peaks were evident at 0.27 and 0.71 V. The dominant feature at 0.08 V was assigned to PCR(−) droplets since both small peaks disappeared, but the large one remained, in the no template control. The peak at 0.71 V was assigned to BCKDHA since it was the sole feature arising with the addition of just BCKDHA, and the peak at 0.27 V appeared on subsequent addition of SMN2, completing the assignments. A very small peak appeared at ~0.9 V, not visible on the scale of FIG. 11*a*, that corresponded to droplets occupied by both genes. As another method of the invention, once the different peaks are identified, droplets within each peak were counted corresponding to each possible state (PCR(+) for either BCKDHA or SMN2, or both, or PCR(−)), and the gene copy number was then determined from the ratio of occupancies. Gene copy numbers for each sample in the serial dilution are plotted in FIG. 11*b* against expected values (observed ratios of SMN2 to BCKDHA to expected ratios of SMN2 to BSKDHA), with an excellent linear fit (y=1.01×) across the full range (R2=0.9997, slope=1.01), demonstrating accurate and precise measurement of the equivalent of 0 to 16 copies of SMN2 per cell.

Detection of Alternatively Spliced Transcripts

The same principle can be used to detect and count alternatively spliced transcripts. TaqMan assays can be designed that are specific for each of the exons in an RNA transcript. After the RNA is turned into cDNA it can be encapsulated into a droplet at 1 copy or less per droplet. The droplet would also contain the multiplexed TaqMan assay for each of the exons. Each of the TaqMan assays would contain a different probe but all the probes would have the same fluorescent dye attached. The droplets would be thermocycled to generate signal for each of the TaqMan assays. If there are multiple splice variants in the sample they each will contain a different number of exons depending on the splicing events. The fluorescent intensity of each droplet would be different depending on the number of exons present. By counting the number of droplets with different intensities it would be possible to identify the presence arid abundance of different splice variants in a sample.

Copy Number Variants in a Heterogeneous Sample

It would be possible to determine if a heterogeneous sample contained components with different copy level numbers. If the copy number variants to be assayed were spaced close enough along the chromosome, the DNA from a sample could be fragmented and encapsulated in droplets at a level of one haploid genomic equivalent or less per droplet. The droplet would also contain a TaqMan assay specific for the copy number variant. The intensity of the signal in each droplet would depend on the number of copy number variants are present for the sample. Counting of the number of droplets of different intensities would indicate things like how many cells in a particular sample had what level of copy number variants.

Tuning TaμMan® Probe Fluorescence Intensity

Identifying probes by fluorescence intensity often requires adjusting the brightness of the probes, particularly for higher-plex assays with dense probe patterns. In the previous section the probes for the gene copy number assay yielded very well resolved peaks (FIG. 11*a*). Clearly room exists to accommodate one or multiple extra probes in the copy number assay within the resolution of the measurement, but a method for adjusting the fluorescence intensity of the new probes is required to avoid interference with the existing assay. One method of the invention involves varying the probe and primer concentrations together as a very simple technique to optimize relative intensities in higher-plex reactions.

FIGS. 12A-C show a schematic for tuning the intensity of a detectable label to a particular target with a microfluidic device. As shown in FIG. 12A, a template DNA is amplified with two sets of primers: forward primers (F1 and F2) and reverse primers (R1 and R2). Probes (P1 and P2) are labeled with fluorophore of color 1 and bind to target 1 and target 2 respectively. Fluorescence from target 2 is lower in intensity than that from target 1 due to single base mismatch between P2 and target 2. As shown in FIG. 12B, template DNA is amplified with two sets of primers: forward primers (F1 and F2) and reverse primers (R1 and R2) (FIG. 12B). Fluorescence from target 2 is lower in intensity than that from target 1 due to the presence of a competing probe 2 that is not labeled with the fluorophore. As shown in FIG. 12C, template DNA is amplified with two sets of primers: forward primers (F1 and F2) and reverse primers (R1 and R2). Probes (P1 and P2) are labeled with fluorophore of color 1 and bind to target 1 and target 2 respectively. Fluorescence from target 2 is lower in intensity than that from target 1 due to the presence of a competing probe 2 that is labeled with a different fluorophore.

Figure 13:
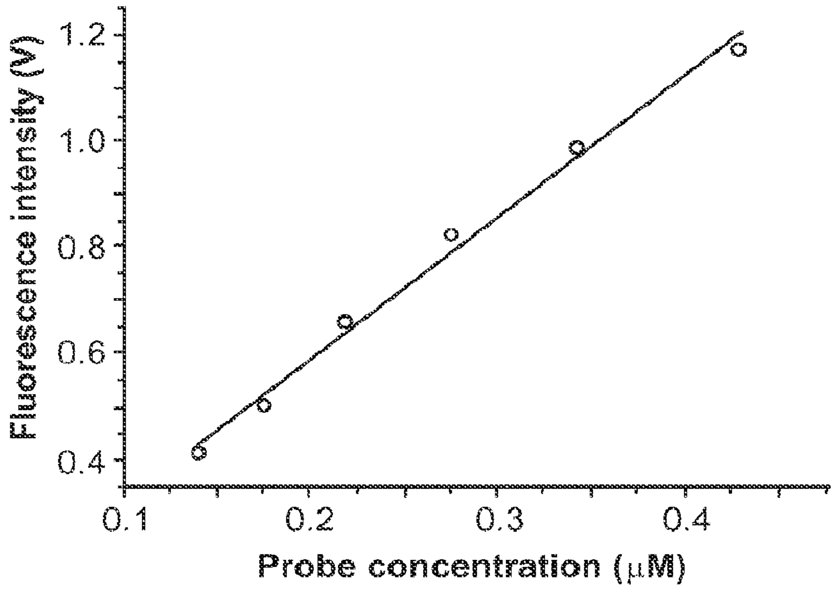
FIG. 13 is a line graph depicting the linear dependence of droplet fluorescence intensity on probe concentration (Line, best linear fit (y=−0.092×+0.082, $R^2$=0.995).

FIG. 13 shows probe fluorescence intensities throughout a serial dilution of the probes and primers for a different reference gene, ribonuclease P (RNaseP), against a constant amount of genomic DNA from the Coriell cell line NA3814 at an occupancy of 0.02 target DNA molecules per droplet. The probe fluorescent intensities varied in direct proportion to probe concentration over a narrow concentration range spanning ~0.15 to 0.4 μM (R2=0.995)—roughly centered about the typical probe concentration of 0.2 μM-after compensation for dilution errors and other run-to-run differences such as optical realignments using the intensity of the PCR(−) droplets as a reference. In summary, probe intensities can be varied by dilution over a small but adequate range for the purpose of tuning multiplexed assays without affecting the amplification itself.

Although the example above for adjusting probe fluorescence intensities involves varying probe and primer concentrations together by the same factor, the invention is not limited to this method alone for varying probe intensity. Other methods known to those familiar with the art for varying probe intensities are also considered. Such methods include varying just the probe concentration; varying just the primer concentrations; varying just the forward primer concentration; varying just the reverse primer concentration; varying the probe, forward, and reverse primers concentrations in any way; varying the thermal cycling program; varying the PCR master mix; incorporating into the assay some fraction of probes that lack fluorophores; or incorporating into the assay any hybridization-based competitive inhibitors to probe binding, such as blocking oligomer nucleotides, peptide nucleic acids, and locked nucleic acids. The invention incorporates the use of these methods adjusting probe fluorescence intensity, or any other methods for adjusting probe fluorescence intensity, used either by themselves or in any combination.

Higher-Plex Reactions

One method of the invention involves performing higher-plex assays with a single probe color (i.e. fluorophore). As described above, probe fluorescent intensities can be adjusted by a variety of means such that each intensity level uniquely identifies a DNA target. For example, targets Ti, T2, T3, and T4 might be uniquely identified by intensity levels I1, I2, I3, and I4. Not intending to be bound by theory, the maximum number of intensity levels possible for unique identification of targets is related to the resolution of the different intensity levels—that is the spread of intensities for each particular probe compared to the separation between the average intensities of the probes—and it is also related to the intensity of the empty droplets that tends to grow with increasing numbers of probes. The number of intensity levels can be 0, or 1, or 2, or 3, or 4, or up to 10, or up to 20, or up to 50, or up to 100. The number of intensity levels can be higher than 100. In the examples show below, as many as three intensity levels are demonstrated.

Another method of the invention involves performing higher-plex assays using multiple different probe colors (i.e. fluorophores). As above for the monochromatic multiplexing assay, for each color probe, multiple targets can be identified based on intensity. Additionally, multiple colors that are spectrally separable can be used simultaneously. For example, a single droplet might contain four different probes for measuring four different targets. Two probes might be of color A with different intensities (say, A1 and A2), and the other two probes of color B with different intensities (say B1 and B2). The corresponding targets are Ti, T2, T3, and T4 for A1, A2, BI, and B2 respectively. If a droplet shows an increase in fluoresce in color A, the droplet therefore contained either targets T1 or T2. Then, based on the fluorescence intensity of color A, the target could be identified as T1 or the target could be identified as T2. If, however, a droplet shows an increase in fluorescence in color B, the droplet therefore contained either targets T3 or T4. Then, based on the fluorescence intensity of color B, the target could be identified as T3 or the target could be identified as T4. Not intending to be bound by theory, the maximum number of different colors possible is limited by spectral overlap between fluorescence emission of the different fluorophores. The maximum number of colors can be 1, or 2, or 3, or 4, or up to 10, or up to 20. The maximum number of colors can be higher than 20. In the demonstrations that follow, the largest number of colors is two.

Another method of the invention involves performing higher-plex assays using multiple different probe colors (i.e. fluorophores), however unlike the strategy above where each target is identified by single type of probe with a unique color and intensity, instead in this method a single target may be identified by multiple probes that constitute a unique signature of both colors and intensities. For example, a single droplet might contain four different probes for measuring three different targets (say, Ti, T2, and T3). Two probes might be of color A (say, Al, and A2), and two probes might be of color B (say, B1 and B2). T1 is measured by probe Al, T2 is measured by probe Bl, but T3 is measured by both probes A2 and B2. Thus, when a droplet contains T1 only increased fluorescence appears in color A. When a droplet contains T2 only increased fluorescence appears in color B. However when a droplet contains T3, increased fluorescence appears in both colors A and B.

Generally, without wishing to be constrained by theory, the above three methods for higher-plex dPCR are simplest to implement under conditions of terminal dilution, that is when the probability of multiple different target molecules co-occupying the same droplet is very low compared to the probability of any single target occupying a droplet. With multiple occupancy arises the complexity of simultaneous assays competing within the same reaction droplet, and also complexity of assigning the resulting fluorescence intensity that involves a combination of fluorescence from two different reaction products that may or may not be equal to the sum of the two fluorescence intensities of the individual reaction products. However, methods of the invention can accommodate these complications arising from multiple occupancy.

Methods of the invention for higher-plex reactions also include methods for primer and probe pairing. In the simplest case targets are unlikely to reside on the same DNA fragments, such as when targets are from different cells; or when targets are from different chromosomes within a single cell type; or when targets are distant from each other within a single chromosome such that they become physically separated during DNA fragmentation; or when targets are very close to each other within a chromosome, but nevertheless become separated by targeted cleavage of the DNA, such as by restriction enzyme digestion; or for any other reason. In such cases each probe can be paired with a single set of primers (forward and reverse). However, in other cases the target regions might frequently reside on the same DNA fragments, for example when targets reside within the same codon, or for any other reason. In such cases, a single set of primers might serve for multiple probes (for an example, see Pekin et al.).

Figure 22:
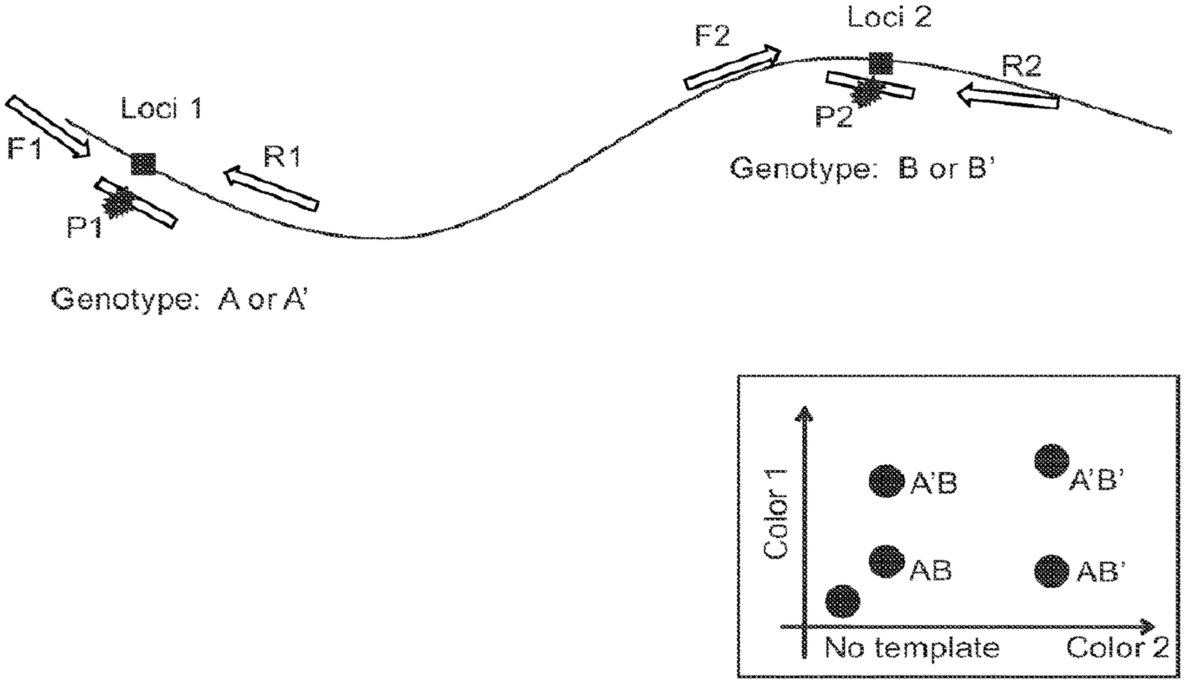
FIG. 22 is a schematic showing haplotype detection in droplets.

Higher multiplex reactions can be performed to distinguish the haplotypes of two SNPs. For example, assume that at position one there can be genotypes A or A' and at position two there can be genotypes of B or B'. In a diploid genome four unique haplotypes are possible (A,B; A,B';A',B; and A',B'). If for example A‘ and B’ represent drug resistant mutations for infection, it is often the case that A‘B and AB’ are less sever and treated differently than A‘B’ which represents a significant drug resistance that must be treated with extreme care. Digital PCR with intensity discrimination is ideally suited for identifying low prevalence of A‘B’ in a background of mixtures of the other three haplotypes. Haplotyping information is also important for construction of haplotypes in HLA. One way that the present example can be constructed is by assay design such that color one is used for A and is of high or low intensity indicative of allele A or A' respectively and color two is used for B and is of high or low intensity respectively indicative of B or B'. Populations of [color1,color2] corresponding to [Low, Low] would be a measure of an allele of AB and [high, low] allele A'B and an allele of [A‘B’] will be readily distinguishable as [high, high] even in a background that is predominately a mixture of A‘B and AB’. See FIG. 22. In some cases it will be advantageous to start by encapsulating into the droplets long single molecules of nucleic acid that contain both A and B SNP location and in other cases it will be desirable to start by encapsulating single cells, bacteria or other organism within the droplets prior to releasing the nucleic acid from the organism. In still other embodiments the multiplex intensity detection of multiple simultaneous targets can be used as surrogate markers for multiple types of binding interactions or labeling of target materials. This technique is also not limited to single molecule detection and can be used for haplotype detection in single cells (e.g., bacteria, somatic cells, etc.). In single cell analysis, a sorting step may be applied prior to haplotyping.

5-Plex Assay for Spinal Muscular Atrophy

An aspect of the invention was reduced to practice in an example demonstration of the quantitation of several genetic markers for spinal muscular atrophy (SMA). SMA was selected for one of the example demonstrations due to both its important clinical significance as well as its complicated genetics. It is the second-most prevalent fatal neurodegenerative disease and affects ~1 in 10,000 live births. SMA is most often caused by homozygous absence of exon 7 within the survival of motor neuron 1 gene (SMN1, reviewed by Wirth et al.), however the severity of the condition is modulated by the number of gene copies of SMN2 with prognosis ranging from lethal to asymptomatic over 1-5 copy numbers (reviewed by Elsheikh et al.). Hence accurate quantitation of SMN2 copy number is important for clinical prognosis and genetic counseling. Aside from large deletions of SMN1, a number of single point mutations or short deletions/duplications within the same gene also account for ~4% of cases of SMA. In a significant step toward a comprehensive SMA assay, the multiplexed dPCR assay demonstrated here contains both copy number assays (for SMN1 & 2) and an assay for one of the prevalent SNPs (c.815A>G).

One embodiment of the invention is a 5-plex assay for SMA diagnostics. The 5-plex assay quantifies common genetic variants impacting SMA including two copy number assays for the SMN1 and SMN2 genes with BCKDHA as a reference, and a SNP assay for the c.815A>G mutation. Two differently colored fluorophores, FAM and VIC, were used to uniquely identify each of the assays. The probes for SMN1 and SMN2 contained only FAM, and for c.815A only VIC. However, mixtures of VIC and FAM-labeled probes were used for BCKDHA and c.815G. The use of VIC and FAM fluorophores in this example does not limit the invention, rather the 5-plex assay can be used with any spectrally separable fluorophores compatible with the TaqMan assay, or any other fluorogenic hybridization-based probe chemistries. For validating the assay, a model chromosome was synthesized containing a single target region for each of the different primer/probe pairs. EcoRV restriction sites flanked each target, allowing separation of the fragments.

Figure 14A:
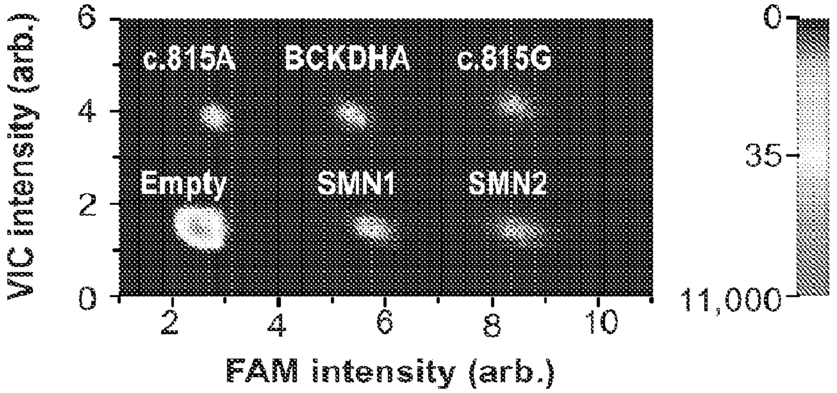
FIGS. 14*a*-*b* depict a 5-plex dPCR assay for spinal muscular atrophy with only-two fluorophores.

As another method of the invention, histogram-based data presentation and analysis is incorporated into the invention for identifying and characterizing statistically similar populations of droplets that arise from one probe signature (color and intensity), and for discriminating one population of droplets from the others. FIG. 14*a* shows a 2-dimensional histogram of droplet fluorescence intensities as a contoured heat map, with hotter colors representing higher occurrences. Standard techniques were used to compensate for spectral overlap of the FAM and VIC signals. Samples were run at 0.006 occupancy per target. Six populations were clearly evident, five for the assay and one for PCR(−) droplets. As one method of the invention, the populations were assigned by selective exclusion of assay components. For example, excluding the SMN2 primers and probe eliminated the population at the bottom right in the histogram, but otherwise the distribution remained unchanged. Assignments are labeled in FIG. 14*a*. As we have found to be generally true for this method of multiplexing, the assay worked immediately with well resolved or at least distinguishable populations for each target. As another method of the invention, the relative positions of the different populations in the histogram were then adjusted into a regularly spaced rectangular array by tuning the probe concentration as described in the previous section. Usually no more than two iterations are required for optimization.

Figure 14B:
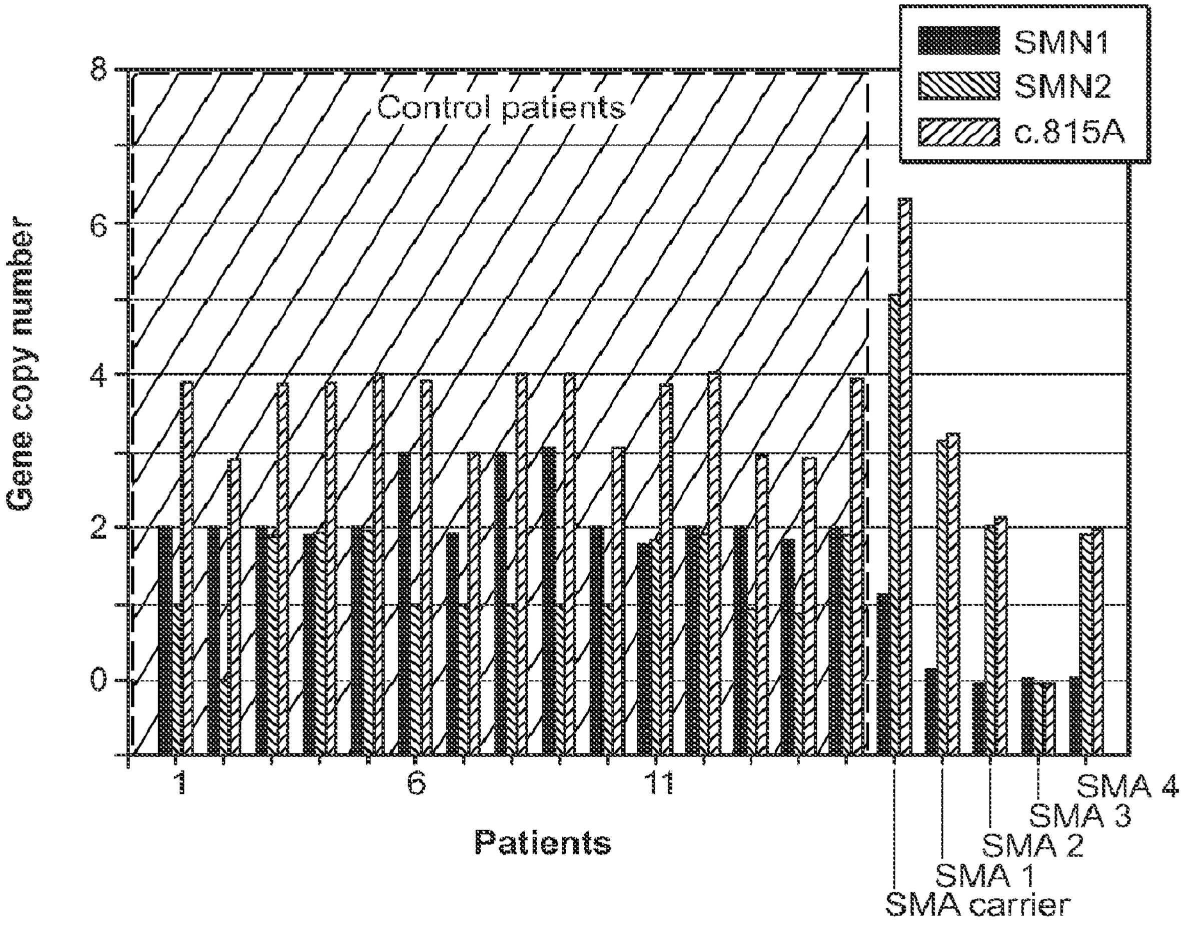

In another method of the invention, the different populations were sufficiently well resolved to allow droplets within each population to be counted by integration across rectangular boundaries. The boundaries were positioned at midsections between neighboring peaks. The methods of the invention are not constrained to rectangular boundaries, or to specific boundary locations between peaks. Rather, any closed or unclosed boundary condition can suffice. Boundary conditions do not need to be "binary" either, in the sense that weighted integrations can also be performed across the boundaries to arrive at droplet counts. The peak position of each cluster varied by no more than 2% from run to run after normalization to the intensity of the empty droplets to account for variations in detection efficiency (data not shown). Hence, once identified, the same boundaries for integration could be reused between samples. The methods of the invention are not limited to fixed boundary positions. Dynamic population identification and boundary selection in between samples or studies is anticipated. Twenty different patient samples from the Coriell cell repositories were analyzed with this assay: 4 afflicted with SMA, 1 SMA carrier, and 15 negative controls. Assay results are shown in FIG. 14*b*. Gene copy number was calculated as before, as the ratio of occupancies derived from the number of target droplets vs. reference droplets. Like the copy number measurement in FIGS. 11*a-b*, each assay yielded ratios very close to the expected integer values, but when all of the patient data was plotted as actual ratio vs. expected integer ratio a small systematic deviation from the ideal slope of 1 was observed. Measured slopes were 0.92, 0.92, and 0.99 for SMN1, SMN2, and c.815A respectively. For clarity, the data in FIG. 14*b* was scaled to the ideal slope of 1.

The measured genotypes of the different patients were consistent with their disease conditions (unafflicted, carrier, or afflicted). The patients afflicted with SMA each had zero copies of SMN1 (numbers SMA 1-4 in FIG. 14*b*), the carrier had just one copy, and the negative controls all had two or three copies (numbers 1-15). Three unrelated individuals (numbers 6, 8, and 9) had three copies of SMN1, occurring at a rate of 20% which is similar to a previous report for healthy individuals. Variability in SMN1 copy number is not surprising since it lies within an unstable region of chromosome 5q13. A larger variety of SMN2 copy numbers was observed. One to two copies were most common in the control group, although one individual had zero copies, a distribution consistent with expectations for normal individuals. The SMA carrier and afflicted patients had elevated copy numbers of SMN2 on average: 5 for the carrier, two afflicted with 3 copies, and the others with 2 copies. The afflicted patients were all diagnosed as SMA Type I, the most severe form, based on clinical observations according to the Coriell repository. The strong genotype/phenotype correlation between SMN2 copy number and disease severity suggests that the two individuals with three copies of SMN2 might have an improved Type II prognosis, especially for the patient SMA 1 who had survived to three years at the time of sampling, much beyond the typical maximum life expectancy for SMA Type I of 2 years. However there remains reluctance to predict disease outcome based on SMN2 copies alone since other less well characterized or unknown modifying genes may impact prognosis and because not all SMN2 copies may be complete genes. Furthermore some Type I patients have begun surviving longer in newer clinical settings. Hence, with little clinical information regarding the patients available to us, we can conclude that our SMN2 assay results were consistent with broad expectations for disease severity.

The SNP assay revealed that all patients carried the normal c.815A genotype and no instances of c.815G were observed. The mutation is relatively rare and hence was not expected to appear in a small patient panel. Of interest, however, was the presence of an apparent extra gene fragment in two unrelated individuals that was uncovered with the SNP assay. The c.815A>G assay does not discriminate between SMN1 and SMN2 due to their high sequence similarity, and hence the total copies of c.815A and G should equal the sum of the copies of SMN1 and SMN2. This was true for all patients except for healthy patients number 1 and 2, both of whom had one extra copy of c.815A. c.815 lies on exon 6, and the SNP that discriminates between the SMN1 and SMN2 genes lies on exon 7, hence the extra genes may be fragments of SMN1 lacking exon 7. This seems reasonable because the deletion of exon 7 is the common mutation causing 95% of cases of SMA (reviewed by Wirth et al.) and it is carried by 1/40 to 1/60 adults. Thus these patients might have been typical carriers of SMA but for the acquisition of at least one compensating healthy copy of SMN1 on the same chromosome.

9-Plex Assay for Spinal Muscular Atrophy

Figure 15:
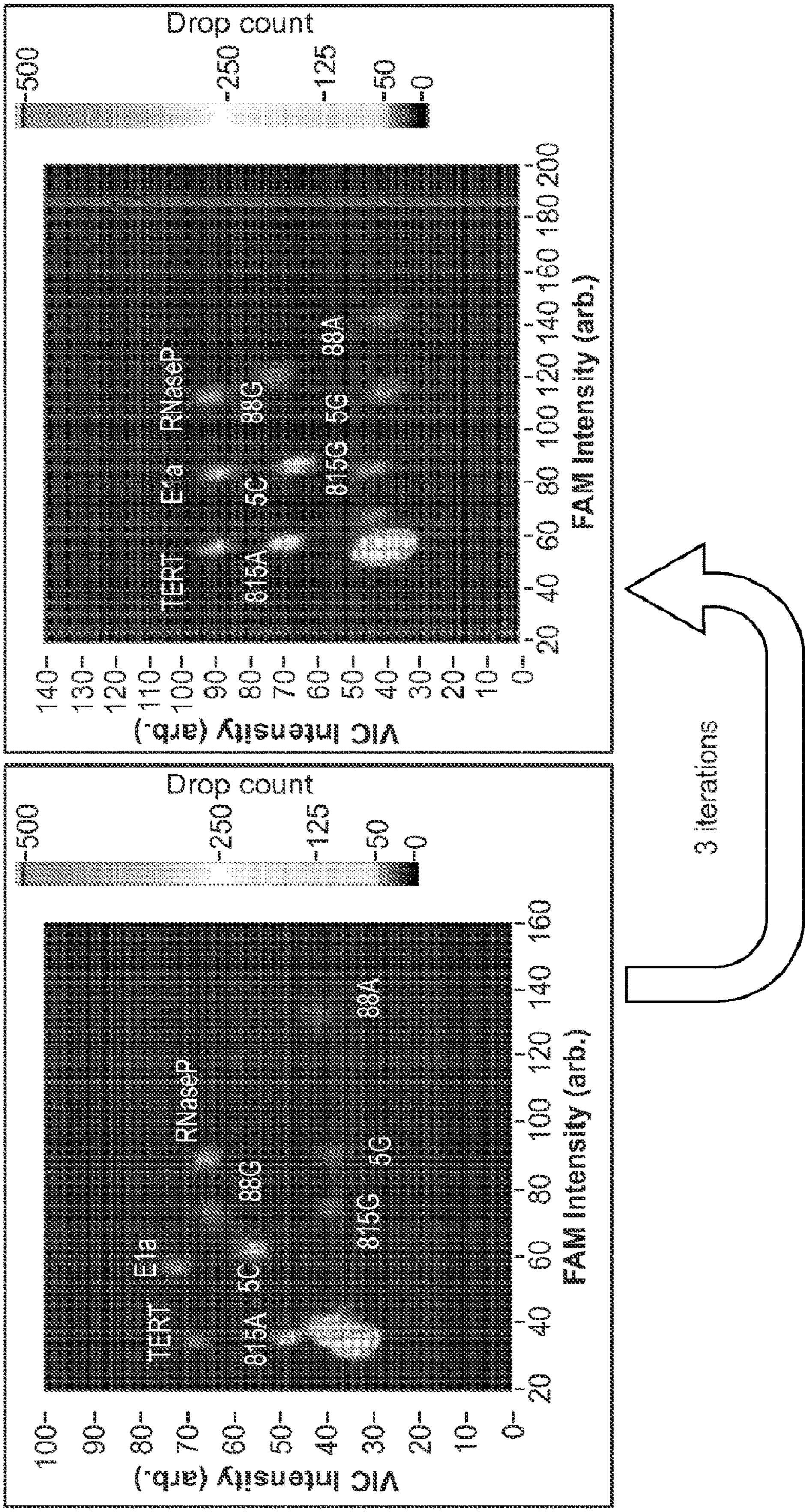
FIG. 15 depicts a 9-plex dPCR assay for spinal muscular atrophy with only two fluorophores, showing the process of optimizing droplet intensities.

A 9-plex assay for certain SMA related targets was also demonstrated with just two colors (probes containing FAM and VIC fluorophores). Aside from the optimized primer and probe concentrations, assay conditions and experimental procedures were identical to the 5-plex assay above. FIG. 15*a* shows the various droplet populations in 2-D histograms before optimization of probe concentrations. The identity of the different targets is shown on the figure itself. As one method of the invention, the identification of the different populations was made as before, by selective exclusion and/or addition of one or more assays. Most of the populations were already well resolved, with the exception of the probe for the c.815A genotype that was in close proximity with the cluster corresponding to empty droplets. After three iterations of optimization of probe concentrations, all of the target populations were well resolved from each other, and well resolved from the empty droplets (FIG. 15*b*). Three methods of the invention were highlighted in this demonstration: (1) nine DNA targets were uniquely identified in a two-dimensional histogram, far beyond the capabilities of conventional qPCR; (2) target DNA molecules were distinguished on the basis of some combination of both color and intensity arising from one or multiple probes against the same target; and (3) the relative positions of the target molecules within the histogram were adjusted by varying the probe concentrations to optimize the pattern of colors and intensities for increased resolution amongst the various droplet populations.

As one method of the invention, different droplet populations were identified by selective addition or exclusion of assays in the examples above. However the invention is not limited to this method alone. Rather, any method for population assignments known to those in the art are considered. Methods of the invention include any method that can cause an identifiable displacement, appearance, or disappearance of one or more populations within the histograms including changing the probe and primer concentrations together, either by the same factor or by different factors; changing the probe concentration alone; changing the primer concentrations alone; changing the thermal cycling conditions; and changing the master mix composition. Another method of the invention takes advantage of prior knowledge of the position of an assay within a histogram to assist assignment.

Multiplexing Capacity

The level of multiplexing demonstrated in the preceding SMA example was 9×, significantly exceeding the maximum practicable number with qPCR. Without wishing to be constrained by theory, the two main limitations are the resolution between assays and the increasing fluorescence intensity of empty droplets with higher loading of probes. A method of the invention involves optimizing the pattern of colors and intensities of the different probes for maximum multiplexing while still achieving adequate specificity for each individual reaction. Although rectangular arrays of droplet populations were demonstrated for the 5- and 9-plex reactions, another desirable pattern is the tight-packed hexagonal array. However the invention is not constrained to any particular array strategy.

Adding extra colors would increase the capability even further, however with some diminishing returns because the fluorescence of the empty droplets would continue to rise. The capacity could be yet further increased with better probes yielding larger differential signals, such as hybrid 5'-nuclease/molecular beacon probes that reduce background by contact quenching yet exhibit the bright signals typical of free unquenched fluorophores. With such improvements multiplexing capacity exceeding 50× can be envisioned.

Combined Multiplexing with Optical Labeling

Using droplet-based microfluidics, multiple targets can also be measured simultaneously by a different method. According to the alternative method, primers and probes can be loaded individually into droplets along with an optical label to uniquely identify the assay. Typically the optical label is a fluorophore, or a combination of different fluorophores, that are spectrally distinct from the probe fluorophore. Various different types of droplets, each containing different assays that are uniquely identified by different optical labels, can be mixed into a "library" of droplets. Then, according to methods of the invention above, library droplets are merged one-to-one with droplets containing template DNA. After thermal cycling, some droplets that contain template DNA will exhibit brighter fluorescence at the emission wavelengths of the probes. The specific target DNA molecules giving rise to these PCR(+) signals are subsequently identified by the optical probes. In one study, the six common mutations in KRAS codon 12 were screened in parallel in a single experiment by one-to-one fusion of droplets containing genomic DNA with any one of seven different types of droplets (a seven-member library), each containing a TaqMan® probe specific for a different KRAS mutation, or wild-type KRAS, and an optical code.

In one method of the invention, optical labeling can be combined with the various methods for multiplexing dPCR already incorporated into this invention. For example, a single optical label might code for the entire 5-plex SMA assay, above, instead of just a single assay as in the KRAS example above. In this manner, other optical labels might code for different screening assays for newborn infants. According to other methods of the invention, above, a single DNA sample from an infant could then be analyzed with all of the assays simultaneously by merging droplets containing the DNA one-to-one with library droplets containing the optically encoded assays.

Figure 16:
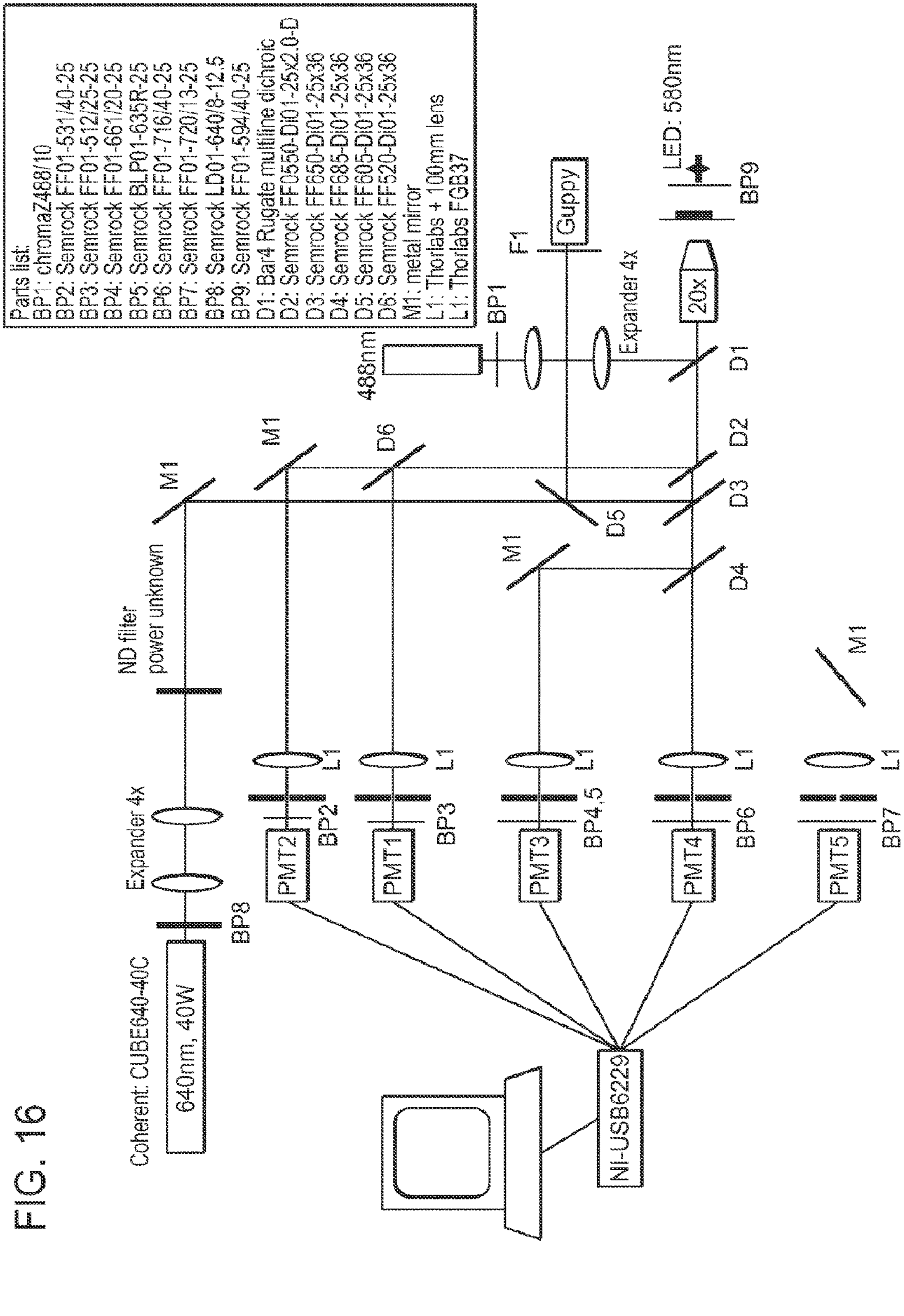
FIG. 16 depicts an optical schematic for combining optical labels with multiplexing.

As an example of combining multiplexing with optical labels, a so called 3×3×3 combination multiplex reaction with optical labeling was demonstrated (3×3 optical labeling with two fluorophores, each encoding a triplex assay, for a total of 27-plex). Two fluorophores were employed for optical labeling, Alexa633 and CF680 (excited by a 640 nm laser), with three intensity levels each producing nine total optical labels. As before with the 5- and 9-plex assays for SMA, TaqMan assays were used with FAM and VIC fluorophores (excited by a 488 nm laser). The fluorescence from the FAM and VIC fluorophores were recorded simultaneously with the fluorescence from the optical labels, requiring modifications to the optical layout of the instrumentation described for the SMA assay (the optical schematic for two-laser excitation and 4-color detection is shown in entirety in FIG. 16). Also, co-flow microfluidics were used in this example (the use of co-flow based microfluidics for this application is one of the methods of the invention described above). In this case, the template DNA was introduced into the chip in one flow, and the PCR master mix, the primers and probes for one triplex assay, and the unique composition of fluorophores for the optical label were introduced into the chip in another flow simultaneously. The two flow streams converged in a fluidic intersection upstream from the droplet forming module, and thus each droplet formed contained the contents of both flow streams. Methods to implement co-flow microfluidics are well known to those in the art. The droplets were collected, and then the procedure was repeated with the next triplex assay and optical label. The procedure was repeated a total of nine times, once for each pair of assays and optical labels. All of the droplets were collected into a single PCR tube and thermally cycled off chip. The mixture of thermally cycled droplets was reinjected into the same read-out chip as used for the SMA assay, above, and the fluorescence intensities of the assays from all four fluorophores was recorded.

Figure 17:
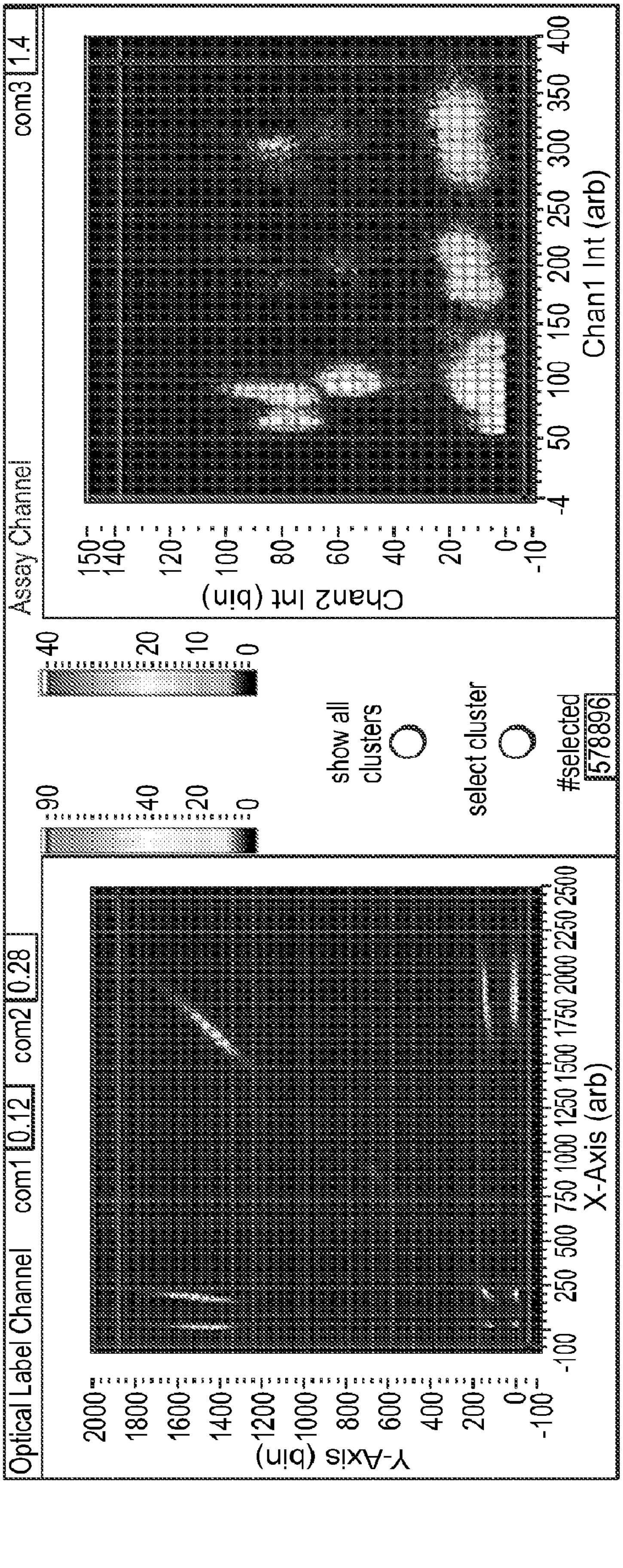
FIG. 17 depicts a dPCR assay combining multiplexing with optical labels using co-flow microfluidics. The contributions from all droplets are shown, that is, from three different triplex assays. (Both panels) 2-D histograms shown as heat maps with hotter colors representing higher droplet counts. (Left panel) histogram of optical labels, i.e. fluorescence intensities of droplets measured at wavelengths for the two fluorophores comprising the optical labels. (Right panel) assay histogram, i.e. fluorescence intensities of droplets measured at wavelengths suitable for FAM detection (x-axis), and VIC detection (y-axis). Both histograms were compensated for spectral overlap by standard techniques.

FIG. 17 shows the cumulative results from all droplets in the 3×3×3 assay using co-flow microfluidics. The figure shows two 2-D histograms of droplet fluorescence intensities, the histogram on the left from all of the optical labels, and the histogram on the right from the assays. Standard methods were used to compensate for spectral overlap. The histograms are shown as a heat maps, with hotter colors designating larger numbers of droplets. Nine different clusters of droplets were clearly evident in the histogram of the optical labels, corresponding to each of the nine different optical labels: there is a small group of four clusters at the bottom left corner of the histogram, corresponding to optical labels with the lowest fluorescent intensities; and there are five clusters appearing as linear streaks at the higher intensities. The droplet clusters were less distinct in the histogram for the assay, but this was as expected because the droplets shown contained all of the triplex assays. The individual assays became clearly distinct once a single type of assay was selected by using the optical labels, as follows.

Methods of the invention involve selecting individual populations of droplets all containing the same optical labels, or groups of optical labels. In some methods of the invention, boundaries of fluorescence intensity were used to specify populations. In the example shown here, a rectangular boundary was used specifying the minimum and maximum fluorescence intensities for each fluorophore. However the methods of the invention are not restricted to rectangular boundaries. Any boundary, closed or unclosed, can be employed. Furthermore, according to methods of the invention, selections of droplet populations can be made by any method, and is not restricted to threshold-based methods such as boundary selection.

Figure 18A:
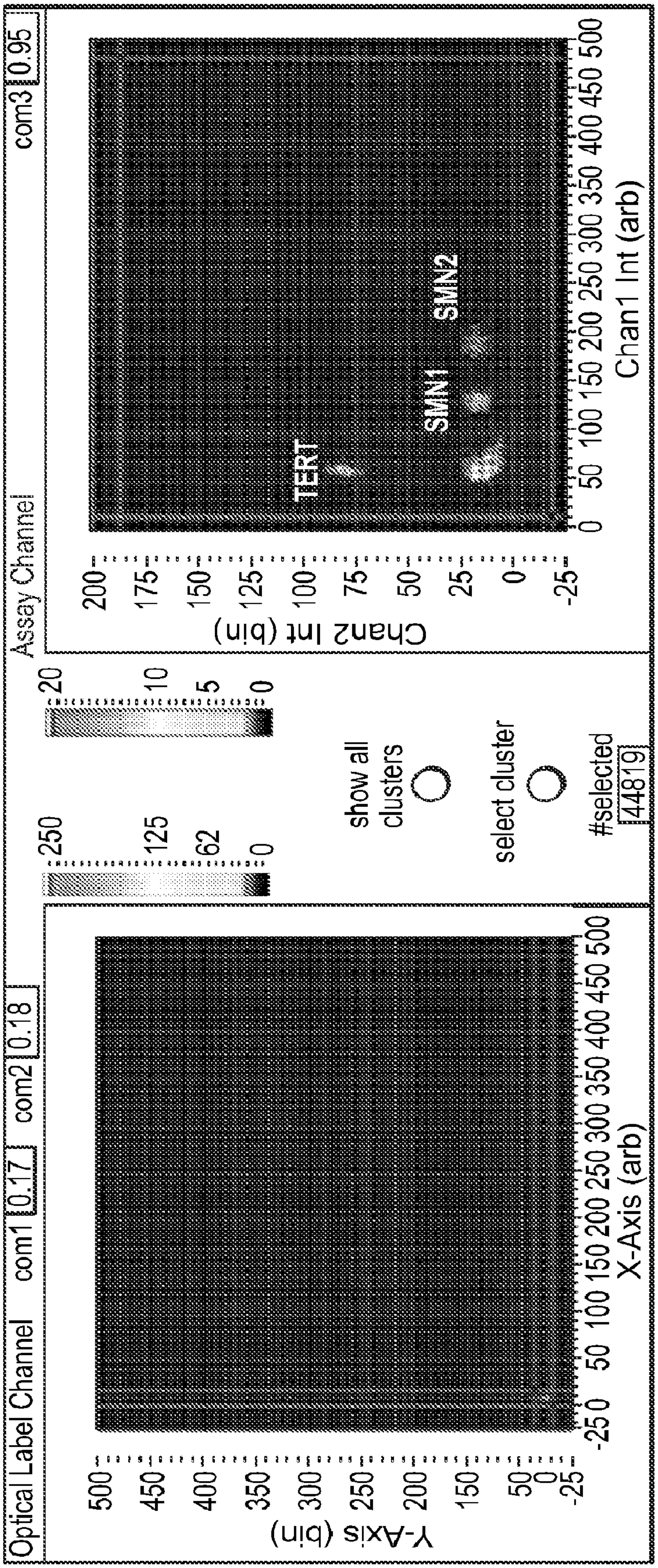
FIGS. 18A-C show single assay selections using optical labels. Selections were taken from all of the droplets from FIG. 17. Each of the three different selections in FIGS. 18A-C were for optical labels encoding the same assay (TERT, SMN1, and SMN2). Histograms are as described in FIG. 17. (Left histograms, optical labels) Superimposed lines demark the bounding box for selecting a single optical label. (Right histograms, assay) Only droplets containing the selected optical label are displayed.
Figure 18B:
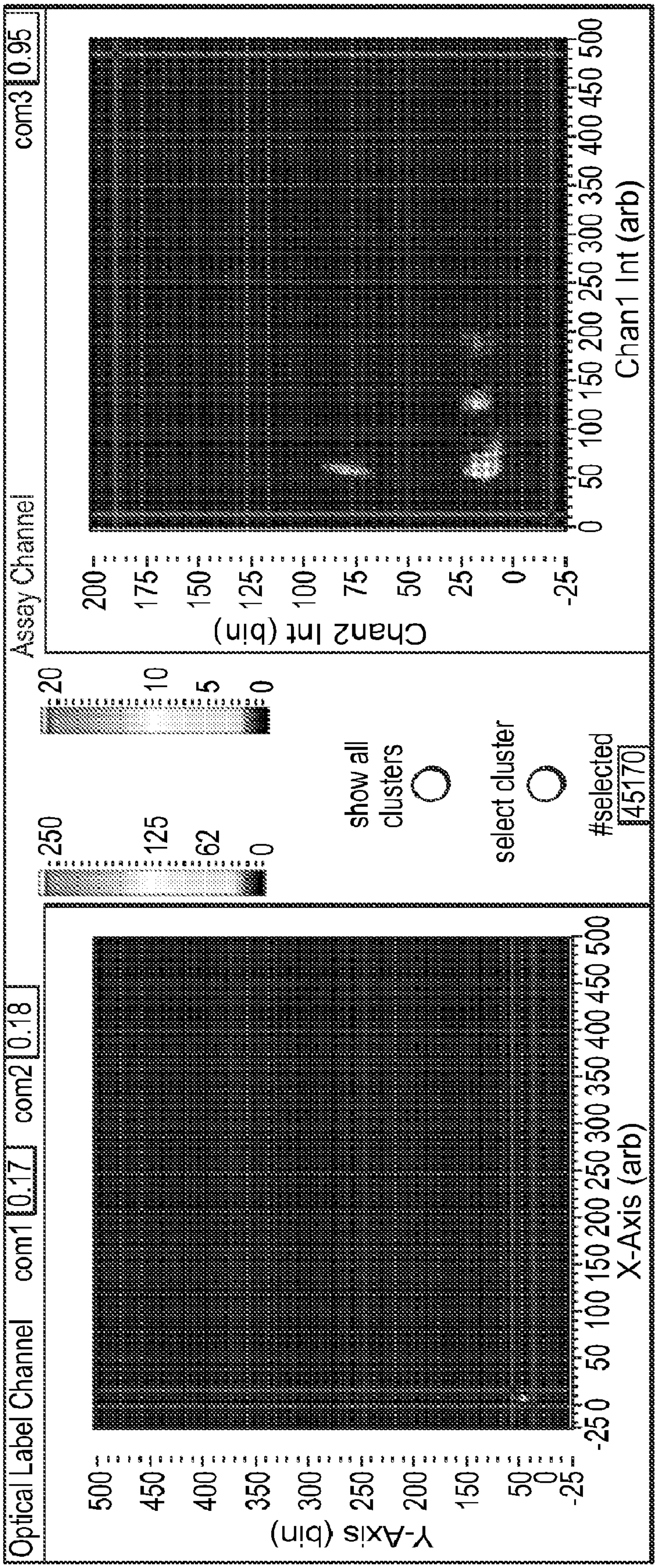
Figure 18C:
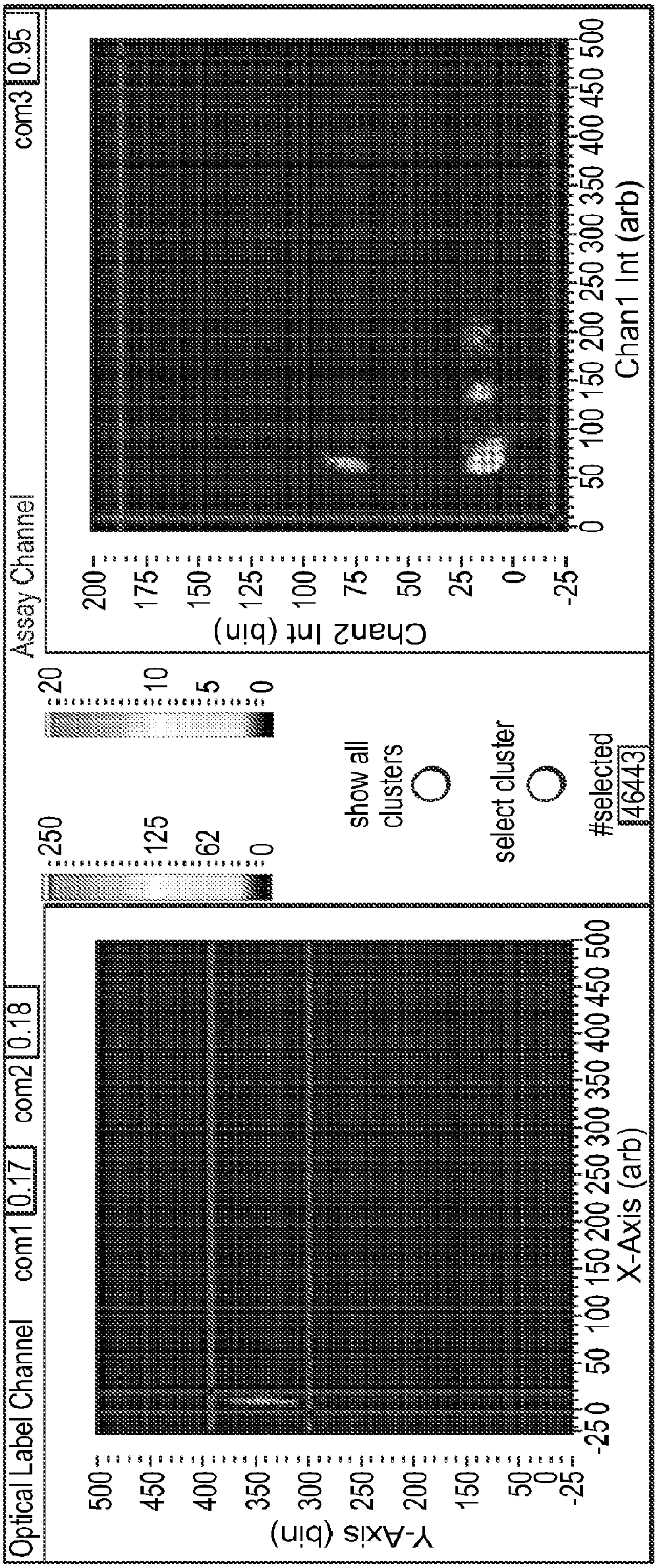

FIG. 18A shows the droplet fluorescence intensities for the assay (right histogram) when only one optical label was selected (left histogram). The lines overlaid on the histogram of the optical labels identify the rectangular boundary used to select just the optical label with the lowest fluorescence for both fluorophores. Both histograms showed only the droplets that were selected. After selection, four distinct clusters of droplets appeared in the assay histogram, three for the different assays (in this case, assays for SMN1, SMN2, and TERT, where TERT is another common reference gene) and one for the empty droplets. The copy numbers for SMN1 and SMN2 were measured by the same methods of the invention as described above for the 5-plex SMA assay, with values of 1.8 and 0.94 close to the expected values of 2 and 1, respectively. The same assay was encoded with two other optical labels, and their selections are shown in FIGS. 18B and C. Similar results were achieved, with an overall measurement of 1.9±0.1 and 0.9±0.1 copies of SMN1 and SMN2 respectively, showing the measurement to be accurate within experimental uncertainty.

Figure 19A:
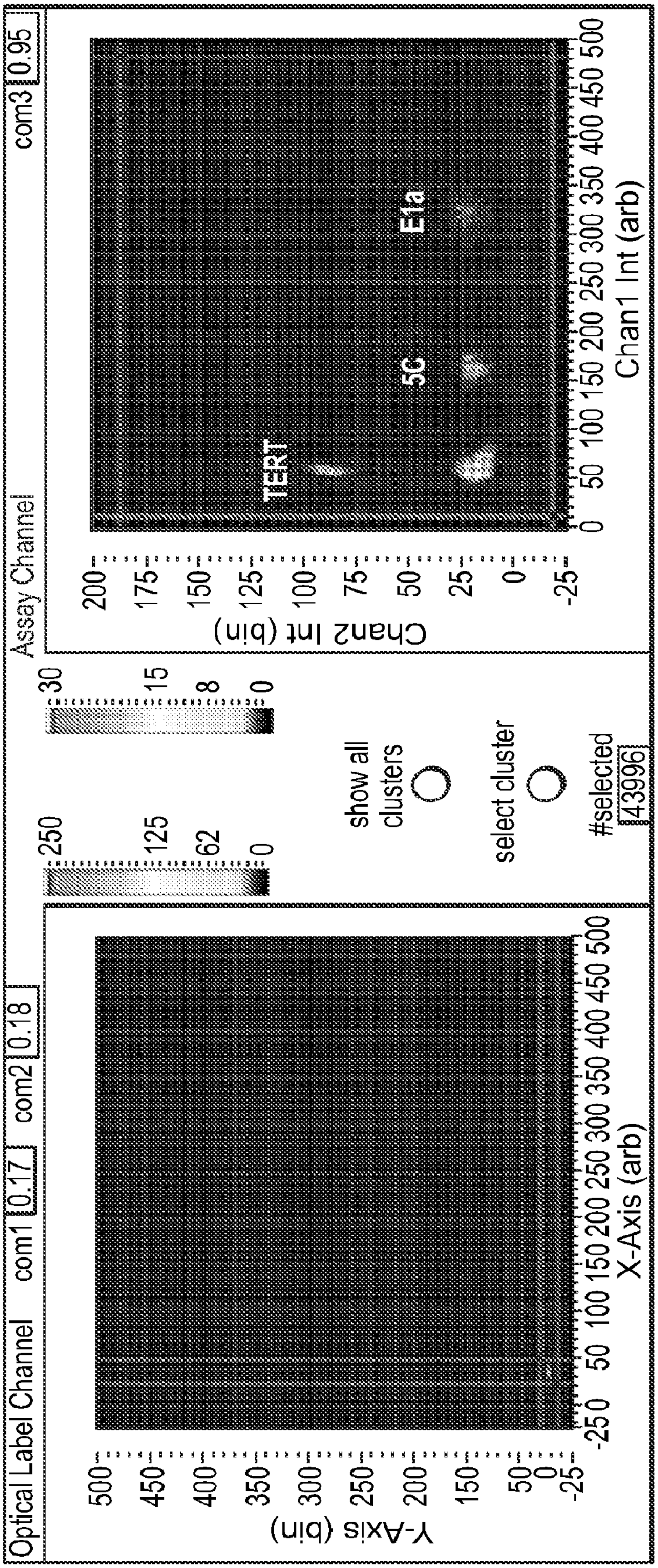
FIGS. 19A-C show single assay selections using optical labels. Selections were taken from all of the droplets from FIG. 17. Each of the three different selections in FIGS. 19A-C was for optical labels encoding the same assay (TERT, c.5C from SMN1, and BCKDHA). Histograms are as described in FIG. 17. (Left histograms, optical labels) Superimposed lines demark the bounding box for selecting a single optical label. (Right histograms, assay) Only droplets containing the selected optical label are displayed.
Figure 19B:
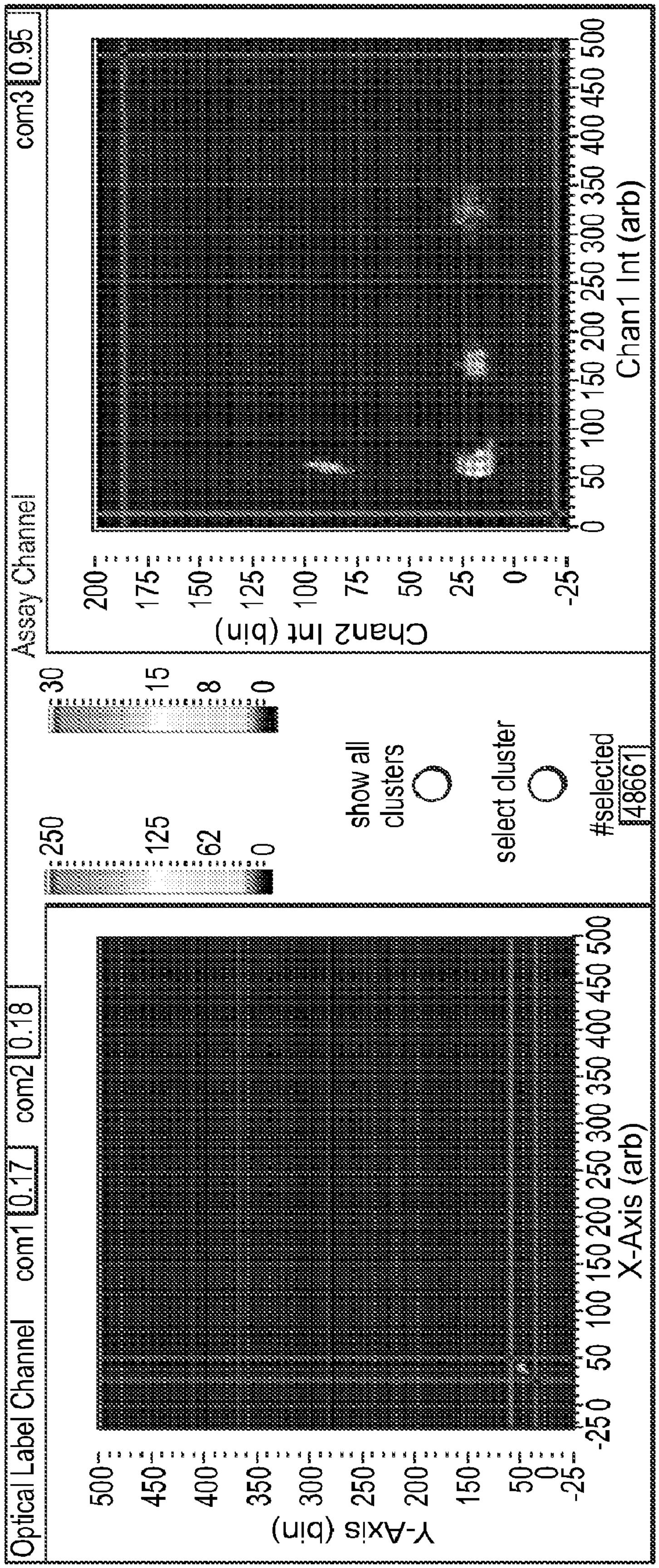
Figure 19C:
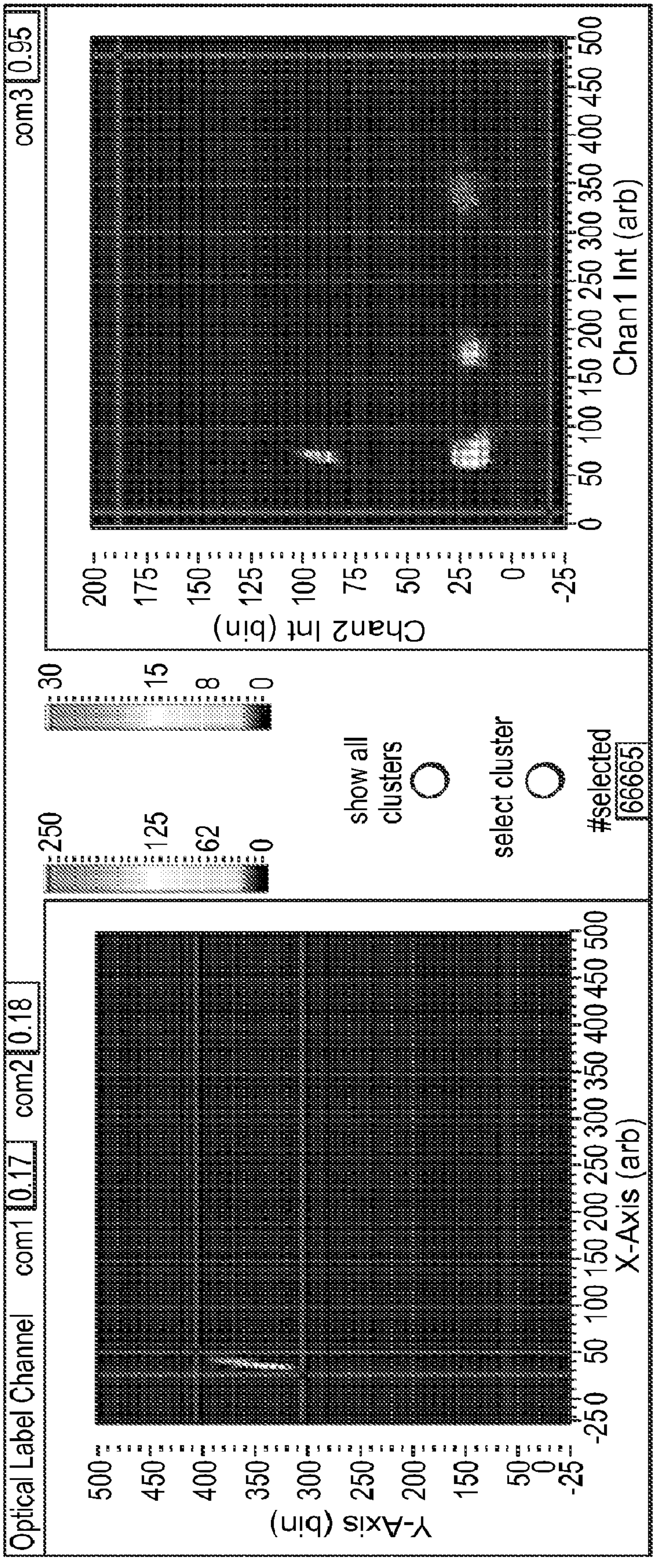
Figure 20A:
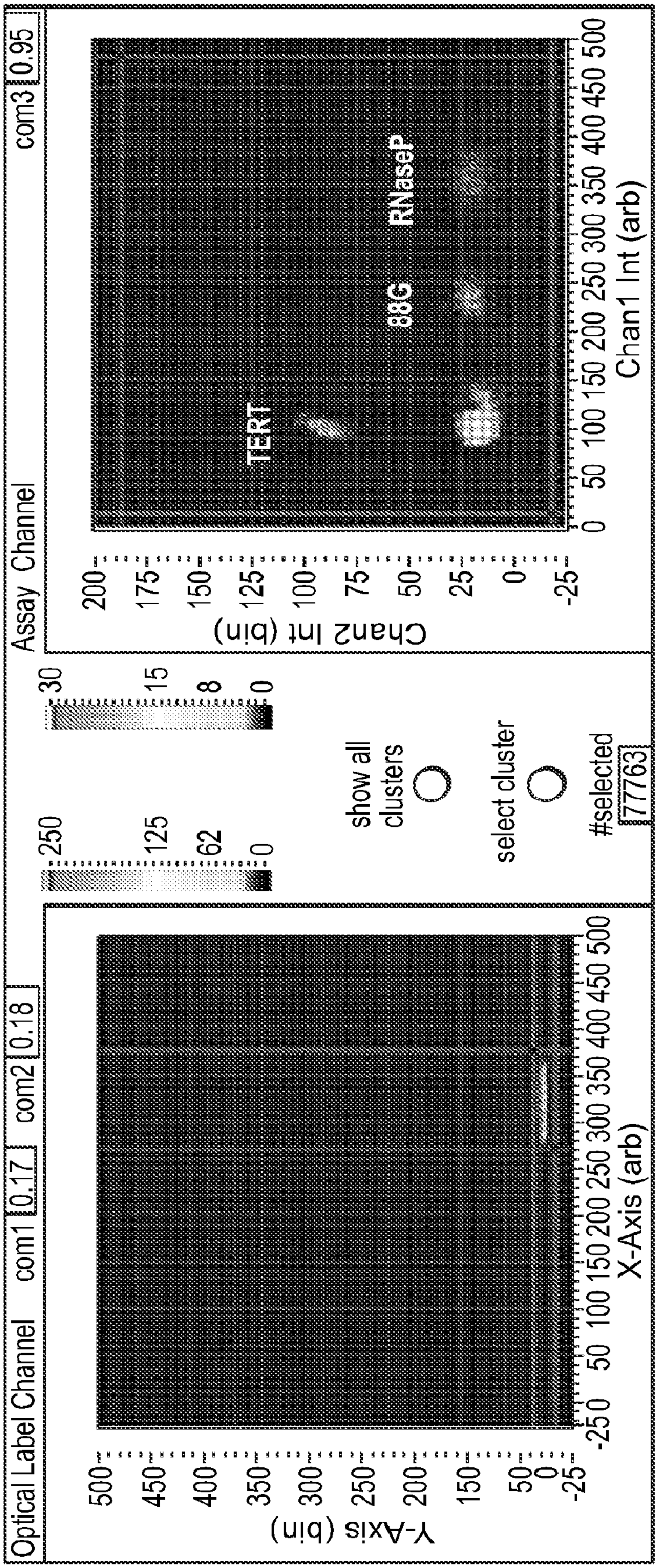
FIGS. 20A-C show single assay selections using optical labels. Selections were taken from all of the droplets from FIG. 17. Each of the three different selections in FIGS. 20A-C was for optical labels encoding the same assay (TERT, c.88G from SMN1, and RNaseP). Histograms are as described in FIG. 17. (Left histograms, optical labels) Superimposed lines demark the bounding box for selecting a single optical label. (Right histograms, assay) Only droplets containing the selected optical label are displayed.
Figure 20B:
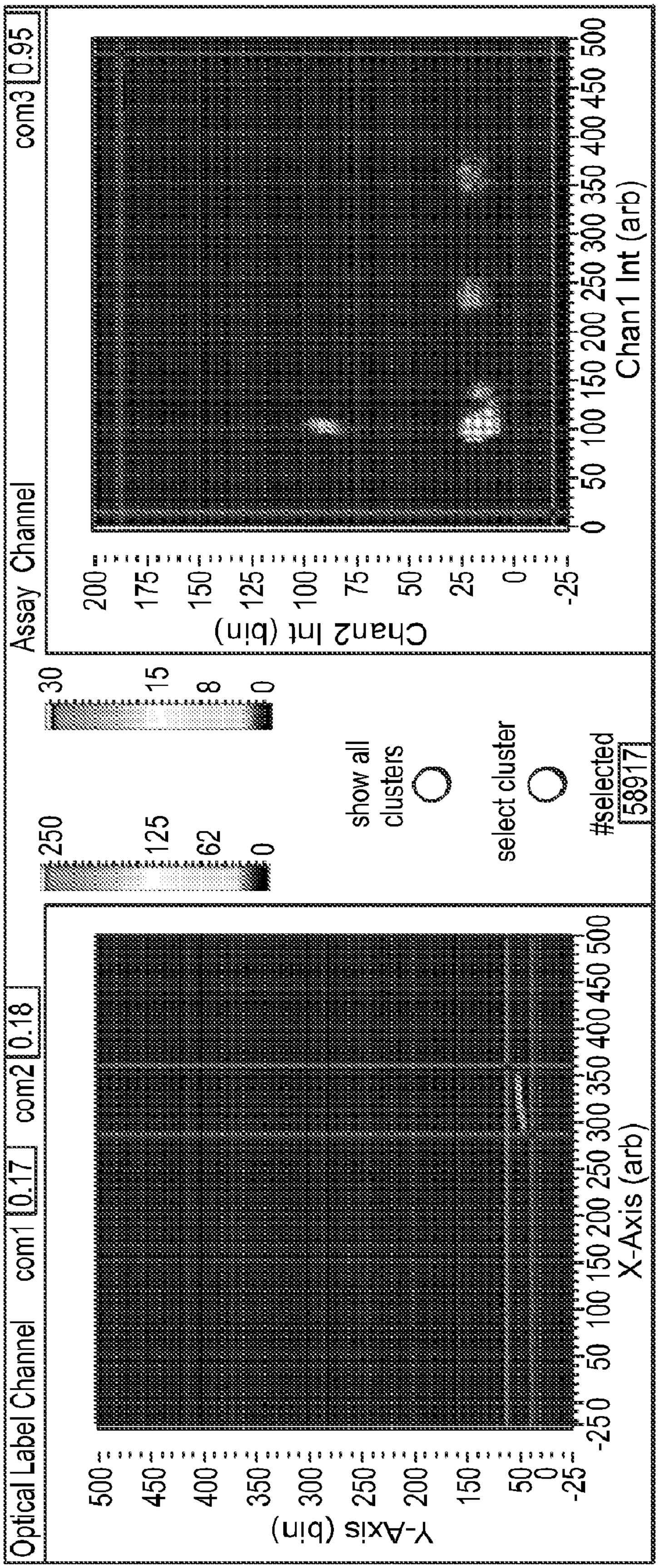
Figure 20C:
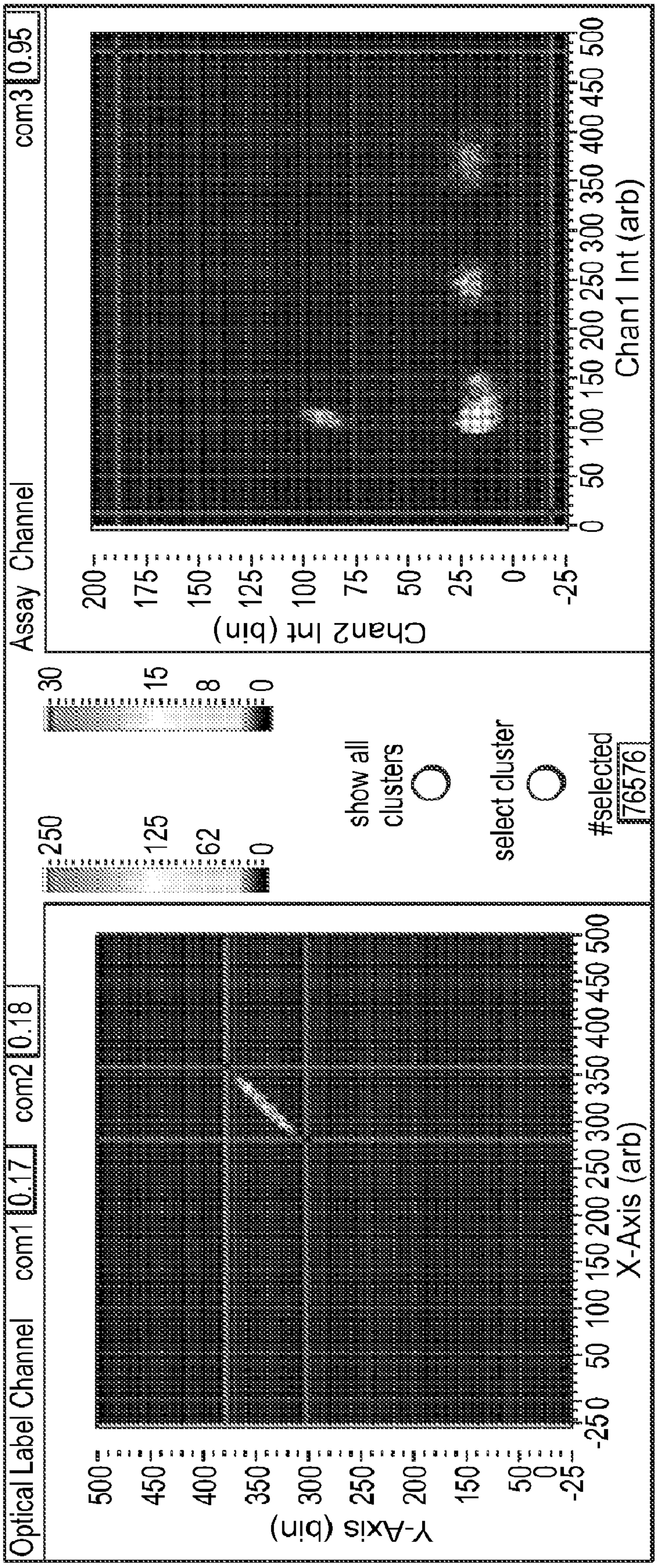
Figure 21A:
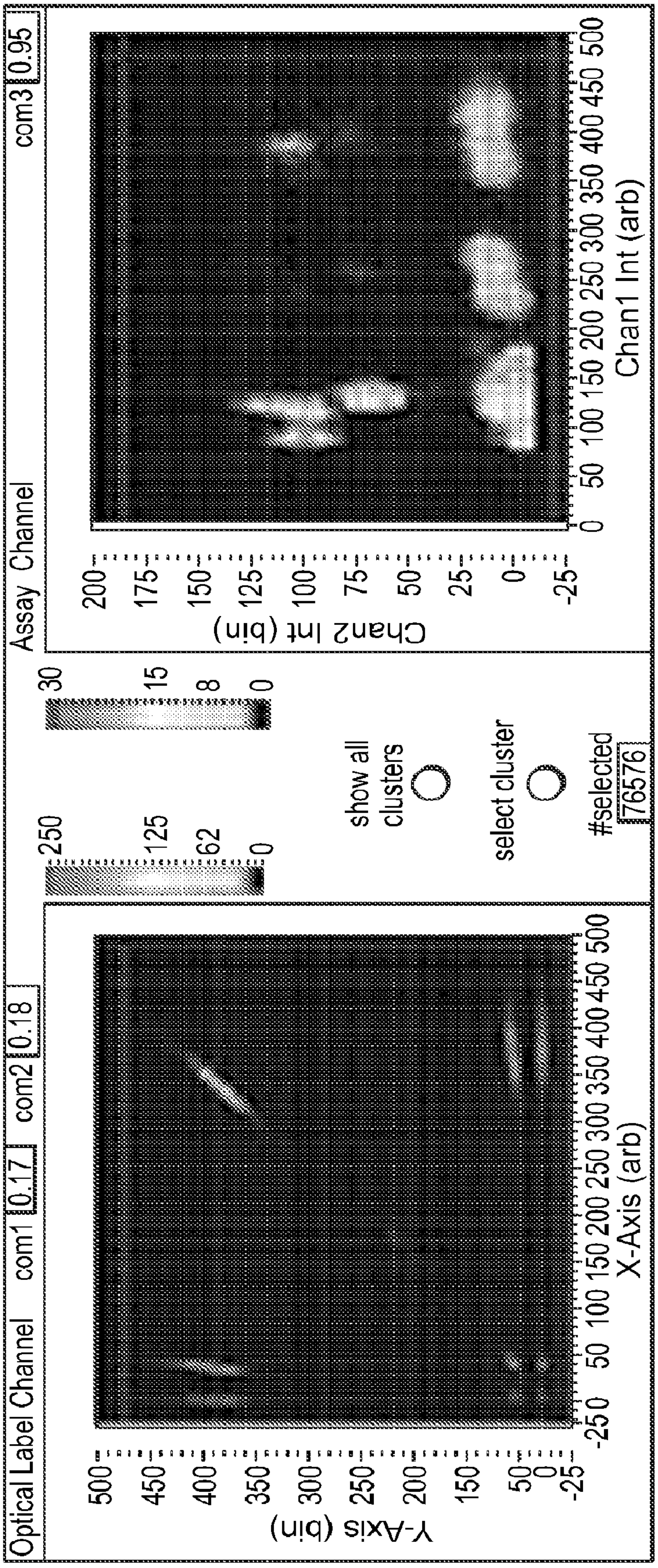
FIGS. 21A-J depict a dPCR assay combining multiplexing with optical labels using droplet merging.
Figure 21B:
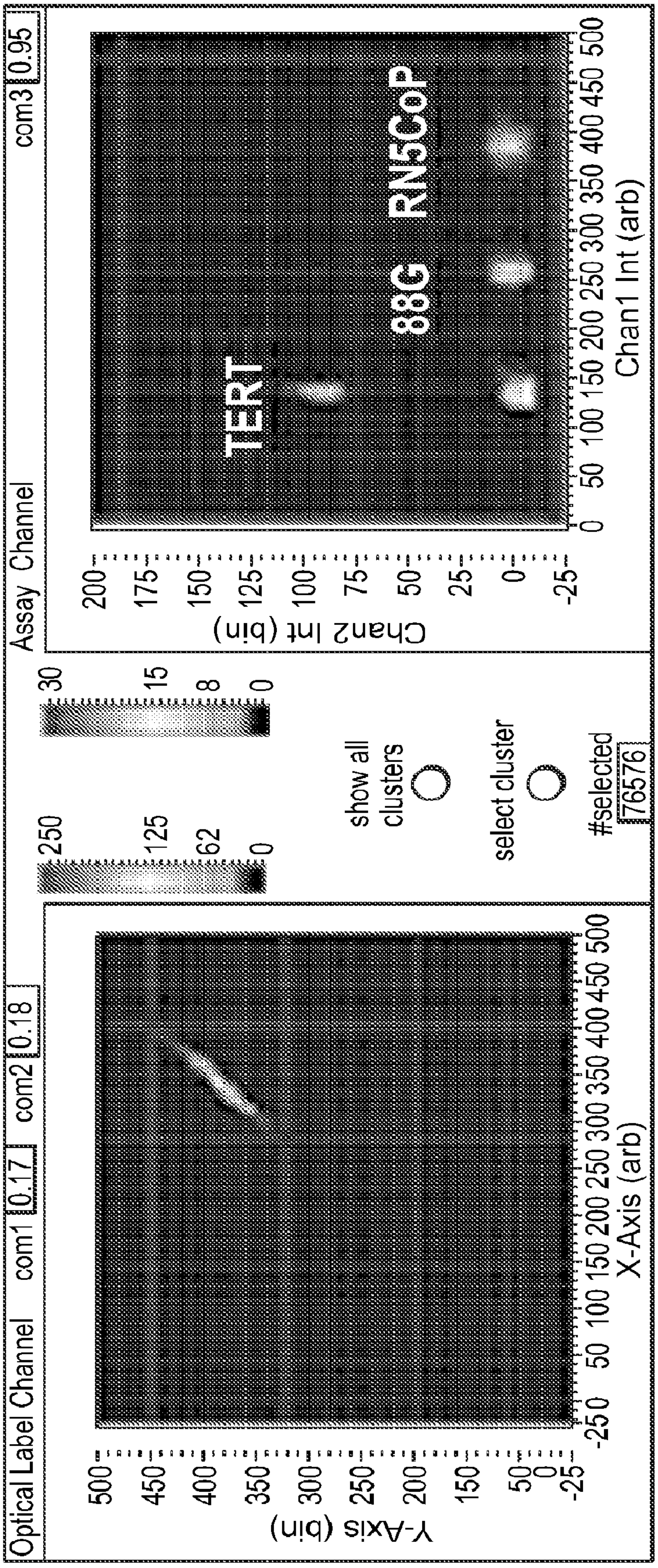
Figure 21C:
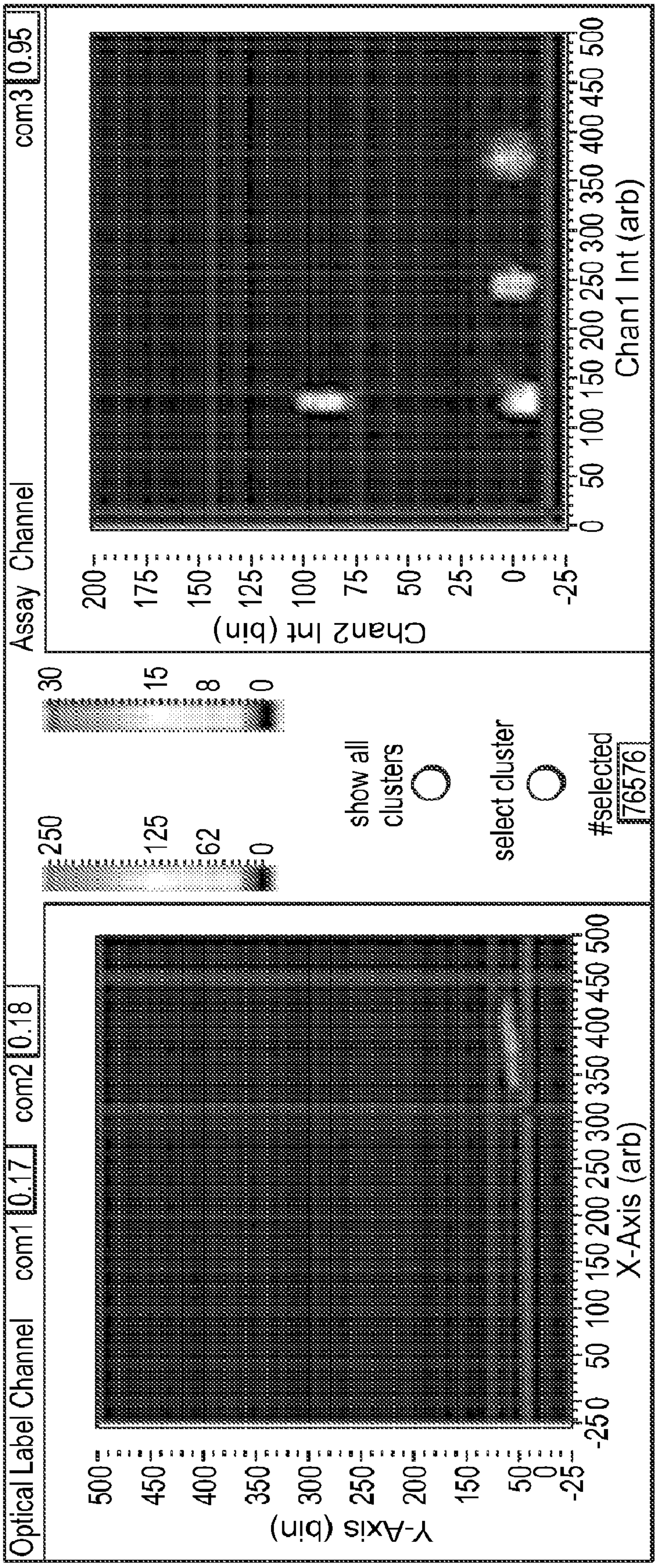
Figure 21D:
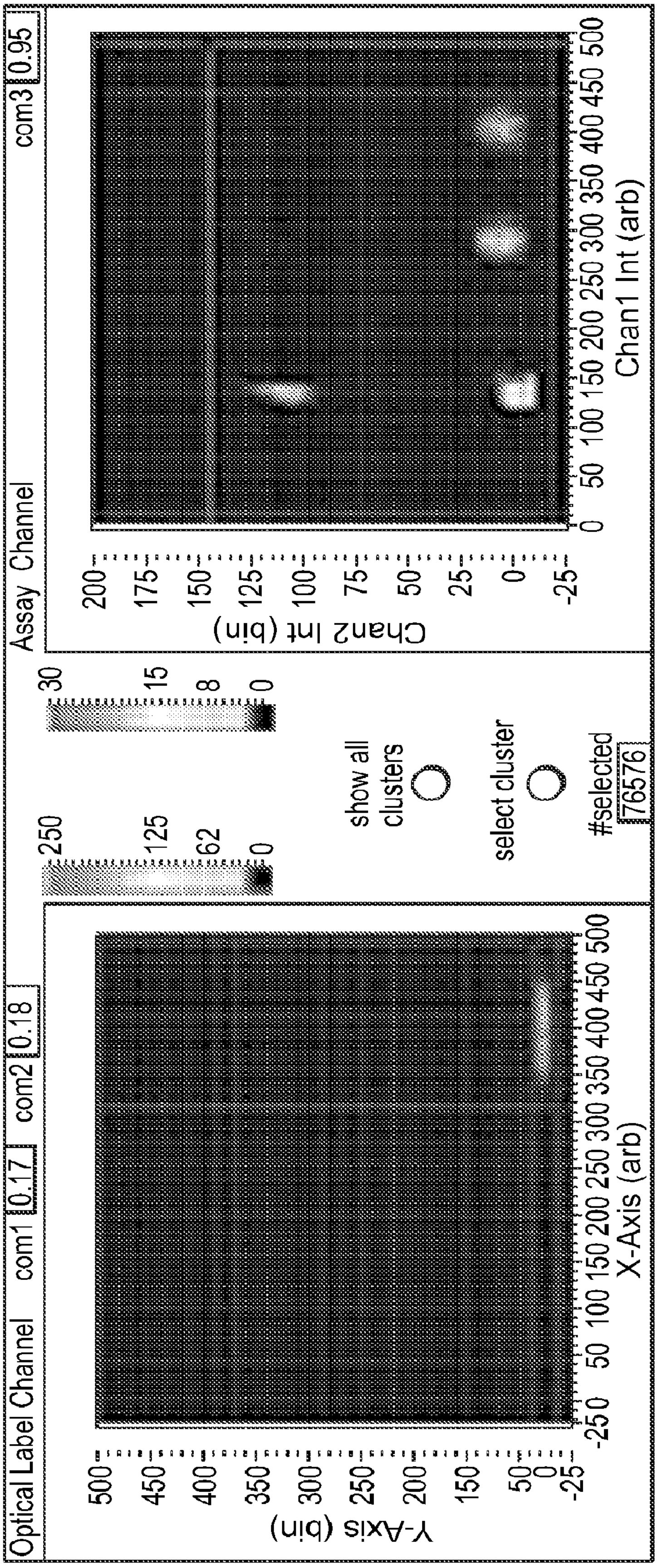
Figure 21E:
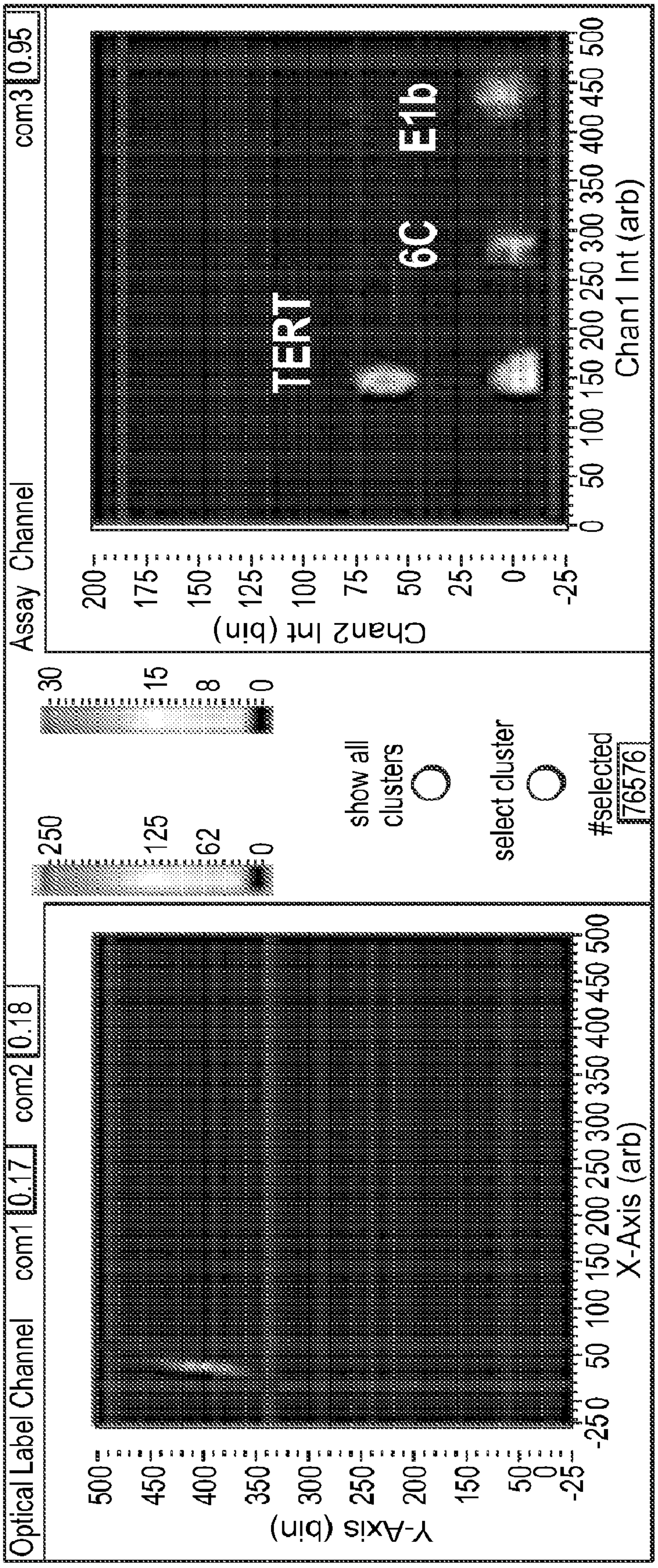
Figure 21F:
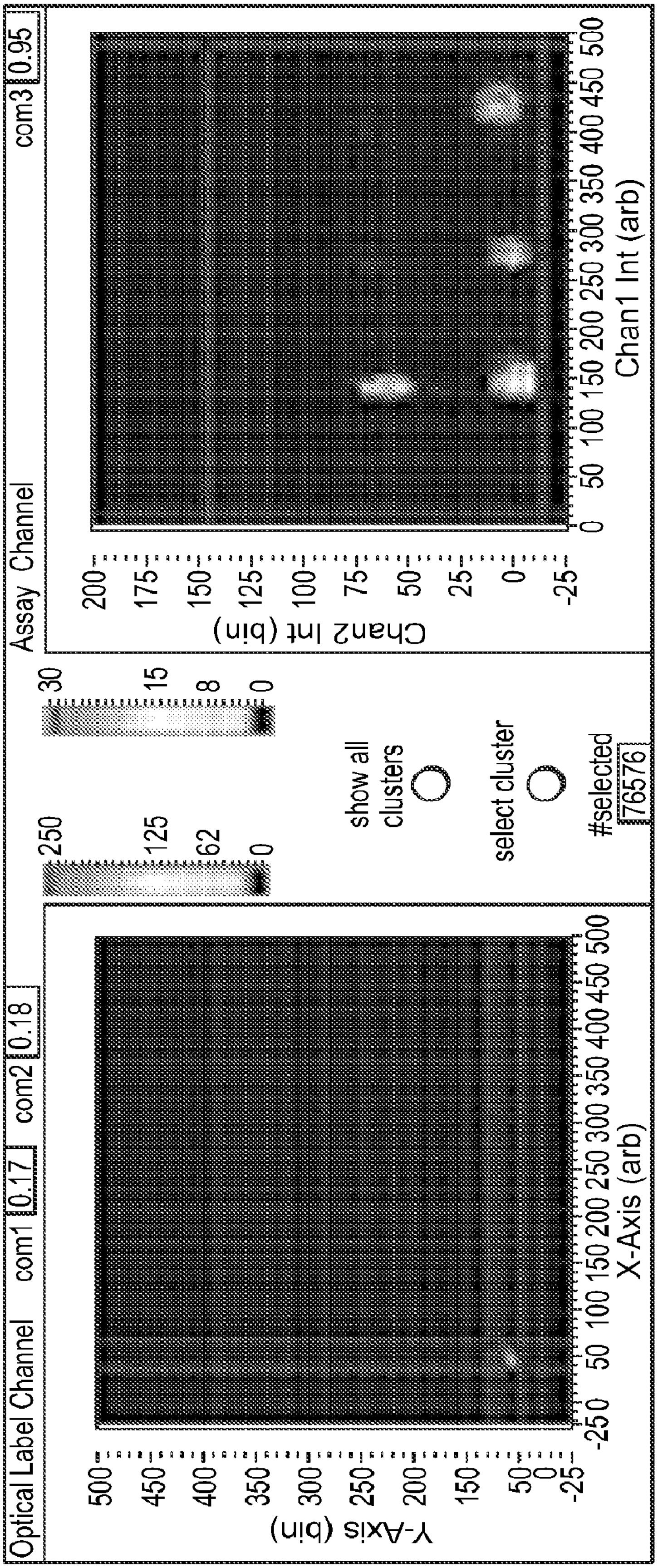
Figure 21G:
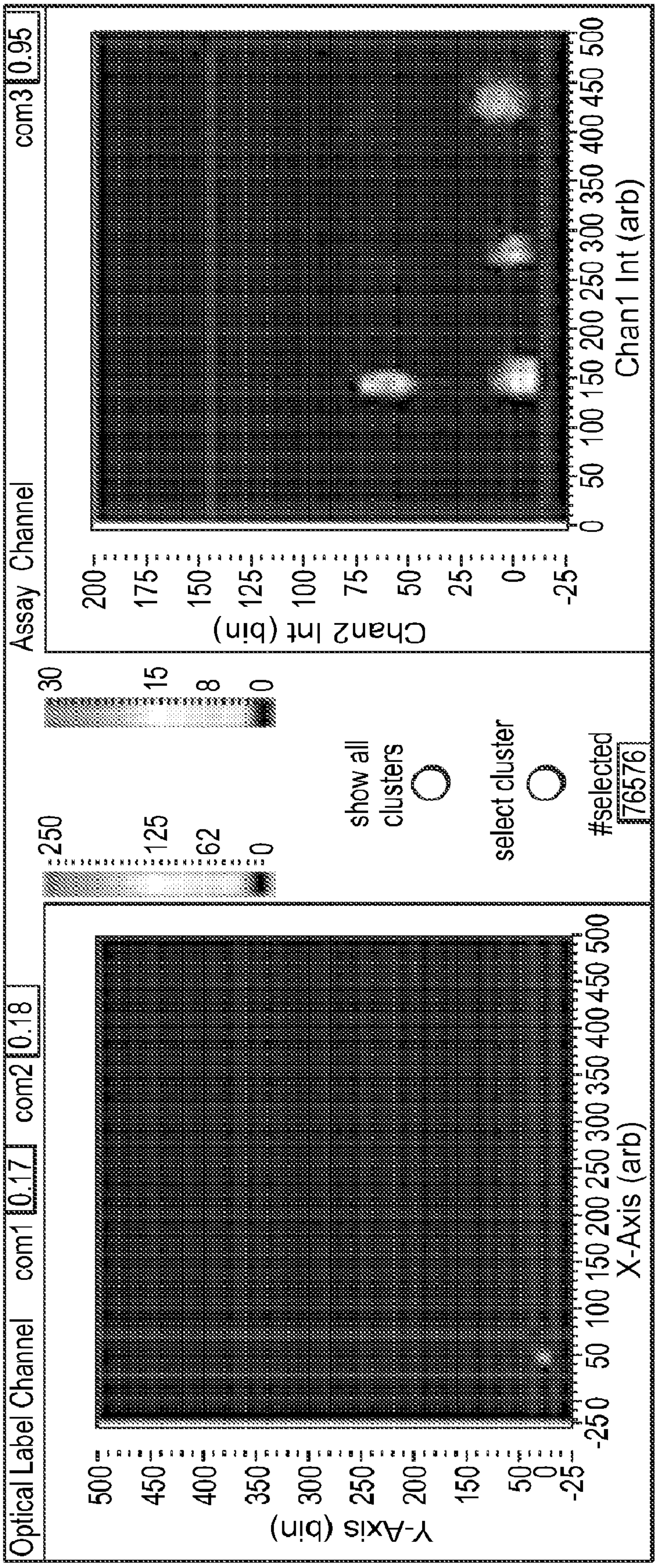
Figure 21H:
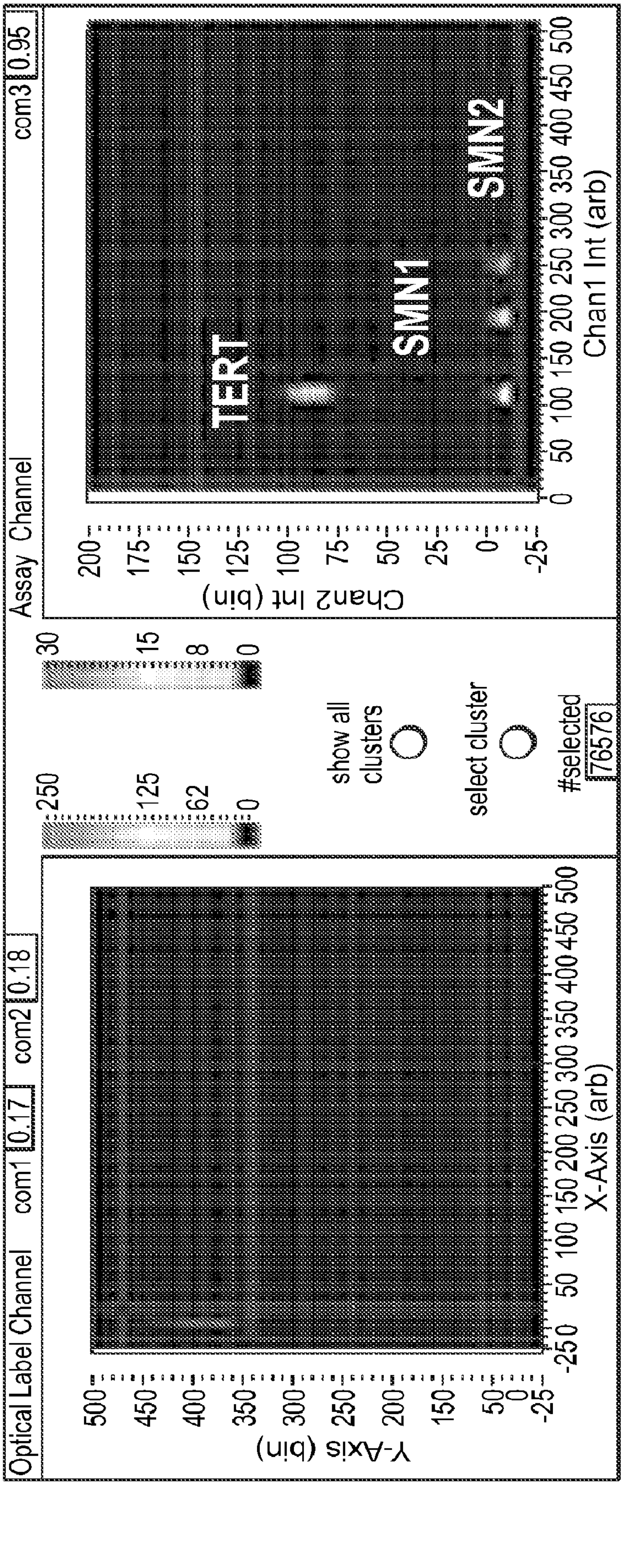
Figure 21I:
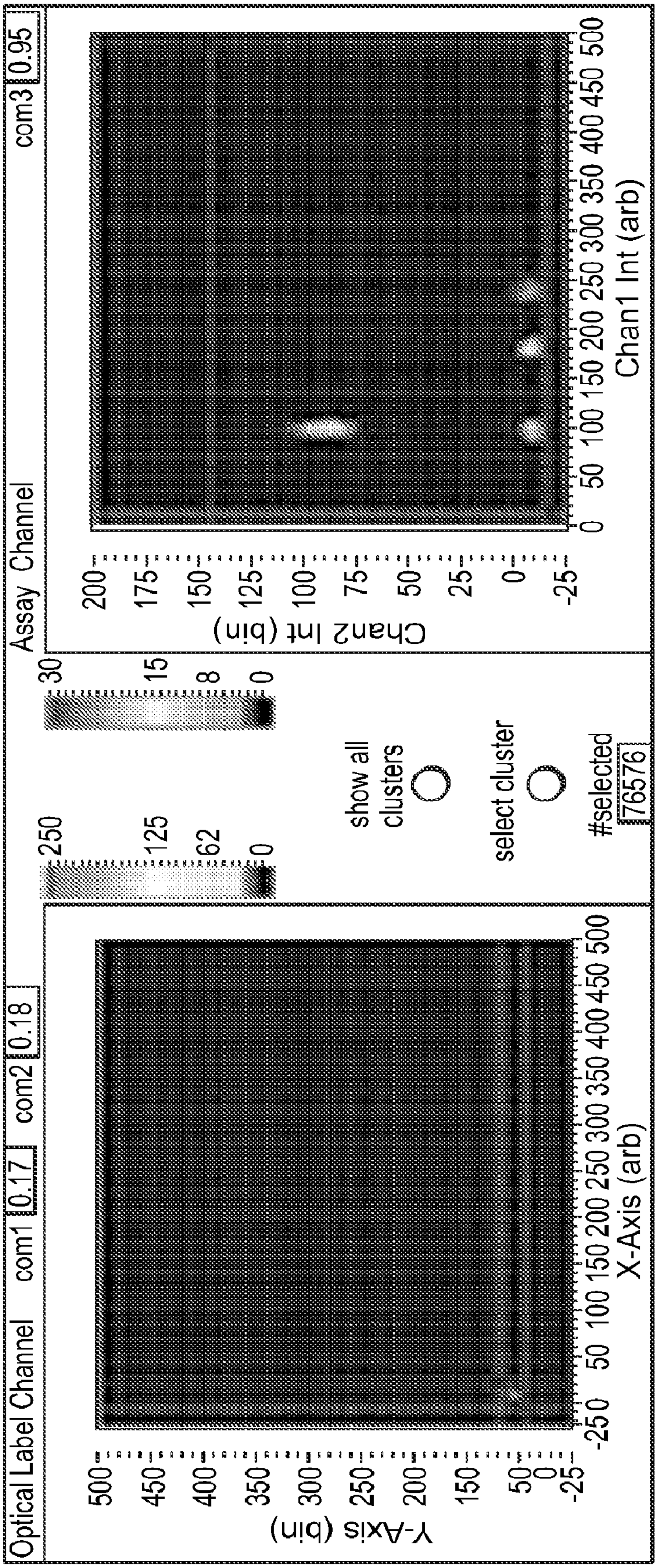
Figure 21J:
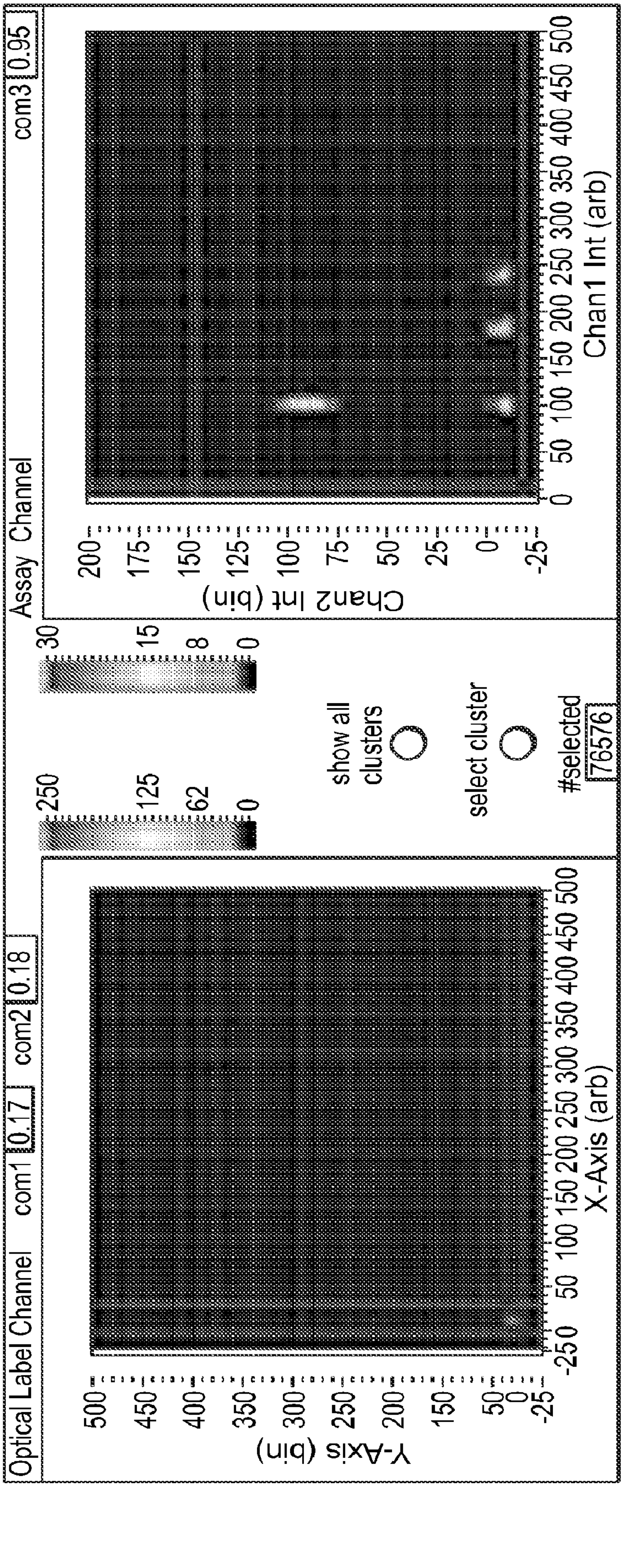

FIGS. 19A, B, and C show optical label selections for a different assay (TERT, c.5C in the SMN1 gene, and BCKDHA (labeled El a in the figure)). In each case four distinct clusters also appeared, and by the same methods of the invention above, accurate measurements of gene copy number were made for c.5C and BCKDHA, referenced to TERT, of 2.9±0.1 and 2.0±0.2 compared to 3 and 2, respectively. FIGS. 20A, B, and C show optical label selections for a third assay (TERT, c.88G in the SMN1 gene, and RNaseP, where RNaseP is a common reference gene). Accurate gene copy numbers of 2.1±0.1 were measured for both c.88G and RNaseP, referenced to TERT, compared to the expected value of 2.

In summary, the demonstration here shows use of nine different optical labels to enable independent measurement of three triplex assays in a single experiment. Although some of the optical labels encoded for redundant assays in this example (there were only three different assays despite having nine optical labels), the invention is not constrained to any particular formatting of assays and optical labels. Embodiments of the invention include formats where all of the assays are the same across all of the optical labels; where none of the assays are the same across all of the optical labels; where some of the assays are the same across all of the optical labels; where some of the assays have greater plexity than others across all of the optical labels; where all of the assays have the same plexity across all of the optical labels; and any other arrangements of assays across all of the optical labels are considered.

Although two different fluorophores were used to create the optical labels in this example, the invention is not constrained to any particular number of fluorophores comprising the optical labels. Embodiments of the invention include optical labels comprised of 1 fluorophore, or 2 fluorophores, or 3 fluorophores, or 4 fluorophores, or up to 10 fluorophores, or up to 20 fluorophores. Optical labels can also comprise more than 20 fluorophores.

Although solely triplex assays were used in the example demonstration here, the invention is not constrained to use of triplex assays with optical labels. Embodiments of the invention include plexities of the following amounts when used with optical labels: single plex, duplex, triplex, 4-plex, up to 10-plex, up to 20-plex, up to 50-plex, and up to 100-plex. Embodiments of the invention also include plexities exceeding 100 when used with optical labels.

Another method of the invention involves the use of droplet merging, instead of co-flow, for combining multiplexing with optical labels. A demonstration using droplet merging was performed with the same 3×3×3 assay as in the preceding example with co-flow. The assays (probes and primers) combined with their unique optical labels were first encapsulated into droplets along with the PCR master mix. Subsequently, according to methods of the invention described above, a library containing a mixture of droplets from all nine optically labeled assays was merged one-to-one with droplets containing template DNA from the same patient as in the preceding example. As another method of the invention, the droplet merge was performed using a lambda-injector style merge module, as described in U.S. Provisional Application, Ser. No. 61/441,985, incorporated by reference herein. Aside from the differences between co-flow and merge, the assays and experimental procedures were identical to those above for the co-flow experiment. FIGS. 21A-J show 2-D histograms of droplet fluorescence intensity for the optical labels and the assays that are similar to those in FIGS. 17-20. As in the case for co-flow, upon selection of droplets containing individual optical labels, the expected distinct clusters of droplets corresponding to each assay were clearly evident. Furthermore for each assay the measured gene copy number matched or very nearly matched the expected values within experimental uncertainty (See Table 1).

TABLE 1

Gene copy number measurements from the 3 × 3 × 3 assay.

| Gene or genotype | Measured copy number | Expected copy number |
|---|---|---|
| SMN1 | 1.98 ± 0.09 | 2 |
| SMN2 | 0.99 ± 0.04 | 1 |
| c.5C in SMN1 | 3.01 ± 0.06 | 3 |
| c.88G in SMN1 | 2.15 ± 0.08 | 2 |
| BCKDHA | 2.00 ± 0.05 | 2 |
| RNaseP | 2.11 ± 0.16 | 2 |

Although methods of the invention include using either microfluidics with co-flow or droplet merging, the invention is not limited in this regard. Any fluidic method capable of generating optically labeled droplets that also contain fluorogenic DNA hybridization probes are considered. For example, other embodiments well known in the art are mixing optical labels and assays in the macrofluidic environment before injection into a droplet generating chip; and mixing optical labels and assays thoroughly upstream from the droplet forming module in dedicated mixing modules, such as with a serpentine mixer.

Data Analysis

One method of the invention involves histogram-based data presentation and analysis for identifying and characterizing populations of statistically similar droplets that arise from unique probe signatures (color and intensity), and for discriminating one population of droplets from the others. Another method of the invention involves histogram-based data presentation and analysis for identifying and selecting populations of droplets based on unique signatures from optical labels. Examples of one and two-dimensional histograms have been provided for these methods, but the invention is not limited in this regard. As described above, it is anticipated that greater numbers of colors will be used for both multiplexing and for optical labels. Hence, embodiments of the invention include histograms of dimensionality greater than two, such as 3, or 4, or up to 10, or up to 20. Histograms of dimensionality greater than 20 are also incorporated into the invention.

Another method of the invention involves the selection of droplets within histograms, either for counting, or for assay selection as in the use of optical labels, or for any other purpose. Methods of the invention include selections by boundaries, either closed or unclosed, of any possible shape and dimension. Methods of the invention also include selections of droplets that exhibit fluorescence from single types of fluorophores, or from multiple types of fluorophores, such as arising from multiple probes against a common DNA target.

Polymerase Error Correction

For applications requiring very high sensitivity, such as searching for rare mutations amidst an abundance of wild-type DNA, false positive results can arise from errors from the DNA polymerase itself. For example, during one of the early thermal cycles the polymerase might synthesize the mutant strand of DNA from a wild-type template. This type of error is most likely to occur when the difference between the mutant and the wild-type is very small, such as single nucleotide polymorphism (SNP). In this method of the invention, each droplet contains only a single target nucleic acid, if any at all. In the preferred embodiment, this is accomplished under the conditions of terminal dilution. Droplets that contain amplification products that are a wild-type of the target are detected based on emission from the fluorophore that is released from the probe that hybridizes to the wild-type of the target. Droplets that contain the variant of the target are detected based on emission from the fluorophore that is released from the probe that hybridizes to the variant of the target. Since each droplet starts with only a single nucleic acid molecule, the resultant amplification products in each droplet are either homogeneous for the target or homogenous for the variant of the target.

However, certain droplets will contain a heterogeneous mixture of both target and target variant due to polymerase errors during the PCR reaction. Error rates in PCR vary according to the precise nucleic acid sequence, the thermostable enzyme used, and the in vitro conditions of DNA synthesis. For example, the error frequency (mutations per nucleotide per cycle) during PCR catalyzed by the thermostable *Thermus aquaticus* (Taq) DNA polymerase vary more than 10-fold, from –2×10' to <1×10-5. Eckert et al. (Genome Res. 1:17-24, 1991), the content of which is incorporated by reference herein in its entirety. Polymerase-mediated errors at a frequency of 1 mutation per 10,000 nucleotides per cycle are an important consideration for any PCR application that begins with a small amount of starting material (e.g., less than a total of 10,000 nucleotides of target DNA) or that focuses on individual DNA molecules in the final PCR population.

The proportion of DNA molecules that contain sequence changes is a function of the error rate per nucleotide per cycle, the number of amplification cycles and the starting population size. The population of altered DNA molecules arises during PCR from two sources: (1) new errors at each PCR cycle; and (2) amplification of DNA molecules containing errors from previous cycles. The formula $f=np/2$ describes the average mutation frequency (f) for PCR amplification as a function of the polymerase error rate per nucleotide per cycle (p) and the number of cycles (n), assuming that p is constant at each cycle. Due to the exponential nature of PCR, the occurrence of an early error can increase the final error frequency above the average described by $f=np/2$, because the variant DNA molecule will be amplified with each cycle, resulting in populations with a larger than average number of variants.

A polymerase error that converts a wild-type of the target to a variant of the target during an early round of amplification results in a heterogeneous population of target and target variant in a droplet, and may lead to a droplet being incorrectly identified as containing a variant of the target, i.e., a false positive. Such false positives greatly impact the validity and precision of digital PCR results.

Methods of the invention are able to detect which droplets contain a heterogeneous population of molecules and are able to exclude those droplets from analysis. As droplets containing amplified product flow in a channel through the detector module, the module is able to detect the fluorescent emission in each droplet. Droplets that produce only a single signal are classified as droplets that contain a homogeneous population of target. Since probes that hybridize to the wild-type of the target have a different fluorophore attached than probes that hybridize to a variant of the wild-type of the target, methods of the invention can classify each droplet as containing either a homogeneous population of amplicons of the target or a homogeneous population of amplicons of the variant of the target.

Droplets that produce two signals are classified as droplets that contain a heterogeneous population of molecules. Since each droplet started with at most a single target nucleic acid, a droplet that includes amplification products that are both amplicons of the target and amplicons of a variant of the target are droplets in which the variant of the target was produced by a polymerase error during the PCR reaction, most likely a polymerase error during an early cycle of the PCR reaction. Such droplets are detected and excluded from analysis.

Analysis

Analyze is then performed on only the droplets that contain a homogeneous population of molecules. The analysis may be based on counting, i.e., determining a number of droplets that contain only wild-type target, and determining a number of droplets that contain only a variant of the target. Such methods are well known in the art. See, e.g., Lapidus et al. (U.S. Pat. Nos. 5,670,325 and 5,928,870) and Shuber et al. (U.S. Pat. Nos. 6,203,993 and 6,214,558), the content of each of which is incorporated by reference herein in its entirety.

Generally, the presence of droplets containing only variant is indicative of a disease, such as cancer. In certain embodiments, the variant is an allelic variant, such as an insertion, deletion, substitution, translocation, or single nucleotide polymorphism (SNP).

Biomarkers that are associated with cancer are known in the art. Biomarkers associated with development of breast cancer are shown in Erlander et al. (U.S. Pat. No. 7,504,214), Dai et al. (U.S. Pat. Nos. 7,514,209 and 7,171,311), Baker et al. (U.S. Pat. Nos. 7,056,674, 7,081,340), Erlander et al. (US 2009/0092973). The contents of the patent application and each of these patents are incorporated by reference herein in their entirety. Biomarkers associated with development of cervical cancer are shown in Patel (U.S. Pat. No. 7,300,765), Pardee et al. (U.S. Pat. No. 7,153,700), Kim (U.S. Pat. No. 6,905,844), Roberts et al. (U.S. Pat. No. 6,316,208), Schlegel (US 2008/0113340), Kwok et al. (US 2008/0044828), Fisher et al. (US 2005/0260566), Sastry et al. (US 2005/0048467), Lai (US 2008/0311570) and Van Der Zee et al. (US 2009/0023137). Biomarkers associated with development of vaginal cancer are shown in Giordano (U.S. Pat. No. 5,840,506), Kruk (US 2008/0009005), Hellman et al. (Br J Cancer. 100(8):1303-1314, 2009). Biomarkers associated with development of brain cancers (e.g., glioma, cerebellum, medulloblastoma, astrocytoma, ependymoma, glioblastoma) are shown in D'Andrea (US 2009/0081237), Murphy et al. (US 2006/0269558), Gibson et al. (US 2006/0281089), and Zetter et al. (US 2006/0160762). Biomarkers associated with development of renal cancer are shown in Patel (U.S. Pat. No. 7,300,765), Soyupak et al. (U.S. Pat. No. 7,482,129), Sahin et al. (U.S. Pat. No. 7,527,933), Price et al. (U.S. Pat. No. 7,229,770), Raitano (U.S. Pat. No. 7,507,541), and Becker et al. (US 2007/0292869). Biomarkers associated with development of hepatic cancers (e.g., hepatocellular carcinoma) are shown in Home et al. (U.S. Pat. No. 6,974,667), Yuan et al. (U.S. Pat. No. 6,897,018), Hanausek-Walaszek et al. (U.S. Pat. No. 5,310,653), and Liew et al. (US 2005/0152908). Biomarkers associated with development of gastric, gastrointestinal, and/or esophageal cancers are shown in Chang et al. (U.S. Pat. No. 7,507,532), Bae et al. (U.S. Pat. No. 7,368,255), Muramatsu et al. (U.S. Pat. No. 7,090,983), Sahin et al. (U.S. Pat. No. 7,527,933), Chow et al. (US 2008/0138806), Waldman et al. (US 2005/0100895), Goldenring (US 2008/0057514), An et al. (US 2007/0259368), Guilford et al. (US 2007/0184439), Wirtz et al. (US 2004/0018525), Filella et al. (Acta Oncol. 33(7):747-751, 1994), Waldman et al. (U.S. Pat. No. 6,767,704), and Lipkin et al. (Cancer Research, 48:235-245, 1988). Biomarkers associated with development of ovarian cancer are shown in Podust et al. (U.S. Pat. No. 7,510,842), Wang (U.S. Pat. No. 7,348,142), O'Brien et al. (U.S. Pat. Nos. 7,291,462, 6,942,978, 6,316,213, 6,294,344, and 6,268,165), Ganetta (U.S. Pat. No. 7,078,180), Malinowski et al. (US 2009/0087849), Beyer et al. (US 2009/0081685), Fischer et al. (US 2009/0075307), Mansfield et al. (US 2009/0004687), Livingston et al. (US 2008/0286199), Farias-Eisner et al. (US 2008/0038754), Ahmed et al. (US 2007/0053896), Giordano (U.S. Pat. No. 5,840,506), and Tchagang et al. (Mol Cancer Ther, 7:27-37, 2008). Biomarkers associated with development of head-and-neck and thyroid cancers are shown in Sidransky et al. (U.S. Pat. No. 7,378,233), Skolnick et al. (U.S. Pat. No. 5,989,815), Budiman et al. (US 2009/0075265), Hasina et al. (Cancer Research, 63:555-559, 2003), Kebebew et al. (US 2008/0280302), and Ralhan (Mol Cell Proteomics, 7(6): 1162-1173, 2008). The contents of each of the articles, patents, and patent applications are incorporated by reference herein in their entirety. Biomarkers associated with development of colorectal cancers are shown in Raitano et al. (U.S. Pat. No. 7,507,541), Reinhard et al. (U.S. Pat. No. 7,501,244), Waldman et al. (U.S. Pat. No. 7,479,376); Schleyer et al. (U.S. Pat. No. 7,198,899); Reed (U.S. Pat. No. 7,163,801), Robbins et al. (U.S. Pat. No. 7,022,472), Mack et al. (U.S. Pat. No. 6,682,890), Tabiti et al. (U.S. Pat. No. 5,888,746), Budiman et al. (US 2009/0098542), Karl (US 2009/0075311), Arjol et al. (US 2008/0286801), Lee et al. (US 2008/0206756), Mori et al. (US 2008/0081333), Wang et al. (US 2008/0058432), Belacel et al. (US 2008/0050723), Stedronsky et al. (US 2008/0020940), An et al. (US 2006/0234254), Eveleigh et al. (US 2004/0146921), and Yeatman et al. (US 2006/0195269). Biomarkers associated with development of prostate cancer are shown in Sidransky (U.S. Pat. No. 7,524,633), Platica (U.S. Pat. No. 7,510,707), Salceda et al. (U.S. Pat. Nos. 7,432,064, 7,364,862), Siegler et al. (U.S. Pat. No. 7,361,474), Wang (U.S. Pat. No. 7,348,142), Ali et al. (U.S. Pat. No. 7,326,529), Price et al. (U.S. Pat. No. 7,229,770), O'Brien et al. (U.S. Pat. No. 7,291,462), Golub et al. (U.S. Pat. No. 6,949,342), Ogden et al. (U.S. Pat. No. 6,841,350), An et al. (U.S. Pat. No. 6,171,796), Bergan et al. (US 2009/0124569), Bhowmick (US 2009/0017463), Srivastava et al. (US 2008/0269157), Chinnaiyan et al. (US 2008/0222741), Thaxton et al. (US 2008/0181850), Dahary et al. (US 2008/0014590), Diamandis et al. (US 2006/0269971), Rubin et al. (US 2006/0234259), Einstein et al. (US 2006/0115821), Paris et al. (US 2006/0110759), Condon-Cardo (US 2004/0053247), and Ritchie et al. (US 2009/0127454). Biomarkers associated with development of pancreatic cancer are shown in Sahin et al. (U.S. Pat. No. 7,527,933), Rataino et al. (U.S. Pat. No. 7,507,541), Schleyer et al. (U.S. Pat. No. 7,476,506), Domon et al. (U.S. Pat. No. 7,473,531), McCaffey et al. (U.S. Pat. No. 7,358,231), Price et al. (U.S. Pat. No. 7,229,770), Chan et al. (US 2005/0095611), Mitchl et al. (US 2006/0258841), and Faca et al. (PLoS Med 5(6):e123, 2008). Biomarkers associated with development of lung cancer are shown in Sahin et al. (U.S. Pat. No. 7,527,933), Hutteman (U.S. Pat. No. 7,473,530), Bae et al. (U.S. Pat. No. 7,368,255), Wang (U.S. Pat. No. 7,348,142), Nacht et al. (U.S. Pat. No. 7,332,590), Gure et al. (U.S. Pat. No. 7,314,721), Patel (U.S. Pat. No. 7,300,765), Price et al. (U.S. Pat. No. 7,229,770), O'Brien et al. (U.S. Pat. Nos. 7,291,462, 6,316,213), Muramatsu et al. (U.S. Pat. No. 7,090,983), Carson et al. (U.S. Pat. No. 6,576,420), Giordano (U.S. Pat. No. 5,840,506), Guo (US 2009/0062144), Tsao et al. (US 2008/0176236), Nakamura et al. (US 2008/0050378), Raponi et al. (US 2006/0252057), Yip et al. (US 2006/0223127), Pollock et al. (US 2006/0046257), Moon et al. (US 2003/0224509), and Budiman et al. (US 2009/0098543). Biomarkers associated with development of skin cancer (e.g., basal cell carcinoma, squamous cell carcinoma, and melanoma) are shown in Roberts et al. (U.S. Pat. No. 6,316,208), Polsky (U.S. Pat. No. 7,442,507), Price et al. (U.S. Pat. No. 7,229,770), Genetta (U.S. Pat. No. 7,078,180), Carson et al. (U.S. Pat. No. 6,576,420), Moses et al. (US 2008/0286811), Moses et al. (US 2008/0268473), Dooley et al. (US 2003/0232356), Chang et al. (US 2008/0274908), Alani et al. (US 2008/0118462), Wang (US 2007/0154889), and Zetter et al. (US 2008/0064047). Biomarkers associated with development of multiple myeloma are shown in Coignet (U.S. Pat. No. 7,449,303), Shaughnessy et al. (U.S. Pat. No. 7,308,364), Seshi (U.S. Pat. No. 7,049, 072), and Shaughnessy et al. (US 2008/0293578, US 2008/0234139, and US 2008/0234138). Biomarkers associated with development of leukemia are shown in Ando et al. (U.S. Pat. No. 7,479,371), Coignet (U.S. Pat. Nos. 7,479,370, 7,449,303), Davi et al. (U.S. Pat. No. 7,416,851), Chiorazzi (U.S. Pat. No. 7,316,906), Seshi (U.S. Pat. No. 7,049,072), Van Baren et al. (U.S. Pat. No. 6,130,052), Taniguchi (U.S. Pat. No. 5,643,729), Insel et al. (US 2009/0131353), and Van Bockstaele et al. (Blood Rev. 23(1):25-47, 2009). Biomarkers associated with development of lymphoma are shown in Ando et al. (U.S. Pat. No. 7,479,371), Levy et al. (U.S. Pat. No. 7,332,280), and Arnold (U.S. Pat. No. 5,858,655). Biomarkers associated with development of bladder cancer are shown in Price et al. (U.S. Pat. No. 7,229,770), Orntoft (U.S. Pat. No. 6,936,417), Haak-Frendscho et al. (U.S. Pat. No. 6,008,003), Feinstein et al. (U.S. Pat. No. 6,998,232), Elting et al. (US 2008/0311604), and Wewer et al. (2009/0029372). The content of each of the above references is incorporated by reference herein in its entirety. Devices and methods described herein may be used to assess the quality of a sample to be analyzed for methylation. DNA methylation is a chemical modification of DNA performed by enzymes called methyltransferases, in which a methyl group (m) is added to certain cytosines (C) of DNA, to yield 5-methylcytosine. This non-mutational (epigenetic) process (mC) is a critical factor in gene expression regulation. See, e.g., J. G. Herman, Seminars in Cancer Biology, 9: 359-67, 1999. Research suggests genes with high levels of 5-methylcytosine in a promoter region are transcriptionally silent, which allows unchecked cell proliferation. Additionally, it is likely that there a correlation between gene transcription and undermethylation. Methylation patterns of DNA from cancer cells are significantly different from those of normal cells. Therefore, detection of methylation patterns in appropriately selected genes of cancer cells can lead to discrimination of cancer cells from normal (i.e., non-cancerous) cells, thereby providing an approach to early detection of cancer.

A common method for assessing methylation status, e.g., the presence of CpG islands, is methylation specific PCR, also known as MSP. In MSP a nucleic acid sample is treated with a methylation reactant, typically bisulfite, and then amplified in the presence of two sets of primers. One primer set is complimentary to sequences with converted Cs and the second primer set is complimentary to non-converted Cs. Using these two separate primer sets, both the methylated and unmethylated DNA can be simultaneously amplified, and the amplification products compared (e.g., sequenced) to determine methylation sites in a given sequence. The MSP method, and variations on the MSP method, are described in greater detail in U.S. Pat. Nos. 6,265,171, 6,331,393, 6,977,146, 7,186,512, and 7,229,759 all of which are incorporated by reference herein in their entireties.

In some instances, a bisulfite treatment to convert unmethylated Cs to Us degrades the sample, making the later amplification and sequencing steps of little value because the resulting sample is no longer contiguous in the region(s) of interest. Using the techniques described herein, it is possible to assess the post bisulfite treatment sample to determine the quality of the sample, for example the amount of contiguous DNA. Thus, a bisulfite treated sample can be partitioned into samples comprising nucleic acids of different lengths, primer pairs can be introduced along with appropriate probes, the nucleic acids amplified, and the make-up, e.g., the continuity of the nucleic acid sample can be determined. Because the sample may contain unmethylated Cs which are converted to Us as well as methylated Cs which are not converted to Us, it may be necessary to use additional primer sets which are complimentary to targets having Cs as well as primer sets complimentary to targets having Us.

In certain embodiments, methods of the invention may be used to monitor a patient for recurrence of a cancer. Since the patient has already been treated for the cancer, the genetic profile and particular mutation(s) associated with that patient's cancer are already known. Probes may be designed that specifically hybridize to the region of the nucleic acid that contains the mutation(s) that is indicative of the cancer for which the patient was previously treated. A patient's sample (e.g., pus, sputum, semen, urine, blood, saliva, stool, or cerebrospinal fluid) may then be analyzed as described above to determine whether the mutant allele(s) is detected in the sample, the presence of which being indicative of recurrence of the cancer.

Droplet Sorting Methods of the invention may further include sorting the droplets based upon whether the droplets contain a homogeneous population of molecules or a heterogeneous population of molecules. A sorting module may be a junction of a channel where the flow of droplets can change direction to enter one or more other channels, e.g., a branch channel, depending on a signal received in connection with a droplet interrogation in the detection module. Typically, a sorting module is monitored and/or under the control of the detection module, and therefore a sorting module may correspond to the detection module. The sorting region is in communication with and is influenced by one or more sorting apparatuses.

A sorting apparatus includes techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A branch channel is a channel that is in communication with a sorting region and a main channel. The main channel can communicate with two or more branch channels at the sorting module or branch point, forming, for example, a T-shape or a Y-shape. Other shapes and channel geometries may be used as desired. Typically, a branch channel receives droplets of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In certain embodiments, a fluidic droplet is sorted or steered by inducing a dipole in the uncharged fluidic droplet (which may be initially charged or uncharged), and sorting or steering the droplet using an applied electric field. The electric field may be an AC field, a DC field, etc. For example, a channel containing fluidic droplets and carrier fluid, divides into first and second channels at a branch point. Generally, the fluidic droplet is uncharged. After the branch point, a first electrode is positioned near the first channel, and a second electrode is positioned near the second channel. A third electrode is positioned near the branch point of the first and second channels. A dipole is then induced in the fluidic droplet using a combination of the electrodes. The combination of electrodes used determines which channel will receive the flowing droplet. Thus, by applying the proper electric field, the droplets can be directed to either the first or second channel as desired. Further description of droplet sorting is shown for example in Link et al. (U.S. patent application numbers 2008/0014589, 2008/0003142, and 2010/0137163) and European publication number EP2047910 to Raindance Technologies Inc.

Based upon the detected signal at the detection module, droplets containing a heterogeneous population of molecules are sorted away from droplets that contain a homogeneous population of molecules. Droplets may be further sorted to separate droplets that contain a homogeneous population of amplicons of the target from droplets that contain a homogeneous population of amplicons of the variant of the target.

Release of Target from Droplet

Methods of the invention may further involve releasing amplified target molecules from the droplets for further analysis. Methods of releasing amplified target molecules from the droplets are shown in for example in Link et al. (U.S. patent application numbers 2008/0014589, 2008/0003142, and 2010/0137163) and European publication number EP2047910 to RainDance Technologies Inc.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and the further analyzed.

The released amplified material can also be subjected to further amplification by the use tailed primers and secondary PCR primers. In this embodiment the primers in the droplet contain an additional sequence or tail added onto the 5' end of the sequence specific portion of the primer. The sequences for the tailed regions are the same for each primer pair and are incorporated onto the 5' portion of the amplicons during PCR cycling. Once the amplicons are removed from the droplets, another set of PCR primers that can hybridize to the tail regions of the amplicons can be used to amplify the products through additional rounds of PCR. The secondary primers can exactly match the tailed region in length and sequence or can themselves contain additional sequence at the 5' ends of the tail portion of the primer. During the secondary PCR cycling these additional regions also become incorporated into the amplicons. These additional sequences can include, but are not limited to adaptor regions utilized by sequencing platforms for library preparation and sequencing, sequences used as a barcoding function for the identification of samples multiplexed into the same reaction. molecules for the separation of amplicons from the rest of the reaction materials such as biotin, digoxin, peptides, or antibodies and molecules such as fluorescent markers that can be used to identify the fragments.

In certain embodiments, the amplified target molecules are sequenced. In a particular embodiment, the sequencing is single-molecule sequencing-by-synthesis. Single-molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Briefly, a single-stranded nucleic acid (e.g., DNA or cDNA) is hybridized to oligonucleotides attached to a surface of a flow cell. The single-stranded nucleic acids may be captured by methods known in the art, such as those shown in Lapidus (U.S. Pat. No. 7,666,593). The oligonucleotides may be covalently attached to the surface or various attachments other than covalent linking as known to those of ordinary skill in the art may be employed. Moreover, the attachment may be indirect, e.g., via the polymerases of the invention directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

Determining the Nucleic Acid Make-Up of a Sample

Further aspects of the invention include methods for determining the nucleic acid make-up of a sample. Specifically, the method can determine the presence of a contiguous, intact nucleic acid, i.e., an unbroken chain of nucleotides, between two locations on the nucleic acid. Presence of a contiguous nucleic acid is determined via detection of both a first and second detectably labeled probe that hybridizes to a first and second location on the nucleic acid (e.g., a sequence, an oligomer, a polymer, a template, dsDNA). The detection of only one probe indicates a fragmented nucleic acid, in other words, a nucleic acid that is not contiguous through the entirety of the two aforementioned locations on the nucleic acid. In some embodiments, the method involves partitioning a sample comprising nucleic acid of different lengths into a plurality of partitioned portions, wherein each portion comprises, on average, a single nucleic acid molecule, introducing first and second primer pairs and first and second detectably labeled probes to the partitioned portions, wherein the first and second primer pairs are specific for first and second locations on the nucleic acid, the first and second locations being spaced apart from each other, and wherein the first probe hybridizes to the first location and the second probe hybridizes to the second location, amplifying the nucleic acid in the partitioned portions, the presence of signal from both probes indicating the presence of a nucleic acid that is contiguous between the first and second locations, and determining a nucleic acid make-up of the sample based upon results of the detecting step.

Specific methods for the partitioning, introducing, amplifying, and detecting steps have been presented throughout the present disclosure. Further detail on determination step is now presented. As mentioned above, determination of contiguous or intact nucleic acid involves detecting a first and second detectably labeled probe that hybridizes to a first and second location on a nucleic acid. The detection of only one probe indicates the presence of a fragment of the longer nucleic acid. In some embodiments, the determining step may involve comparing relative amounts of contiguous nucleic acid to relative amounts of non-contiguous nucleic acid. In other embodiments, the determining step involves comparing amount of contiguous nucleic acid or non-contiguous nucleic acid to a total amount of amino acid.

For sequencing and other extensive molecular biology studies, a sample comprising mostly intact nucleic acid is desirable and is conducive to accurate results. The presence of a relatively large population of nucleic acid fragments, i.e., non-contiguous nucleic acids, may indicate that a sample is not suitable for sequencing. Because sequencing is relatively expensive, knowing the make-up of the sample prior to testing is advantageous. This is especially so when the sample is an FFPE sample or some other form of preserved sample in which the nucleic acid of interest has degraded into fragments. In some embodiments, if less than 90% of the nucleic acid sample, e.g., less than 80% of the nucleic acid sample, e.g., less than 70% of the nucleic acid sample, e.g., less than 50% of the nucleic acid sample, e.g., less than 40% of the nucleic acid sample, e.g., less than 30% of the nucleic acid sample, e.g., less than 20% of the nucleic acid sample, e.g., less than 10% of the nucleic acid sample is fragmented, the nucleic acid sample is suitable for further sequencing. Accordingly, once the nucleic acid make-up of a sample is determined, a further step may involve sequencing the sample, enriching the sample, or sequencing the sample after enrichment. Furthermore, because the method of determining the nucleic acid make-up incorporates the dPCR methods described throughout the present disclosure, extremely small amounts of sample can be tested successfully. In some embodiments, the test sample may contain 50 ng or less of DNA or RNA.

Figure 23:
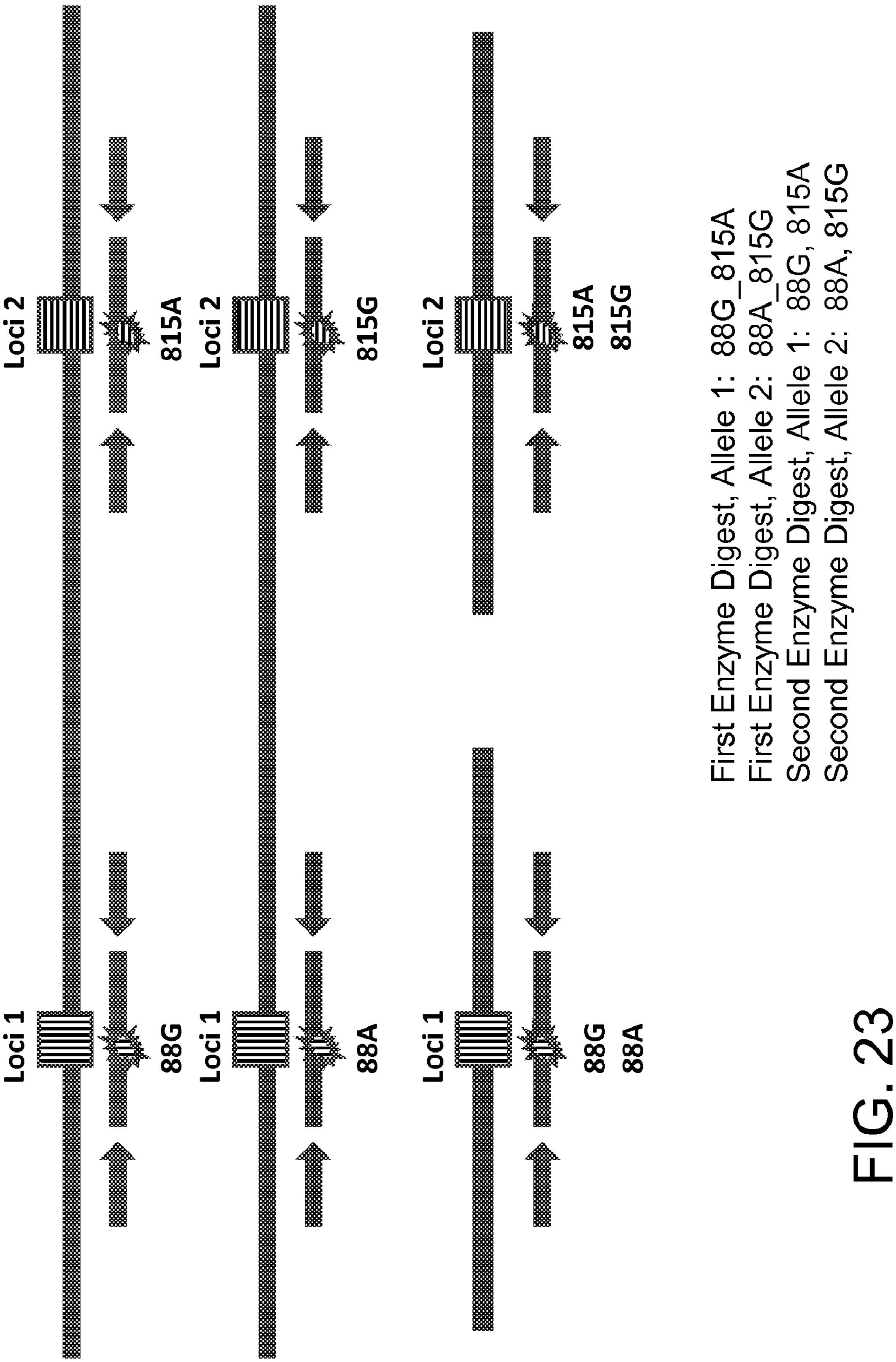
FIG. 23 is a schematic showing several loci of interest on a pair of alleles and fragments of those alleles resulting from enzymatic digestion.

A demonstration of concept in accordance with the invention is presented schematically in FIG. 23. Two alleles are presented: Allele 1, comprising genes 88G and 815A, and Allele 2, comprising genes 88A and 815G. Alleles 1 and 2 were digested with a first enzyme to produce a first nucleic acid containing 88G and 815A ("88G 815A") and a second nucleic acid containing 88A and 815G ("88A 815G"). A portion of these products were then subjected to a second digestion with a second enzyme to obtain four additional fragments, each containing only one gene of interest ("88G," "815A", "88A", and "815G"). Methods of performing enzymatic digestion as well as selecting the proper enzymes are well-known in the art. While enzymatic digestion was used in this example, other methods of fragmenting or shearing the nucleic acid prior to partitioning the samples can be used. Such means may include, for example, sonication, the use of commercially available shearing devices, such as a Covaris® shearing device, or other means known in the art. In this demonstration of concept, the fragmentation is performed to simulate the degradation of a nucleic acid that may naturally occur in a sample, such as a FFPE sample. In certain embodiments of the invention, however, the nucleic acid is fragmented prior to partitioning the sample.

The six nucleic acids were then partitioned into a plurality of partitioned portions, each portion containing on average, a single nucleic acid molecule. Partitioning may involve any methods known in the art, such as serial or terminal dilution. Partitioning may also involve the methods described in in the present disclosure, including forming droplets from a sample present in an aqueous fluid. Additional details on droplet formation have been described throughout the present disclosure.

As further shown in FIG. 23, a first and second primer pair and a first and second detectably labeled probe specific for the regions of interest were introduced to the partitioned portions. In this example, the probes were labeled with either VIC™ or FAM. Further detail on probe embodiments has been described throughout the present disclosure. The nucleic acid was then amplified and the amplicons detected through the hybridized probes.

Figure 24:
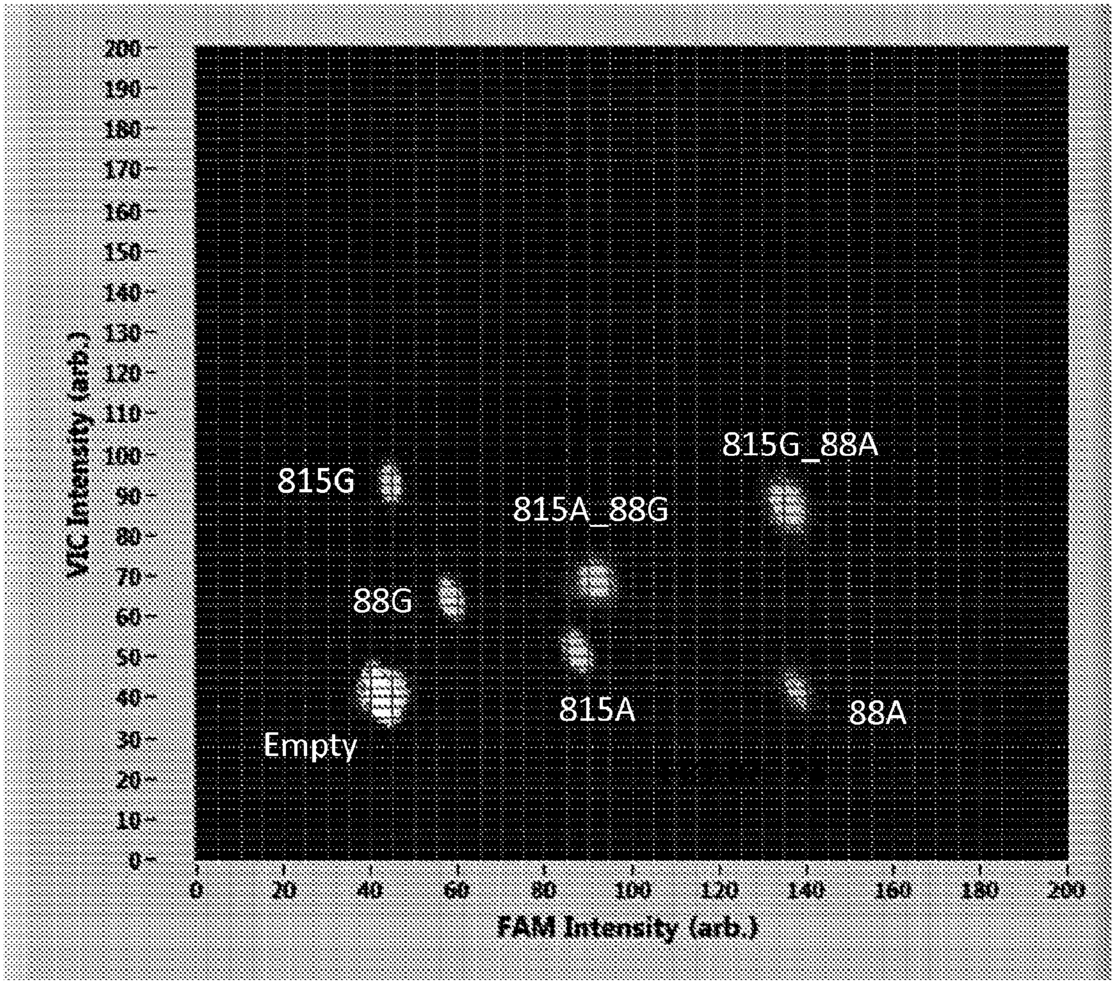
FIG. 24 depicts a multiplex dPCR assay to determine the nucleic acid make-up of a sample containing nucleic acids shown schematically in FIG. 23.

Sample data is presented in FIG. 24, which shows the six populations of nucleic acids along with the empty droplets as peaks on a graph. 815A 88G and 815G 88A, oriented approximately along the diagonal axis, are the longer nucleic acids. 815G, 88G, 815A, and 88A, arranged primarily along the y-axis and x-axis, respectively, are the shorter fragments.

Accordingly, the invention encompasses a method for determining the nucleic acid make-up of a sample. The method can determine the presence of intact or contiguous nucleic acids, represented in this experiment by peaks corresponding to 815A 88G and 815G 88A, as well as the presence of non-contiguous nucleic acids, represented by peaks corresponding to 815G, 88G, 815A, and 88A. In this example, the nucleic acid make-up can be assessed by looking at the number of counts in all the peaks. In a sample where the level of fragmentation is unknown, for example, in a FFPE sample, a prevalence of nucleic acid where only one probe has bound would indicate the presence of non-contiguous nucleic acid and sample degradation. In contrast, the prevalence of nucleic acid where both the first and second probe has bound would indicate the presence of a contiguous nucleic acid and a relatively more intact sample.

The methods described herein are not limited to the use of two probes, however. In some embodiments a plurality of probes are used to give additional information about the properties of nucleic acids in a sample. For example, three probes could be used wherein one probe was one color (e.g., VICT™), and two probes were another color (e.g., FAM). Differences in intensity or polarization make it possible to distinguish between the probes of the same color, as discussed previously. Analysis using such a method may make it possible to determine the presence of multiple different contiguous lengths of nucleic acid molecules.

While methods described herein can encompass the use of several primer pairs, methods in accordance with the invention also encompass the use of a single primer pair. In some embodiments, the method includes providing a fluid comprising the sample nucleic acid and a plurality of one or more primer pairs, wherein each primer pair has at least one unique related probe and is selected to be complementary to one or more sequences of known length. The method also includes partitioning the fluid into a plurality of partitions, wherein at least a first portion of the partitions comprise one molecule of the nucleic acid sample having sequences complementary to one or more of the primer pairs, and at least one related probe, and a second portion of the partitions comprise no molecules of the sample nucleic acid having sequences complementary to one or more of the primer pairs. The method further includes conducting a PCR reaction in the partitions, thereby changing a fluorescent property of the first portion of the partitions, detecting the fluorescent property of each partition, and determining the number of occurrences in the sample nucleic acid of one or more sequences of known length based on the detecting step. In some aspects of the invention, the method further includes comparing a first number of occurrences of a first sequence of known length to a second number of occurrences of a second sequence of a second known length.

Additional embodiments of the invention may also contemplate the use of a single primer pair as well as rely on something other than a probe for detecting the amplified sequence. In certain embodiments, the method comprises partitioning a sample comprising nucleic acid of different lengths into a plurality of partitioned portions, wherein each portion comprises, on average a single nucleic acid molecule. The method further includes introducing at least one primer pair, in which each primer of the pair is specific for a first and second location on the nucleic acid, the first and second locations being spaced apart from each other. The method further includes amplifying the nucleic acid in the partitioned portions, detecting the amplicons in the partitioned portions, and determining a nucleic acid make-up of the sample based on the results of the detecting step. In certain embodiments, the amplicons may be detected with a probe, for example, a fluorescently labeled probe. In other embodiments, the amplicon may be detected with a dye that intercalates within the nucleic acid. The invention also contemplates any other means of detecting nucleic acid sequences known in the art that do not interfere with the other steps described herein.

Figure 25:
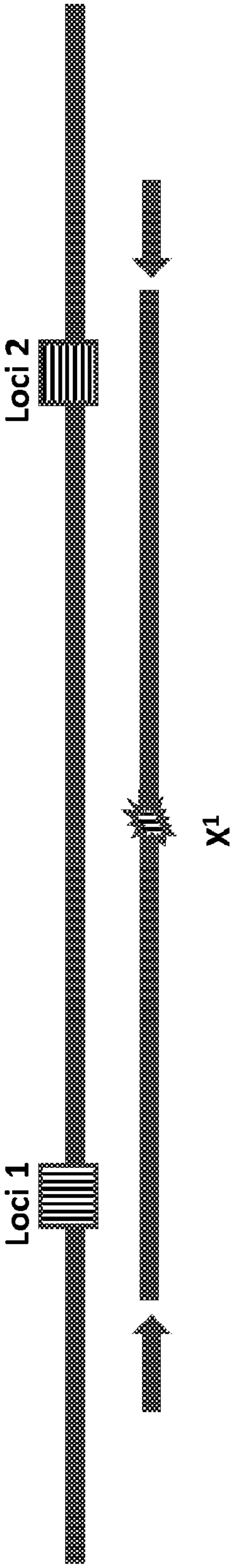
FIG. 25 is a schematic showing a nucleic acid and a pair of primers, each primer specific for a separate location on the nucleic acid, and probe specific for a region of interest on the nucleic acid.

A demonstration of concept using a single primer pair is shown in FIG. 25. Each primer within the primer pair is specific for a first and second location on the nucleic acid. The distance between the two primers for this sequence is known beforehand so that the resulting amplicons will be of a known length. The sequence between the primers is then amplified by PCR. In this particular demonstration of concept, the amplicons are detected via a fluorescent probe, specific for region X' on the nucleic acid sequence. As discussed above, other means of detection are encompassed by the invention.

Figure 26:
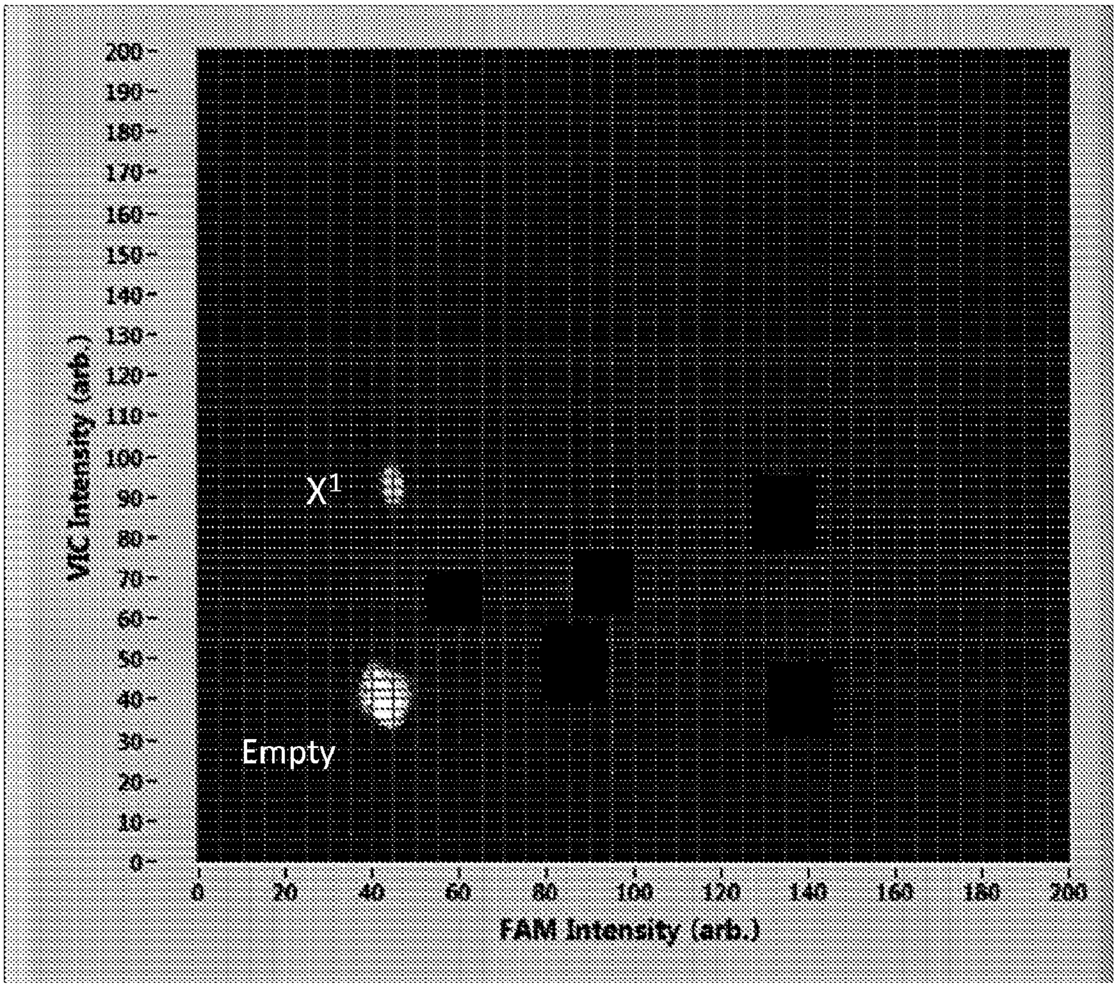
FIG. 26 depicts dPCR assay conducted with a single pair of primers and a nucleic acid shown schematically in FIG. 25.

Sample data is presented in FIG. 26, which shows as peaks, the hybridization of the fluorescent probe to the amplified sequences along with the empty wells, i.e, partitions containing no molecules of sample nucleic acid. The amplicons, as detected by the X' specific probe, appear primarily along the Y-axis. Accordingly, the method encompasses a method of analyzing a sample nucleic acid or determining the nucleic acid make-up of a sample with just one pair of primers. As in the earlier experiment, the nucleic acid make-up of the sample can be assessed by looking at the number of the counts in the peaks. In this case, by looking at the counts, one could determine the number of occurrences in the sample nucleic acid of a sequence of predetermined length. Accordingly, one could determine whether or not the sample was suitable for further testing based on the number of nucleic acids within the sample having the desired length.

Methods in accordance with the invention also encompass the analysis of cell-free nucleic acids. Collecting and assaying cell-free nucleic acids provides advantages over analysis of cellular nucleic acids in that anomalies, e.g., mutations, are easier to identify in the absence of massive quantities of normal nucleic acids. For example, circulating cell-free tumor DNA has been detected in the serum, plasma, and blood of cancer patients. Cell-free nucleic acids are versatile in that they can be analyzed to detect the presence of mutations, or epigenetic markers of a disease. Cell-free nucleic acids can also be used to identify the presence of foreign pathogens, e.g., a bacterial infection. In some embodiments, the biological sample can be blood, saliva, sputum, urine, semen, transvaginal fluid, cerebrospinal fluid, sweat, breast milk, breast fluid (e.g., breast nipple aspirate), stool, a cell or a tissue biopsy.

The methods of the invention can also be used to evaluate the quality of cell-free nucleic acids, for example cell-free DNA or RNA, which can be obtained from a biological sample. In some instances cell-free nucleic acid is greatly degraded, for example, because the nucleic acid was partially digested by normal metabolic processes in the body. The invention allows the cell-free nucleic acid to be evaluated for quality, e.g., continuity, prior to amplification and sequencing. Thus, a cell-free nucleic acid sample can be partitioned into samples comprising nucleic acids of different lengths, primer pairs can be introduced along with appropriate probes, the nucleic acids amplified, and the make-up, e.g., the continuity of the cell-free nucleic acid sample can be determined.

Experimental Detail

What follows is experimental detail for most of the experiments detailed above.

Primers and Probes

All TaqMan® primers and probes used here are listed in Table 2. Unless otherwise noted by reference in the table, the primers and probes were designed with the "Custom TaqMan® Assay Design Tool" from Applied Biosystems Inc. (ABI) and procured through ABI (Carlsbad, CA). Probes were labeled with 6-carboxyfluorescein (FAM, λex 494 nm/λem 494 nm) or VIC™ (from ABI, λex 538 nm/λem 554 nm).

TABLE 1

| Target | Assay | Primers (5' to 3') | Probe (5' to 3') | 5-plex assay conditions | Ref. |
|---|---|---|---|---|---|
| SMN1 | Copy number | (f) AATGCTTTTTAA-CATCCATATAAAGCT (SEQ ID NO: 1) | FAM-CAGGGTTTC*AGACAA A(SEQ ID NO: 2)-MGBNFQ | 0.37x | Anhuf et al., 2003 |
| | | (r) CCTTAATTTAAG-GAATGTGAGCACC (SEQ ID NO: 3) | | | |
| SMN2 | Copy number | (f) AATGCTTTTTAA-CATCCATATAAAGCT (SEQ ID NO: 4) | FAM-TGATTTTGTCTA*AAA-CCC(SEQ ID NO: 5)-MGBNFQ | 0.76x | Anhuf et al., 2003 |
| | | (r) CCTTAATTTAAG-GAATGTGAGCACC (SEQ ID NO: 6) | | | |

TABLE 1-continued

| Target | Assay | Primers (5' to 3') | Probe (5' to 3') | 5-plex assay conditions | Ref. |
|---|---|---|---|---|---|
| BCKDHA | Copy number | (f) CAACCTACTCTT CTCAGACGTGTA (SEQ ID NO: 7) | (FAM/VIC)-CAGGAGATGCCCG-CCCAGCTC(SEQ ID NO: 8)-TAMRA | FAM: 0.18x VIC: 0.56x | DiMatteo et al., 2008 |
| | | (r) TCGAAGTGATCC AGTGGGTAGTG (SEQ ID NO: 9) | | | |
| c.815A>G | SNP | (f) TGCTGATGCTTT-GGGAAGTATGTTA (SEQ ID NO: 10) | (A)(FAM/VIC)-CATGAGTGG-CTA*TCATAC(SEQ ID NO: 11)-MGBNFQ | 0.9x | |
| | | (r) TGTCAGGAAAAG-ATGCTGAGTGATT (SEQ ID NO: 12) | (G)FAM-ATGAGTGGCTG*TC-ATAC(SEQ ID NO: 13)-MGBNFQ; | FAM: 0.9x VIC: 0.45x | |
| | | | VIC-CATGA-GTGGCTG*TCATAC (SEQ ID NO: 14)-MGBNFQ | | |
| RNaseP | Copy number | Unknown | unknown | n/a | Standard product, 4403326, ABI |

5'-exonuclease genotyping assay design. Assay conditions in column 5 are specific to the multiplexed SMA assay. References: D. Anhuf, T. Eggermann, S. Rudnik-Schöneborn and K. Zerres, Hum Mutat., 2003, 22, 74-78; D. DiMatteo, S. Callahan and E. B. Kmiec, Exp Cell Res., 2008, 15, 878-886.

Target DNA

For some genetic targets, BCKDHA and SMN2, plasmid DNA was synthesized (GeneArt, Regensburg, Germany) containing the sequence spanning between the primers (see Table 2) and cloned into the GeneArt standard vector (2.5 kb). The target fragment was released from the cloning vector by restriction digestion with SfiI to avoid any DNA supercoiling that might affect the assay. For simplicity, these gene fragments are called "plasmid DNA" throughout the text. A string of different gene fragments was also synthesized (GeneArt) and cloned into the GeneArt standard vector for demonstration of multiplexed reactions, called an "artificial chromosome" in the text. In this case, the fragments were separated from each other by restriction digestion at flanking EcoRV sites. Human DNA was obtained in already purified form from cell lines (See Table 3; Coriell, Camden, NJ) and fragmented before use with a K7025-05 nebulizer following manufacturer's instructions (Invitrogen, Carlsbad, CA). DNA concentration was quantified by measuring absorbance at 260 nm on a Nanodrop 2000 spectrophotometer (Thermo Scientific, Wilmington, DE).

TABLE 3

Map of patient numbers used in the text to Coriell cell lines.

| Patient number | Coriell cell line | Patient number, cont'd. | Coriell cell line, cont'd. |
|---|---|---|---|
| 1 | NA14638 | 11 | NA13714 |
| 2 | NA14637 | 12 | NA13712 |
| 3 | NA14097 | 13 | NA13709 |
| 4 | NA14096 | 14 | NA13707 |
| 5 | NA14094 | 15 | NA13705 |
| 6 | NA14093 | SMA carrier | NA03814 |
| 7 | NA14092 | SMA 1 | NA03813 |
| 8 | NA14091 | SMA 2 | NA00232 |

TABLE 3-continued

Map of patient numbers used in the text to Coriell cell lines.

| Patient number | Coriell cell line | Patient number, cont'd. | Coriell cell line, cont'd. |
|---|---|---|---|
| 9 | NA14090 | SMA 3 | NA09677 |
| 10 | NA13715 | SMA 4 | NA10684 |

Microfluidics

Microfluidic chips were manufactured by conventional soft lithography. Molding masters were fabricated by spin coating SU-8 negative photoresist (MicroChem Corp., Newton, MA) onto 6 inch silicon wafers and transferring the fluidic features from photomasks (CAD/Art Services, Bandon, OR) by contact lithography with an OAI Hybralign Series 200 aligner (OAI, San Jose, CA). Chips contained channels with two depths: deep channels with low hydrodynamic resistance (100±10 um) for transporting fluid from external ports to the functional regions of the chip, and shallow channels (20±1 um) for droplet manipulation and detection. SU-8 photoresists 2100 and 2025 were used for deep and shallow channels respectively. Polydimethylsiloxane (PDMS) (Sylgard® 184, Dow Corning, Midland, MI) chips were molded from the negative masters within mold housings of custom design. Glass cover slides were permanently bonded to the fluidic side of the chips by surface activation in an AutoGlow™ oxygen plasma system (Glow Research, Phoenix, AZ) followed by immediate contact bonding. To create hydrophobic surfaces, the microfluidic channels were exposed for ~2 min to 1H,1H,2H,2H-perfluorodecyltrichlorosilane (Alfa Aesar, Ward Hill, MA) dissolved in FC-3283 (3M Specialty Materials, St. Paul, MN) prepared as a mixture of 18 g silane in 100 uL solvent.

Two different microfluidic devices were used, one for droplet generation and the other for fluorescence readout after thermal cycling. The droplet generation chip created an emulsion of uniformly sized aqueous droplets of template DNA and PCR master mix that were suspended in an inert fluorinated oil with an emulsion stabilizing surfactant, called "carrier oil" from this point forward (REB carrier oil; RainDance Technologies, Lexington, MA). Droplets were generated in a cross-shaped microfluidic intersection, or "nozzle". As shown in FIG. 3*a*, under typical operation the aqueous phase flowed into the nozzle from the right (160 uL/hr), joining flows of the carrier oil from the top and bottom (750 uL/hr of total oil), and producing 4 pL droplets at a rate of 11 kHz. The channel widths at the intersection measured 15 um for the aqueous inlet, 12.5 for the oil inlets, and 15 um widening to 40 um at the outlet. Flow was driven by custom OEM pumps (IDEX Corporation, Northbrook, IL).

Approximately 25 μL of the PCR reaction mixture was collected as an emulsion from the droplet generation chip and thermally cycled in a DNA Engine (Bio-Rad, Hercules, CA). The reaction mixture contained 1× TaqMan® universal PCR master mix (Applied Biosystems, Carlsbad, CA), 0.2 mM dNTP (Takara Bio, Madison, WI), and various amounts of primer pairs and probes as described in the results. 1× assay concentration is defined as 0. μM probes with 0.9 μM primers. In all cases, when varied from the 1× concentration, the primers and probes were varied by the same amount. The cycler program included a 10 min hot start at 95° C., and 45 cycles of 15 sat 95° C. and 60 s at 60° C.

The droplets became concentrated during off-chip handling because the carrier oil is more dense than the aqueous phase and drained down from the emulsion. Hence the droplets were reinjected into the readout chip as a tightly packed emulsion that required dilution prior to readout to properly distinguish one droplet from another. A "spacer" nozzle similar to the droplet generation nozzle above was used to inject uniform plugs of extra carrier oil between droplets immediately before readout. As shown in FIG. 3*b*, the droplet entrance into the nozzle tapered down into a constriction about the size of an individual droplet forcing the droplets to enter the nozzle in single file and consequently at a stable rate. Opposed flow of the carrier oil from the top and bottom channels separated the droplets uniformly. The channel leaving the spacer nozzle increased in width along the direction of flow, and the droplets were interrogated by laser induced fluorescence at the location along the channel where the width was smaller than or equal to the droplet diameter (marked with an arrow in FIG. 3*b*). The nozzle dimensions were 15 um for the droplet entrance and exit, and 20 um for the oil lines.

Instrumentation

Fluorescence readout was performed by conventional epifluorescence microscopy with a custom microscope. A 20 mW, 488 nm laser source (Cyan; Picarro, Sunnyvale, CA) was expanded 2× and focused by the objective lens (20×/0.45 NA; Nikon, Japan) onto the microfluidic channel. Two band pass filters discriminated the fluorescence collected through the objective lens: 512/25 nm and 529/28 nm for FAM and VIC fluorophores respectively (Semrock, Rochester, NY). Fluorescence was detected by two H5784-20 photomultipliers (Hamamatsu, Japan) and was typically recorded at a 200 kHz sampling rate with a USB-6259 data acquisition card (National Instruments, Austin, TX). The data traces were smoothed by a seven-point, second-order Savitzky-Golay algorithm before subsequent analysis. Concurrent with the fluorescence read out, the droplets were imaged through the same objective lens with backside illumination from an 850 nm LED (TSHG6200; Vishay Semiconductors, Shelton, CT), a short pass filter to separate the optical paths for fluorescence detection and imaging, and a Guppy CCD camera (Allied Vision Technologies, Newburyport, MA). Droplets were imaged with short illumination pulses (5-20 us) to avoid image streaking.

Data Analysis

Data was analyzed with custom LabView software (National Instruments, Austin, TX) that interpreted droplet events as contiguous bursts of fluorescence intensity above a threshold value. The signal-to-noise ratio was generally quite high and the signal levels were consistent from day to day, hence a fixed threshold value of 50 mV was used predominantly, otherwise the threshold was set by eye. The peak fluorescence intensity was recorded for each droplet event for both VIC and FAM fluorophores. Some coalescence of droplets did occur during thermal cycling, typically as isolated events between two intact droplets forming "doublets." Doublets and the rare larger coalesced events were easily filtered from the data set on based on the duration of the fluorescence burst.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method of analyzing a sample nucleic acid, the method comprising the steps of:

preparing a sample fluid by mixing a nucleic acid molecule isolated from a biological sample with a plurality of primers pair types and a plurality of probe types, wherein each primer pair type and each probe type targets a variant at one of a plurality of loci on the nucleic acid molecule, wherein the plurality of probe types comprises probes of a first type of probes that targets a first variant at a first locus and probes of a second type of probes that targets a second variant at a second locus, wherein the first type of probes and the second type of probes are present in different concentrations and include a first fluorescent label;

conducting a polymerase chain reaction (PCR) on the sample fluid;

detecting one or more fluorescent signals emitted by the first fluorescent label as a result of the PCR, wherein signal intensity of the first fluorescent label from the first type of probes is distinct from signal intensity of the first fluorescent label from the second type of probes due to the different concentrations among the first and second types of probes; and determining the presence of a haplotype of interest based on detecting the one or more fluorescent signals.

2. The method of claim 1, wherein the haplotype of interest comprises a grouping of more than two genomic variants associated with the nucleic acid molecule.

3. The method of claim 2, wherein the genomic variants comprise single nucleotide polymorphisms.

4. The method of claim 1, wherein the nucleic acid molecule comprises a single nucleic acid strand.

5. The method of claim 1, wherein the biological sample is tissue or body fluid.

6. The method of claim 5, wherein the body fluid is selected from the group consisting of blood, saliva, urine, feces, spinal fluid, aspirate, and sputum.

7. The method of claim 1, further comprising sequencing the sample nucleic acid molecule.

* * * * *

SEQUENCE LISTING

```
<160> NUMBER OF SEQ ID NOS: 14

<210> SEQ ID NO 1
<211> LENGTH: 27
<212> TYPE: DNA
<213> ORGANISM: Artificial Sequence
<220> FEATURE:
<223> OTHER INFORMATION: synthetic sequence

<400> SEQUENCE: 1

aatgcttttt aacatccata taaagct                                        27
```

<210> SEQ ID NO 2
<211> LENGTH: 25
<212> TYPE: DNA
<213> ORGANISM: Artificial Sequence
<220> FEATURE:
<223> OTHER INFORMATION: synthetic sequence

<400> SEQUENCE: 2
ccttaattta aggaatgtga gcacc 25

<210> SEQ ID NO 3
<211> LENGTH: 27
<212> TYPE: DNA
<213> ORGANISM: Artificial Sequence
<220> FEATURE:
<223> OTHER INFORMATION: synthetic sequence

<400> SEQUENCE: 3
aatgcttttt aacatccata taaagct 27

<210> SEQ ID NO 4
<211> LENGTH: 25
<212> TYPE: DNA
<213> ORGANISM: Artificial Sequence
<220> FEATURE:
<223> OTHER INFORMATION: synthetic sequence

<400> SEQUENCE: 4
ccttaattta aggaatgtga gcacc 25

<210> SEQ ID NO 5
<211> LENGTH: 24
<212> TYPE: DNA
<213> ORGANISM: Artificial Sequence
<220> FEATURE:
<223> OTHER INFORMATION: synthetic sequence

<400> SEQUENCE: 5
caacctactc ttctcagacg tgta 24

<210> SEQ ID NO 6
<211> LENGTH: 23
<212> TYPE: DNA
<213> ORGANISM: Artificial Sequence
<220> FEATURE:
<223> OTHER INFORMATION: synthetic sequence

<400> SEQUENCE: 6
tcgaagtgat ccagtgggta gtg 23

<210> SEQ ID NO 7
<211> LENGTH: 25
<212> TYPE: DNA
<213> ORGANISM: Artificial Sequence
<220> FEATURE:
<223> OTHER INFORMATION: synthetic sequence

<400> SEQUENCE: 7
tgctgatgct ttgggaagta tgtta 25

<210> SEQ ID NO 8
<211> LENGTH: 25
<212> TYPE: DNA
<213> ORGANISM: Artificial Sequence
<220> FEATURE:

<223> OTHER INFORMATION: synthetic sequence

<400> SEQUENCE: 8
tgtcaggaaa agatgctgag tgatt 25

<210> SEQ ID NO 9
<211> LENGTH: 16
<212> TYPE: DNA
<213> ORGANISM: Artificial Sequence
<220> FEATURE:
<223> OTHER INFORMATION: synthetic sequence

<400> SEQUENCE: 9
cagggtttca gacaaa 16

<210> SEQ ID NO 10
<211> LENGTH: 18
<212> TYPE: DNA
<213> ORGANISM: Artificial Sequence
<220> FEATURE:
<223> OTHER INFORMATION: synthetic sequence

<400> SEQUENCE: 10
tgattttgtc taaaaccc 18

<210> SEQ ID NO 11
<211> LENGTH: 21
<212> TYPE: DNA
<213> ORGANISM: Artificial Sequence
<220> FEATURE:
<223> OTHER INFORMATION: synthetic sequence

<400> SEQUENCE: 11
caggagatgc ccgcccagct c 21

<210> SEQ ID NO 12
<211> LENGTH: 18
<212> TYPE: DNA
<213> ORGANISM: Artificial Sequence
<220> FEATURE:
<223> OTHER INFORMATION: synthetic sequence

<400> SEQUENCE: 12
catgagtggc tatcatac 18

<210> SEQ ID NO 13
<211> LENGTH: 17
<212> TYPE: DNA
<213> ORGANISM: Artificial Sequence
<220> FEATURE:
<223> OTHER INFORMATION: synthetic sequence

<400> SEQUENCE: 13
atgagtggct gtcatac 17

<210> SEQ ID NO 14
<211> LENGTH: 18
<212> TYPE: DNA
<213> ORGANISM: Artificial Sequence
<220> FEATURE:
<223> OTHER INFORMATION: synthetic sequence

<400> SEQUENCE: 14
catgagtggc tgtcatac 18